(12) United States Patent
Zhang et al.

(10) Patent No.: US 8,980,908 B2
(45) Date of Patent: *Mar. 17, 2015

(54) NON-PEPTIDYL, POTENT, AND SELECTIVE MU OPIOID RECEPTOR ANTAGONISTS AND THEIR USE IN TREATING OPIOID ADDICTION AND OPIOID INDUCED CONSTIPATION

(71) Applicant: Virginia Commonwealth University, Richmond, VA (US)

(72) Inventors: Yan Zhang, Glen Allen, VA (US); Dana E. Selley, Richmond, VA (US); William Dewey, Richmond, VA (US)

(73) Assignee: Virginia Commonwealth University, Richmond, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/287,254

(22) Filed: May 27, 2014

(65) Prior Publication Data

US 2014/0371255 A1 Dec. 18, 2014

Related U.S. Application Data

(63) Continuation-in-part of application No. 13/144,788, filed as application No. PCT/US2010/021157 on Jan. 15, 2010, now Pat. No. 8,772,308.

(60) Provisional application No. 61/912,662, filed on Dec. 6, 2013, provisional application No. 61/145,379, filed on Jan. 16, 2009.

(51) Int. Cl.
*A61K 31/485* (2006.01)
*C07D 489/08* (2006.01)
*G01N 33/53* (2006.01)

(52) U.S. Cl.
CPC .............. *C07D 489/08* (2013.01); *G01N 33/53* (2013.01); *G01N 2500/04* (2013.01)
USPC .............................................. 514/282; 546/44

(58) Field of Classification Search
USPC ............................................ 514/282; 546/44
See application file for complete search history.

(56) References Cited

U.S. PATENT DOCUMENTS 8,772,308 B2 * 7/2014 Zhang et al. .................. 514/282

* cited by examiner

*Primary Examiner* — Charanjit Aulakh
(74) *Attorney, Agent, or Firm* — Whitham, Curtis, Christofferson & Cook, P.C.

(57) ABSTRACT

Selective, non-peptide antagonists of the mu opioid receptor (MOR) and methods of their use are provided. The antagonists may be used, for example, to identify MOR agonists in competitive binding assays, and to treat conditions related to addiction in which MOR is involved, e.g. heroin, prescription drug and alcohol addiction, as well as in the treatment of opioid induced constipation (OIC).

15 Claims, 37 Drawing Sheets

R = Me, OMe, CN, Cl etc;
X = CH₂, C₂H₄, CH₂NHCO;
Y/Y' = N;
Z = N or NMe;

SEQUENCE LISTING

```
<160> NUMBER OF SEQ ID NOS: 7

<210> SEQ ID NO 1
<211> LENGTH: 285
<212> TYPE: PRT
<213> ORGANISM: Mus musculus

<400> SEQUENCE: 1

Val Thr Ala Ile Thr Ile Met Ala Leu Tyr Ser Ile Val Cys Val Val
1               5                   10                  15

Gly Leu Phe Gly Asn Phe Leu Val Met Tyr Val Ile Val Arg Tyr Thr
            20                  25                  30

Lys Met Lys Thr Ala Thr Asn Ile Tyr Ile Phe Asn Leu Ala Leu Ala
        35                  40                  45

Asp Ala Leu Ala Thr Ser Thr Leu Pro Phe Gln Ser Val Asn Tyr Leu
    50                  55                  60

Met Gly Thr Trp Pro Phe Gly Asn Ile Leu Cys Lys Ile Val Ile Ser
65                  70                  75                  80

Ile Asp Tyr Tyr Asn Met Phe Thr Ser Ile Phe Thr Leu Cys Thr Met
                85                  90                  95

Ser Val Asp Arg Tyr Ile Ala Val Cys His Pro Val Lys Ala Leu Asp
            100                 105                 110

Phe Arg Thr Pro Arg Asn Ala Lys Ile Val Asn Val Cys Asn Trp Ile
        115                 120                 125

Leu Ser Ser Ala Ile Gly Leu Pro Val Met Phe Met Ala Thr Thr Lys
    130                 135                 140
```

```
Tyr Arg Gln Gly Ser Ile Asp Cys Thr Leu Thr Phe Ser His Pro Thr
145                 150                 155                 160

Trp Tyr Trp Glu Asn Leu Leu Lys Ile Cys Val Phe Ile Phe Ala Phe
                165                 170                 175

Ile Met Pro Val Leu Ile Ile Thr Val Cys Tyr Gly Leu Met Ile Leu
            180                 185                 190

Arg Leu Lys Ser Val Arg Met Leu Ser Gly Ser Lys Glu Lys Asp Arg
        195                 200                 205

Asn Leu Arg Arg Ile Thr Arg Met Val Leu Val Val Val Ala Val Phe
210                 215                 220

Ile Val Cys Trp Thr Pro Ile His Ile Tyr Val Ile Lys Ala Leu
225                 230                 235                 240

Ile Thr Ile Pro Glu Thr Thr Phe Gln Thr Val Ser Trp His Phe Cys
                245                 250                 255

Ile Ala Leu Gly Tyr Thr Asn Ser Cys Leu Asn Pro Val Leu Tyr Ala
                260                 265                 270

Phe Leu Asp Glu Asn Phe Lys Arg Cys Phe Arg Glu Phe
            275                 280                 285

<210> SEQ ID NO 2
<211> LENGTH: 288
<212> TYPE: PRT
<213> ORGANISM: Mus musculus

<400> SEQUENCE: 2

Ala Ile Pro Val Ile Ile Thr Ala Val Tyr Ser Val Val Phe Val Val
1               5                   10                  15

Gly Leu Val Gly Asn Ser Leu Val Met Phe Val Ile Ile Arg Tyr Thr
            20                  25                  30

Lys Met Lys Thr Ala Thr Asn Ile Tyr Ile Phe Asn Leu Ala Leu Ala
        35                  40                  45

Asp Ala Leu Val Thr Thr Thr Met Pro Phe Gln Ser Ala Val Tyr Leu
50                  55                  60

Met Asn Ser Trp Pro Phe Gly Asp Val Leu Cys Lys Ile Val Ile Ser
65                  70                  75                  80

Ile Asp Tyr Tyr Asn Met Phe Thr Ser Ile Phe Thr Leu Thr Met Met
                85                  90                  95

Ser Val Asp Arg Tyr Ile Ala Val Cys His Pro Val Lys Ala Leu Asp
            100                 105                 110

Phe Arg Thr Pro Leu Lys Ala Lys Ile Ile Asn Ile Cys Ile Trp Leu
        115                 120                 125

Leu Ala Ser Ser Val Gly Ile Ser Ala Ile Val Leu Gly Gly Thr Lys
130                 135                 140

Val Arg Glu Asp Val Asp Val Ile Glu Cys Ser Leu Gln Phe Pro Asp
145                 150                 155                 160

Asp Glu Tyr Ser Trp Trp Asp Leu Phe Met Lys Ile Cys Val Phe Val
                165                 170                 175

Phe Ala Phe Val Ile Pro Val Leu Ile Ile Ile Val Cys Tyr Thr Leu
            180                 185                 190

Met Ile Leu Arg Leu Lys Ser Val Arg Leu Leu Ser Gly Ser Arg Glu
        195                 200                 205

Lys Asp Arg Asn Leu Arg Arg Ile Thr Lys Leu Val Leu Val Val Val
210                 215                 220

Ala Val Phe Ile Ile Cys Trp Thr Pro Ile His Ile Phe Ile Leu Val
```

```
                225                 230                 235                 240
            Glu Ala Leu Gly Ser Thr Ser His Ser Thr Ala Ala Leu Ser Ser Tyr
                                245                 250                 255

Tyr Phe Cys Ile Ala Leu Gly Tyr Thr Asn Ser Ser Leu Asn Pro Val
                                260                 265                 270

Leu Tyr Ala Phe Leu Asp Glu Asn Phe Lys Arg Cys Phe Arg Asp Phe
                                275                 280                 285

<210> SEQ ID NO 3
<211> LENGTH: 286
<212> TYPE: PRT
<213> ORGANISM: Mus musculus

<400> SEQUENCE: 3

Ala Leu Ala Ile Ala Ile Thr Ala Leu Tyr Ser Ala Val Cys Ala Val
1               5                   10                  15

Gly Leu Leu Gly Asn Val Leu Val Met Phe Gly Ile Val Arg Tyr Thr
            20                  25                  30

Lys Leu Lys Thr Ala Thr Asn Ile Tyr Ile Phe Asn Leu Ala Leu Ala
        35                  40                  45

Asp Ala Leu Ala Thr Ser Thr Leu Pro Phe Gln Ser Ala Lys Tyr Leu
    50                  55                  60

Met Glu Thr Trp Pro Phe Gly Glu Leu Leu Cys Lys Ala Val Leu Ser
65                  70                  75                  80

Ile Asp Tyr Tyr Asn Met Phe Thr Ser Ile Phe Thr Leu Thr Met Met
                85                  90                  95

Ser Val Asp Arg Tyr Ile Ala Val Cys His Pro Val Lys Ala Leu Asp
            100                 105                 110

Phe Arg Thr Pro Ala Lys Ala Lys Leu Ile Asn Ile Cys Ile Trp Val
        115                 120                 125

Leu Ala Ser Gly Val Gly Val Pro Ile Met Val Met Ala Val Thr Gln
    130                 135                 140

Pro Arg Asp Gly Ala Val Val Cys Met Leu Gln Phe Pro Ser Pro Ser
145                 150                 155                 160

Trp Tyr Trp Asp Thr Val Thr Lys Ile Cys Val Phe Leu Phe Ala Phe
                165                 170                 175

Val Val Pro Ile Leu Ile Ile Thr Val Cys Tyr Gly Leu Met Leu Leu
            180                 185                 190

Arg Leu Arg Ser Val Arg Leu Leu Ser Gly Ser Lys Glu Lys Asp Arg
        195                 200                 205

Ser Leu Arg Arg Ile Thr Arg Met Val Leu Val Val Val Gly Ala Phe
    210                 215                 220

Val Val Cys Trp Ala Pro Ile His Ile Phe Val Ile Val Trp Thr Leu
225                 230                 235                 240

Val Asp Ile Asn Arg Arg Asp Pro Leu Val Val Ala Ala Leu His Leu
                245                 250                 255

Cys Ile Ala Leu Gly Tyr Ala Asn Ser Ser Leu Asn Pro Val Leu Tyr
            260                 265                 270

Ala Phe Leu Asp Glu Asn Phe Lys Arg Cys Phe Arg Gln Leu
        275                 280                 285

<210> SEQ ID NO 4
<211> LENGTH: 264
<212> TYPE: PRT
<213> ORGANISM: Homo sapiens
```

-continued

```
<400> SEQUENCE: 4

Val Trp Val Val Gly Met Gly Ile Val Met Ser Leu Ile Val Leu Ala
1               5                   10                  15

Ile Val Phe Gly Asn Val Leu Val Ile Thr Ala Ile Ala Lys Phe Glu
            20                  25                  30

Arg Leu Gln Thr Val Thr Asn Tyr Phe Ile Thr Ser Leu Ala Cys Ala
        35                  40                  45

Asp Leu Val Met Gly Leu Ala Val Val Pro Phe Gly Ala Ala His Ile
    50                  55                  60

Leu Met Lys Met Trp Thr Phe Gly Asn Phe Trp Cys Glu Phe Trp Thr
65                  70                  75                  80

Ser Ile Asp Val Leu Cys Val Thr Ala Ser Ile Glu Thr Leu Cys Val
                85                  90                  95

Ile Ala Val Asp Arg Tyr Phe Ala Ile Thr Ser Pro Phe Lys Tyr Gln
            100                 105                 110

Ser Leu Leu Thr Lys Asn Lys Ala Arg Val Ile Ile Leu Met Val Trp
        115                 120                 125

Ile Val Ser Gly Leu Thr Ser Phe Leu Pro Ile Gln Met His Trp Tyr
    130                 135                 140

Arg Ala Thr His Gln Glu Ala Ile Asn Cys Tyr Ala Asn Glu Thr Cys
145                 150                 155                 160

Cys Asp Phe Phe Thr Asn Gln Ala Tyr Ala Ile Ala Ser Ser Ile Val
                165                 170                 175

Ser Phe Tyr Val Pro Leu Val Ile Met Val Phe Val Tyr Ser Arg Glu
            180                 185                 190

His Lys Ala Leu Lys Thr Leu Gly Ile Ile Met Gly Thr Phe Thr Leu
        195                 200                 205

Cys Trp Leu Pro Phe Phe Ile Val Asn Ile Val His Val Ile Gln Asp
    210                 215                 220

Asn Leu Ile Arg Lys Glu Val Tyr Ile Leu Leu Asn Trp Ile Gly Tyr
225                 230                 235                 240

Val Asn Ser Gly Phe Asn Pro Leu Ile Tyr Ile Tyr Cys Arg Ser Pro
                245                 250                 255

Asp Phe Arg Ile Ala Phe Gln Glu
            260

<210> SEQ ID NO 5
<211> LENGTH: 286
<212> TYPE: PRT
<213> ORGANISM: Bos primigenius

<400> SEQUENCE: 5

Trp Gln Phe Ser Met Leu Ala Ala Tyr Met Phe Leu Leu Ile Met Leu
1               5                   10                  15

Gly Phe Pro Ile Asn Phe Leu Thr Leu Tyr Val Thr Val Gln His Lys
            20                  25                  30

Lys Leu Arg Thr Pro Leu Asn Tyr Ile Leu Leu Asn Leu Ala Val Ala
        35                  40                  45

Asp Leu Phe Met Val Phe Gly Gly Phe Thr Thr Thr Leu Tyr Thr Ser
    50                  55                  60

Leu His Gly Tyr Phe Val Phe Gly Pro Thr Gly Cys Asn Leu Glu Gly
65                  70                  75                  80

Phe Phe Ala Thr Leu Gly Gly Glu Ile Ala Leu Trp Ser Leu Val Val
                85                  90                  95
```

```
Leu Ala Ile Glu Arg Tyr Val Val Cys Lys Pro Met Ser Asn Phe
            100                 105                 110

Arg Phe Gly Glu Asn His Ala Ile Met Gly Val Ala Phe Thr Trp Val
        115                 120                 125

Met Ala Leu Ala Cys Ala Ala Pro Pro Leu Val Gly Trp Ser Arg Tyr
    130                 135                 140

Ile Pro Glu Gly Met Gln Cys Ser Cys Gly Ile Asp Tyr Tyr Thr Pro
145                 150                 155                 160

His Glu Glu Thr Asn Asn Glu Ser Phe Val Ile Tyr Met Phe Val Val
                165                 170                 175

His Phe Ile Ile Pro Leu Ile Val Ile Phe Phe Cys Tyr Gly Gln Leu
            180                 185                 190

Val Phe Thr Val Lys Glu Ala Ala Ala Gln Gln Gln Glu Ser Ala Thr
        195                 200                 205

Thr Gln Lys Ala Glu Lys Glu Val Thr Arg Met Val Ile Ile Met Val
    210                 215                 220

Ile Ala Phe Leu Ile Cys Trp Leu Pro Tyr Ala Gly Val Ala Phe Tyr
225                 230                 235                 240

Ile Phe Thr His Gln Gly Ser Asp Phe Gly Pro Ile Phe Met Thr Ile
                245                 250                 255

Pro Ala Phe Phe Ala Lys Thr Ser Ala Val Tyr Asn Pro Val Ile Tyr
            260                 265                 270

Ile Met Met Asn Lys Gln Phe Arg Asn Cys Met Val Thr Thr
        275                 280                 285

<210> SEQ ID NO 6
<211> LENGTH: 8
<212> TYPE: PRT
<213> ORGANISM: Artificial Sequence
<220> FEATURE:
<223> OTHER INFORMATION: Synthetic mu opioid receptor selective
      antagonist
<220> FEATURE:
<221> NAME/KEY: misc_feature
<222> LOCATION: (1)..(1)
<223> OTHER INFORMATION: D amino acid
<220> FEATURE:
<221> NAME/KEY: misc_feature
<222> LOCATION: (4)..(4)
<223> OTHER INFORMATION: D amino acid
<220> FEATURE:
<221> NAME/KEY: misc_feature
<222> LOCATION: (5)..(5)
<223> OTHER INFORMATION: ornithine
<220> FEATURE:
<221> NAME/KEY: misc_feature
<222> LOCATION: (7)..(7)
<223> OTHER INFORMATION: Penicillamine (Pen)
<220> FEATURE:
<221> NAME/KEY: misc_feature
<222> LOCATION: (8)..(8)
<223> OTHER INFORMATION: thr is sulfated and forms a disulfide with cys
      at position 2

<400> SEQUENCE: 6

Phe Cys Tyr Trp Xaa Thr Xaa Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic mu opioid receptor selective
      antagonist
```

```
<220> FEATURE:
<221> NAME/KEY: MISC_FEATURE
<222> LOCATION: (1)..(1)
<223> OTHER INFORMATION: D non-natural amino acid
      1,2,3,4-Tetrahydroisoquinoline-3-Carboxylic Acid (Tic)
<220> FEATURE:
<221> NAME/KEY: MISC_FEATURE
<222> LOCATION: (4)..(4)
<223> OTHER INFORMATION: D amino acid
<220> FEATURE:
<221> NAME/KEY: MISC_FEATURE
<222> LOCATION: (7)..(7)
<223> OTHER INFORMATION: Penicillamine (Pen)
<220> FEATURE:
<221> NAME/KEY: MISC_FEATURE
<222> LOCATION: (8)..(8)
<223> OTHER INFORMATION: Thr is sulfated and forms a disulfide with Cys
      at position 2

<400> SEQUENCE: 7

Xaa Cys Tyr Trp Arg Thr Xaa Thr
1               5
```

NON-PEPTIDYL, POTENT, AND SELECTIVE MU OPIOID RECEPTOR ANTAGONISTS AND THEIR USE IN TREATING OPIOID ADDICTION AND OPIOID INDUCED CONSTIPATION

CROSS-REFERENCE TO RELATED APPLICATIONS

This application is a continuation-in-part (CIP) application of U.S. Ser. No. 13/144,788 filed Sep. 1, 2011, as a national stage filing of PCT/US2010/021157 filed Jan. 15, 2010, claiming priority to U.S. Ser. No. 61/145,379 filed Jan. 16, 2009. This application also claims priority to U.S. Ser. No. 61/912,662 filed Dec. 6, 2013. The complete contents of each of these applications is herein incorporated by reference.

BACKGROUND OF THE INVENTION

1. Field of the Invention

The invention generally relates to selective, non-peptide antagonists of the mu opioid receptor (MOR) and methods of their use including, without limitation, in treating opioid induced constipation.

2. Background

Opioid dependence is one of the most serious chronic and relapsing medical disorders. Heroin and prescription opioid abuse and dependence are very common and still increasing. According to the National Household Survey on Drug Abuse 2001, there are about 800,000 persons addicted to heroin and 3.5 million prescription opioid abusers in the United States. For many clinically available opiates, not only their analgesic function but also their notorious side effects (such as addiction and abuse liability) are primarily due to their interaction with the mu opioid receptor (MOR). There is an ongoing need to develop selective antagonists for MOR, and to develop analgesics without or with less addiction and abuse liability.

SUMMARY OF THE INVENTION

The invention provides selective, non-peptide antagonists of the mu opioid receptor (MOR) and methods of using the antagonists to identity MOR agonists, or as agents to treat various disorders that involve MOR (e.g. drug addiction, opioid induced constipation (OIC), etc.).

In preferred embodiments, the selective, non-peptide MOR antagonist is represented by formula

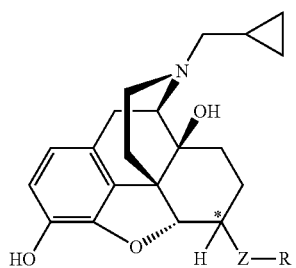

where
the MOR antagonist may be a racemic mixture or a purified racemate;
the nitrogen (N) at the 17N position may be charged and substituted with a $C_{1-10}$ alkyl or alkaryl (e.g, methylated), or may be uncharged (e.g., unmethylated);
Z is selected from the group consisting of a substituted or unsubstituted aliphatic moiety; NH; CO; (NHCO)n where n=1-5; (CONH)n where n=1-5; (NHCO)(CH$_2$)n(NHCO), where n=1-5; (NHCO)(CH$_2$)n where n=1-5; (CH$_2$)n(NHCO), where n=1-5; and O;
R is selected from the group consisting of substituted and unsubstituted heteroaromatic rings including without limitation

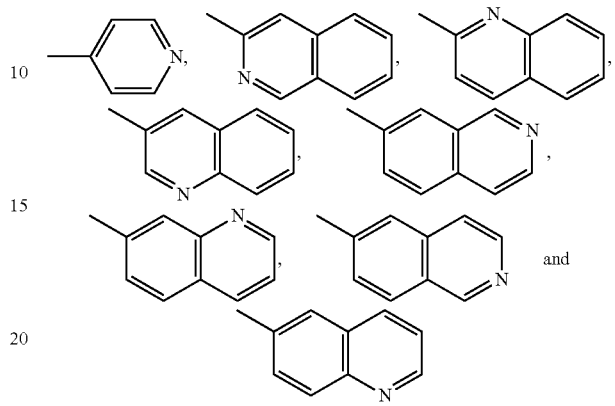

and wherein any carbon of said heteroaromatic ring may be bonded to a hydrogen or be substituted with a substitution selected from the group consisting of substituted or unsubstituted C1-5 alkyl (e.g., methyl), C1-5 alyleether (e.g., O-methyl), carboxylic acid (COOH), nitrogen (N), cyano (CN), nitro (NO$_2$), halogen (e.g., chloro), or amino moiety, and where the substitution may be the same or different when more than one carbon is substituted, and wherein the nitrogen moiety in the heteroaromatic ring may be charged and substituted with a C1-10 alkyl or alkaryl, and wherein in addition to the nitrogen substitution in said heteroaromatic ring, one or more carbons within said heteroaromatic ring may be replaced by a substitution with a ring selected from the group consisting of N, S, P, and O. Exemplary moieties that may be included as substitutions to the aromatic ring(s) include but are not limited to N, methyl and various branched and unbranched aliphatic chains; COOH, halogen, CN, NO$_2$, OCH$_3$, etc., and combinations thereof, e.g. (CH$_2$)nCOOH where n=1-5), (CH$_2$)nNO$_2$ where n=1-5, (CH$_2$)nNH$_2$ where n=1-5, etc. If multiple substitutions are present, they may be the same or different. Furthermore, the heteroaromatic rings may also include more than one substitution within the rings (e.g., two or more nitrogens in the rings, as well as S, P, or O substitutions within the rings, and the heteroaromatic rings, when substituted with more than one substitution may be substituted with the same or different moieties (e.g., an N and a P).

Examples of non-peptide MOR antagonists include without limitation:

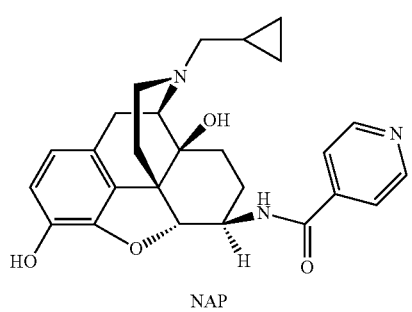

NAP

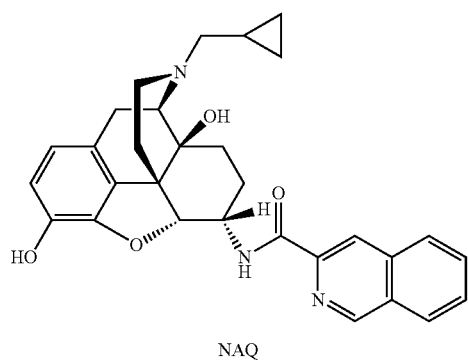
NAQ
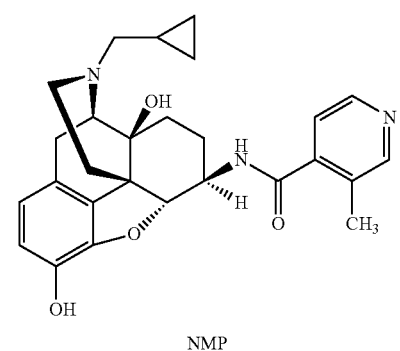
NMP
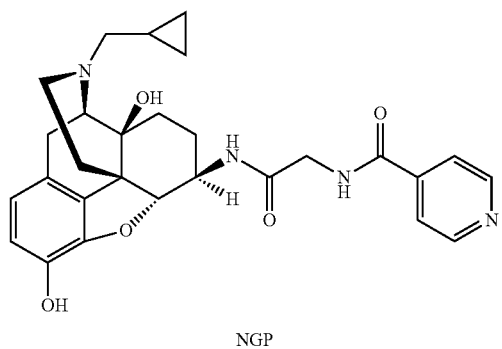
NGP
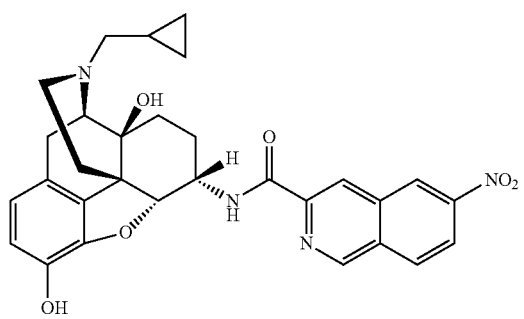
NNQ
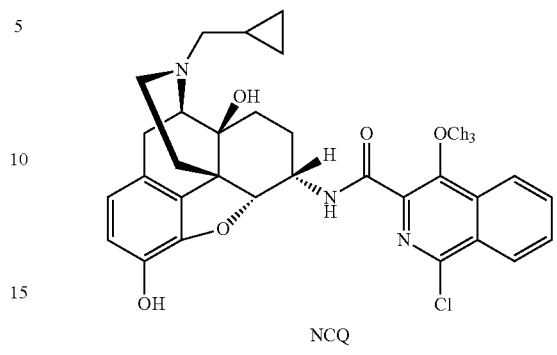
NCQ
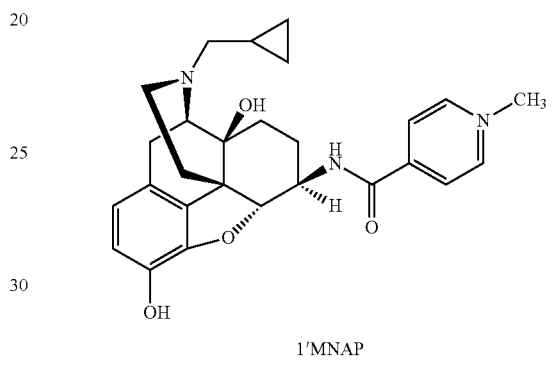
1′MNAP
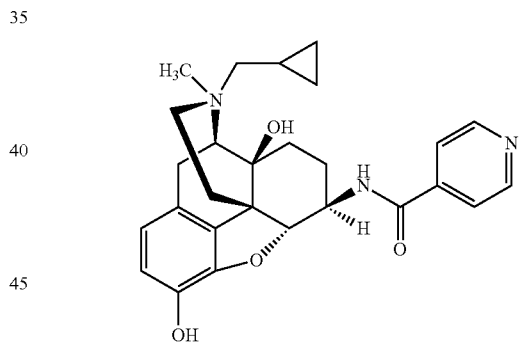
17MNAP
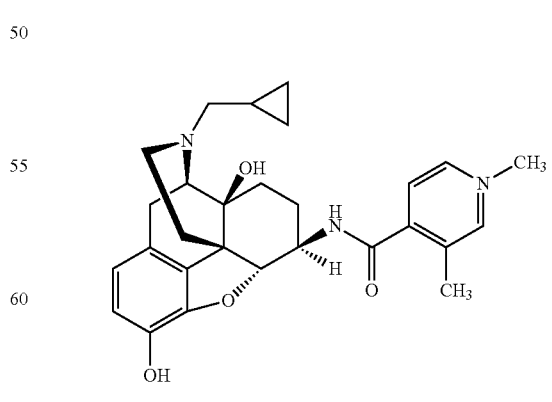
1′MNMP

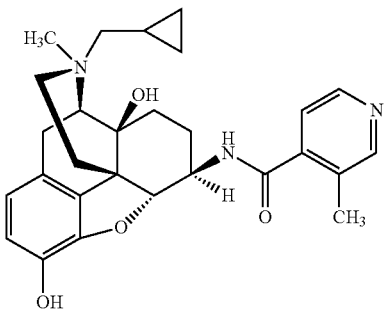

17MNMP

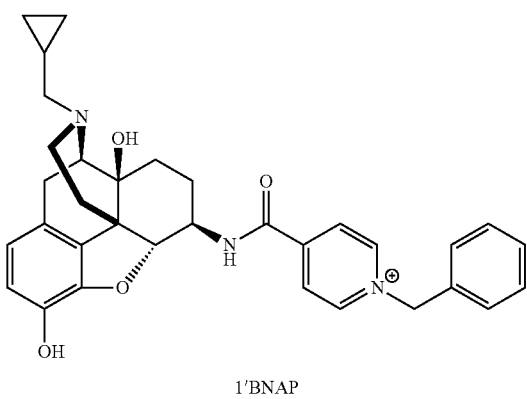

1'BNAP

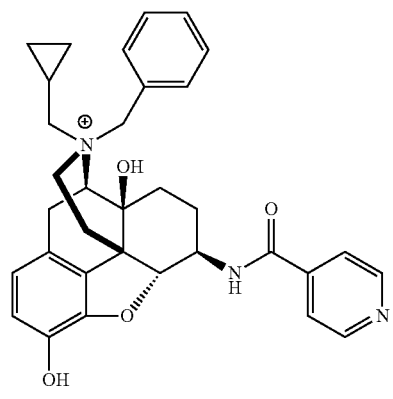

17 BNAP

Embodiments of the invention contemplate use of the compounds for combating opiate drug addition, opiate induced constipation, as well as in other clinical applications, and in screening for whether or not a compound is a suitable candidate as a MOR antagonist (e.g., by performing a competitive inhibition test with the candidate and one or more of the non-peptidyl MOR antagonist. Notably, 1'MNAP, 17MNAP, 1'MNMP, and 71MNMP are essentially different methylation products of NAP and NMP, but have relatively more promising therapeutic potential in treating symptoms of opioid induced constipation. When used to treat symptoms of addiction related to MOR or opioid induced constipation in a human or animal subject, the subject is administered with one or multiple doses of the non-peptidyl MOR antagonist of general formula

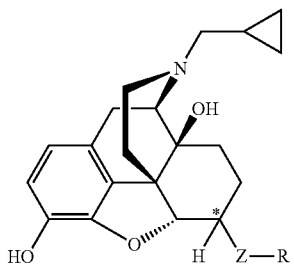

where administration may be via any suitable route including oral, nasal, injection (i.p., i.v., i.m., s.c., etc.) and transdermal, and where, if multiple doses of the non-peptidyl MOR antagonist are employed the specific non-peptidyl MOR antagonist may be the same or different at each dosing.

DETAILED DESCRIPTION

Figure 1:
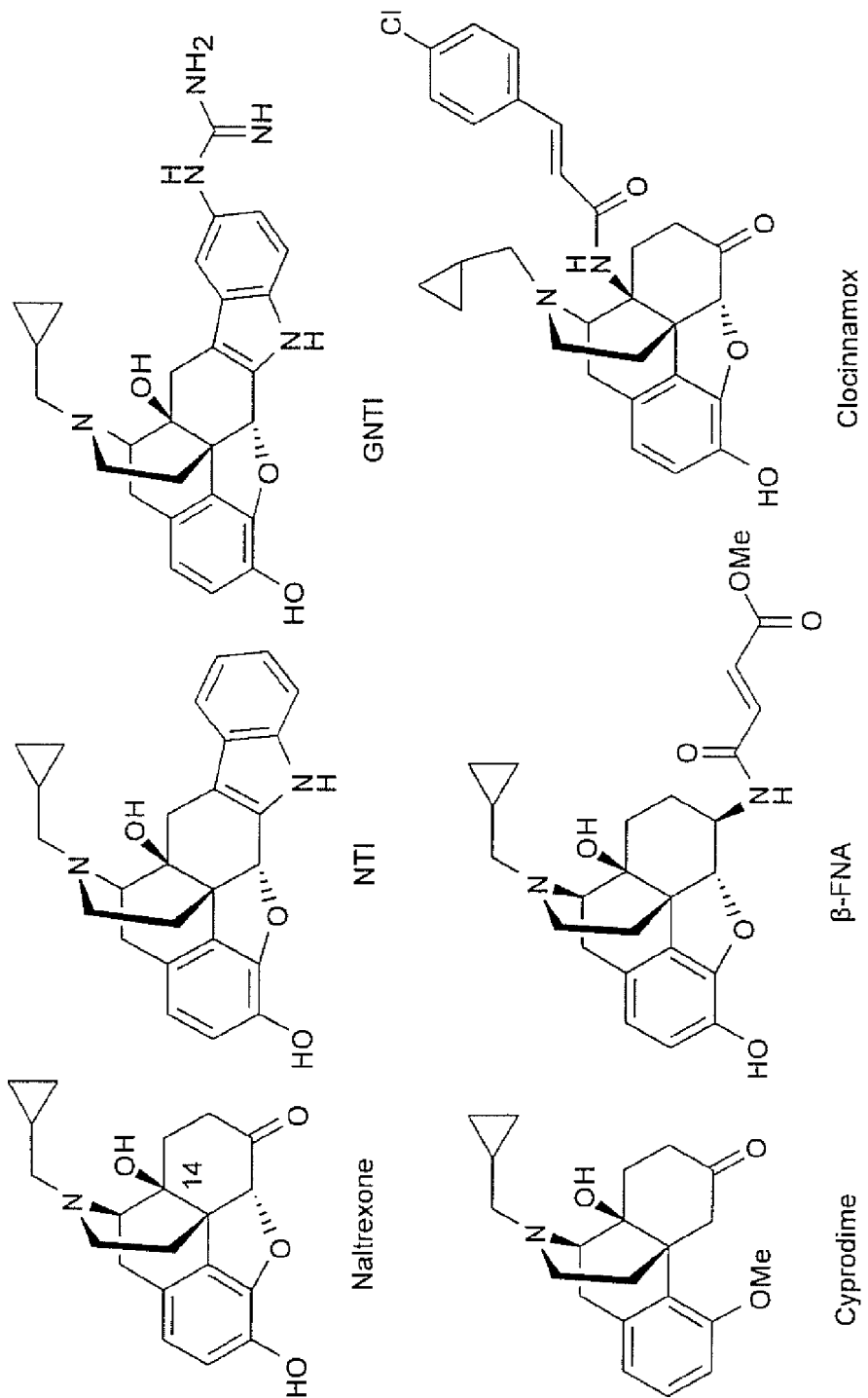
FIG. 1. Morphinan derivatives as opioid selective antagonists

The present invention provides novel non-peptide selective mu opioid receptor (MOR) antagonists. The molecules display high affinity for MOR and, because they do not include amino acids, they are relatively stable in vivo. The ligands carry structural features that enable them to interact with the aromatic binding locus built by the amino acid residues which form the extracellular part of MOR, and may also satisfy hydrogen binding requirements from the binding locus. The molecules will find use in methods for identifying MOR agonists. In addition, the molecules themselves may be used to treat addiction symptoms, such as heroin or prescription opioid drug addiction, as well as in the treatment of opioid induced constipation (OIC).

In some embodiments of the invention, then the compounds are C-14 substituted compounds represented by Formula 1:

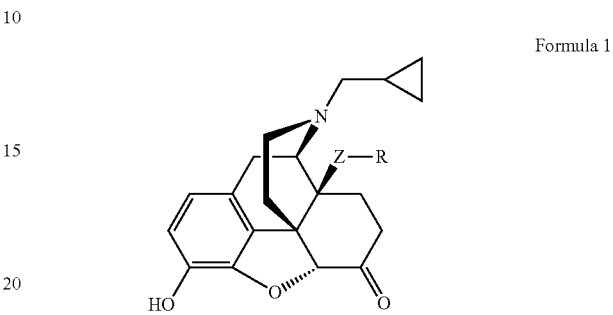

Formula 1 where Z is a spacer element and R is an aromatic or aliphatic moiety, which may be substituted or unsubstituted. Z may be present or absent. If Z is present, Z may be: aliphatic (e.g. short aliphatic chain (CH$_2$)n where n=1-5); NH; CO; (NHCO)n where n=1-5; (CONH)n where n=1-5; (NHCO)(CH$_2$)n(NHCO), where n=1-5; (CONH)(CH$_2$)n(CONH), where n=1-5; (NHCO)(CH$_2$)n where n=1-5; (CONH)(CH$_2$)n where n=1-5; (CH$_2$)n(NHCO), where n=1-5; (CH$_2$)n(CONH), where n=1-5; O (in which case Z is a single atom); CxHy (x=1-5, y=0-10).

Examples of unsubstituted aromatic moieties that may be R include but are not limited to phenyl or naphthalene. The aromatic substituent R may be an aromatic or a heteroaromatic moiety, and may be substituted at one or more positions, either within the ring (e.g., 1 or 2 nitrogens within the ring structure), or by having substituents (e.g., c-1-5 alkyl, C1-5 alkylether, halogen, nitrogen, nitro, amino, cyano, carboxylic acid, and combinations thereof) bonded or attached to the ring. Aromatic ring sizes (i.e. number of carbon atoms in the ring) are generally in the range of from about 3 to about 6.

Exemplary moieties that may be included in the aromatic ring(s) include but are not limited to N, methyl and various branched and unbranched aliphatic chains; COOH, halogen, CN, NO$_2$, OCH$_3$, etc., and combinations thereof, e.g. (CH$_2$)nCOOH where n=1-5), (CH$_2$)nNO$_2$ where n=1-5, (CH$_2$)nNH$_2$ where n=1-5, etc. If multiple substitutions are present, they may be the same or different.

Examples of aliphatic moiety that may be R include but are not limited to various branched and unbranched aliphatic chains and various sizes and numbers of aliphatic rings (e.g. various sizes of cycloalkanes). The chains or rings can also be substituted with different types of heteroatoms, including but not limited to N, S, P, O, etc. Aliphatic ring sizes (i.e. number of carbon atoms in the ring) are generally in the range of from about 3 to about 6. Rings may contain one or more double bonds, and may be substituted (i.e. may be heterocyclic rings) or branched (i.e. may have various substitutions attached to the ring system).

In some embodiments of the invention, the compounds are C-6 substituted compounds represented by Formula 2:

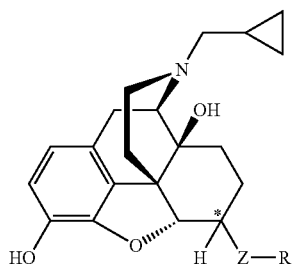

Formula 2 where Z is a spacer element; R is an aromatic or aliphatic moiety (as described for Formula 1), which may be substituted or unsubstituted; and * indicates a chiral carbon. The invention encompasses all stereoisomers (e.g. α and β isomers) of C6. In this embodiment, Z may be present or absent. If Z is present, Z may be: aliphatic (e.g. short aliphatic chain ($CH_2$)n where n=1-5); NH; CO; (NHCO)n where n=1-5; (CONH)n where n=1-5; (NHCO)($CH_2$)n(NHCO), where n=1-5; (CONH)($CH_2$)n(CONH), where n=1-5; (NHCO)($CH_2$)n where n=1-5; (CONH)($CH_2$)n where n=1-5; ($CH_2$)n(NHCO), where n=1-5; ($CH_2$)n(CONH), where n=1-5; O (in which case Z is a single atom), $C_xH_y$ (x=1-5, y=0-10), etc; with the caveat that if Z=NHCO, then R cannot be phenyl or naphthalene.

Examples of unsubstituted aromatic moieties that may be R include but are not limited to phenyl, naphthalene, and other aromatic moieties. The aromatic substituent R may be a substituted aromatic (i.e. a heteroaromatic) and may be substituted at one or more positions, either within the ring, or bonded or attached to the ring. Exemplary moieties that may be included in the aromatic ring(s) include but are not limited to N, methyl and various branched and unbranched aliphatic chains; COOH, halogen, CN, $NO_2$, $OCH_3$, etc., and combinations thereof, e.g. ($CH_2$)nCOOH where n=1-5), ($CH_2$)n$NO_2$ where n=1-5, ($CH_2$)n$NH_2$ where n=1-5, etc. If multiple substitutions are present, they may be the same or different.

Examples of aliphatic moiety that may be R include but are not limited to various branched and unbranched aliphatic chains and various sizes of aliphatic rings (e.g. cycloalkanes). The chains or rings can also be substituted with different type of heteroatoms, including but not limited to N, S, P, O, etc., or as described for the aromatic rings, or branched (e.g. may have various substitutions attached to the ring system).

For Formulas 1, 2 and 3 (below), aromatic and aliphatic ring sizes (i.e. the number of carbon atoms in the ring) are generally in the range of from about 3 to about 6, and R may be a single ring or may contain two or more (generally from about 2 to about 5, e.g. 2, 3, 4, or 5) fused rings. Aliphatic rings may contain one or more double bonds, and may be substituted at one or more positions, either by substituting a constituent of the ring (i.e. the rings may be heterocyclic rings), or by attaching a modifying chemical group to the ring (e.g. may have various substitutions attached to the ring system).

With respect to Formula 2

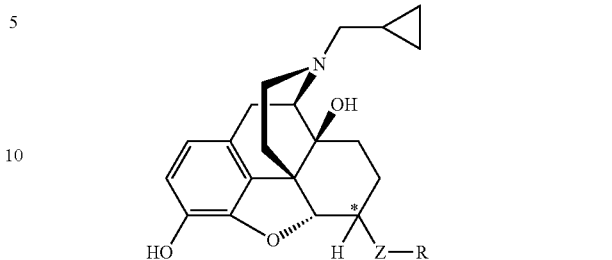

Formula 2

In preferred embodiments,
the MOR antagonist may be a racemic mixture or a purified racemate;
the nitrogen (N) at the 17N position may be charged and methylated, or may be uncharged and unmethylated;
Z is selected from the group consisting of a substituted or unsubstituted aliphatic moiety; NH; CO; (NHCO)n where n=1-5; (CONH)n where n=1-5; (NHCO)($CH_2$)n(NHCO), where n=1-5; (NHCO)($CH_2$)n where n=1-5; ($CH_2$)n(NHCO), where n=1-5; and O;
R is selected from the group consisting of substituted and unsubstituted heteroaromatic rings including without limitation

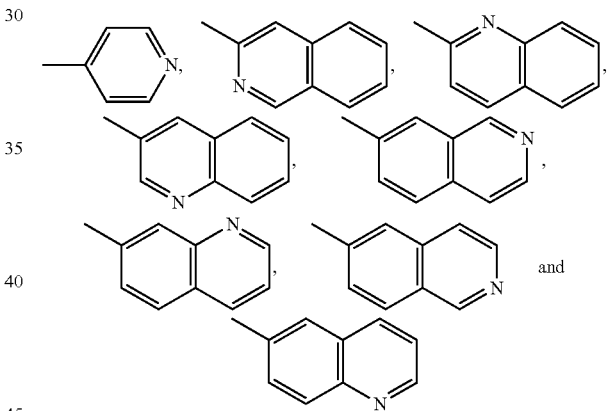

and wherein any carbon on any of the heteroaromatic rings may be a hydrogen, substituted or unsubstituted C1-5 alkyl (e.g., methyl), C1-5 alyleether (e.g., O-methyl), carboxylic acid (COOH), nitrogen (N), cyano (CN), nitro ($NO_2$), halogen (e.g., chloro), or amino moiety, and where the substitution may be the same or different when more than one carbon is substituted. Exemplary moieties that may be included as substitutions to the aromatic ring(s) include but are not limited to N, methyl and various branched and unbranched aliphatic chains; COOH, halogen, CN, $NO_2$, $OCH_3$, etc., and combinations thereof, e.g. ($CH_2$)nCOOH where n=1-5), ($CH_2$)n$NO_2$ where n=1-5, ($CH_2$)n$NH_2$ where n=1-5, etc. If multiple substitutions are present, they may be the same or different. Furthermore, the heteroaromatic rings may also include more than one substitution within the rings (e.g., two or more nitrogens in the rings, as well as S, P, or O substitutions within the rings, and the heteroaromatic rings, when substituted with more than one substitution may be substituted with the same or different moieties (e.g., an N and a P).

In yet further embodiments of the invention, the compounds are substituted at both the C6 and C14 positions, as depicted in Formula 3:

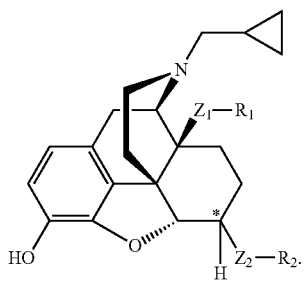

Formula 3

In Formula 3, Z1 and Z2 may be the same or different and R1 and R2 may also be the same or different (i.e. all these groups may vary independently). Possible equivalents for Z1 and Z2 are the same as those listed for Z of Formulas 1 and 2, and, as noted above, may the spacers Z1 and Z2 may be present or absent. Possible equivalents for R1 and R2 are the same as those listed for R of Formulas 1 and 2. All stereoisomers of the compound represented by Formula 3 are also contemplated. For this formula, the following caveat applies: if Z1 and R1 are absent, and if Z2=NHCO, then R2 cannot be phenyl or naphthalene.

In some embodiments of the invention, the compounds substituted at C14 may also be represented as in Formula 4:

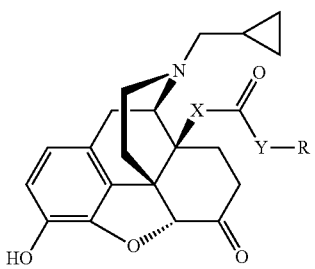

Formula 4 where X=O or NH; Y=an aliphatic moiety, or, in some embodiments, absent; and R is defined as for Formula 1.

Examples of suitable aliphatic moieties that may be Y include but are not limited to unbranched aliphatic moieties such as $(CH_2)n$, where n ranges from about 0 to about 10. For example, n may be 0 (i.e. Y is absent), or n may be 1, 2, 3, 4, 5, or more, and is preferably 0, 1, 2 or 3. Other possible Y equivalents include but are not limited to $C_xH_y$ (x=1-5, y=0-10).

With respect to Formula 4, when X=O, the resulting compound is represented as in Formula 5:

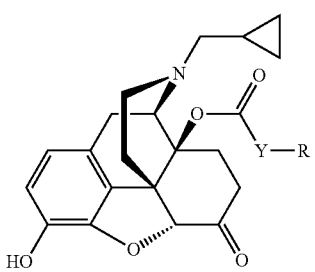

Formula 5 and when X=NH, the compounds are represented as in Formula 6:

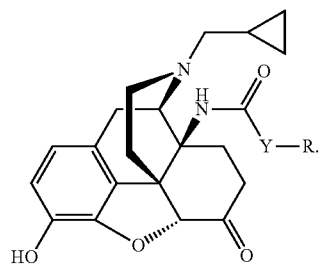

Formula 6

For Formulas 5 and 6, Y and R are as represented in Formula 4.

In some embodiments of the invention, the compounds substituted at C6 may be represented as in Formula 7:

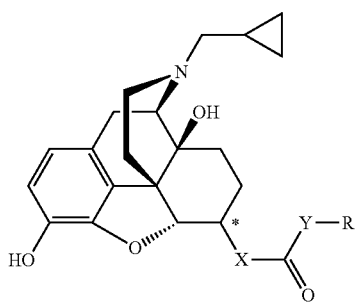

Formula 7 where X=O or NH; Y=an aliphatic moiety (as defined for Formula 4 above), or, in some embodiments, absent; and R is defined as for Formula 2, with the caveat that if X=NH and Y is absent, then R cannot be phenyl or naphthalene.

With respect to Formula 7, when X=O, the compounds may be represented as in Formula 8:

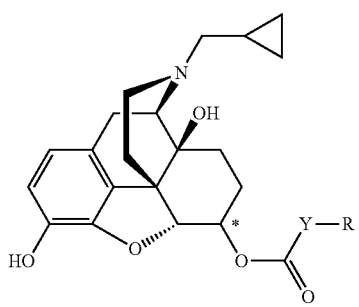

Formula 8 and when X=NH, they are represented as in Formula 9:

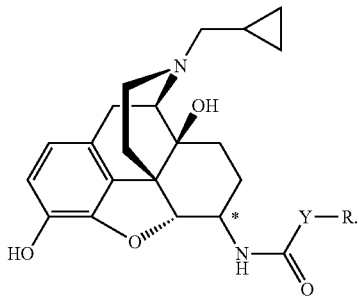

Formula 9

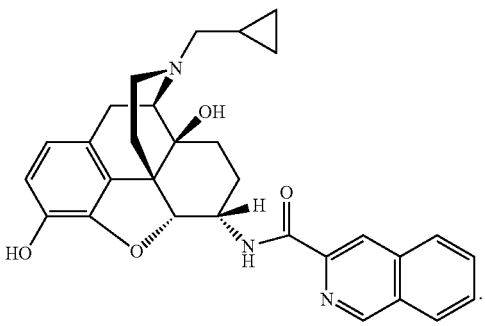

9

For Formulas 8 and 9, Y and R are as described for Formula 7. For Formula 9, if Y is absent, then R cannot be phenyl or naphthalene.

In some embodiments of the invention, the R group is phenyl or naphthalene or a substituted phenyl or naphthalene (for example, N substituted phenyl or naphthalene, as follows:

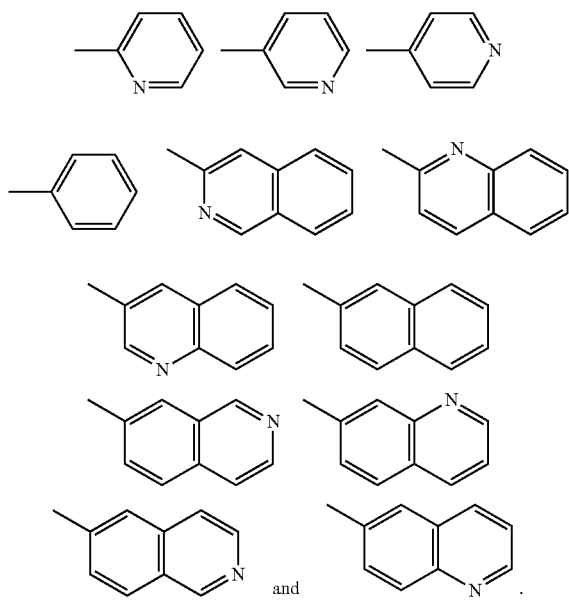

Particular embodiments of the compounds of the invention include:

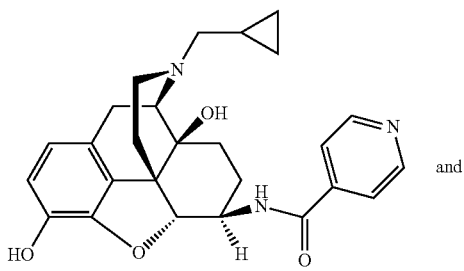

6 and

The compounds of the invention display selectivity for MOR in comparison to other receptors, e.g. other related receptors of interest such as one or both or DOR and KOR. By "selective" or "selectivity" we mean that the compounds of the invention display at least a 10-fold greater binding affinity for MOR than for one or more other receptors (at least one other receptor) of interest. In some cases, the compounds display binding affinities that are about 10, about 50, about 100, about 500 or about 1000-fold or greater for MOR than for other receptors, as measured by standard techniques that are known to those of skill in the art, and described, for example, in the Examples section herein. Further, in some embodiments, the antagonists may be used to identify or characterize other receptors as well.

The compounds of the invention are generally MOR antagonists. By "antagonist" we mean a receptor ligand that does not provoke a biological response upon binding to a receptor, but which blocks or dampens (decreases, lessens, etc.) agonist-mediated responses. (An "agonist" is a ligand that binds to a receptor and triggers a response, i.e. an agonist produces an action, often mimicking the action of a naturally occurring substance.) Antagonists thus have affinity but no efficacy for their cognate receptors, and binding of an antagonist to a receptor will disrupt the interaction and inhibit the function of an agonist or inverse agonist at receptors. Antagonist activity may be reversible or irreversible depending on the longevity of the antagonist-receptor complex, which, in turn, depends on the nature of antagonist receptor binding.

The MOR opioid antagonists of the invention have a variety of applications. For example, they may be used in competitive assays to identify MOR agonists. MOR agonists are, in fact, defined as opoid agonists only if their effect is competitively inhibited by a known opioid antagonist. The application thus provides methods of identifying a substance as a MOR opioid agonist by analyzing the results of competitive binding assays. Those of skill in the art are familiar with such competition experiments, which are typically carried out under controlled conditions in the absence of antagonist (to establish a baseline of binding by the possible agonist) and also in the presence of antagonist at a variety of concentrations of antagonist while the concentration of candidate agonist is held constant. Levels of binding of the candidate agonist in the absence of the antagonist and at increasing concentrations of antagonist are measured by any suitable means, and may be measured directly or indirectly. If the presence of the antagonist interferes with (inhibits) the binding of the test substance to the receptor (i.e. if the presence of antagonist prevents or decreases binding of the test substance to the receptor), then the substance being tested is deemed to be a receptor agonist. Variations of competitive assays, the mathematical and statistical analysis of results obtained in this manner, and the interpretation of such analyses, are well known.

Compounds of the invention may be used and administered as agonists or partial agonists of MOR. In some embodiments of the invention, the selective antagonists of the invention may be used, for example, in medical applications such as in the treatment of opioid addiction or in the treatment of opioid induced constipation (OIC). In a particular application, the antagonists of the invention may be administered to a subject or patient in need of treatment for addictions that involve the MOR receptor, such as drug and alcohol addictions. MOR is the receptor that is accessed by heroin and by several other opioids (e.g. commercial or prescription opioids such as morphine, oxycodone, oxymophone, etc.). Other naturally occurring opiates and semi-synthetic opioids also access this receptor. Several such substances are known and patients to whom they are prescribed and/or more frequently subjects who obtain them illegally for recreational use are liable to become addicted, and to exhibit symptoms of addiction. Symptoms of addiction which may be lessened or treated by the administration of the antagonists of the invention include but are not limited to craving for the addictive substance, physical and psychological dependence, CNS-mediated respiration depression, dysphoria, sweating, nausea, rhinorrea, depression, severe fatigue, vomiting and pain, insomnia, etc. The MOR selective antagonists of the invention may be used to treat such addictions, e.g. to lessen or alleviate symptoms of withdrawal, e.g. during addiction treatment.

In addition, the MOR antagonists of the invention may be used to treat conditions such as pain, neuropathic pain, OIC, alcoholism, cocaine addiction, amphetamine/methamphetamine addiction, Methyelenedioxypyrovalerone (MDPV) (known as "bath salts"), Parkinson's disease, gambling addiction, obesity, epilepsy, depression, schizophrenia, bipolar disorder, schizoaffective disorder, inflammation, gastrointestinal tract disturbance, AIDS, etc.

The invention thus also provides compositions and formulations comprising the antagonists. The compositions include one or more substantially purified antagonists and a pharmacologically suitable carrier. The preparation of such compositions is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of antagonist in the formulations may vary. However, in general, the amount in the formulations will be from about 1 to about 99% by weight, (e.g., 5% or 10% to 20%, 30%, 40%, 50%, or 60% of one or more MOR antagonists with the remainder being pharmaceutical carriers, excipients and/or other ingredients)

The antagonist compositions (preparations) of the present invention may be administered by any of the many suitable means which are well known to those of skill in the art, including but not limited to by injection, inhalation, orally, intranasally, by ingestion of a food product containing the antagonist, topically, as eye drops, via sprays, etc. In preferred embodiments, the mode of administration is orally or by injection. In addition, the compositions may be administered in conjunction with other treatment modalities such as other medicaments, other types of therapy (e.g. psychological or psychiatric treatment), and the like.

The amount of antagonist that is administered to an individual (who is usually a mammal, typically a human) will vary based on several factors, as will be understood by those of skill in the art. For example, the dose and frequency of administration may vary according to the gender, age, weight, general physical condition, ethnic background, etc. of the individual, as well as whether or not the individual has other diseases or conditions that might impinge on the treatment. Generally, the dose will be in the range of from about 0.01 to about 1000 mg/kg of body weight (e.g., 1 to 50, 100, 250 or 500 mg/kg, etc.).

The ensuing Examples are intended to further illustrate the present invention, but should not be interpreted as limiting in any way.

EXAMPLES

Example 1

14-O-Heterocyclic-Substituted Naltrexone Derivatives as Non-Peptide Mu Opioid Receptor (MOR) Selective Antagonists: Design, Synthesis and Biological Studies Abstract: Mu opioid receptor antagonists have clinical utility and are important research tools. In order to develop non-peptide and highly selective mu opioid receptor antagonist, a series of 14-O-heterocyclic substituted naltrexone derivatives were designed, synthesized and evaluated. These compounds showed subnanomolar to nanomolar binding affinity for the mu opioid receptor. Among them, compound 1 exhibited the highest selectivity for the mu opioid receptor over the delta and kappa receptors. These results implicated an alternative "address" domain in the extracellular loops of the mu opioid receptor.

Opioid receptors were generally classified into three subtypes based on the pharmacological, behavioral, and biochemical studies.[1-3] Opioid antagonists have played very important roles in the study of opioid receptors. In fact, an agonist is characterized as opioid-receptor-mediated only if its effect is competitively inhibited by an opioid antagonist.[4,5] It is important to have receptor-selective opioid antagonists as tools to identify the receptor types related to the interaction with opioid agonists.[4-6] The mu opioid receptor (MOR) is the major type that mediates opioid analgesic effects of morphine, although all three opioid receptors can be involved in analgesia. The characterization of the MOR structure-function relationship is essential because it has been found that morphine's analgesic effect, addictive properties, and other major side effects are abolished in MOR knock-out mice.[7,8] Moreover, it has been demonstrated that the analgesic effects and the adverse side effects (including addiction and abuse liability) of morphine are primarily due to its interaction with the MOR.4 In fact, naltrexone, an opioid antagonist with moderate selectivity for the MOR, has been shown to block relapse and curb drug craving in post-dependent opiate addicts.[9,10] Recent research results also indicate that MOR antagonists can be used in the treatment of obesity, psychosis and Parkinson's disease.[11] Furthermore, highly selective MOR antagonists can be used as probes to characterize the MOR binding pocket. Yet the lack of a non-peptidyl, highly selective, and potent MOR antagonist limits our understanding of the structure-function relationship of the MOR, the interaction of non-peptidyl MOR agonists with the receptor, and more specifically, the activation mechanism of the receptor related to its role in drug abuse and addiction.

Schwyzer et al proposed the "message-address" concept in his analysis of the structure-activity relationship of ACTH, adrenocorticotropic hormone, and related hormones.[12] By applying the "message-address" concept, highly selective non-peptide antagonists for the kappa opioid receptor (KOR) (e.g. norbinaltorphimine (norBNI) and 5'-guanidinonaltrindole (GNTI)),[13,14] and for the delta opioid receptor (DOR) (e.g. naltrindole (NTI))[15] were designed and synthesized several years ago. (FIG. 1) Thus far no potent and highly selective antagonist derived from morphinan's structural skeleton has been developed for the MOR, although some moderately potent ligands, e.g. cyprodime,[16] are available. Compared with the high selectivity of GNTI for the KOR (Ki value ratios are mu/kappa≈120, delta/kappa≈250)[14] and NTI for the DOR (Ki value ratios are mu/delta≈152, kappa/delta≈276),[15] cyprodime only has a moderate selectivity for the MOR over the DOR and KOR (Ki value ratios are kappa/mu≈45, delta/mu≈40).[17] At the same time, β-funaltrexamine (β-FNA), clocinnamox, and other compounds, act as selective but irreversible antagonists for the MOR.[18] Therefore, the development of a highly selective, non-peptidyl, and reversible MOR antagonist is highly desired.

It was reported that the extracellular loop (EL) domains of the MOR are critical for the binding of MOR selective agonists, such as morphine, sufentanil, lofentanil and DAMGO.[19] At the same time, site-directed mutagenesis studies have revealed that certain amino acid residues in this domain may be essential for ligand (including agonist and antagonist) selectivity for the MOR over the other two opioid receptor types.[20] Therefore, a non-peptide ligand with potential interaction with the EL domains of the MOR, would be favorable for its selectivity for the MOR.

Due to the lack of the crystal structure of the MOR, so far most molecular design efforts directed toward development of selective opioid ligands have been based on structure-activity-relationship studies. As a matter of fact, in the entire superfamily of GPCRs, only the X-ray crystal structures of bovine rhodopsin,[21-24] opsin,[25] and the human β2[26-29] and β1-adrenergic receptor[30] have been successfully obtained with high resolution. Thus far, most of the molecular models of other GPCRs have been constructed using rhodopsin's structure as a template via homology modeling. Homology modeling of GPCRs has been successfully applied to further understand ligand-protein interactions, and to identify new and potent ligands. It is believed that with all the lessons learned from previous experience, GPCR homology modeling based on the bovine rhodopsin X-ray crystal structure can aid in structure-based drug design and virtual screening for therapeutic applications.[31-38] For example, a homology model of the Angiotensin II Type 1 (AT1) receptor was used to further explore the binding sites of several non-peptide AT1 receptor antagonists.[39] A homology model of the M1 muscarinic acetylcholine receptor was applied to understand the mechanism by which the agonist-receptor complex activates G proteins.[40]

Figure 2:
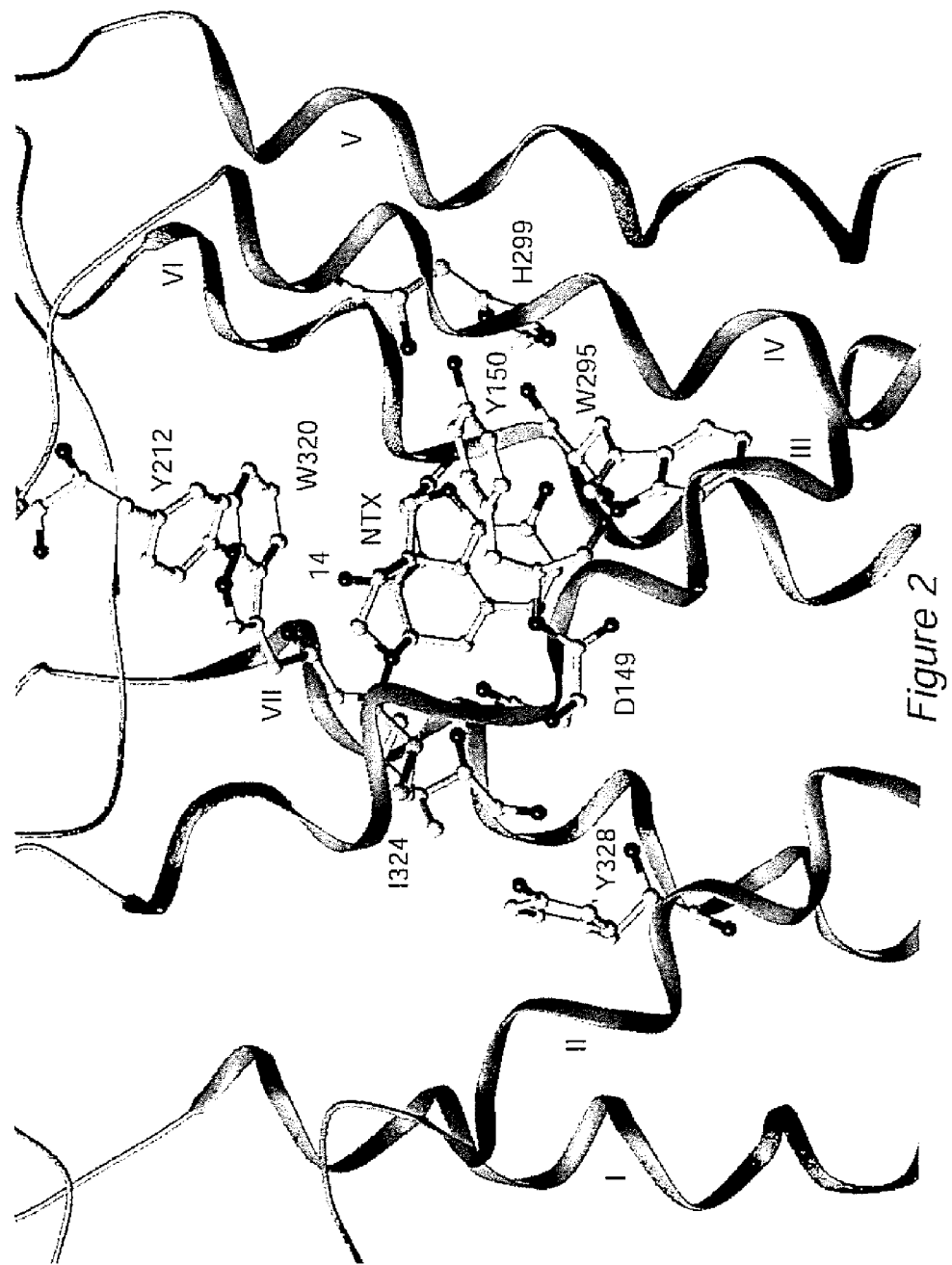
FIG. 2. Naltrexone in MOR Binding pocket: Mu opioid receptor model: ribbon=the residues in mu opioid receptor: ball and stick=Naltrexone molecule.

Recently, we reported the construction of a MOR homology model based on the crystal structure of bovine rhodopsin.[41] This model contained not only the transmembrane helical domains, but also the extracellular and intracellular loops so that the model we obtained was integrated and complete. This model was further optimized in a membrane-aqueous system by molecular dynamics simulations. Similar homology models of the DOR and KOR were then constructed (see supplementary information for details). Naltrexone is a good template for the design of selective MOR antagonists because it has subnanomolar to nanomolar affinity for all three opioid receptor types and shows moderate selectivity for the MOR over the other two opioid receptor types. FIG. 2 shows that in a representative binding mode of naltrexone in the MOR, the 14-hydroxyl group of naltrexone is pointing to the EL3 loop and the upper-level region of TM6/7. Compared to the amino acid residues in the corresponding domains of the KOR and DOR, some non-conserved residues, e.g. Tyr212 and Trp320, in MOR could act as hydrogen bonding donor/acceptors. This unique feature in the MOR antagonist binding locus might form an alternative "address" domain to differentiate the antagonist binding mode of the MOR over the DOR and KOR. Therefore, a new compound containing specific structural features to interact with these amino acid residues may have increased selectivity for the MOR over the DOR and KOR.

Figure 3:
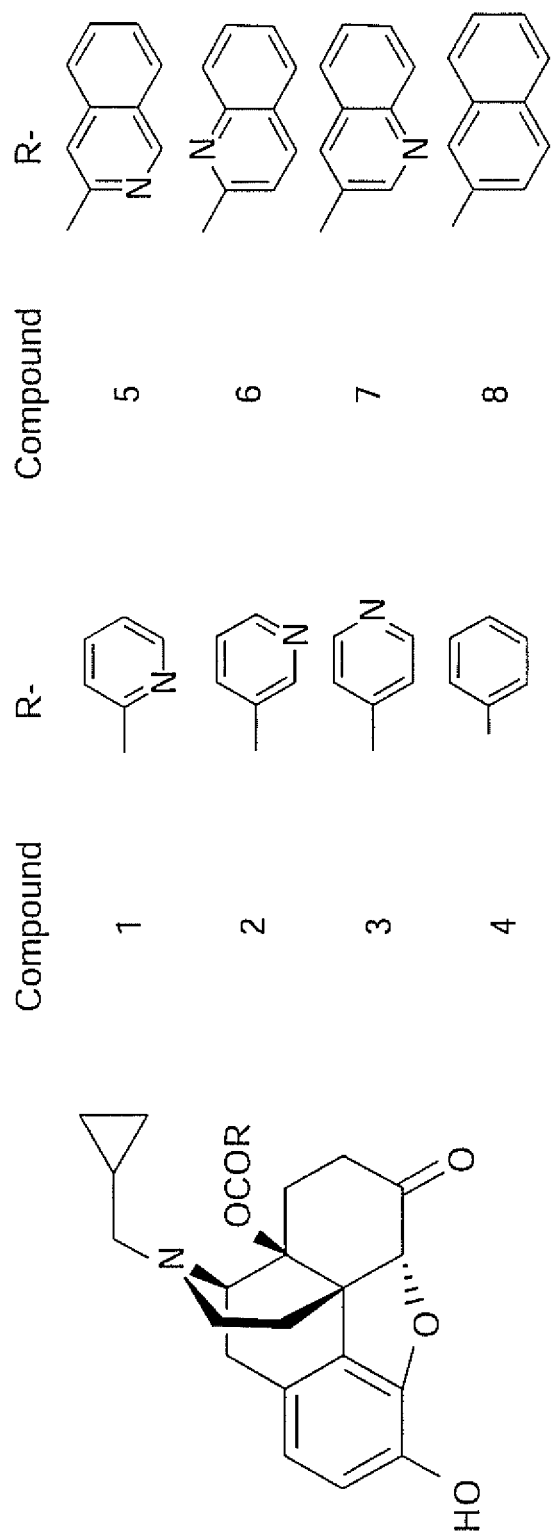
FIG. 3. The designed ligand for a primary study.

Based on this hypothesis of ours, a series of novel 14-O-substituted naltrexone derivatives (FIG. 3) have been designed and synthesized. The ester bond in these novel ligands was assumed to provide a flexible conformation for the whole side chain. The nitrogen atom in the hetero-aromatic moiety on the 14-O-position of naltrexone was introduced to provide an opportunity for hydrogen bonding and/or aromatic stacking interaction with the amino acid residues Tyr212 and Trp320 in the MOR binding pocket (compound 1-3 and 5-7). Compound 4 and 8 were designed as control compounds to test this hypothesis. These ligands could also be considered as derivatives of clocinnamox without the Michael acceptor character.

Figure 4:
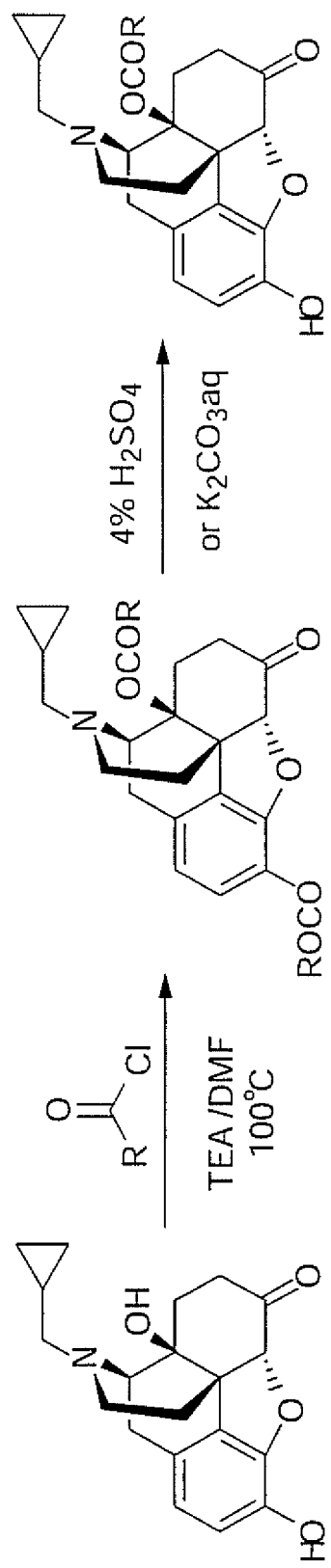
FIG. 4. The synthetic route for the 14-O-substituted naltrexone derivatives.

Using naltrexone as the starting material, the syntheses of these 14-O-heterocyclic substituted derivatives was straightforward (FIG. 4). To be noticed, in the second step of the synthesis route, $K_2CO_3$ aqueous solution was used to prepare the control compounds 4 and 8 instead of using the acidic condition. All the final compounds were obtained with reasonable yield and characterized with NMR, IR, MS, and HPLC.

The primary biological studies of these ligands included competitive radioligand-binding assays using mono-cloned opioid receptors expressed in CHO cell lines. [$^3$H]DAMGO, [$^3$H] NTI and [$^3$H] norBNI were used to label the MOR, DOR and KOR respectively. The binding affinities of these ligands for the MOR, DOR and KOR, and comparative selectivities were summarized in Table 1. These compounds showed binding affinities in the subnanomolar to nanomolar range for the MOR.

TABLE 1

Binding affinity and functional assay results for the 14-O-substituted naltrexone derivatives.

| | Ki ± SEM(nM) | | | Selectivity | | Percent Max of |
|---|---|---|---|---|---|---|
| Compounds | [3H]DAMGO (μ) | [3H] NTI (δ) | [3H] norBNI (κ) | δ/μ | κ/μ | DAMGO |
| Naltrexone | 0.26 ± 0.02 | 117.00 ± 8.90 | 5.15 ± 0.26 | 450 | 20 | 0.00 |
| β-FNA | 0.41 ± 0.04 | 27.78 ± 4.60 | 0.94 ± 0.05 | 68 | 2 | 0.00 |
| CTAP | 2.02 ± 0.71 | 1441.00 ± 106.10 | 1012.70 ± 174.80 | 713 | 501 | 0.00 |
| 1 | 0.14 ± 0.03 | 117.38 ± 17.97 | 25.50 ± 6.50 | 838 | 182 | 0.00 |
| 2 | 1.59 ± 0.61 | 170.30 ± 12.64 | 47.81 ± 8.48 | 107 | 30 | 0.00 |
| 3 | 5.58 ± 1.34 | 405.32 ± 234.68 | 49.21 ± 20.37 | 73 | 9 | 0.00 |
| 4 | 123.23 ± 38.23 | >10,000.00 | 586.42 ± 32.39 | >81 | 5 | 0.00 |
| 5 | 68.40 ± 6.04 | >10,000.00 | >10,000.00 | >146 | >146 | 0.00 |
| 6 | 1.44 ± 0.32 | 22.81 ± 19.52 | 67.15 ± 36.72 | 16 | 47 | 0.00 |
| 7 | 2.69 ± 0.72 | 818.43 ± 507.23 | 148.23 ± 55.53 | 304 | 55 | 22.00 ± 10.30 |
| 8 | 225.27 ± 46.6 | 907.18 ± 192.99 | 46.57 ± 13.53 | 4 | <1 | 0.00 |

The Ki values for the mu, delta and kappa opioid receptors were n=3. The averages were reported along with their standard error of the means, SEM, for each compound. The comparison to percent stimulation of DAMGO was the Emax of the compound compared to the Emax of DAMGO (normalized to 100%). The DAMGO $EC_{50}$ value was 45.1±6.63 nM and its Emax value was 366±23% stimulation over basal using a [$^{35}$S] GTPγS functional assay. Naltrexone, β-FNA and CTAP were tested along as positive controls under the same conditions.

Also as shown above, all of these compounds exhibited different levels of selectivity for the MOR over the KOR and DOR. Among these, compound 1 had approximately 800-fold selectivity for the MOR over the DOR and nearly 200-fold selectivity over the KOR. Compound 5 also showed over 100-fold selectivity for the MOR over the other two receptor types, although its binding affinity for the MOR was significantly lower than compound 1. In addition, all of these compounds acted as MOR antagonists in $^{35}$[S]GTPγS functional assays except for compound 7, which was a partial agonist.

Compared to the control compounds 4 and 8, the MOR selectivity over DOR and KOR had been enhanced greatly in all of the other compounds. This result suggested that the 14-O-substitutions introduced onto the naltrexone skeleton might interact with the proposed alternative "address" domain in the MOR, and the nitrogen atom in the heterocyclic ring might act as a hydrogen bond acceptor and play an important role for the selectivity. Among all of these ligands, compound 1 showed the highest selectivity, which suggested that it had the most favorable orientation of its side chain towards this plausible "address" binding domain in the MOR. For compound 5, its side chain might confer selectivity for the MOR, whereas the bulkiness of its side chain also might have reduced its binding affinity for the MOR. To further characterize compound 1 as the lead for our next generation molecular design, its antagonism was evaluated against DAMGO in $^{35}$[S]GTPγS functional assay. The concentration of compound 1 was 1.5 nM while DAMGO was in the range of 10 nM to 10,000 nM. The Ke value of compound was 0.20±0.04 nM and apparent pA2 value was 9.72±0.10. This observation was consistent with the binding affinity results and further verified that compound 1 could be used as the lead for future molecular design.

It has been reported by Schmidhammer et al., that 14-alkoxymorphinans showed very high opioid receptor affinity. These compounds exhibited significantly increased binding affinities at all opioid receptors without any specific preference for any one receptor type.[42-44] Recently, Husbands et al. investigated the SAR of the analogs of clocinnamox, 14-aminodihydromorphinones and 14-aminodihydrocodeinones, in order to explore the effect of changing the chain linking and substitution in the aromatic ring of cinnamoylaminomorphinones and codeinones.[45-47] These authors found that a modest selectivity for the MOR over the DOR and KOR was achieved when the side chain on the 14 positions was comparably rotatable in these 14-aminiodihydromorphinone compounds.

Comparing to the compounds reported by Schmidhammer and Husbands, the compounds reported here showed similar affinity for the MOR, but much higher selectivity over the DOR and KOR. One possible explanation might be that the introduction of a shorter side chain and a more flexible ester bond in our compounds might lead to a more favorable conformation and orientation of the side chain to target the "address" locus and thereby improve selectivity for the MOR. Certainly this "address" locus needs to be further verified, e.g. by site-directed mutagenesis, in future studies.

In summary, a series of 14-O-heterocyclic substituted naltrexone derivatives were designed, synthesized and evaluated as selective MOR antagonists. Most of these novel ligands exhibited subnanomolar to nanomolar binding affinity for the MOR, with compound 1 showing the highest selectivity for the MOR over the DOR and KOR. These results implicated a plausible "address" domain in the extracellular loops of the MOR. The knowledge gained from these studies will enrich the "message-address" concept that has been applied successfully in opioid research and may lead to the identification of potent MOR selective non-peptide antagonists.

REFERENCES FOR EXAMPLE 1

1. Goldstein, A.; Naidu, A. Mol. Pharmacol. 1989, 36, 265-272;
2. Dhawan, B. N.; Cesselin, F.; Raghubir, R.; Reisin, T.; Bradley, P. B.; Portoghese, P. S.; Hamon, M. Pharmacol. Rev. 1996, 48(4), 567-592;
3. Minami, M.; Satoh, M. Neurosci. Res. 1995, 23, 121-145;
4. Zimmerman, D. M.; Leander, J. D. J. Med. Chem., 1990, 33, 895-902.
5. Schmidhammer, H. Progress in Medicinal Chemistry, 1998, 35, 83-132.
6. Eguchi, M. Med. Res. Rev. 2004, 24(2), 182-212;
7. Skoubis, P. D.; Matthes, H. W.; Walwyn, W. M.; Kieffer, B. L.; Maidment, N. T. Neuroscience, 2001, 106, 757-63.

8. Matthes, H. W.; Maldonado, R.; Simonin, F.; Valverde, O.; Slowe, S.; Kitchen, I.; Befort, K.; Dierich, A.; Le Meur, M.; Dolle, P.; Tzavara, E.; Hanoune, J.; Roques, B. P.; Kieffer, B. L. Nature, 1996, 383(6603), 819-23;
9. Gold, M. S.; Dackis, C. A.; Pottash, A. L.; Sternbach, H. H.; Annitto, W. J.; Martin, D.; Dackis, M. P. Med. Res. Rev. 1982, 2(3), 211-46;
10. Gonzalez, J. P.; Brogden, R. N. Drugs, 1988, 35, 192-213;
11. Goodman, A. J.; Le Bourdonnec, B.; Dolle, R. E. ChemMedChem, 2007, 2. 1552-1570;
12. Schwyzer, R. Ann. N. Y. Acad. Sci. 1977, 297, 3-26;
13. Portoghese, P. S.; Lipkowski, A. W.; Takemori, A. E. Life Sci. 1987, 40, 1287-92;
14. Jones, R. M.; Hjorth, S. A.; Schwartz, T. W.; Portoghese, P. S. J. Med. Chem. 1998, 41(25), 4911-4;
15. Portoghese, P. S.; Sultana, M.; Nagase, H.; Takemori, A. E. J. Med. Chem., 1988, 31, 281-82;
16. a) Schmidhammer, H.; Burkard, W. P.; Eggstin-Aeppli, L.; Smith, C. F. C. J. Med. Chem., 1989, 32, 418-421; b) Schmidhammer. H.; Smith, C. F.; Erlach, D.; Koch, M.; Krassnig, R.; Schwetz, W.; Wechner, C. J. Med. Chem. 1990, 33(4), 1200-6; c) Schmidhanmmer, H.; Smith, C. F.; Erlach, D.; Koch, M.; Krassnig, R.; Schwetz, W.; Wechner, C. Prog. Clin. Biol. Res. 1990, 328, 37-40. d) Spetea, M.; Schullner, F.; Moisa, R. C.; Berzetei-Gurske, I. P.; Schraml, B.; Dorfler, C.; Aceto, M. D.; Harris, L. S.; Coop, A; Schmidhammer, H. J. Med. Chem. 2004, 47(12), 3242-7;
17. Schmidhammer, H.; Burkard, W. P.; Eggstin-Aeppli, L.; Smith, C. F. C. J. Med. Chem., 1989, 32, 418-421.
18. a) Lewis, J. W.; Smith, C. F. C.; McCarthy, P. S.; Kobylecki, R. J.; Myers, M.; Haynes, A. S.; Lewis, C. J.; Waltham, K. NIDA Res. Monogr. 1988, 90, 136-143; b) Portoghese, P. S.; Takemori, A. E. NIDA Res. Monogr. 1986, 69, 157-68; c) Burke, T. F.; Woods, J. H.; Lewis, J. W.; Medzihradsky, F. J. Pharmacol. Exp. Ther. 1994, 271 (2), 715-21;
19. a) Xue, J.-C.; Chen, C.; Zhu, J.; Kunapuli, S. P.; De Riel, J. K.; Yu, L.; Liu-Chen, L-Y. J. Biol. Chem. 1995, 270(22), 12977-12979; b) Zhu, J.; Xue, J.-C.; Law, P.-Y.; Claude, P. A.; Luo, L.-Y.; Yin, J.; Chen, C.; Liu-Chen, L.-Y. FEBS Lett. 1996, 384, 198-202;
20. a) Bonner, G.; Meng, F.; Akil, H. Eur. J. Pharmcol. 2000, 403, 37-44; b) Xu, H.; Lu, Y. F.; Partilla, J. S.; Zheng, Q. X.; Wang, J. B.; Brine, G. A.; Carroll, F. I.; Rice, K. C.; Chen, K. X.; Chi, Z. Q.; Rothman, R. B. Synapse (New York), 1999, 32(1), 23-28;
21. Okada, T.; Le Trong, 1.; Fox, B. A.; Behnke, C. A.; Stenkamp, R. E.; Palczewski, K. J. Struct. Biol. 2000, 130(1), 73-80;
22. Teller, D. C.; Okada, T.; Behnke, C. A.; Palczewski, K.; Stenkamp, R. E. Biochemistry. 2001, 40(26), 7761-72;
23. Salom, D.; Le Trong, I.; Pohl, E.; Ballesteros, J. A.; Stenkamp, R. E.; Palczewski, K.; Lodowski, D. T. J. Struct. Biol. 2006, 156(3), 497-504;
24. Salom, D.; Lodowski, D. T.; Stenkamp, R. E.; Le Trong, I.; Golczak, M.; Jastrzebska, B.; Harris, T.; Ballesteros, J. A.; Palczewski, K. Proc. Natl. Acad. Sci. USA. 2006, 103 (44), 16123-8;
25. Park, J. H.; Scheerer, P.; Hofmann, K. P.; Choe, H. W.; Ernst, O. P. Nature. 2008, 454, 183-7;
26. Rasmussen, S. G.; Choi, H. J.; Rosenbaum, D. M.; Kobilka, T. S.; Thian, F. S.; Edwards, P. C.; Burghammer, M.; Ratnala, V. R.; Sanishvili, R.; Fischetti, R. F.; Schertler, G. F.; Weis, W. I.; Kobilka, B. K. Nature, 2007, 450(7168), 383-7;
27. Rosenbaum, D. M.; Cherezov, V.; Hanson, M. A.; Rasmussen, S. G.; Thian, F. S.; Kobilka, T. S.; Choi, H.-J.; Yao, X.-J.; Weis, W. I; Stevens, R. C.; Kobilka, B. K. Science, 2007, 318(5854), 1266-73;
28. Cherezov, V.; Rosenbaum, D. M.; Hanson, M. A.; Rasmussen, S. G.; Thian, F. S.; Kobilka, T. S.; Choi, H.-J.; Kuhn, P.; Weis, W. I; Kobilka, B. K.; and Stevens, R. C. Science, 2007, 318(5854), 1258-65;
29. Hanson, M. A.; Cherezov, V.; Griffith, M. T.; Roth, C. B.; Jaakola, V. P.; Chien, E. Y.; Velasquez, J.; Kuhn, P.; Stevens, R. C. Structure, 2008, 16(6), 897-905;
30. Warne, T.; Serrano-Vega, M. J.; Baker, J. G.; Moukhametzianov, R.; Edwards, P. C.; Henderson, R.; Leslie, A. G.; Tate, C. G.; Schertler, G. F. Nature, 2008 Jun. 25. [Epub ahead of print]
31. Patny, A.; Desai, P. V.; Avery, M. A. Curr Med Chem. 2006, 13(14), 1667-91;
32. Ballesteros, J. A.; Shi, L.; Javitch, J. A. Mol Pharmacol. 2001, 60(1), 1-19;
33. Becker, O. M.; Shacham, S.; Marantz, Y.; Noiman, S. Curr. Opin. Drug. Discov. Devel. 2003, 6(3), 353-61;
34. Moro, S.; Spalluto, G.; Jacobson, K. A. Trends Pharmacol. Sci. 2005, 26(1), 44-51;
35. Nowak, M.; Kolaczkowski, M.; Pawlowski, M.; Bojarski, A. J. J. Med. Chem. 2006, 49(1), 205-14;
36. McLean, T. H.; Chambers, J. J.; Parrish, J. C.; Braden, M. R.; Marona-Lewicka, D.; Kurrasch-Orbaugh, D.; Nichols, D. E. J. Med. Chem. 2006, 49(14), 4269-74;
37. Hobrath, J. V.; Wang, S. J. Med. Chem. 2006, 49(15), 4470-6;
38. Singh, S.; Malik, B. K.; Sharma, D. K. Chem. Biol. Drug. Des. 2007, 69(3), 191-203;
39. Patny, A.; Desai, P. V.; Avery, M. A. Proteins. 2006, 65(4), 824-42;
40. Lu, Z. L.; Saldanha, J. W.; Hulme, E. C. Trends Pharmacol. Sci. 2002, 23(3), 140-6;
41. Zhang, Y.; Sham, Y. Y.; Rajamani, R.; Gao, J. L.; Portoghese, P. S. ChemBioChem, 2005, 6, 859;
42. Lattanzi, R.; Spetea, M.; Schullner, F.; Rief, S. B.; Krassnig, R.; Negri, L.; Schmidhammer, H. J Med. Chem. 2005, 48(9), 3372-8;
43. Spetea, M.; Schillne, F.; Moisa, R. C.; Berzetei-Gurske, I. P.; Schraml, B.; Dorfler, C.; Aceto, M. D.; Harris, L. S.; Coop, A.; Schmidhammer, H. J. Med. Chem. 2004, 47(12), 3242-7;
44. Greiner, E.; Spetea, M.; Krassnig, R.; Schullne, F.; Aceto, M.; Harris, L. S.; Traynor, J. R; Woods, J. H.; Coop, A.; Schmidhammer, H. J. Med. Chem. 2003, 46(9), 1758-63;
45. Rennison, D.; Moynihan, H.; Traynor, J. R.; Lewis, J. W.; Husbands, S. M. J. Med. Chem. 2006, 49(20), 6104-10;
46. Nieland, N. P.; Moynihan, H. A.; Carrington, S.; Broadbear, J.; Woods, J. H.; Traynor, J. R.; Husbands, S. M.; Lewis, J. W. J. Med. Chem. 2006, 49(17), 5333-8;
47. Grundt, P.; Jales, A. R.; Traynor, J. R.; Lewis, J. W.; Husbands, S. M. J. Med. Chem. 2003, 46(8), 1563-6.

Example 2

Design, Synthesis and Biological Evaluation of 6α- and 6β-N-Heterocyclic Substituted Naltrexamine Derivatives as Mu Opioid Receptor Selective Antagonists Abstract Opioid receptor selective antagonists are important pharmacological probes in opioid receptor structural characterization and opioid agonist functional study. Thus far a non-peptidyl, highly selective, and reversible mu opioid receptor (MOR) antagonist is unavailable. Based on our modeling studies, a series of novel naltrexamine derivatives have been designed and synthesized. Among them, two compounds were identified as leads based on the results of in vitro and in vivo assays. Both of them displayed high binding affinity for the MOR (Ki=0.37 nM and 0.55 nM). Compound 6 (NAP) showed over 700-fold selectivity for the MOR over the delta receptor (DOR) and more than 150-fold selectivity over the kappa receptor (KOR). Compound 9 (NAQ) showed over 200-fold selectivity for the MOR over the DOR and approximately 50-fold selectivity over the KOR. Thus these two novel ligands will serve as leads to further develop more potent and selective antagonists for the MOR.

Introduction

Opioid antagonists have played very important roles in the study of opioid receptors. In fact, the action of an agonist is characterized as opioid-receptor-mediated only if it is competitively antagonized by an opioid antagonist.[1,2] Receptor-selective opioid antagonists are important tools to identify the receptor types that mediate the effects of opioid agonists.[3] The characterization of the mu opioid receptor (MOR) is essential because the analgesic function and addiction/abuse liability of many clinically available opiates are primarily due to their interaction with the MOR.[1,2,4] Thus, MOR selective antagonists are essential for the study of MOR function in drug abuse and addiction. In fact, some antagonists with relatively low selectivity for MOR, e.g. naltrexone, have been shown to inhibit relapse and curb drug craving in opiate addicts.[5-7]

Based on the "message-address concept", highly selective non-peptide antagonists for the kappa opioid receptor (e.g. norbinaltorphimine (norBNI) and 5'-guanidinonaltrindole (GNTI)),[8,9] and for the delta receptor (e.g. naltrindole (NTI))[10] (FIG. 5) were designed and synthesized several years ago. These compounds are widely used as selective ligands in pharmacological studies.

Figure 6:
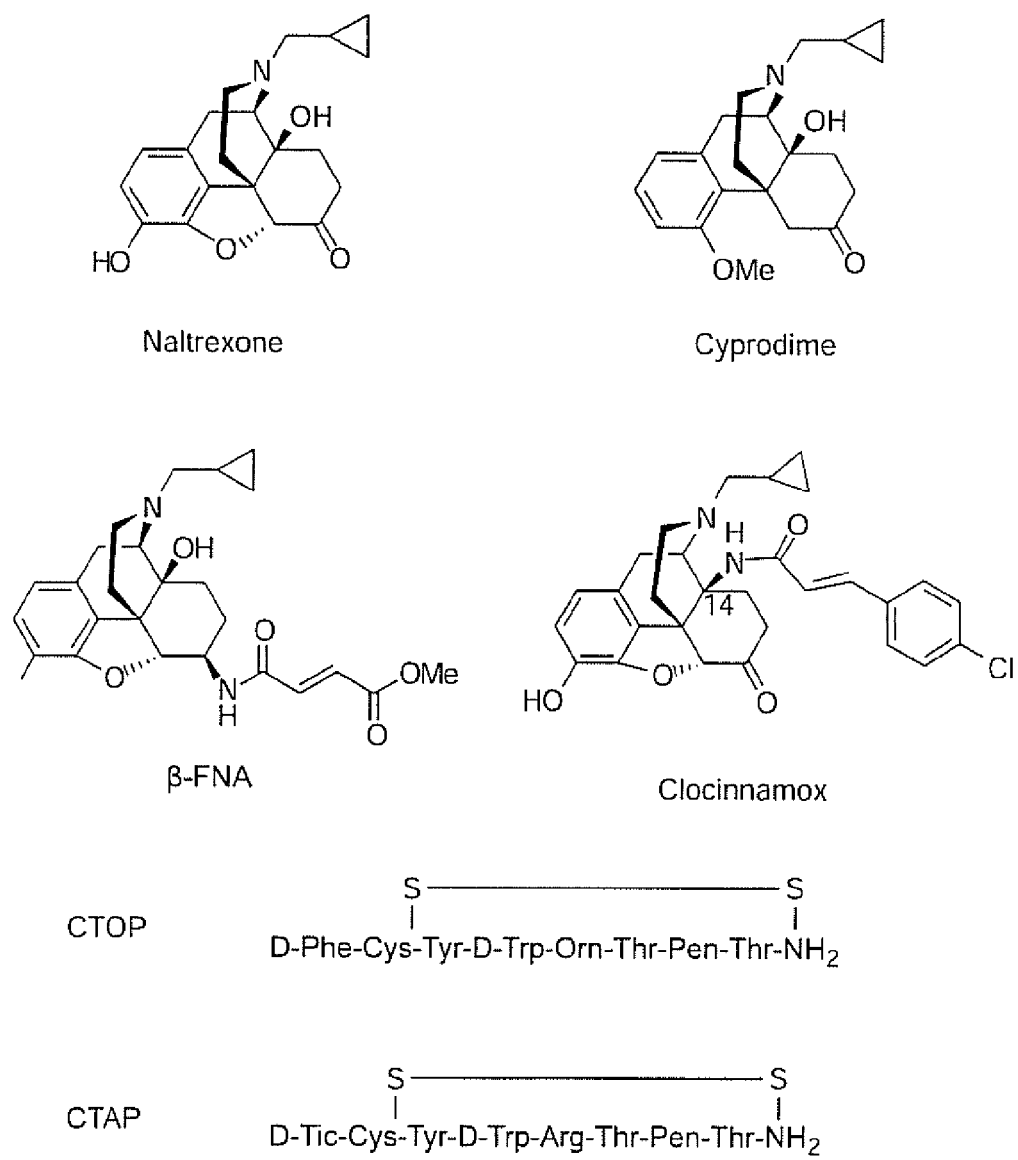
FIG. 6. The mu opioid receptor selective antagonists naltroxone, cyprodime, β-FNA, Clocinnamox, CTOP (SEQ ID NO: 6) and CTAP (SEQ ID NO: 7).

Thus far, however, no optimal non-peptide antagonist has been developed for the MOR, although some moderately potent ligands, e.g. cyprodime[11] are available. Compared with the high selectivity of GNTI for the kappa opioid receptor (KOR) (Ki values ratios are mu/kappa≈120, delta/kappas≈250)9 and NTI for the delta opioid receptor (DOR) (Ki values ratios are mu/delta≈152, kappa/delta≈276),[10] cyprodime only has a moderate selectivity of the MOR over the DOR and KOR (Ki values ratios are kappa/mu≈45, delta/mu≈40).[12] Another drawback of cyprodime is that it has much lower affinity for the MOR than naloxone and naltrexone,[11] which limits its utility. Further structure-activity relationship studies of cyprodime derivatives did not generate any additional antagonist with significantly improved affinity or selectivity for the MOR.[13-17] Although β-funaltrexamine (β-FNA), clocinnamox, and others (FIG. 6), have been reported as selective and irreversible non-peptide antagonists for MOR,[18-21] the fact that they bind covalently with the receptor largely limits their utility. In most cases, a reversible antagonist would be preferred because it can inhibit the receptors temporarily for pharmacological study and then can be washed out from the binding locus to "revive" the receptors afterwards.

Most highly selective and reversible mu opioid receptor antagonists currently available are conformation-constrained peptides, e.g. CTOP and CTAP.[22-28] They are relatively metabolically stable and have been used to target the MOR in in vitro and in vivo studies while their limited bioavailability may not be suitable for many types of in vivo studies and for medical applications. Optimal utility of antagonists as pharmacological tools requires both in vitro and in vivo activity. Non-peptide ligands are preferred due to their ability to penetrate the CNS and lesser vulnerability to metabolic inactivation compared to the peptide agents. Therefore, the development of a non-peptide, potent, selective and reversible antagonist for the mu opioid receptor is highly desirable.

Naltrexone is a promising template for the design of the opioid receptor selective ligands. The successful modification of naltrexone in the synthesis of NTI, norBNI and GNTI are good examples. While naltrexone has nanomolar affinity for all three opioid receptors, it also shows moderate selectivity for the MOR over DOR and KOR. Some chemical structure features are essential for its high affinity for the opioid receptors and should not be abolished. For example, the addition of a 3-hydroxyl group onto cyprodime and its derivatives will "markedly enhance affinity at all three opioid receptors".[13] In addition, the chemistry related to the structural modification of naltrexone has been thoroughly studied.

In this Example, we report the design, synthesis and biological evaluation of two series of novel naltrexone-derived ligands as selective MOR antagonists. Molecular modeling of the naltrexone binding pocket in the homology models of the three opioid receptors led to the identification of an alternative "address" domain in the MOR that may enhance selectivity for the MOR over the DOR and KOR. Two series of ligands were designed and synthesized as proof-of-concept. Biological evaluation of these two series of compounds revealed some ligands with high affinity and selectivity for the MOR. Based on these results, two exemplary compounds have been identified for future optimization.

Results and Discussion

Molecular Modeling

Figure 7:
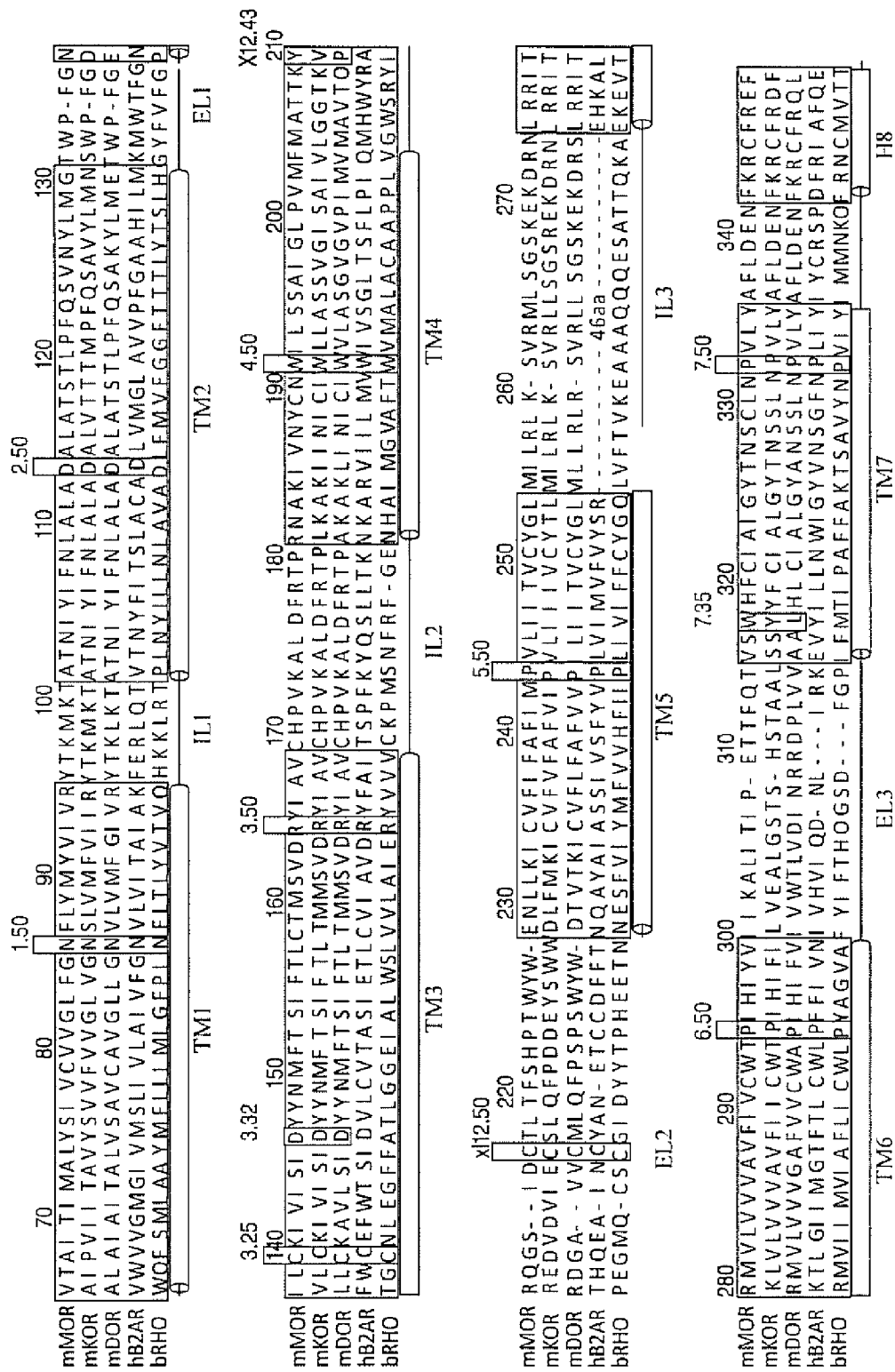
FIG. 7. The sequence alignment of the MOR (SEQ ID NO: 1), DOR(SEQ ID NO: 2), and KOR (SEQ ID NO: 3), with human β2AR (SEQ ID NO: 4), and bovine rhodposin(SEQ ID NO: 5). The Ballesteros-Weinstein numbering system was adopted to mark all the conserved amino acid residues among most of the GPCRs and colored in red. The extracellular loop 2 (EL2) was numbered following the assignment proposed by Johnson (Xhaard, H.; Nyrönen, T.; Rantanen, V. V.; Ruuskanen, J. O.; Laurila, J.; Salminen, T.; Scheinin, M.; Johnson, M. S. Model structures of alpha-2 adrenoceptors in complex with automatically docked antagonist ligands raise the possibility of interactions dissimilar from agonist ligands. J Struct. Biol. 2005, 150(2), 126-43.) The MOR protein was numbered accordingly above its sequence. The secondary structure of the MOR receptor 3D conformation based on bovine rhodopsin crystal structure was marked out below all the sequences. The conserved aspartate residues among all three opioid receptors are residues 3 and 32. The two non-conserved residues xl2.43 and 7.35 are also indicated.

To facilitate ligand design, homology models of all three opioid receptors were constructed. To date, in the whole superfamily of G-protein coupled receptors (GPCRs), only the X-ray crystal structures of bovine rhodopsin,[29-32] opsin,[33] and the human β2- and β1-adrenergic receptor[34-38] have been successfully obtained with high resolution. Most molecular models of other GPCRs have been constructed using the rhodopsin structure as a template. Therefore, homology models of the mu, delta and kappa opioid receptors were constructed based on the X-ray crystal structure of bovine rhodopsin after sequence alignment (FIG. 7). Molecular dynamics simulations were conducted to optimize the conformation of the models. The models contain not only the transmembrane helices, but also the extracellular and intracellular domains so that these models were integrated and complete. The MOR model was also optimized in a membrane-aqueous system.[39] The DOR and KOR models were also optimized following the same method. All amino acid residues in these three models have reasonable bond lengths and bond angles. The analysis of $\phi$, $\psi$, $\chi 1$, $\chi 2$ angles of the resulting protein conformations was further conducted with Procheck 4.1.

Figure 8A:
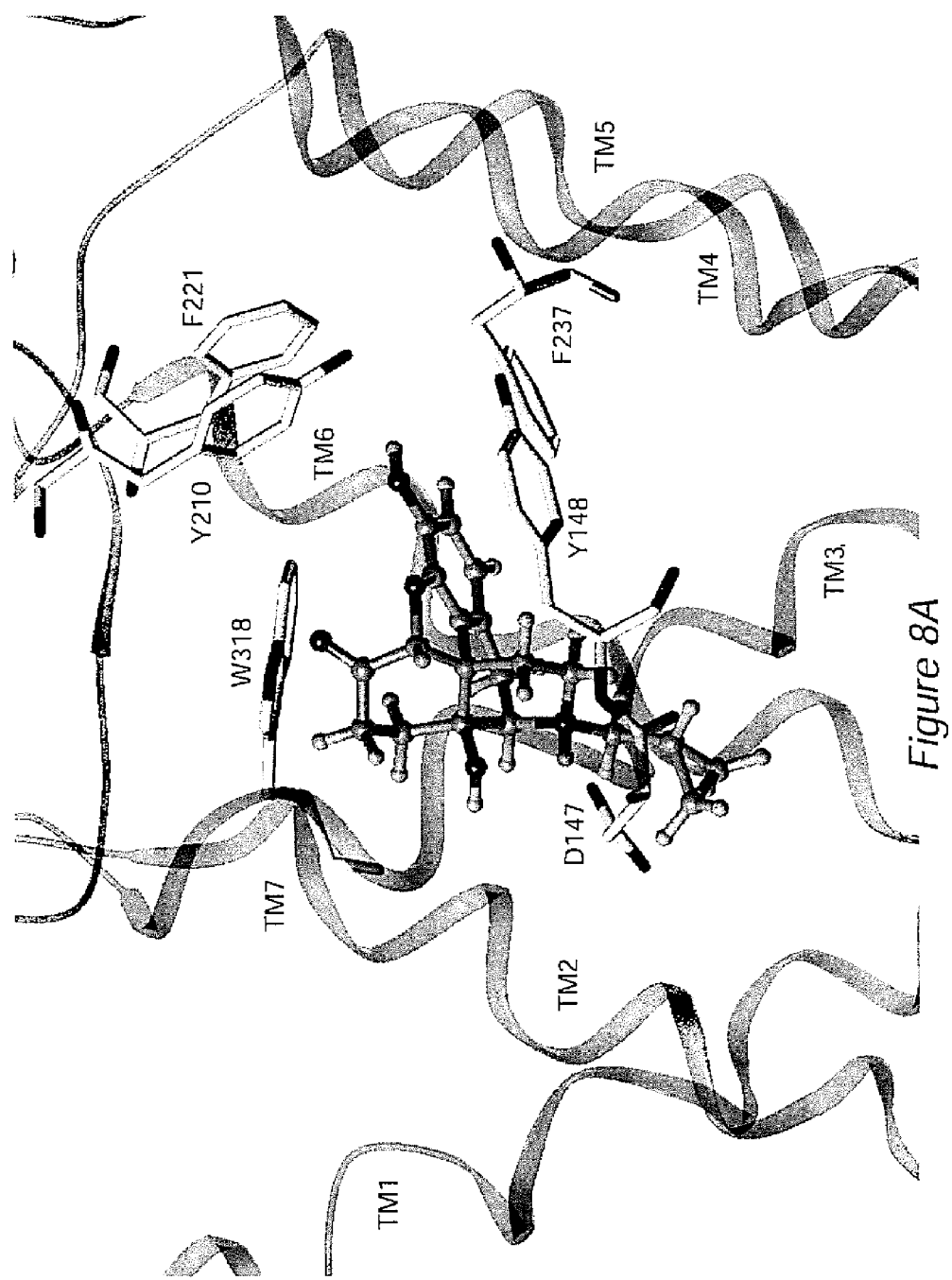
FIG. 8A-C Naltrexone (NTX) docked in the homology models in the MOR, DOR and KOR. NTX and the amino acid residues are in stick form. The receptor homology models are in ribbon. NTX is in A) MOR, B) DOR and C) KOR.
Figure 8B:
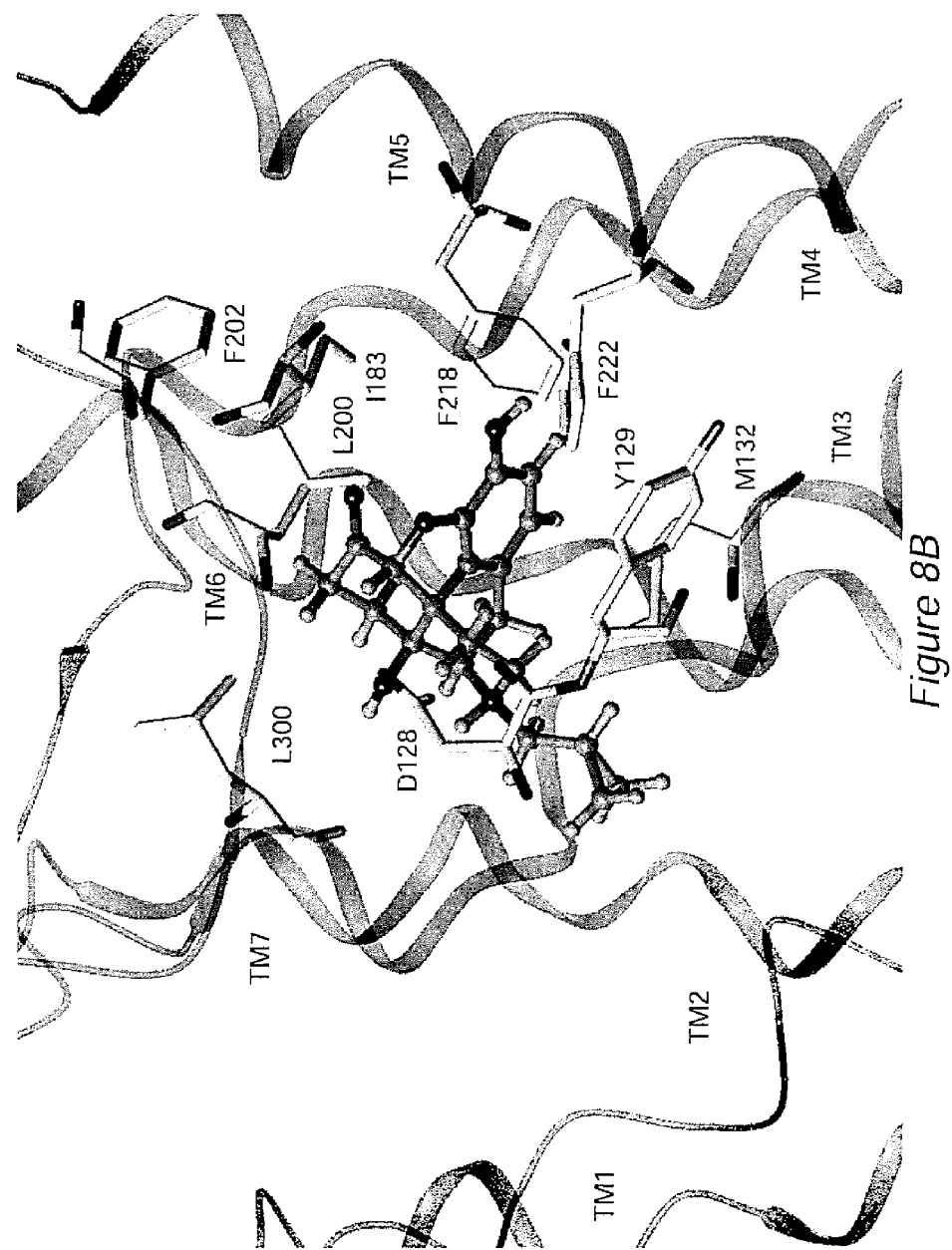
Figure 8C:
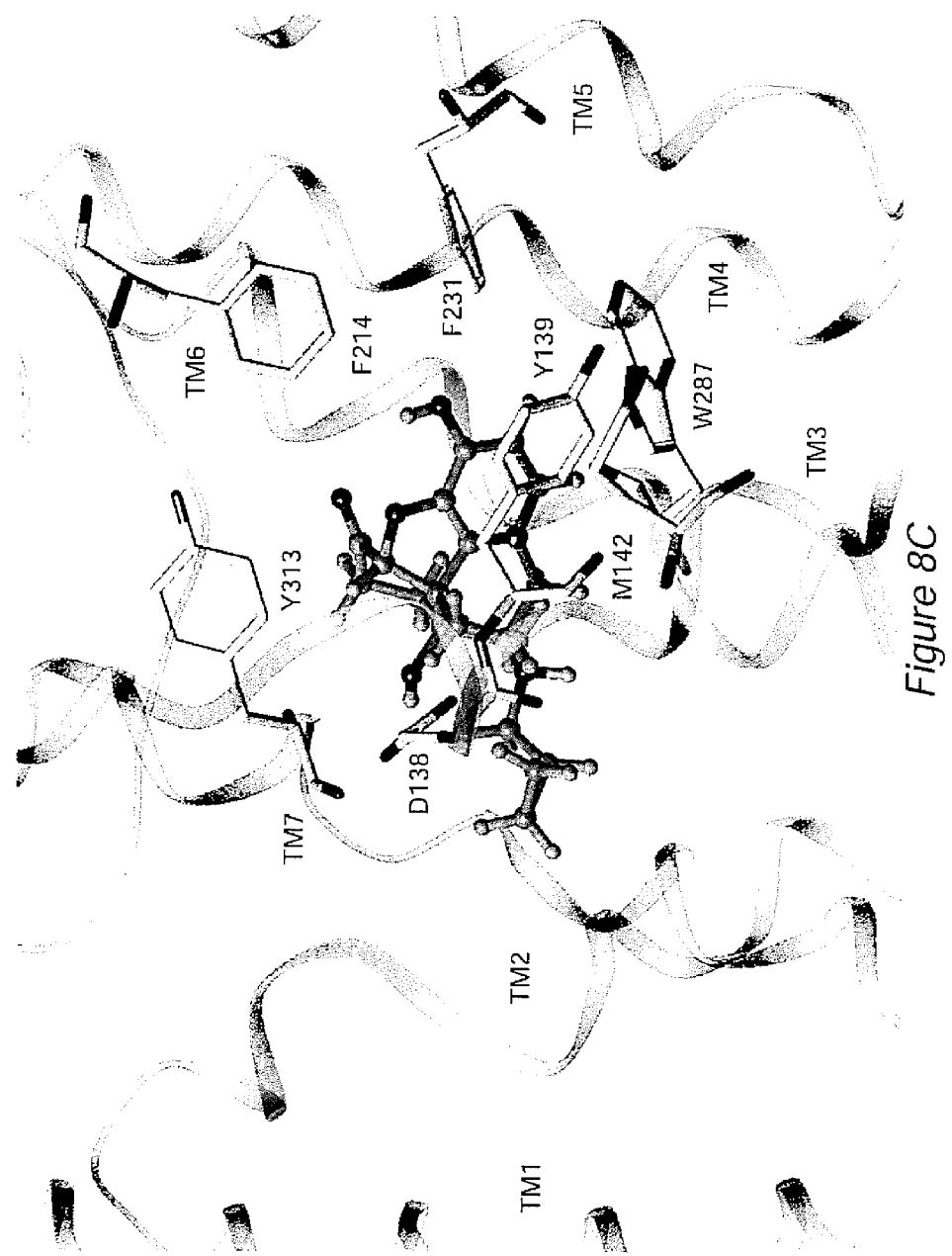

Because naltrexone is a universal antagonist at all three opioid receptors with moderate selectivity for the MOR, we decided to use it as a probe molecule to identify the antagonist binding site in all three opioid receptors. By comparison of the differences among these three binding pockets, we attempted to identify the amino acid residues that are critical to ligand selectivity for the MOR. Three steps were involved in the identification of the critical amino acid residues that differentiate the binding affinity of naltrexone in the three opioid receptors. The first step was the interactive docking of naltrexone into the binding locus of the receptor to form the ligand-receptor complex. The second step was energy minimization and molecular dynamics carried out for the ligand-receptor system to relax and optimize binding interactions between the ligand and amino acid residues in the binding cavity. The third step is the identification and comparison of the naltrexone binding locus in all the three receptors. The ligand-receptor complex structure obtained after 11 ps of molecular dynamics simulation is depicted in FIG. 8A-C. In these complexes, the distance between the protonated nitrogen atom in the 17-amino group of NTX and the carboxyl group of Asp147 (D3.32) was initially anchored at 4.0 Å and retained at this value by a weak harmonic restraint (2 kcal/Å) during the molecular dynamics simulation to represent the putative salt bridge that has been inferred from experimental studies.[53] In the lowest energy conformation of the complex extracted from the last 5 ps molecular dynamics simulation, the distance (4.1 Å) was compatible with the initial setting.

As shown in FIG. 8A, the binding pocket of naltrexone the entire molecule in the MOR was mainly composed of aliphatic amino acid residues. The positively charged amino moiety of the ligand was within the range of an ionic interaction with Asp 147 (D3.32). We also noticed that the carbonyl group on C(6) of naltrexone was orientating towards an aromatic binding pocket formed mainly by amino acid residues from the extracellular loops (ELs) of the receptor, including Tyr210 (Yxl2.43) and Phe221 (Fxl2.54) from EL2 and Trp318 (W7.35) at the border of EL3 and Helix 7.

In FIG. 8B, the naltrexone's binding pocket in the DOR was very similar to that in the MOR except that there existed no aromatic binding locus formed by multiple amino acid residues to which the C(6) carbonyl group of naltrexone pointed. At the conserved region, only Phe202 (Fxl2.54) from EL2 was in the vicinity while Pro191 (Pxl2.43) and Leu300 (L7.35) are not aromatic ones. This difference might be applicable in the design of ligands that are selective for the MOR over the DOR.

Further study of the naltrexone binding pocket in the KOR (FIG. 8C) showed that there was an aromatic/aliphatic binding pocket formed with the contribution of Phe214 (Fxl2.54) from EL2, Phe231 (F5.37) on Helix 5, and Tyr313 (Y7.35) from Helix 7. However, only one residue Tyr313 (Y7.35) may form hydrogen bond with the ligand, while in the MOR binding locus at least two of them are available to be considered.

Therefore, our molecular modeling study of the MOR antagonist binding pocket using naltrexone as the probe has revealed an aromatic binding locus at the extracellular loop region. Further comparison with the DOR and KOR antagonist binding pockets indicated that the existence of amino acid residues acting as potential hydrogen bonding donors and/or acceptors may be a unique structural feature of this aromatic binding locus in the MOR. Therefore, this binding domain may serve as an alternate "address" motif in the MOR that contributes to ligand recognition of the MOR selectively over DOR and KOR. Molecular design targeting to this "address" domain could lead to the identification of selective MOR antagonists. To be noticed, accumulated evidence has shown that the extracellular loops of GPCRs may play a critical role in the binding pocket of their small molecule ligands, including a number of opioid receptor agonists and antagonists.[39-46] It has been found that EL3 of the MOR is critical for the binding of MOR-selective agonists by comparing their binding affinities for MOR/DOR and MOR/KOR chimeric receptors with those for the wild-type MOR, DOR and KOR.[43,44] Site-directed mutagenesis studies have revealed that certain amino acid residues in EL3 could be essential for ligand (including agonist and antagonist) selectivity for the MOR.[45-47] More specifically, Trp318 from EL3 has been identified as an important residue for the binding affinity and selectivity of varies ligands for the MOR.[40,41,43,48] These reports are consistent with the observation from our modeling studies.

Molecular Design

Based on the molecular modeling study, two series of ligands were designed as MOR selective antagonists (Table 2). None of them have been discussed in the literature as selective opioid receptor ligands.

TABLE 2

The ligands designed as the mu opioid receptor selective antagonists.

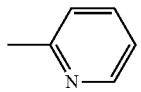

| Compound | R | C6-configuration |
|---|---|---|
| 1 | 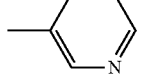 | α |
| 2 | | β |
| 3 | 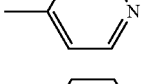 | α |
| 4 | | β |
| 5 | 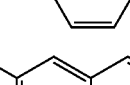 | α |
| 6 | | β |
| 7 | 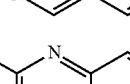 | α |
| 8 | | β |
| 9 | 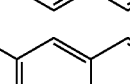 | α |
| 10 | | β |
| 11 | 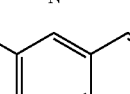 | α |
| 12 | | β |
| 13 | 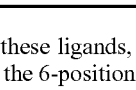 | α |
| 14 | | β |
| 15 | 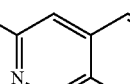 | α |
| 16 | | β |

In the structure of these ligands, we introduced a heteroaromatic moiety onto the 6-position of naltrexone. An amide bond was adopted as the linkage of the side chain moiety to the morphinan skeleton. Therefore, these ligands can be considered derivatives of naltrexamine. The configuration of C(6) will be either α or β. Such a stereochemical arrangement may play an important role for the affinity and the selectivity of the ligand, as has been demonstrated by β-FNA and β-FNA.[49] Alternatively, the stereochemical arrangement may not have an important functionality, and racemic mixtures, as well as compositions with one or the other racemate, may have comparable effects. The aromatic character of this side chain was designed to have aromatic stacking interaction with the aromatic binding locus in the MOR in order to differentiate from the DOR. The nitrogen atom in the aromatic system will act as a hydrogen bond acceptor to probe for the potential formation of a hydrogen bond with Tyr210 or Trp318 in the binding locus from the ELs of the MOR in order to possibly differentiate from the KOR. Compounds with phenyl and naphthalenyl substitutions were designed as control compounds to test our hypothesis. These two series of ligands served as proof-of-concept to test the identification of the alternate "address" domain in MOR.

Chemical Synthesis

For the synthesis of these 6-substituted derivatives of naltrexamine, the starting material was naltrexone. The stereoselective synthesis of α- and β-naltrexamine has been applied successfully in the synthesis of their derivatives in the literature.[50]

Figure 9:
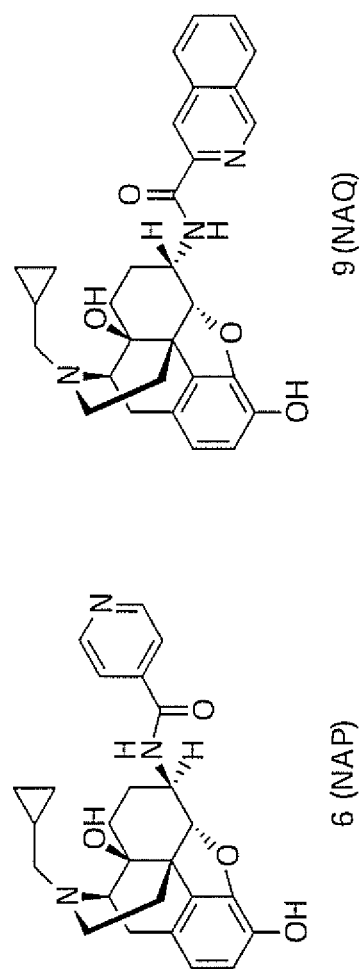
FIG. 9. Chemical structures of exemplary compounds 6 (NAP) and 9 (NAQ).

In our case, α-naltrexamine was obtained with a yield of 60% in three steps, while β-naltrexamine was obtained with a yield of 63% in three steps. The amide bond formation between the naltrexamine and the side chain moiety was straightforward. Depending on the commercial availability of the aromatic moiety, either in acyl chloride or acid form, condition 1 or 2 was adopted. Under mild basic condition, the intermediate, 3,6-disubstituted naltrexamine, was converted to the 6-mono-substituted target compound (FIG. 9) with reasonable yield. All the ligands were fully characterized before submitting for biological studies.

Biological Evaluation

Biological screening for the synthesized ligands was focused on in vitro radioligand binding assay and functional assays, and in vivo behavioral tests. Basically, the radioligand binding assay was adopted to characterize the affinity and selectivity of new ligands for the MOR, DOR and KOR, whereas the $^{35}$S-GTP[γS]-binding functional assay was applied to determine whether each new ligand acted as an agonist, partial agonist or antagonist of the MOR by determining its efficacy for G-protein activation relative to a full agonist at the MOR. Agonist efficacy were measured at the level of G-protein activation because efficacy is most accurately determined at this proximal level of signal transduction.[51-53] The use of cell lines heterologously expressing each of the cloned receptors has become standard practice because it provides a pure source of each opioid receptor type free of other opioid receptor types. Furthermore, these systems express the receptor at high density to provide optimal signal-to-noise ratios in the radioligand and $^{35}$S-GTP[γS] binding assays. The in vivo tests were focused on the inhibition of morphine's antinociception activity and behavioral properties of those compounds showing high selectivity and low agonist efficacy at the MOR.

In Vitro Pharmacological Study

The primary testing of these ligands included the competitive radioligand binding assay using the mono-cloned opioid receptors expressed in CHO cell lines. [$^3$H]naloxone, [3H] NTI and [$^3$H]norBNI were used to label the MOR, DOR and KOR, respectively. The binding affinities of these ligands to the mu, delta and kappa opioid receptors are summarized in Table 3. Most of these ligands showed sub-nanomolar affinity for the MOR and significant selectivity for the MOR over DOR and KOR. These results demonstrated that our primary molecular design was successful.

TABLE 3

The binding affinity and selectivity of C(6) naltrexamine derivatives (n = 3)

| Compound | Ki (nM) ± SEM | | | Selectivity ratio | |
| --- | --- | --- | --- | --- | --- |
| | MOR | DOR | KOR | delta/mu | kappa/mu |
| NTX | 0.26 ± 0.02 | 117.06 ± 8.94 | 5.15 ± 0.26 | 450 | 20 |
| β-FNA | 0.41 ± 0.04 | 27.78 ± 4.60 | 0.94 ± 0.05 | 68 | 2 |
| CTAP | 2.02 ± 0.71 | 1441.0 ± 106.1 | 1012.7 ± 174.8 | 713 | 501 |
| 1 | 2.6579 ± 0.424 | 64.467.85 ± 15.976.81 | 222.5834.3 ± 11.972.60 | 24 | 84 |
| 2 | 5.856.46 ± 1.4156 | 215.1837.5 ± 21.023.2 | 277.96306.8 ± 67.7774.8 | 37 | 47 |
| 3 | 0.157 ± 0.078 | 40.785.01 ± 8.399.26 | 7785.234 ± 224.4376 | 265 | 501 |
| 4 | 0.145 ± 0.04 | 211.91.98 ± 15.587.2 | 5.4298 ± 1.1830 | 1413 | 40 |
| 5 | 0.4853 ± 0.123 | 186.64206.0 ± 32.075.4 | 19.5621.59 ± 9.0610.00 | 389 | 41 |
| 6 (NAP) | 0.3741 ± 0.078 | 277.51306.3 ± 7.978.8 | 607.702 ± 56.5816 | 747 | 163 |
| 7 | 1.4155 ± 0.628 | 385.84425.4 ± 83.9992.6 | 41.695.96 ± 6.0668 | 274 | 30 |
| 8 | 0.921.03 ± 0.304 | 47538.820 ± 19.9422.4 | 7.798.75 ± 1.5372 | 522 | 8 |
| 9 (NAQ) | 0.556 ± 0.15 | 135.2.50 ± 27.015 | 26.4593 ± 5.2232 | 241 | 48 |
| 10 | 0.101 ± 0.067 | 15.42 17.13 ± 10.829.74 | 1.5875 ± 0.768 | 156 | 16 |
| 11 | 0.213 ± 0.112 | 148.2059.4 ± 64.809.7 | 9.8410.58 ± 0.961.03 | 693 | 46 |
| 12 | 0.11 ± 0.03 | 3.8694 ± 1.213 | 5.0414 ± 1.303 | 36 | 47 |
| 13 | 0.123 ± 0.03 | 32.196.01 ± 1.0113 | 1.812.03 ± 0.112 | 277 | 16 |
| 14 | 0.078 ± 0.02 | 11.612.52 ± 2.993.23 | 0.5762 ± 0.202 | 157 | 8 |
| 15 | 8.3678 ± 1.7180 | 518.3245.6 ± 14.068 | 640.8.76 ± 15.776.6 | 62 | 73 |
| 16 | 55.67.5 ± 3.67 | 29.2630.17 ± 4.7489 | 657.268 ± 17.2679 | 0.5 | 1 |

The Ki values for the mu, delta and kappa opioid receptors are n=3. The averages are reported along with their standard error of the means, SEM, for each compound. The comparison to percent stimulation of DAMGO is the Emax of the compound compared to the Emax of DAMGO (normalized to 100%). Naltrexone, 1-FNA and CTAP were tested along as positive controls under the same conditions.

As shown in Table 4, target compound 1 to 6 all have sub-nanomolar or nanomolar affinity for the MOR while much lower affinity for the DOR and KOR. Specifically, compound 4 showed over 1,000-fold selectivity for the MOR over DOR, whereas compound 6 showed over 700-fold selectivity for the MOR over DOR, and over 150-fold selectivity for the MOR over KOR. The control compound 7 and 8 showed somewhat lower affinity for MOR and lower selectivity for MOR over KOR. These results suggest the possibility of hydrogen bonding or other polar interactions between the target compounds and the MOR because the only unique chemical structure in the target compounds is the nitrogen atom in the pyridine ring. Similarly, target compounds 9 to 14 all showed high sub-nanomolar affinity for MOR whereas compound 9 and 11 exhibited the highest selectivity for the MOR over both the DOR and KOR. Again we observed significantly lower affinity and selectivity of the control compounds 15 and 16 for the MOR. This finding further supported the possibility of hydrogen bonding or some other polar interaction between the target compounds and the MOR because of the existence of a quinoline or isoquinoline ring in the target compounds verses the pure aromatic ring system of the naphthalene moiety in the control compounds.

TABLE 4

The efficacy and potency of target compounds in $^{35}$S-GTP[γS]-binding functional assay in the MOR expressing CHO cells (n = 3)

| Compound | $EC_{50}$ (nM) | Emax (% Stim) | Percent Max of DAMGO |
|---|---|---|---|
| DAMGO | 45.06 ± 6.63 | 366.5 ± 23.0 | 100.0 ± 6.2 |
| 1 | 23.905.16 ± 4.6690 | 133.5 ± 9.8 | 37.79 ± 2.68 |
| 2 | 269.2801 ± 8.0588 | 150.6 ± 15.8 | 41.09 ± 4.32 |
| 3 | 1.0112 ± 0.404 | 164.3 ± 16.5 | 44.82 ± 4.50 |
| 4 | 0.336 ± 0.145 | 106.7 ± 18.3 | 29.11 ± 5.00 |
| 5 | 1.2639 ± 0.6774 | 136.8 ± 17.8 | 37.32 ± 4.87 |
| 6 (NAP) | 1.149 ± 0.3842 | 83.3 ± 3.1 | 22.72 ± 0.84 |
| 9 (NAQ) | 4.3644 ± 0.723 | 58.008.0 ± 9.303 | 15.8383 ± 2.5353 |
| 10 | 0.2730 ± 0.067 | 120.9 ± 9.0 | 32.99 ± 2.46 |
| 11 | 0.0910 ± 0.04 | 239.6 ± 22.5 | 65.38 ± 6.13 |
| 12 | 0.6970 ± 0.199 | 149.8 ± 26.1 | 40.87 ± 7.20 |
| 13 | 2.2956 ± 0.7281 | 164.3 ± 14.5 | 44.83 ± 3.96 |
| 14 | 0.2931 ± 0.02 | 195.8 ± 32.0 | 53.41 ± 8.74 |

All of these ligands except the controls (which showed lower affinity for the MOR) were then tested in the $^{35}$S-GTP[γS] binding functional assay using the MOR-expressing CHO cell line (Table 4). The $^{35}$S-GTP[γS] binding results were analyzed in such a way as to normalize the stimulation produced by each novel ligand to that obtained with the full agonist DAMGO, which provided a measurement of relative efficacy. These results demonstrated that all of the novel ligands showed partial agonism.

Specifically, compounds 6 and 9 showed the lowest relative efficacy, with approximately 20% of the maximal stimulation produced by DAMGO. Compounds 6 and 9 produced stimulation similar to nalbuphine, a ligand with very low efficacy to activate the MOR. With a goal of a neutral antagonist of the MOR, their (compounds 6 and 9) high affinity and selectivity for the MOR and very low agonism at the MOR provides guidance for molecular design. In order to further characterize their pharmacological profile, we conducted in vivo study of these compounds.

In Vivo Pharmacological Evaluation

The potential MOR selective antagonists were evaluated for acute agonistic and antagonistic effects in mice. In detail, they were tested for their ability to produce antinociception and to antagonize the antinociceptive effects of morphine in the mouse tail immersion test. The data are summarized in Table 5. As shown, both compounds 6 and 9 (FIG. 9), were found to be potent antagonists of morphine. Their antagonist $AD_{50}$ values were 4.51 and 0.45 nM, and neither of these ligands produced any agonist effect in this test at doses up to 100 mg/kg. This is in agreement with our original molecular design hypothesis as well as the in vitro functional assays. Therefore, these two compounds good lead candidates and enable additional molecular design and synthesis to identify pure, potent and highly selective antagonists for the MOR. In addition, compounds 1 and 2 had similar $ED_{50}$ values to compound 9 and compounds 4, 5 and 13 were equally potent to compound 6 as a morphine antagonist. On the other hand, compound 12 was more potent than morphine and compounds 10 and 11 were equally potent to morphine in producing antinociception in this test.

TABLE 5

$AD_{50}$ values for Naloxone naloxone and the two series of C6-naltrexamine derivatives versus morphine in the warm-water tail immersion test in vivo.

| Compound | $AD_{50}$ value (mg/kg (95% C.L.)) for Blockade of morphine antinociception |
|---|---|
| Naloxone | 0.05 (0.03 to 0.09) |
| 1 | 0.8994 (0.759 to 1.0713) |
| 2 | 0.336 (0.269 to 0.4347) |
| 3 | 36.7740.59 (29.9933.10 to 44.9849.65) |
| 4 | 1.3852 (0.7886 to 2.4368) |
| 5 | 8.69.55 (5.3591 to 13.975.42) |
| 6 (NAP) | 4.5198 (2.4570 to 8.269.12) |
| 9 (NAQ) | 0.456 (0.277 to 0.789) |
| 10[a] | Inactive |
| 11[b] | Inactive |
| 12[c] | Inactive |
| 13 | 4.4598 (2.4170 to 8.159.12) |
| 14 | 42.555.90 (235.6753 to 76.5182.53) |

[a]Agonist, $ED_{50}$ 1.19 mg/kg (morphine $ED_{50}$ 2.59 mg/kg);
[b]Agonist, $ED_{50}$ 4.57 mg/kg;
[c]Agonist, $ED_{50}$ 0.04 mg/kg.

Interestingly, some of the target compounds did not show parallel functional activity between the in vitro and the in vivo studies. For example, both compounds 6 and 9 showed partial agonism in the $^{35}$S-GTP[γS] binding assay while acting as full antagonists in the warm-water tail immersion test. On the other hand, compounds 10, 11 and 12 showed only moderately higher partial agonism in the $^{35}$S-GTP[γS] binding assay but acted as full agonists in the in vivo assays. To our understanding, there are several factors that might have contributed to these observations. First, it has been reported that the level of antinociception produced by an opioid is dependent on both the intrinsic efficacy of the drug and the stimulus intensity. Some low efficacy MOR partial agonists, such as butorphanol, produced maximal levels of antinociception at a lower temperature nociceptive stimulus (50° C.) but not at a higher temperature (56° C.) stimulus.[54] On the other hand, butorphanol acted as an antagonist and shifted the dose-effect curve of the high-efficacy opioid alfentanil to the right in a competitive manner at a higher temperature (55° C.) stimulus.[55] This may explain why the two exemplary compounds did not show any efficacy at the higher temperature (56° C.) stimulus and thereby acted as full antagonists in the in vive study. Second, some ligands could have significant intrinsic efficacy at the DOR or KOR, while acting as low efficacy partial agonists at the MOR which might explain why compounds 10, 11 and 12 acted as full agonists in vivo.

Additional Molecular Modeling

In order to verify that the two compounds that acted as selective MOR ligands utilized the alternate "address" domain identified from the previous modeling study, further molecular modeling study was conducted. First, compound 6 and 9 were built using the InsightII/Discover program and their conformation energy minimization was conducted. Then, as we have described for the docking study of naltrexone in the three opioid receptor homology models, they were docked into the homology model of MOR interactively. The orientation of the newly introduced C(6) side chain was not deliberately considered originally. The lowest energy conformation after the minimization and the dynamics simulation of the ligand/receptor complex is illustrated in FIGS. 10A and B.

Figure 10A:
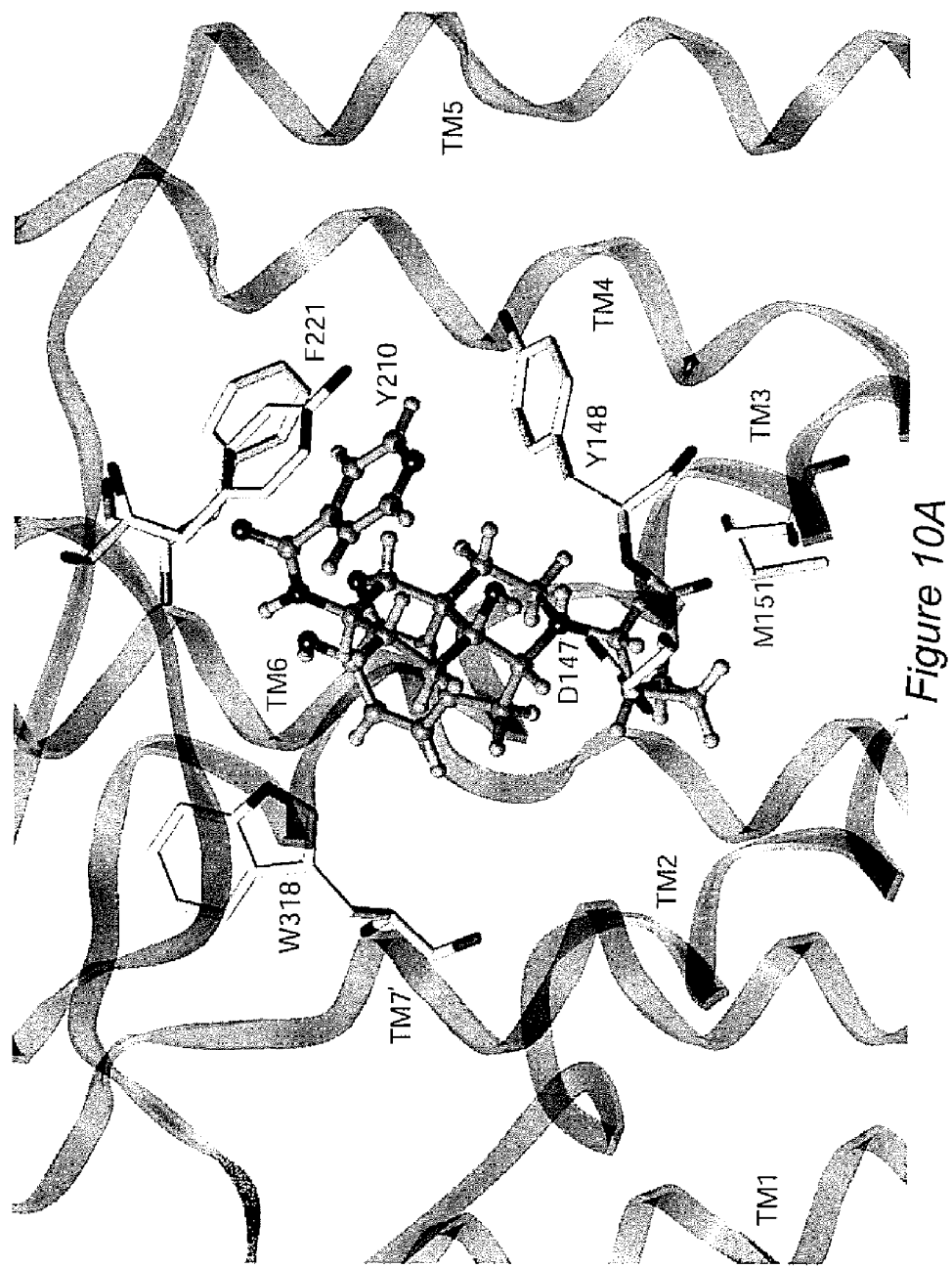
FIGS. 10A and B The docking of compounds 6 and 9 in the mu opioid receptor model. The ligands and the amino acid residues are in stick. The receptor homology models are in ribbon. A) Lead 6 (NAP) and B) lead 9 (NAQ) in MOR.
Figure 10B:
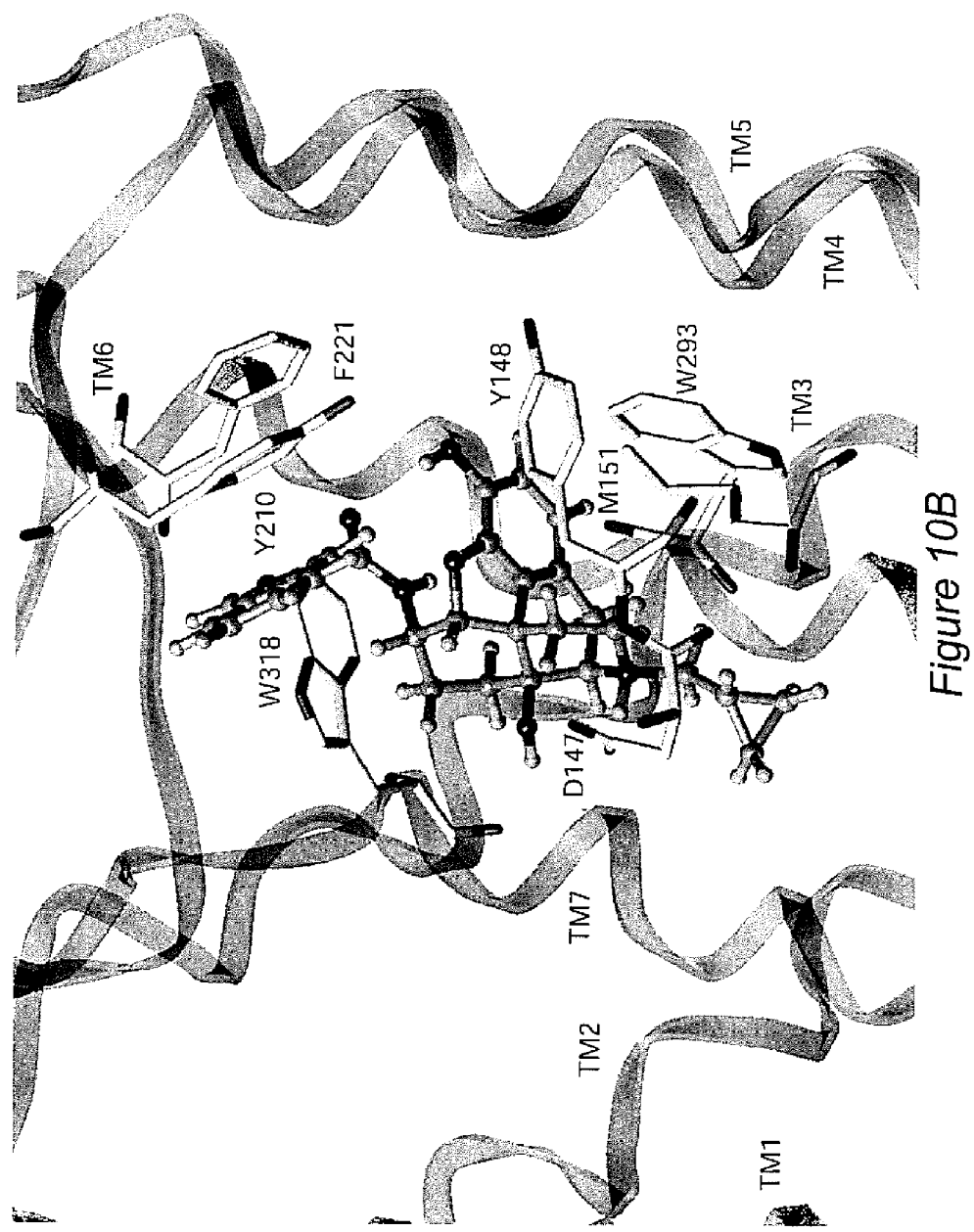

As shown in FIG. 10A, the C(6) side chain in compound 6 pointed to the aromatic binding locus at the extracellular loop region of the MOR. The pyridinyl moiety was in the vicinity of Tyr210 (Yxl2.43) while the distance between the nitrogen atom in the pyridine ring and the oxygen atom in the hydroxyl group of Tyr210 (Yxl2.43) was 3.37 Å. Similarly, the C(6) side chain in compound 9 also pointed to the aromatic binding locus at the extracellular loop region of the MOR while the isoquinolinyl moiety in 9 was in the vicinity of Trp318 (W7.35) (FIG. 10B). The distance between the nitrogen atom in the isoquinoline ring and the nitrogen atom in the indole ring of Trp318 (W7.35) was 3.64 Å. Both distances could be plausible for hydrogen bonding interaction between the C(6) side chains in the ligands and the specified amino acid residue.

Because these two residues (Tyr210 (Yxl2.43) and Trp318 (W7.35)) are not conserved in the DOR and KOR, these two residues could act as an alternate "address" domain in MOR, and this plausible hydrogen bonding could contribute to the selectivity of the exemplary compounds 6 and 9 for the MOR. Site-directed mutagenesis and radioligand binding analysis with the mutated MOR can be conducted for confirmation.[56]

Conclusions

In summary, based on the molecular modeling study of the opioid receptor antagonist binding pocket using naltrexone as a probe molecule, an alternative "address" binding domain has been identified in the MOR antagonist binding pocket. Two series of novel ligands have been designed and synthesized to target on this "address" domain as proof-of-concept. Competition binding and in vitro functional assays have identified two compounds with sub-nanomolar affinity for the MOR and high selectivity over the DOR and KOR. Both compounds showed partial agonism in the in vitro G-protein activation test and potent antagonism in the in vivo antinociceptive test. Further molecular modeling study has implicated that the selectivity of these two ligands for the MOR could be the result of potential hydrogen bonding between the ligand and the "address" binding locus in the MOR. Moreover, we have also observed that some of the compounds in these series showed a range of efficacies as MOR partial agonists. These ligands would serve as pharmacological tools to obtain information on MOR activation mechanisms and on structural parameters that affect ligand efficacy at the MOR.

Experimental Section

Molecular Modeling

A Silicon Graphics Octane 2 workstation, equipped with two parallel R12000 processors, was used for all computational studies. InsightII (Accelrys)[57] package was used for modeling. InsightII/Homology module was used to construct the homology models of three opioid receptors based on the X-ray crystal structure of bovine rhodopsin, as reported previously.[39] InsightII/Discover module was applied to construct all the small molecules in their nitrogen-protonated form. Minimization with the steepest descent and then the conjugate gradient algorithm were performed to generate the lowest energy conformation for each ligand studied. Then a molecular dynamics simulation was performed (an equilibration phase of 1,000 fs at 300 K, followed by a collection phase of 5,000 fs at the same temperature) to further study the small molecule conformation. The lowest energy conformation of the molecule from the last 2 ps molecular dynamics simulation was extracted and applied as the initial configuration for docking into the proposed binding site of the opioid receptors. The docking of the small molecule was conducted interactively using InsightII/Discover. Experimental studies[47] suggest that the protonated nitrogen moiety interacts with the carboxyl group of Asp 147 to form a putative salt bridge. In detail, the molecule was docked in the upper level of transmembrane part in each receptor. The orientation of the molecule skeleton in the binding locus was mainly decided by: first, the putative ionic interaction between the tertiary amino group in naltrexone and the carboxylic group of aspartate on the transmembrane helix 3 in each opioid receptor (Asp147 in mu, Asp128 in delta and Asp138 in kappa); Second, the hydrophobic portion of the ligand intend to face the hydrophobic transmembrane helices while the hydrophilic portion to the more polar extracellular loop region. The ligand-receptor complex was minimized in gas phase first with the backbone of the receptor fixed, but all the side chain atoms were left unconstrained. The optimized conformation was then used as the initial configuration for the molecular dynamics simulations. A short-term steepest descent energy minimization (5,000 iterations) and dynamics simulation (10,000 step, 1 fs each step) was conducted to validate the docking primarily followed by a more vigorous minimizations (50,000 iterations) and dynamics simulation (100,000 steps) was conducted with 2000 steps equilibration for the initial dynamics. The total simulation time was 102 ps. In both processes, the backbone of the receptor was fixed to prevent the disruption of the α-helical bundle of the receptor and a generic distance constraint (4 to 4.2 Å) was applied between the negatively charged oxygen atom in aspartate on TM3 and the positively charged nitrogen atom in the ligand. After the dynamics simulation, the lowest energy conformation of the complex was extracted and saved for analysis.

Chemical Synthesis

General Methods: All reagents were purchased from Sigma-Aldrich or as otherwise states. Melting points were obtained with a Fisher scientific micro melting point apparatus and were uncorrected. All IR spectra were recorded on a Nicolet Avatar 360 FT-IR Instruments. Proton (300 MHz) and Carbon-13 (75 MHz) nuclear magnetic resonance (NMR) spectra were recorded at ambient temperature with tetramethylsilane as the internal standard on either a Varian Gemini-300 MHz "Tesla" spectrometer or Varian Mercury-300 MHz NMR spectrometer. GC/MS analysis was performed on a Hewlett Packard 6890 (Palo Alto, Calif.). TLC analyses were carried out on the Analtech Uniplate F254 plates. Chromatographic purification was carried out on silica gel columns (230~400 mesh, Merck). Yields were not maximized. The final target compounds' purity was tested by HPLC and elemental analysis, and satisfying purity of >95% was achieved from both methods. Varian ProStar HPLC System was used on Microsorb-MV 100-5 C18 column (250×4.6 mm) with injection volume at 10 μL and sample concentrations at 1-2 mg/0.5 mL in 100% acetonitrile; The sample was detected at single wavelength of 210 nm with eluent system of acetonitrile:water (75:25) at 1 mL/min over 50 min. Elemental analysis was conducted in Atlantic Microlab, Inc. All spectral data reported here were obtained from the hydrochloride salt form of the products while compound 1-6 and 9-14 were dihydrochloride salts, and compound 7, 8, 15 and 16 monohydrochloride salts.

General procedure 1: A solution of 6α-naltrexamine or 6β-naltrexamine (1 equivalent) in $CH_2Cl_2$ was added acyl chloride (2 equivalent), and triethylamine (4 equivalent) on an ice-water bath under $N_2$ protection. The mixture was allowed to stir overnight at room temperature. After concentrated to remove $CH_2Cl_2$, the resulting residue was dissolved in MeOH and added potassium carbonate (2 equivalents). The reaction mixture was stirred overnight at room temperature. After concentrated, the residue was partitioned between water and CH₂Cl₂. The water layer was extracted with CH₂C2. The combined CH₂Cl₂ solution was washed with brine, dried over Na₂SO₄. After concentrated, the residue was purified by silica gel column with a CH₂Cl₂/MeOH (100:1) (1% NH₃H₂O) solvent system as eluent to give the aim product. The product was then transferred into the hydrochloride salt using 1.25 M hydrochloride acid methanol solution at 0° C.

General procedure 2: A solution of carboxylic acid (3 equivalent) in DMF was added N-(3-Dimethylaminopropyl)-N'-ethylcarbodiimide hydrochloride (EDCI, 2.5 equivalent), hydrobenzotriazole (HOBt, 2.5 equivalent), 4 Å Molecular sieve, and triethylamine (5 equivalent) on an ice-water bath under N₂ protection. After 15 min, a solution of 6β-naltrexamine (1 equivalent) in DMF was added. The reaction mixture was filtered over celite after stirring overnight at room temperature. The filtrate was concentrated in vacuum to remove DMF. The residue was dissolved in MeOH and added potassium carbonate (2 equivalent). The resulting mixture was stirred overnight at room temperature. After concentrated, the residue was partitioned between water and CH₂Cl₂. The water layer was extracted with CH₂Cl₂. The combined CH₂Cl₂ solution was washed with H₂O, brine, dried with Na₂SO₄. After concentrated, the residue was purified by silica gel column with a CH₂Cl₂/MeOH (100:1) (1% NH₃H₂O) solvent system as eluent to give the aim product. Then the product was transferred into a hydrochloride salt.

17-Cyclopropylmethyl-3,14β-dihydroxy-4,5α-epoxy-6α-[(2'-pyridyl)acetamido]morphinan (1) was prepared by following the general procedure 1 in 58% yield. $[\alpha]^{25}_D$: −244° (c=0.05, MeOH). M.p.: 212-214° C.; IR (KBr, cm⁻¹) $\nu_{max}$: 3225, 1675, 1521, 1320; ¹H NMR (300 MHz, DMSO): δ 8.90 (b, 1H, exchangeable), 8.71 (b, 1H, Amide-H), 8.39 (m, 1H, Ar—H), 8.09 (m, 2H, Ar—H), 7.68 (m, 1H, Ar—H), 6.77 and 6.62 (2 d, 1H each, J=8.1 Hz, C₁—H, C₂—H), 4.77 (m, 1H, C₆—H), 4.67 (m, 1H, C₅—H), 3.12 (d, J=6.3 Hz, 1H), 3.05 (d, J=18.6 Hz, 1H), 2.67 (m, 1H), 2.63 (m, 1H), 2.57 (m, 1H), 2.35 (m, 1H), 2.27 (m, 1H), 2.17 (m, 2H), 1.84 (m, 1H), 1.74 (m, 1H), 1.49 (m, 1H), 1.14 (m, 1H), 0.86 (m, 1H), 0.54 (m, 2H), 0.12 (m, 2H); ¹³C NMR (75 MHz, DMSO) δ: 163.88, 150.16, 148.34, 145.74, 137.79, 137.61, 130.10, 126.35, 125.99, 122.69, 119.41, 117.61, 90.45, 69.85, 62.36, 59.91, 47.49, 46.49, 43.39, 33.83, 29.45, 23.11, 21.17, 9.60, 4.21, 4.06; MS (ESI) m/z: 447.7 (M⁺). Anal. (C₂₆H₂₉N₃O₄.2HCl.1.5H₂O) C, H.

17-Cyclopropylmethyl-3,14β-dihydroxy-4,5α-epoxy-6β-[(2'-pyridyl)acetamido]morphinan (2) was prepared by following the general procedure 1 in 65% yield. $[\alpha]^{25}_D$: −91° (c=0.07, MeOH). M.p.: 210-212° C.; IR (KBr, cm⁻¹) $\nu_{max}$: 3384 1673, 1526, 1324; ¹H NMR (300 MHz, DMSO): δ 9.07 (b, 1H, Amide-H), 8.86 (b, 1H, exchangeable), 8.69 (m, 1H, Ar—H), 8.03 (m, 2H, Ar—H), 7.65 (m, 1H, Ar—H), 6.73 and 6.68 (2 d, 1H each, J=8.1 Hz, C₁—H, C₂—H), 5.02 (m, 1H, C₆—H), 4.62 (m, 1H, C₅—H), 3.10 (d, J=6.3 Hz, 1H), 3.03 (d, J=18.9 Hz, 1H), 2.65 (m, 1H), 2.63 (m, 1H), 2.58 (m, 1H), 2.37 (m, 2H), 2.25 (m, 1H), 2.19 (m, 1H), 1.95 (m, 1H), 1.82 (m, 1H), 1.61 (m, 1H), 1.45 (m, 1H), 0.84 (m, 1H), 0.54 (m, 2H), 0.12 (m, 2H); ¹³C NMR (75 MHz, DMSO) δ: 160.27, 145.86, 144.30, 138.97, 136.63, 133.54, 127.19, 122.39, 120.28, 118.59, 115.29, 114.35, 89.11, 66.42, 58.54, 55.44, 47.84, 43.91, 41.96, 40.30, 27.00, 26.22, 20.59, 18.88, 6.82, 5.68; MS (ESI) m/z: 448.1 (M+H)⁺. Anal. (C₂₆H₂₉N₃O₄.2HCl.3H₂O) C, H.

17-Cyclopropylmethyl-3,14β-dihydroxy-4,5α-epoxy-6α-[(3'-pyridyl)acetamido]morphinan (3) was prepared by following the general procedure 1 in 54% yield. $[\alpha]^{25}_D$: −273° (c=0.06, MeOH). M.p.: 211-214° C.; IR (KBr, cm⁻¹) $\nu_{max}$: 3215, 1672, 1531, 1507, 1322; ¹H NMR (300 MHz, DMSO): δ 9.23 (m, 1H, Ar—H), 8.94 (b, 1H, exchangeable), 8.92 (s, 1H, Amide-H), 8.75 (d, J=5.1 Hz, 1H, Ar—H), 8.66 (d, J=7.5 Hz, 1H, Ar—H), 7.89 (dd, J=5.1, 7.5 Hz, 1H, Ar—H), 6.73 and 6.58 (2 d, 1H each, J=8.1 Hz, C₁—H, C₂—H), 4.76 (m, 1H, C₅—H), 4.63 (m, 1H, C₆—H), 3.97 (m, 1H), 3.43 (m, 2H), 3.05 (m, 3H), 2.71 (m, 1H), 2.45 (m, 2H), 1.95 (m, 1H), 1.63 (m, 1H), 1.53 (m, 1H), 1.20 (m, 1H), 1.06 (m, 1H), 0.64 (m, 2H), 0.45 (m, 2H); ¹³C NMR (75 MHz, DMSO) δ: 165.25, 151.34, 147.83, 145.94, 138.43, 136.20, 131.16, 130.84, 125.51, 123.82, 119.56, 117.96, 89.49, 69.88, 62.38, 59.89, 47.28, 45.95, 43.45, 33.71, 29.32, 23.08, 21.38, 9.62, 4.20, 4.06; MS (ESI) m/z: 448.9 (M+H)⁺. Anal. (C₂₆H₂₉N₃O₄.2HCl.3H₂O) C, H.

17-Cyclopropylmethyl-3,14β-dihydroxy-4,5α-epoxy-6β-[(3'-pyridyl)acetamido]morphinan (4) was prepared by following the general procedure 1 in 56% yield. $[\alpha]^{25}_D$: −141° (c=0.10, MeOH)). M.p.: 225-227° C.; IR (KBr, cm⁻¹) $\nu_{max}$: 3207, 3057, 1665, 1540, 1326; ¹H NMR (300 MHz, DMSO): δ9.18 (m, 1H, Ar—H), 9.15 (b, 1H, Amide-H), 8.90 (b, 1H, exchangeable), 8.86 (m, 1H, Ar—H), 8.51 (m, 1H, Ar—H), 7.77 (m, 1H, Ar—H), 6.75 and 6.68 (2 d, 1H each, J=8.4 Hz, C₁—H, C₂—H), 4.85 (d, J=8.4H, 1H, C₅—H), 4.47 (s, 1H, C₆—H), 3.89 (m, 1H), 3.73 (m, 1H), 3.38 (m, 1H), 3.12 (m, 2H), 2.85 (m, 1H), 2.45 (m, 2H), 1.93 (m, 1H), 1.80 (m, 1H), 1.64 (m, 1H), 1.47 (m, 2H), 1.09 (m, 1H), 0.64 (m, 2H), 0.46 (m, 2H); ¹³C NMR (75 MHz, DMSO) δ: 161.34, 147.63, 144.05, 139.39, 136.30, 131.90, 126.87, 126.46, 120.29, 119.68, 115.32, 114.28, 88.05, 66.55, 58.39, 55.48, 47.27, 41.88, 40.16, 27.77, 25.51, 19.75, 18.82, 6.98, 5.63, 3.26; MS (ESI) m/z: 448.9 (M+H)⁺. Anal. (C₂₆H₂₉N₃O₄.2HCl.3H₂O) C, H.

17-Cyclopropylmethyl-3,14β-dihydroxy-4,5α-epoxy-6α-[(4'-pyridyl)acetamido]morphinan (5) was prepared by following the general procedure 1 in 45% yield. $[\alpha]^{25}_D$: −213° (c=0.09, MeOH). M.p. 215-217° C.; IR (KBr, cm⁻¹) $\nu_{max}$: 3225, 1653, 1542, 1500, 1318; ¹H NMR (300 MHz, DMSO): δ 8.92 (m, 2H, Ar—H), 8.88 (b, 1H, exchangeable), 8.77 (b, 1H, Amide-H), 8.08 (m, 2H, Ar—H), 6.73 and 6.59 (2 d, 1H each, J=8.1 Hz, C₁—H, C₂—H), 4.78 (m, 1H, C₅—H), 4.62 (m, 1H, C₆—H), 3.95 (m, 1H), 3.40 (m, 2H), 3.06 (m, 2H), 2.74 (m, 1H), 2.46 (m, 2H), 1.91 (m, 1H), 1.65 (m, 1H), 1.52 (m, 1H), 1.18 (m, 2H), 1.09 (m, 1H), 0.69 (m, 2H), 0.49 (m, 2H); ¹³C NMR (75 MHz, DMSO) δ: 164.17, 149.72, 149.72, 145.15, 142.08, 137.77, 130.25, 124.71, 121.12, 121.12, 119.07, 117.28, 88.82, 69.06, 61.74, 59.26, 46.81, 46.54, 45.27, 42.58, 33.29, 28.70, 22.43, 8.17, 7.55, 3.56; MS (ESI) m/z: 448.9 (M+H)⁺. Anal. (C₂₆H₂₉N₃O₄.2HCl.3H₂O) C, H.

17-Cyclopropylmethyl-3,14β-dihydroxy-4,5α-epoxy-6β-[(4'-pyridyl)acetamido]morphinan (6, NAP) was prepared by following the general procedure 1 in 45% yield. $[\alpha]^{25}_D$: −176° (c=0.01, MeOH). M.p.: 258-61° C.; IR (KBr, cm⁻¹) $\nu_{max}$: 3386, 1666, 1548, 1502, 1326; ¹H NMR (300 MHz, DMSO): δ 8.81 (b, 1H, Amide-H), 8.45 (m, 2H, Ar—H), 8.22 (b, 1H, exchangeable), 7.60 (m, 2H, Ar—H), 6.32 and 6.27 (2 d, 1H each, J=7.8 Hz, C₁—H, C₂—H), 4.84 (s, 1H, C₅—H), 4.46 (m, 1H, C₆—H), 3.90 (m, 1H), 3.69 (m, 1H), 3.30 (m, 2H), 3.06 (m, 2H), 2.85 (m, 1H), 2.45 (m, 2H), 1.93 (m, 1H), 1.80 (m, 1H), 1.59 (m, 1H), 1.46 (m, 1H), 1.07 (m, 1H), 0.63 (m, 2H), 0.45 (m, 2H); ¹³C NMR (75 MHz, DMSO) δ: 164.30, 149.27, 142.72, 139.62, 130.15, 128.61, 127.80, 124.87, 123.73, 120.89, 118.86, 117.84, 91.15, 69.90, 61.75, 58.84, 50.68, 46.91, 43.50, 39.98, 31.10, 28.60, 22.18, 8.99, 3.68, 3.37; MS (ESI) m/z: 448.9 (M+H)⁺. Anal. (C₂₆H₂₉N₃O₄.2HCl.3H₂O) C, H.

17-Cyclopropylmethyl-3,14β-dihydroxy-4,5α-epoxy-6α-(benzamido)morphinan (7) was prepared by following the general procedure 1 in 54% yield. $[\alpha]^{25}_D$: −215° (c=0.11, MeOH). M.p.: 182-185° C.; IR (KBr, cm$^{-1}$) $v_{max}$: 3353, 2947, 1638, 1540, 1324; $^1$H NMR (300 MHz, DMSO): δ 7.75 (m, 2H, Ar—H), 7.45 (m, 3H, Ar—H), 6.70 and 6.65 (2 d, 1H each, J=8.4 Hz, C$_1$—H, C$_2$—H), 6.50 (b, 1H, Amide-H), 4.79 (m, 1H, C$_6$—H), 4.77 (m, 1H, C$_5$—H), 3.14 (m, 1H), 3.04 (m, 1H), 2.68 (m, 1H), 2.65 (m, 1H), 2.60 (m, 1H), 2.36 (m, 1H), 2.29 (m, 1H), 2.27 (m, 2H), 1.84 (m, 1H), 1.58 (m, 1H), 1.42 (m, 1H), 1.25 (m, 1H), 0.86 (m, 1H), 0.54 (m, 2H), 0.12 (m, 2H); $^{13}$C NMR (75 MHz, DMSO) δ: 167.72, 145.85, 138.14, 134.53, 131.57, 131.11, 128.60, 127.47, 125.63, 119.38, 117.86, 90.12, 69.91, 62.32, 59.87, 47.38, 46.98, 43.39, 33.69, 29.45, 23.11, 21.17, 9.56, 4.24, 4.08; MS (ESI) m/z: 447.9 (M+H)$^+$. Anal. (C$_{27}$H$_{30}$N$_2$O$_4$.HCl.2.75H$_2$O) C, H.

17-Cyclopropylmethyl-3,14β-dihydroxy-4,5α-epoxy-6β-(benzamido)morphinan (8) was prepared by following the general procedure 1 in 59% yield. [α]$^{25}$$_D$: —157° (c=0.07, MeOH). M.p.: 220-221° C.; IR (KBr, cm$^{-1}$) $v_{max}$: 3242, 1638, 1540, 1324; $^1$H NMR (300 MHz, DMSO): δ 7.84 (m, 2H, Ar—H), 7.50-7.40 (m, 3H, Ar—H), 7.21 (b, 1H, Amide-H), 6.75 and 6.58 (2 d, 1H each, J=8.1 Hz, C$_1$—H, C$_2$—H), 4.52 (m, 1H, C$_5$—H), 4.26 (m, 1H, C$_6$—H), 3.87 (m, 1H), 3.73 (m, 1H), 3.15 (m, 1H), 2.69 (m, 1H), 2.61 (m, 1H), 2.40 (m, 1H), 2.23 (m, 2H), 1.87 (m, 1H), 1.72 (m, 1H), 1.55 (m, 1H), 1.26 (m, 1H), 1.12 (m, 1H), 0.86 (m, 1H), 0.54 (m, 2H), 0.12 (m, 2H); $^{13}$C NMR (75 MHz, DMSO) δ: 168.79, 142.59, 140.78, 134.52, 131.55, 131.18, 128.38, 127.23, 123.87, 119.04, 117.62, 91.82, 70.59, 62.61, 58.92, 52.14, 44.49, 30.45, 30.11, 29.66, 24.35, 22.52, 8.76, 3.61, 3.05; MS (ESI) m/z: 447.9 (M+H)$^+$. Anal. (C$_{27}$H$_{30}$N$_2$O$_4$.HCl-3.25H$_2$O) C, H.

17-Cyclopropylmethyl-3,14β-dihydroxy-4,5α-epoxy-6α-[(3'-isoquinolyl)acetamido]morphinan (9, NAQ) was prepared by following the general procedure 2 in 70% yield. [α]$^{25}$$_D$: −150° (c=0.01, MeOH). M.p.: 210-213° C.; IR (KBr, cm$^{-1}$) $v_{max}$: 3222, 1666, 1529, 1261, 801; $^1$H NMR (300 MHz, DMSO): δ 9.44 (s, 1H, Ar—H), 8.95 (b, 1H, exchangeable), 8.64 (s, 1H, Ar—H), 8.58 (b, 1H, Amide-H), 8.27 (m, 2H, Ar—H), 7.90 (m, 2H, Ar—H), 6.79 and 6.62 (2 d, 1H each, J=7.8 Hz, C$_1$—H, C$_2$—H), 4.81 (s, 1H, C$_5$—H), 4.74 (m, 1H, C$_6$—H), 3.99 (m, 1H), 3.45 (m, 2H), 3.14 (m, 2H), 2.73 (m, 1H), 2.58 (m, 1H), 2.23 (m, 2H), 1.87 (m, 1H), 1.67 (m, 2H), 1.48 (m, 1H), 1.08 (m, 1H), 0.67 (m, 2H), 0.47 (m, 2H); $^{13}$C NMR (75 MHz, DMSO) δ: 159.97, 148.87, 146.15, 139.18, 138.21, 137.40, 134.48, 132.47, 131.01, 128.93, 128.86, 128.37, 124.16, 122.44, 120.07, 118.39, 87.91, 69.86, 62.26, 57.93, 47.15, 46.05, 30.51, 29.43, 23.88, 19.57, 19.56, 5.75, 5.18, 2.26; MS (ESI) m/z: 498.1 (M+H)$^+$. Anal. (C$_{30}$H$_{31}$N$_3$O$_4$.2HCl.0.5H$_2$O) C, H.

17-Cyclopropylmethyl-3,14β-dihydroxy-4,5α-epoxy-6β-[(3'-isoquinolyl)acetamido]morphinan (10) was prepared by following the general procedure 2 in 50% yield. [α]$^{25}$$_D$: −166° (c=0.10, MeOH)). M.p.: 235-237° C.; IR (KBr, cm$^{-1}$) $v_{max}$: 3069, 1665, 1537, 1328, 901; $^1$H NMR (300 MHz, DMSO): δ 9.46 (s, 1H, Ar—H), 9.27 (b, 1H, Amide-H), 9.15 (s, 1H, Ar—H), 8.92 (b, 1H, exchangeable), 8.21 (m, 2H, Ar—H), 8.00 (m, 1H, Ar—H), 7.81 (m, 1H, Ar—H), 6.76 and 6.68 (2 d, 1H each, J=8.4 Hz, C$_1$—H, C$_2$—H), 5.06 (m, 1H, C$_6$—H), 4.90 (d, J=7.8 Hz, 1H, C$_5$—H), 3.91 (m, 1H), 3.78 (m, 1H), 3.37 (m, 2H), 3.10 (m, 2H), 2.89 (m, 1H), 2.45 (m, 1H), 2.00 (m, 1H), 1.83 (m, 1H), 1.69 (m, 1H), 1.49 (m, 2H), 1.12 (m, 1H), 0.68 (m, 2H), 0.48 (m, 2H); $^{13}$C NMR (75 MHz, DMSO) δ: 164.63, 151.51, 143.09, 142.94, 140.57, 135.84, 131.37, 131.26, 129.64, 129.01, 128.16, 128.06, 124.62, 120.53, 119.48, 118.30, 92.95, 62.55, 59.43, 52.26, 44.35, 36.71, 31.66, 30.85, 30.42, 24.69, 22.92, 9.68, 4.22, 4.02; MS (ESI) m/z: 498.8 (M+H)$^+$. Anal. (C$_{30}$H$_{31}$N$_3$O$_4$.2HCl3.5H$_2$O) C, H.

17-Cyclopropylmethyl-3,14β-dihydroxy-4,5α-epoxy-6α-[(2'-quinolyl)acetamido]morphinan (11) was prepared by following the general procedure 1 in 93% yield. The product was transferred into a HCl salt. [α]$^{25}$$_D$: −186° (c=0.03, MeOH). M.p.: 212-214° C.; IR (KBr, cm$^{-1}$) $v_{max}$: 3199, 1673, 1528, 1321, 785; $^1$H NMR (300 MHz, DMSO): δ 8.90 (b, 1H, Amide-H), 8.60 (m, 2H, Ar—H), 8.21 (b, 1H, exchangeable), 8.13 (m, 2H, Ar—H), 7.92 (m, 1H, Ar—H), 7.75 (m, 1H, Ar—H), 6.76 and 6.63 (2 d, 1H each, J=7.8 Hz, C$_1$—H, C$_2$—H), 4.84 (s, 1H, C$_5$—H), 4.68 (m, 1H, C$_6$—H), 3.94 (m, 1H), 3.65 (m, 1H), 3.35 (m, 1H), 3.05 (m, 1H), 2.71 (m, 1H), 2.45 (m, 2H), 1.93 (m, 2H), 1.82 (m, 1H), 1.65 (m, 1H), 1.48 (m, 2H), 1.06 (m, 1H), 0.63 (m, 2H), 0.44 (m, 2H); $^{13}$C NMR (75 MHz, DMSO) δ: 160.77, 146.72, 146.08, 145.15, 141.05, 139.27, 134.49, 134.49, 130.24, 130.24, 128.88, 123.95, 122.35, 120.10, 119.33, 118.51, 87.79, 69.88, 62.24, 57.95, 47.18, 46.06, 30.51, 29.42, 23.91, 19.68, 19.68, 5.79, 5.22, 2.31; MS (ESI) m/z: 498.1 (M+H)$^+$. Anal. (C$_{30}$H$_{31}$N$_3$O$_4$.2HCl.2.5H$_2$O) C, H.

17-Cyclopropylmethyl-3,14β-dihydroxy-4,5α-epoxy-6β-[(2'-quinolyl)acetamido]morphinan (12) was prepared by following the general procedure 1 in 83% yield. [α]$^{25}$$_D$: −112° (c=0.1, MeOH). M.p.: 227-229° C.; IR (KBr, cm$^{-1}$) $v_{max}$: 3110, 1671, 1533, 1329, 770; $^1$H NMR (300 MHz, DMSO): δ9.26 (m, 1H, Ar—H), 8.94 (b, 1H, Amide-H), 8.61 (m, 1H, Ar—H), 8.16 (m, 2H, Ar—H), 8.12 (b, 1H, exchangeable), 7.92 (m, 1H, Ar—H), 7.78 (m, 1H, Ar—H), 6.79 and 6.68 (2 d, 1H each, J=7.81 Hz, C$_1$—H, C$_2$—H), 5.15 (s, 1H, C$_5$—H), 5.12 (m, 1H, C$_6$—H), 3.93 (m, 1H), 3.77 (m, 1H), 3.43 (m, 1H), 3.10 (m, 2H), 2.90 (m, 1H), 2.45 (m, 2H), 2.09 (m, 1H), 1.83 (m, 1H), 1.62 (m, 1H), 1.48 (m, 1H), 1.08 (m, 1H), 0.86 (m, 1H), 0.65 (m, 2H), 0.50 (m, 2H); $^{13}$C NMR (75 MHz, DMSO) δ: 163.98, 149.09, 145.84, 141.98, 139.75, 136.87, 130.48, 129.60, 129.12, 128.72, 127.40, 127.26, 123.60, 118.64, 118.44, 117.41, 93.02, 69.83, 61.83, 58.76, 51.23, 47.33, 43.66, 30.11, 29.71, 24.20, 22.20, 8.99, 3.62, 3.36; MS (ESI) m/z: 497.8 (M+H)$^+$ Anal. (C$_{30}$H$_{31}$N$_3$O$_4$.2HCl.0.5H$_2$O) C, H.

17-Cyclopropylmethyl-3,14β-dihydroxy-4,5α-epoxy-6α-[(3'-quinolyl)acetamido]morphinan (13) was prepared by following the general procedure 2 in 61% yield: [α]$^{25}$$_D$: −192° (c=0.05, MeOH). M.p.: >270° C.; IR (KBr, cm$^{-1}$) $v_{max}$: 3221, 1660, 1537, 1318, 777; $^1$H NMR (300 MHz, DMSO): δ 9.39 (s, 1H, Ar—H), 9.06 (s, 1H, Ar—H), 8.90 (b, 1H, Amide-H), 8.66 (b, 1H, exchangeable), 8.19 (m, 2H, Ar—H), 7.97 (m, 1H, Ar—H), 7.79 (m, 1H, Ar—H), 6.73 and 6.59 (2 d, 1H each, J=8.1H, C$_1$—H, C$_2$—H), 4.83 (m, 1H, C$_5$—H), 4.70 (m, 1H, C$_6$—H), 3.95 (m, 1H), 3.45 (m, 2H), 3.08 (m, 3H), 2.72 (m, 1H), 2.52 (m, 2H), 1.92 (m, 1H), 1.65 (m, 1H), 1.51 (m, 1H), 1.26 (m, 1H), 1.10 (m, 1H), 0.68 (m, 2H), 0.45 (m, 2H); $^{13}$C NMR (75 MHz, DMSO) δ: 164.04, 147.59, 146.84, 144.48, 141.03, 139.52, 134.19, 130.41, 129.48, 128.03, 127.76, 125.83, 122.91, 119.93, 119.24, 116.95, 87.73, 70.15, 61.65, 57.70, 47.08, 45.99, 39.40, 30.92, 29.83, 24.30, 20.10, 6.50, 5.99, 3.34; MS (ESI) m/z: 498.9 (M+H)$^+$. Anal. (C$_{30}$H$_{31}$N$_3$O$_4$.2HCl.3.75H$_2$O) C, H.

17-Cyclopropylmethyl-3,14β-dihydroxy-4,5α-epoxy-6β-[(3'-quinolyl)acetamido]morphinan (14) was prepared by following the general procedure 2 in 87% yield. [α]$^{25}$$_D$: −86° (c=0.07, MeOH). M.p.: 235-238° C.; IR (KBr, cm$^{-1}$) $v_{max}$: 3072, 1660, 1549, 1324, 777; $^1$H NMR (300 MHz, DMSO): δ 9.47 (s, 1H, Ar—H), 9.35 (b, 1H, Amide-H), 8.92 (b, 1H, exchangeable), 8.23 (m, 2H, Ar—H), 8.22 (s, 1H, Ar—H), 8.03 (m, 2H, Ar—H), 6.76 and 6.68 (2 d, 1H each, J=8.4 Hz, C$_1$—H, C$_2$—H), 5.11 (s, 1H, C$_5$—H) 5.01 (m, 1H, C$_6$—H), 3.92 (m, 1H), 3.78 (m, 1H), 3.33 (m, 2H), 3.07 (m, 2H), 2.89 (m, 1H), 1.83 (m, 1H), 1.62 (m, 2H), 1.46 (m, 3H), 1.11 (m, 1H), 0.65 (m, 2H), 0.47 (m, 2H); $^{13}$C NMR (75 MHz, DMSO) δ: 165.68, 147.82, 147.72, 141.71, 140.27, 135.74, 131.00, 130.18, 128.40, 127.21, 127.04, 126.69, 126.50, 122.65, 118.42, 116.87, 99.79, 69.75, 61.90, 57.95, 51.63, 46.22, 44.11, 29.40, 29.24, 23.49, 21.82, 7.55, 2.99, 2.10; MS (ESI) m/z: 498.8 (M+H)$^+$. Anal. ($C_{30}H_{31}N_3O_4 \cdot 2HCl \cdot 2.5H_2O$) C, H.

17-Cyclopropylmethyl-3,14β-dihydroxy-4,5α-epoxy-6α-[(2'-naphthalyl)acetamido]morphinan (15) was prepared by following the general procedure 1 in 46% yield. $[\alpha]^{25}_D$: −218° (c=0.01, MeOH). M.p.: 213-215° C.; IR (KBr, cm$^{-1}$) $v_{max}$: 3399, 1641, 1503, 1460, 1318; $^1$H NMR (300 MHz, DMSO): δ 8.15 (s, 1H, Ar—H), 7.77-7.73 (m, 4H, Ar—H), 7.45 (m, 2H, Ar—H), 6.85 (b, 1H, Amide-H), 6.85 and 6.50 (2 d, 1H each, J=8.1H, C$_1$—H, C$_2$—H), 4.80 (m, 1H, C$_6$—H), 4.71 (m, 1H, C$_5$—H), 3.69 (m, 1H), 3.00 (m, 1H), 2.63 (m, 1H), 2.53 (m, 1H), 2.34 (m, 1H), 2.23 (m, 1H), 2.15 (m, 2H), 1.76 (m, 1H), 1.49 (m, 1H), 1.36 (m, 1H), 1.09 (m, 1H), 1.14 (m, 1H), 0.83 (m, 1H), 0.55 (m, 2H), 0.12 (m, 2H); $^{13}$C NMR (75 MHz, CD$_3$OD) δ: 167.96, 145.46, 138.32, 134.35, 132.03, 130.76, 128.13, 127.44, 127.37, 127.25, 127.17, 127.00, 125.98, 123.30, 121.61, 119.24, 117.59, 87.72, 61.56, 57.25, 44.50, 39.95, 37.39, 29.81, 28.96, 23.29, 18.95, 13.60, 9.87, 5.05, 4.55; MS (ESI) m/z: 496.8 (M$^+$). Anal. ($C_{31}H_{32}N_2O_4 \cdot HCl \cdot 1.5H_2O$) C, H.

17-Cyclopropylmethyl-3,14β-dihydroxy-4,5α-epoxy-6β-[(2'-naphthalyl)acetamido]morphinan (16) was prepared by following the general procedure 1 in 44% yield. $[\alpha]^{25}_D$: −123° (c=0.09, MeOH). M.p.: 212-215° C.; IR (KBr, cm$^{-1}$) $v_{max}$: 3248, 2964, 1640, 1508, 1319, 716; $^1$H NMR (300 MHz, DMSO): δ 8.36 (b, 1H, Amide-H), 7.95-7.86 (m, 5H, Ar—H), 7.56 (m, 2H, Ar—H), 6.76 and 6.59 (2 d, 1H each, J=8.4 Hz, C$_1$—H, C$_2$—H), 4.60 (m, 1H, C$_5$—H), 4.31 (m, 1H, C$_6$—H), 3.88 (m, 1H), 3.75 (m, 1H), 3.19 (m, 1H), 2.70 (m, 1H), 2.42 (m, 1H), 2.27 (m, 2H), 1.96 (m, 1H), 1.70 (m, 1H), 1.54 (m, 1H), 1.24 (m, 1H), 1.49 (m, 1H), 1.14 (m, 1H), 0.88 (m, 1H), 0.50 (m, 2H), 0.12 (m, 2H); $^{13}$C NMR (75 MHz, DMSO) δ: 166.36, 147.21, 142.86, 134.85, 132.86, 131.80, 129.57, 128.98, 128.57, 128.35, 128.25, 128.24, 127.48, 124.85, 121.75, 119.20, 119.10, 91.30, 70.44, 62.43, 51.74, 42.96, 35.67, 33.08, 32.17, 30.45, 24.70, 20.10, 9.50, 6.80, 4.00; MS (ESI) m/z: 497.8 (M+H)$^+$. Anal. ($C_{31}H_{32}N_2O_4 \cdot HCl \cdot H_2O$) C, H.

In Vitro Competitive Radioligand-Binding and Functional Assay

Details of the binding assay was conducted to study the selectivity of the ligands by using mono-cloned opioid receptor expressed in Chinese hamster ovarian (CHO) cell lines as described previously.[44,45] [$^3$H]naloxone, [$^3$H]NTI and [$^3$H]norBNI were used to label the mu, delta and kappa opioid receptors respectively. Aliquots of a membrane preparation were incubated with the radioligands in the presence of different concentrations of the drug under investigation at 30° C. for 1 h. Specific (i.e. opioid receptor related) binding was determined as the difference in binding obtained in the absence and presence of 10 μM naltrexone. The potency of the drugs in displacing the specific binding of the radioligand was determined from data using linear regression analysis of Hill plots. The IC$_{50}$ values will then be determined and corrected to K$_i$ values using the Cheng-Prusoff equation. Functional assays, including $^{35}$S-GTP[γS]-binding assay were conducted in the same cell membranes used for the receptor binding assays. 3 μM of DAMGO was included in the assay for a maximally effective concentration of a full agonist for the mu opioid receptor.

In Vivo Acute Function Test Procedure

Animals. Male Swiss Webster mice (Harlan Laboratories, Indianapolis, Ind.) weighing 25-30 g were housed 6 to a cage in animal care quarters and maintained at 22±2° C. on a 12 hr light-dark cycle. Food and water were available ad libitum. The mice were brought to a test room (22±2° C., 12 hr light-dark cycle), marked for identification and allowed 18 hr to recover from transport and handling. Protocols and procedures were approved by the Institutional Animal Care and Use Committee (IACUC) at Virginia Commonwealth University Medical Center and comply with the recommendations of the IASP (International Association for the Study of Pain).

Tail immersion test. The warm-water tail immersion test was performed according to Coderre and Rollman[58] using a water bath with the temperature maintained at 56±0.1° C. Before injecting the mice, a base-line (control) latency was determined. Only mice with a control reaction time from 2 to 4 second were used. The average baseline latency for these experiments was 3.0±0.1 sec. The test latency after drug treatment was assessed at the appropriate time, and a 10 second maximum cut-off time was imposed to prevent tissue damage. Antinociception was quantified according to the method of Harris and Pierson[59] as the percentage of maximum possible effect (% MPE) which was calculated as: % 0 [(test latency−control latency)/(10−control latency)]×100. Percent MPE was calculated for each mouse using at least 6 mice per drug.

Drugs. Morphine sulfate was purchased from Mallinekrodt, St. Louis, Mo., USA. Naloxone was purchased from Sigma-Aldrich (St. Louis, Mo., USA). All drugs and test compounds were dissolved in pyrogen-free isotonic saline (Baxter Healthcare, Deerfield, Ill.) and were administered to mice subcutaneously (s.c.)

Experimental design and statistical analysis. To test for agonist properties, mice, with pre-determined tail immersion baseline, were injected s.c. with morphine (10 mg/kg; a dose that produces maximal antinociception) or the test compound at increasing doses and were re-assessed for their tail immersion reaction time 20 min later. To test for antagonist properties, mice, with pre-determined tail immersion baseline, were injected s.c. with either naloxone (1 mg/kg; a dose that totally block the antinociception induce by 10 mg/kg morphine) or the test compound at various doses and 5 min later they were administered morphine (10 mg/kg; s.c.). Mice were re-assessed for their tail immersion reaction time 20 min later. Effective dose-50 (ED50) values were calculated using least-squares linear regression analysis followed by calculation of 95% confidence limits (95% C.L.) by the method of Bliss.[60]

Data are expressed as mean values±S.E.M. Analysis of variance (ANOVA) followed by the post hoc "Student-Newman-Keuls" test were performed to assess significance using the Instat 3.0 software (GraphPad Software, San Diego, Calif., U.S.A.). P<0.05 was considered significant.

REFERENCES FOR EXAMPLE 2

1. Zimmerman, D. M.; Leander, J. D. Selective opioid receptor agonists and antagonists: research tools and potential therapeutic agents. J. Med. Chem. 1990, 33, 895-902.
2. Schmidhammer, H. Opioid Receptor Antagonists, Prog. Med. Chem., 1998, 35, 83-132.
3. Snyder, S. H.; Pasternak. G. W. Historical review: Opioid Receptors. TRENDs Pharmacol. Sci., 2003, 24(4), 198-205.
4. Fiellin, D. A.; Kleber, H.; Trumble-Hejduk, J. G.; McLellan, A. T.; Kosten, T. R. Consensus statement in office-based treatment of opioid dependence using buprenorphine, J. Subst. Abuse Treat. 2004, 27, 153-159.

5. Gold, M. S.; Dackis, C. A.; Pottash, A. L.; Sternbach, H. H.; Annitto, W. J.; Martin, D.; Dackis, M. P. Naltrexone, opiate addiction, and endorphins. Med. Res. Rev. 1982, 2(3), 211-46.
6. Gonzalez, J. P.; Brogden, R. N. Naltrexone. A review of its pharmacodynamic and pharmacokinetic properties and therapeutic efficacy in the management of opioid dependence. Drugs, 1988, 35, 192-213.
7. Schwyzer, R. ACTH: a short introductory review. Ann. NY. Acad. Sci., 1977, 297, 3-26.
8. Portoghese, P. S.; Lipkowski, A. W.; Takemori, A. E. Binaltorphimine and nor-binaltorphimine, potent and selective kappa opioid receptor antagonists. Life Sci. 1987, 40, 1287-92.
9. Jones, R. M.; Hjorth, S. A.; Schwartz, T. W. Portoghese, P. S. Mutational evidence for a common kappa antagonist binding pocket in the wild-type kappa and mutant mu[K303E] opioid receptors. J. Med. Chem. 1998, 41(25), 4911-4.
10. Portoghese, P. S.; Sultana, M.; Nagase, H. Takemori, A. E. Application of the message-address concept in the design of highly potent and selective non-peptide delta opioid receptor antagonist. J. Med. Chem., 1988, 31, 281-82.
11. Schmidhammer, H.; Burkard, W. P.; Eggstin-Aeppli, L.; Smith, C. F. C. Synthesis and biological evaluation of 14-alkoxymorphinans. 2. (−)-N-(cyclopropymethyl)-4,14-dimethoxymorphinana-6-one, a selective mu opioid receptor antagonist. J. Med. Chem., 1989, 32, 418-421.
12. Marki, A.; Monory, K.; Otvos, F.; Toth, G.; Krassnig, R.; Schmidhammer, H.; Traynor, J. R.; Roques, B. P.; Maldonado, R.; Borsodi, A. Mu-opioid receptor specific antagonist cyprodime: characterization by in vitro radioligand and [35S]GTPgammaS binding assays. Eur. J Pharmacol. 1999, 383(2), 209-14.
13. Schmidhammer, H.; Jennewein, H. K.; Krassnig, R.; Traynor, J. R.; Patel, D.; Bell, K.; Froschauer, G.; Mattersberger, K.; Jachs-Ewinger, C.; Jura, P.; Fraser, G. L.; Kalinin, V. N. Synthesis and biological evaluation of 14-alkoxymorphinans. 11. 3-Hydroxycyprodime and analogues: opioid antagonist profile in comparison to cyprodime. J. Med. Chem. 1995, 38(16), 3071-7.
14. Schmidhammer, H.; Jennewein, H. K.; Smith, C. F. Synthesis and biological evaluation of 14-alkoxymorphinans. 11. 3-Hydroxycyprodime and analogues: opioid antagonist profile in comparison to cyprodime. Arch. Pharm. (Weinheim). 1991, 324(4), 209-11.
15. Schmidhammer, H.; Smith, C. F.; Erlach, D.; Koch, M.; Krassnig, R.; Schwetz, W.; Wechner, C. Synthesis and biological evaluation of 14-alkoxymorphinans. 3. Extensive study on cyprodime-related compounds. J. Med. Chem. 1990, 33(4), 1200-6.
16. Schmidhammer, H.; Smith, C. F.; Erlach, D.; Koch, M.; Krassnig, R.; Schwetz, W., Wechner, C. Cyprodime analogues: synthesis and pharmacological evaluation. Prog. Clin. Biol. Res. 1989, 328, 37-40.
17. Spetea, M.; Schullner, F.; Moisa, R. C.; Berzetei-Gurske, I. P.; Schraml, B.; Dorfler, C.; Aceto, M. D.; Harris, L. S.; Coop, A.; Schmidhammer, H. Synthesis and biological evaluation of 14-alkoxymorphinans. 21. Novel 4-alkoxy and 4-phenylpropoxy derivatives of the mu opioid receptor antagonist cyprodime. J. Med. Chem. 2004, 47(12), 3242-7.
18. Lewis, J. W.; Smith, C. F. C.; McCarthy, P. S.; Walter, D.; Kobylecki, R. J.; Myers, M.; Haynes, A. S.; Lewis, C. J.; Waltham, K. New 14-aminomorphinones and codeinones. NIDA Res. Monogr. 1988, 90, 136-143.
19. Portoghese, P. S.; Takemori, A. E. Affinity labels as probes for opioid receptor types and subtypes. NIDA Res. Monogr. 1986, 69, 157-68.
20. Burke, T. F.; Woods, J. H.; Lewis, J. W.; Medzihradsky, F. Irreversible opioid antagonist effects of clocinnamox on opioid analgesia and mu receptor binding in mice. J. Pharmacol. Exp. Ther. 1994, 271(2), 715-21.
21. Eguchi, M. Recent advances in selective opioid receptor agonists and antagonists. Med. Res. Rev., 2004, 24(2), 182-212.
22. Pelton, J. T.; Kazmierski, W.; Gulya, K.; Yamamura, H. I.; Hruby, V. J. Design and synthesis of conformationally constrained somatostatin analogues with high potency and specificity for mu opioid receptors. J Med Chem. 1986, 29, 2370-5.
23. Gulya, K.; Pelton, J. T.; Hruby, V. J.; Yamamura, H. I. Cyclic somatostatin octapeptide analogues with high affinity and selectivity toward mu opioid receptors. Life Sci. 1986, 38, 2221-30.
24. Hawkins, K. N.; Knapp, R. J.; Lui, G. K.; Gulya, K.; Kazmierski, W.; Wan, Y. P.; Pelton, J. T.; Hruby, V. J.; Yamamura, H. I. [3H]-[H-D-Phe-Cys-Tyr-D-Trp-Orn-Thr-Pen-Thr-NH2]([3H]CTOP), a potent and highly selective peptide for mu opioid receptors in rat brain. J Pharmacol Exp Ther. 1989, 248(1), 73-81.
25. Kramer, T. H.; Shook, J. E.; Kazmierski, W.; Ayres, E. A.; Wire, W. S.; Hruby, V. J.; Burks, T. F. Novel peptidic mu opioid antagonists: pharmacologic characterization in vitro and in vivo. J Pharmacol Exp Ther. 1989, 249(2), 544-51.
26. Hruby, V. J.; Toth, G.; Gehrig, C. A.; Kao, L. F.; Knapp, R.; Lui, G. K.; Yamamura, H. I.; Kramer, T. H.; Davis, P.; Burks, T. F. Topographically designed analogues of [D-Pen,D-Pen5]enkephalin. J Med Chem. 1991, 34(6), 1823-30.
27. Mulder, A. H.; Wardeh, G.; Hogenboom, F.; Kazmierski, W.; Hruby, V. J.; Schoffelmeer, A. N. Cyclic somatostatin analogues as potent antagonists at mu-, but not delta- and kappa-opioid receptors mediating presynaptic inhibition of neurotransmitter release in the brain. Eur J Pharmacol. 1991, 205(1), 1-6.
27. Abbruscato, T. J.; Thomas, S. A.; Hruby, V. J.; Davis, T. P. Blood-brain barrier permeability and bioavailability of a highly potent and mu-selective opioid receptor antagonist, CTAP: comparison with morphine. J Pharmacol Exp Ther. 1997, 280(1), 402-9.
28. Bonner, G. G.; Davis, P.; Stropova, D.; Edsall, S.; Yamamura, H. I.; Porreca, F.; Hruby, V. J. Opiate aromatic pharmacophore structure-activity relationships in CTAP analogues determined by topographical bias, two-dimensional NMR, and biological activity assays. J Med Chem. 2000, 43(4), 569-80.
29. Okada, T.; Le Trong, I.; Fox, B. A.; Behnke, C. A.; Stenkamp, R. E.; Palczewski, K. X-Ray diffraction analysis of three-dimensional crystals of bovine rhodopsin obtained from mixed micelles. J. Struct. Biol. 2000, 130(1), 73-80.
30. Teller, D. C.; Okada, T.; Behnke, C. A.; Palczewski, K.; Stenkamp, R. E. Advances in determination of a high-resolution three-dimensional structure of rhodopsin, a model of G-protein-coupled receptors (GPCRs). Biochemistry. 2001, 40(26), 7761-72.
31. Salom, D.; Le Trong, I.; Pohl, E.; Ballesteros, J. A.; Stenkamp, R. E.; Palczewski, K.; Lodowski, D. T. Improvements in G protein-coupled receptor purification yield light stable rhodopsin crystals. J. Struct. Biol. 2006, 156(3), 497-504.

32. Salom, D.; Lodowski, D. T.; Stenkamp, R. E.; Le Trong, 1.; Golczak, M.; Jastrzebska, B.; Harris, T.; Ballesteros, J. A.; Palczewski, K. Crystal structure of a photoactivated deprotonated intermediate of rhodopsin. Proc. Natl. Acad. Sci. USA. 2006, 103(44), 16123-8.

33. Park, J. H.; Scheerer, P.; Hofmann, K. P.; Choe, H. W.; Ernst, O. P. Crystal structure of the ligand-free G-protein-coupled receptor opsin. Nature. 2008, 454, 183-7.

34. Rasmussen, S. G.; Choi, H. J.; Rosenbaum, D. M.; Kobilka, T. S.; Thian, F. S.; Edwards, P. C.; Burghammer, M.; Ratnala, V. R.; Sanishvili, R.; Fischetti, R. F.; Schertler, G. F.; Weis, W. I.; Kobilka, B. K. Crystal structure of the human beta(2) adrenergic G-protein-coupled receptor. Nature, 2007, 450(7168), 383-7.

35. Rosenbaum, D. M.; Cherezov, V.; Hanson, M. A.; Rasmussen, S. G.; Thian, F. S.; Kobilka, T. S.; Choi, H.-J.; Yao, X.-J.; Weis, W. I; Stevens, R. C.; Kobilka, B. K. GPCR Engineering Yields High-Resolution Structural Insights into 2 Adrenergic Receptor Function. Science, 2007, 318 (5854), 1266-73.

36. Cherezov, V.; Rosenbaum, D. M.; Hanson, M. A.; Rasmussen, S. G.; Thian, F. S.; Kobilka, T. S.; Choi, H.-J.; Kuhn, P.; Weis, W. I; Kobilka, B. K.; and Stevens, R. C. High-Resolution Crystal Structure of an Engineered Human 2-Adrenergic G Protein-Coupled Receptor. Science, 2007, 318(5854), 1258-65.

37. Hanson, M. A.; Cherezov, V.; Griffith, M. T.; Roth, C. B.; Jaakola, V. P.; Chien, E. Y.; Velasquez, J.; Kuhn, P.; Stevens, R. C. A specific cholesterol binding site is established by the 2.8 Å structure of the human beta2-adrenergic receptor. Structure, 2008, 16(6), 897-905.

38. Warne, T.; Serrano-Vega, M. J.; Baker, J. G.; Moukhametzianov, R.; Edwards, P. C.; Henderson, R.; Leslie, A. G.; Tate, C. G.; Schertler, G. F. Structure of a beta(1)-adrenergic G-protein-coupled receptor. Nature, 2008, 454(7203), 486-91.

39. Zhang, Y.; Sham, Y. Y.; Rajamani, R.; Gao, J. L.; Portoghese, P. S. Homology Modeling of the Mu Opioid Receptor Built in a Complete Membrane-Aqueous System. ChemBioChem, 2005, 6, 853-9.

40. Metzger, T. G.; Paterlini, M. G.; Ferguson, D. M.; Portoghese, P. S. Investigation of the selectivity of oxymorphone- and naltrexone-derived ligands via site-directed mutagenesis of opioid receptors: exploring the "address" recognition locus. J Med Chem., 2001, 44, 857-62.

41. Ulens, C.; Baker, L.; Ratka, A.; Waumans, D.; Tytgat, J. Morphine-6beta-glucuronide and morphine-3-glucuronide, opioid receptor agonists with different potencies. Biochem Pharmacol., 2001, 62, 1273-82.

42. Fowler, C. B.; Pogozheva, I. D.; LeVine, H. 3rd; Mosberg, H. I. Refinement of a homology model of the mu-opioid receptor using distance constraints from intrinsic and engineered zinc-binding sites. Biochemistry, 2004, 43, 8700-10.

43. Xue, J-C.; Chen, C.; Zhu, J.; Kunapuli, S. P.; de Riel, J. K.; Yu, L.; Liu-Chen, L-Y. The third extracellular loop of the mu opioid receptor is important for agonist selectivity. J. Biol. Chem., 1995, 270, 12977-12979.

44. Bonner, G.; Meng, F.; Akil, H. Selectivity of mu-opioid receptor determined by interfacial residues near the third extracellular loop. European J. Pharmcol., 2000, 403, 37-44.

45. Zhu, J.; Xue, J-C.; Law, P-Y.; Claude, P. A.; Luo, L-Y.; Yin, J.; Chen, C.; Liu-Chen; L-Y. The region in the mu opioid receptor conferring selectivity for sufentanil over the delta receptor is different from that over the kappa receptor. FEBS Letters, 1996, 384, 198-202.

46. Xu, W.; Li, J.; Chen, C.; Huang, P.; Weinstein, H.; Javitch, J. A.; Shi, L.; de Riel, J. K.; Liu-Chen, L. Y. Comparison of the amino acid residues in the sixth transmembrane domains accessible in the binding-site crevices of mu, delta, and kappa opioid receptors. Biochemistry, 2001, 40, 8018-29.

47. Law, P. Y.; Wong, Y. H.; Loh, H. H. Mutational analysis of the structure and function of opioid receptors. Biopolymers. 1999, 51(6): 440-55.

48. Xu, H.; Lu, Y. F.; Partilla, J. S.; Zheng, Q. X.; Wang, J. B.; Brine, G. A.; Carroll, F. I.; Rice, K. C.; Chen, K. X.; Chi, Z. Q.; Rothman, R. B. Opioid peptide receptor studies, 11: involvement of Tyr148, Trp318 and His319 of the rat β-opioid receptor in binding of 3-selective ligands. Synapse (New York) 1999, 32(1), 23-28.

49. Griffin, J. F.; Larson, D. L.; Portoghese, P. S. Crystal structures of alpha- and beta-funaltrexamine: conformational requirement of the fumaramate moiety in the irreversible blockage of mu opioid receptors. J. Med. Chem. 1986, 29(5), 778-83.

50. Sayre, L. M.; Portoghese, P. S. Stereospecific synthesis of the 6α- and 6β-amino derivatives of naltrexone and oxymorphone. J. Org. Chem. 1980, 45, 3366-8.

51. Keen, M. Testing models of agonism for G protein-coupled receptors. Trends Pharmacol. Sci. 1991, 12(10), 371-4.

52. Selley, D. E.; Sim, L. J.; Xiao, R.; Liu, Q.; Childers, S. R. Mu-Opioid receptor-stimulated guanosine-5'-O-(gamma-thio)-triphosphate binding in rat thalamus and cultured cell lines: signal transduction mechanisms underlying agonist efficacy. Mol. Pharmacol. 1997, 51(1), 87-96.

53. Selley, D. E.; Liu, Q.; Childers, S. R. Signal transduction correlates of mu opioid agonist intrinsic efficacy: Receptor-stimulated [$^{35}$S]GTPγS binding in mMOR-CHO cells and rat thalamus. J. Pharmacol. Exp. Ther. 1998, 285, 496-505.

54. Morgan, D.; Cook, C. D.; Picker, M. J. Sensitivity to the discriminative stimulus and antinociceptive effects of mu opioids: role of strain of rat, stimulus intensity, and intrinsic efficacy at the mu opioid receptor. J Pharmacol Exp Ther. 1999, 289(2), 965-75.

55. Morgan, D.; Cook, C. D.; Smith, M. A.; Picker, M. J. An examination of the interactions between the antinociceptive effects of morphine and various mu-opioids: the role of intrinsic efficacy and stimulus intensity. Anesth Analg. 1999, 88(2), 407-13.

56. To further verify the role of Tyr210 and Trp318 in the binding of two leads to MOR, we conducted an initial site-directed mutagenesis study with CHO cells transiently transfected with the wild type and mutant MORs (Y210A and W318A). Naltrexone was used as control ligand and its binding affinity did not change much in both wild-type (wt) and mutant MORs (ICs, values were 3.90±2.96 nM (wt), 0.95±0.49 nM (Y210A), and 10.35±1.64 nM (W318A) respectively). Both compound 6 and 9 bound to the Y210A mutant MOR with comparable affinities (IC50, 6, 1.61±0.17 nM; 9, 3.31±1.71 nM) as to the wild-type MOR (IC50, 6, 2.29 t 0.15 nM; 9, 5.42±0.70 nM), whereas their affinities were dramatically lower in binding to the W318A mutant (IC50, 6, >1,000 nM; 9, >1,000 nM). We will revisit these studies with wider concentration range in order to define the IC50 and Ki values for this mutant. These results indicate that these two leads could recognize an "address" locus with potential hydrogen bonding property in the MOR, which could confer their selectivity for the MOR over the DOR and KOR.

57. InsightII User Guide, October 1995. San Diego:MSI, 1995.
58. Coderre, T. J.; Rollman, G. B. Naloxone hyperalgesia and stress-induced analgesia in rats.
Life Sci. 1983, 32(18), 2139-46.
59. Harris, L. S.; Pierson, A. K. Some narcotic antagonists in the benzomorphan series. J. Pharmacol. Exp. Ther. 1964, 143, 141-148.
60. Bliss, C. I. Statistics in Biology; McGraw-Hill: New York, 1967; p 439.

EXAMPLE 3

Exemplary Compound Derivatives: From Compound 6 (NAP) Defined Above in Examples 2 (Referred to as Lead Compound 1 (or "Compound 1" in this Example)

Figure 11:
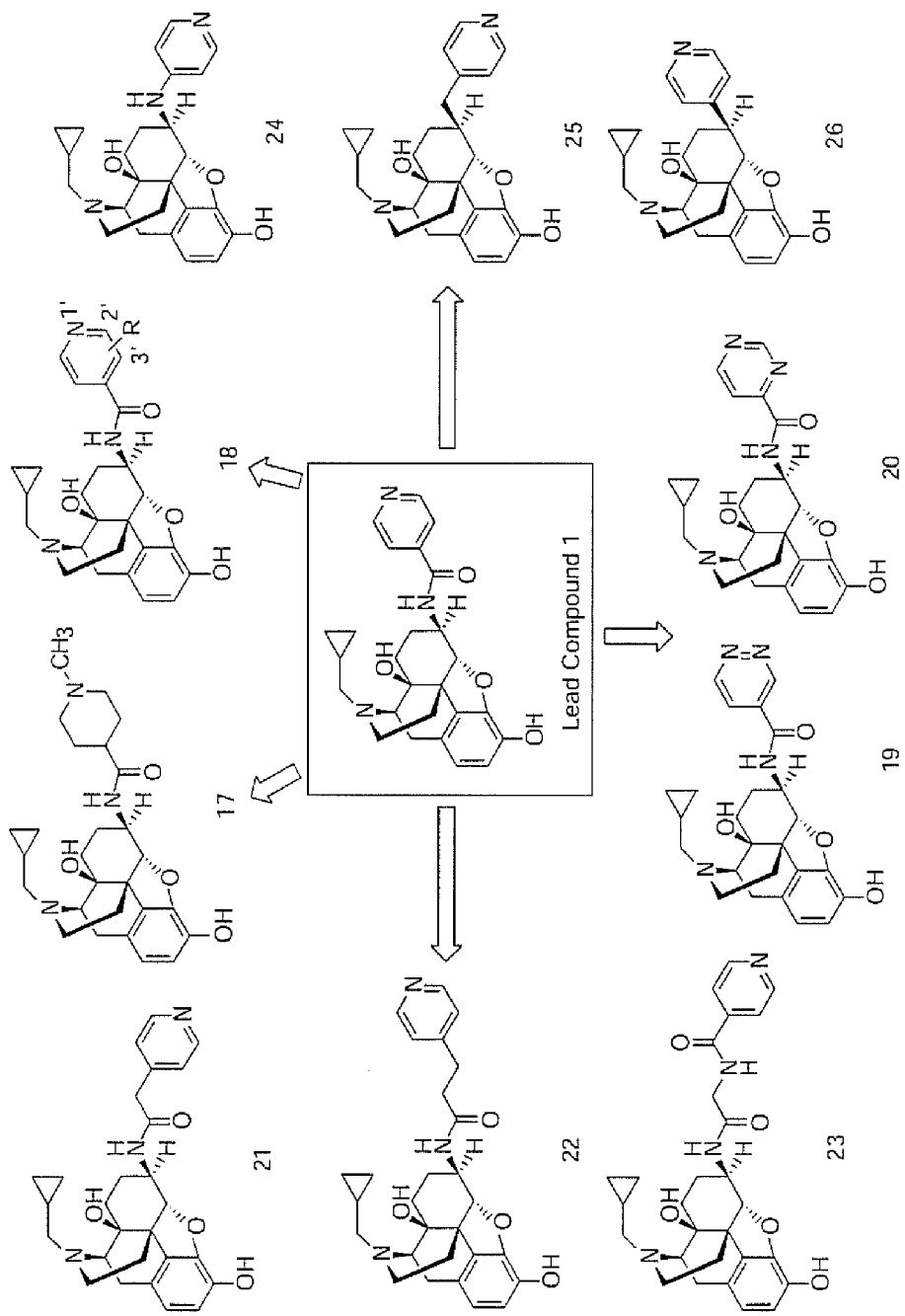
FIG. 11. Exemplary Derivatives of Lead Compound NAP.
Figure 12A:
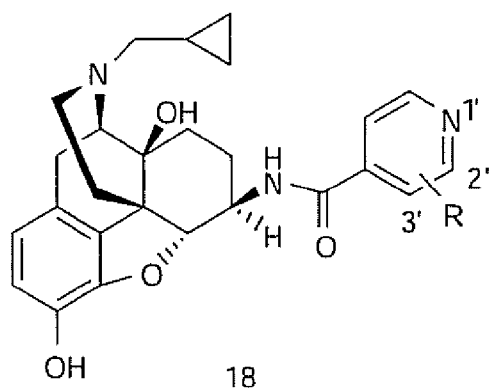
FIGS. 12A and 12B. Possible substitutions on the side chain aromatic system of compound 18.

Exemplary new ligands based on exemplary compound 1 are used to further explore the structure-activity-relationships of these naltrexamine derivatives. The major morphinan skeleton and the C(6)-heterocyclic ring system are retained because they provided very high affinity for the MOR. Some adjustments are introduced to influence the orientation and the distance between these two moieties and to strengthen interactions (e.g. hydrogen bonding) between the ligand and the aromatic amino acid residues in the MOR. These interactions are believed to be important not only to the ligand binding affinity/selectivity for the receptor, but also to the optimization of the antagonism of the ligand. These compounds are synthesized and characterized by NMR, IR, Mass Spectrometry, elemental analysis and biological screening essentially as described in Examples 1 and 2. MOR antogonists based on exemplary compound 1 are depicted in FIG. 11. In addition, for compound 18, (FIG. 12A) various side chain substitutions are made as described in Table 6.

TABLE 6

The possible substitutions on the side chain aromatic system of 18

| | Substitutions |
| --- | --- |
| Position 2' | $CH_3O$, $CH_3$, Cl, Br, CN |
| Position 3' | $CH_3O$, $CH_3$, Cl, Br, CN |

Figure 12B:
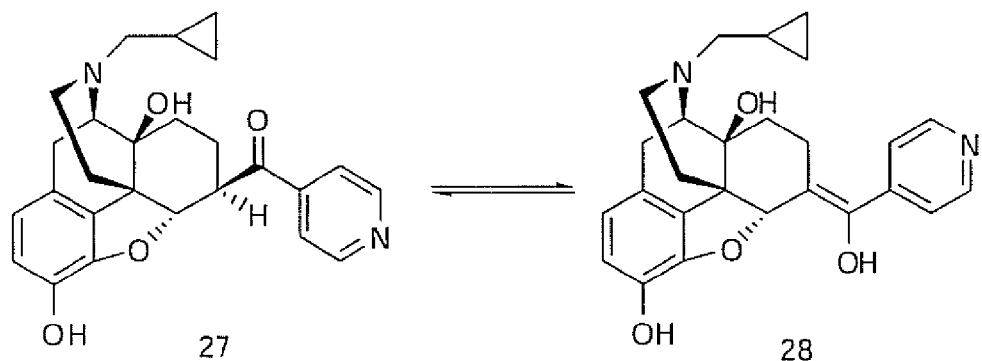

Additional embodiments of antagonists are depicted in FIG. 12B.

For the chemical synthesis of some new ligands conditions described in Examples 1 and 2 (e.g. FIG. 9) are adopted. Some of the proposed side chain moieties are not commercially available and are synthesized via the routes shown in Table 7, whereas others are commercially available in gram quantities.

TABLE 7

The availability of side chain moieties for derivatives of exemplary compound I

| Target compound | Side chain moiety | Commercial availability or chemical synthetic preparation route (references for each step Included) |
| --- | --- | --- |
| 17 | Me—N(piperidine)—COOH | HN(piperidine)—COOH [153] →(1. HCHO, HCO₂H, H₂O; 2. HCl, H₂O)→ HCl Me—N(piperidine)—COOH |
| 19 | pyridazine-COOH | Aldrich USA (in gram scale) |
| 20 | pyrimidine-COOH | pyrimidine-Me →($SeO_2$, t-BuOOH, Dioxane, 50° C.)→ [154] pyrimidine-COOH |
| 21 | pyridine-CH₂-COOH | Aldrich USA (in gram scale) |
| 22 | pyridine-CH₂CH₂-COOH | pyridine-CH₂CH₂-OH →(Swern Oxidation)→ →(m-ClPhCO₃H)→ [155] pyridine-CH₂CH₂-COOH |
| 23 | pyridine-C(=O)-NH-CH₂-COOH | pyridine-COOH →(glycine ethyl ester, EDCI, HOBt, DMF)→ →(NaOH, THF, H₂O)→ [156] pyridine-C(=O)-NH-CH₂-COOH |

TABLE 7-continued

The availability of side chain moieties for derivatives of exemplary compound I

| Target compound | Side chain moiety | Commercial availability or chemical synthetic preparation route (references for each step Included) |
|---|---|---|
| 18 | 2-methoxy-pyridine-4-COOH (MeO) | Matrix Scientific, SC. (in gram scale) or Combi-Blocks, CA. (in gram scale) |
| | 2-methyl-pyridine-4-COOH | chromone-3-CHO [157] + H$_2$NCH$_2$CO$_2$Et $\xrightarrow{\text{p-MeC}_6\text{H}_4\text{SO}_3\text{H}}{\text{Toluene}}$ $\xrightarrow{\text{KOH}}{\text{H}_2\text{O}}$ $\xrightarrow{\text{MCPBA}}{\text{CHCl}_3}$ $\xrightarrow{\text{P(OEt)}_3}{\text{PhBr}}$ $\xrightarrow{\text{H}_2\text{SO}_4}{\text{AcOH}}$ 2-methyl-pyridine-4-COOH |
| | 2-chloro-pyridine-4-COOH (Cl) | Aldrich USA (in gram scale) |
| | 2-bromo-pyridine-4-COOH (Br) | Matrix Scientific, SC. (in gram scale) |
| | 2-cyano-pyridine-4-COOH (NC) | HOOC-pyridine $\xrightarrow{\text{H}_2\text{O}_2, \text{H}_2\text{O}}{\text{AcOH, 90° C.}}$ [158] HOOC-pyridine-N=O $\xrightarrow{\text{Et}_3\text{N}, \text{Me}_3\text{SiCl}_2}{\text{NaCN, DMF, 105° C.}}$ HOOC-pyridine-CN |
| | 3-methoxy-pyridine-4-COOH (OMe) | 3B Medical System Product (in gram scale) |
| | 3-methyl-pyridine-4-COOH | 3-methyl-pyridine $\xrightarrow{\text{KMnO}_4 \text{ or SeO}_2}$ 3-methyl-pyridine-4-COOH [159] |

TABLE 7-continued

The availability of side chain moieties for derivatives of exemplary compound I

| Target compound | Side chain moiety | Commercial availability or chemical synthetic preparation route (references for each step Included) |
|---|---|---|
| | pyridine-COOH with Cl | Aldrich USA (in gram scale) |
| | pyridine-COOH with Br | Matrix Scientific, SC. (in gram scale) |
| | pyridine-COOH with CN | pyridine-CH₃ with CN →(KMnO₄ or SeO₂)→ pyridine-COOH with CN [159] |

Figure 13:
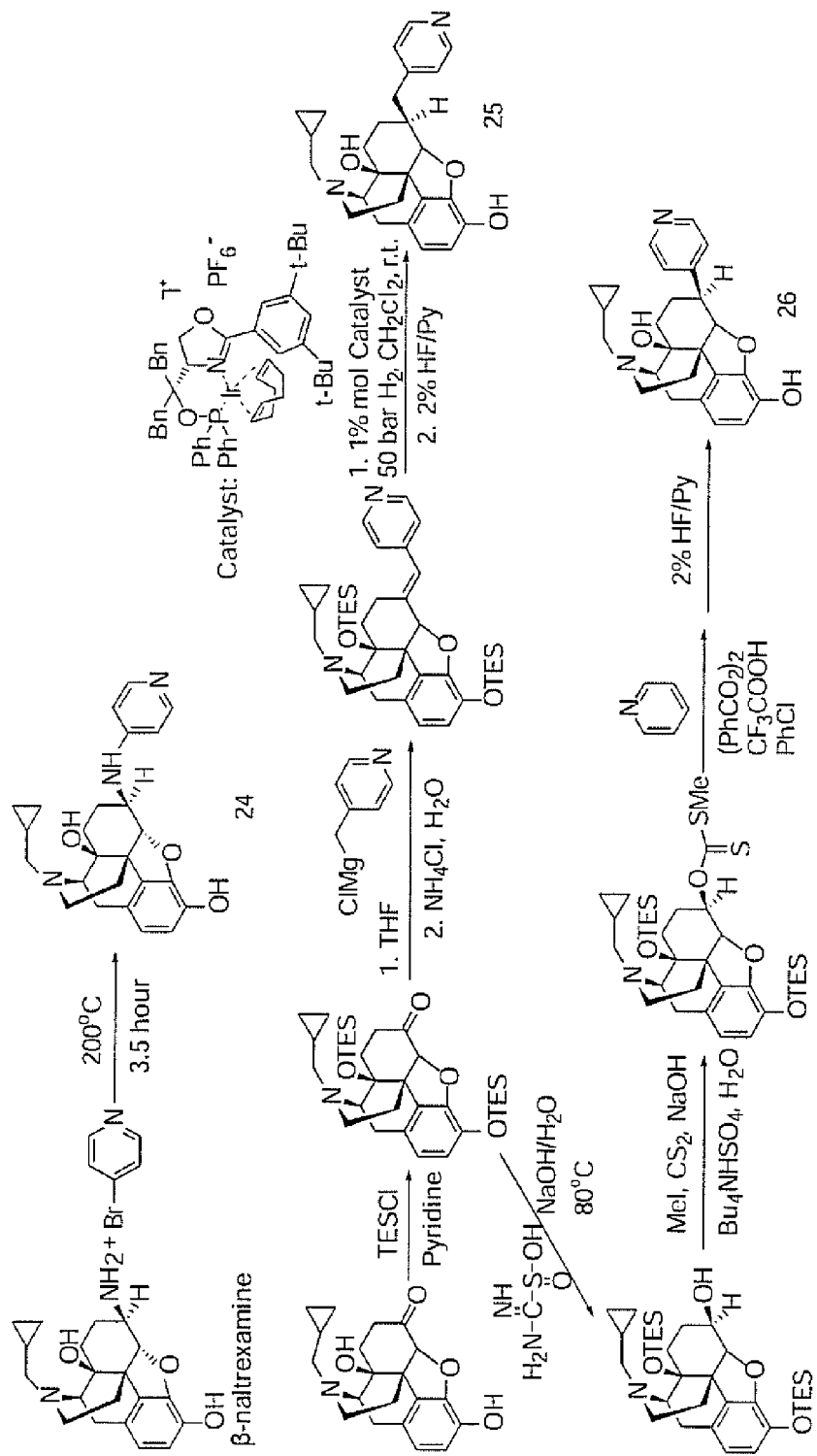
FIG. 13. The chemical synthesis routes for compounds 24, 25, and 26.

The chemical synthesis of Compounds 24, 25 and 26 differs from previously introduced routes. Therefore, synthetic routes have been designed as shown in FIG. 13. As shown, the reaction condition to prepare compound 24 might be too harsh for the opiate starting material [Bailey D M, DeGrazia C G, Hoff S J, Schulenberg P L, O'Connor J R, Paris D A, Slee A M. Journal of Medicinal Chemistry 1984, 27(11), 1457-64]. Alternatively, NaOH is used as the base and the reaction is conducted in dioxane under high-pressure [Kotsuki H, Sakai H, Shinohara T. High-pressure organic chemistry. Part 23. Synlett 2000, (1), 116-118]. For compound 25, the enantioselective reduction of the double bond is challenging. Because the substrate carries a "largely unsubstituted" double bond [Cui X, Burgess K. Chemical Reviews, 2005, 105(9), 3272-96], one of the most reliable methods is the adoption of a cationic Iridium complex catalyst [Lightfoot A, Schnider P, Pfaltz A. Angewandte Chemie, International Edition, 1998, 37(20), 2897-2899; Blackmond D G, Lightfoot A, Pfaltz A, Rosner T, Schnider P, Zimmermann N. Chirality 2000, 12(5-6), 442-9; Blankenstein J, Pfaltz A. Angewandte Chemie, International Edition, 2001, 40(23), 4445-4447; Menges F, Pfaltz A. Advanced Synthesis & Catalysis 2002, 344(1), 40-44; Pfaltz A, Blankenstein J, Hilgraf R, Hormann E, McIntyre S, Menges F, Schonleber M, Smidt S P, Wustenberg B, Zimmermann N. Advanced Synthesis & Catalysis 2003, 345 (1+2), 33-44]. Such a catalyst leads to up to 99% stereoselectivity. The absolute stereochemistry of the new chiral center in the opioid ligand is assigned by ¹HNMR. Alternatively, D-serine, instead of L-serine, is adopted to prepare the enantiomer of the listed catalyst in four steps to give the desired chirality of the designed ligand 25 [Blankenstein, supra]. The starting material to synthesize compound 26 is protected β-naltrexol. It is prepared predominantly by adopting formamidinesulfinic acid under alkaline conditions with approximately 90% yield [Chatterjie N, Inturrisi C E. J Med Chem. 1975, 18(5), 490-2.].

For purposes of example and not limitation, nineteen new compounds have been designed as compound 1 derivatives. The syntheses of these 19 ligands include the multiple-step chemical synthesis of eight essential side chains as the starting material.

Characterization and biological testing of these compounds is carried out as described in Examples 1 and 2.

Example 4

Derivatives of Exemplary Compound 9 (Naq) Defined Above in Example 2 (Referred to as Lead Compound 2 (or "Compound 2") in this Example)

Figure 14:
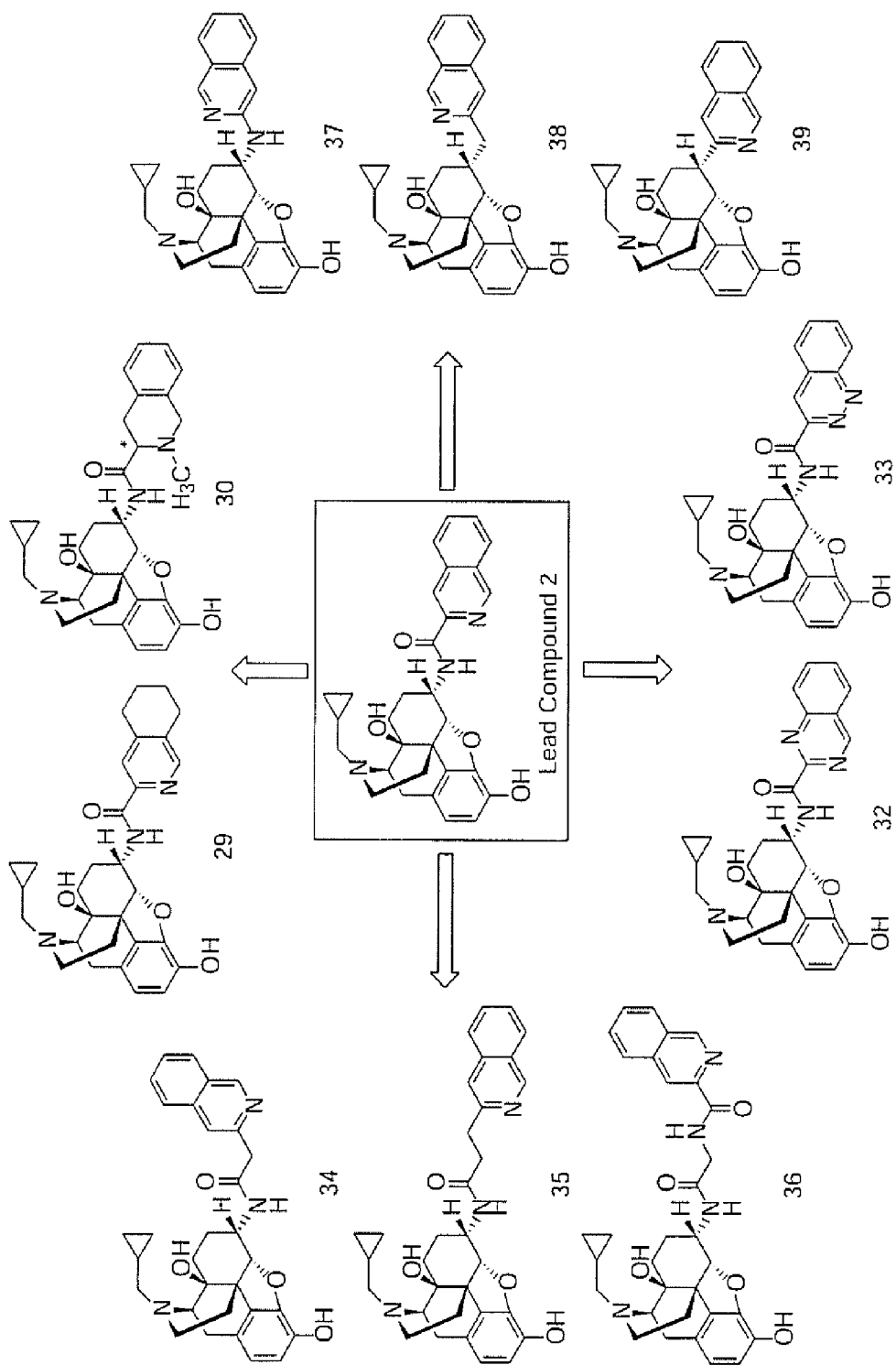
FIG. 14. Exemplary derivatives of Lead Compound NAQ.

Exemplary derivatives of compound 2 are depicted in FIG. 14. Similar to the derivatives of compound 1, compound 29 and 30 are designed to test the necessity of the aromatic system in the side chain for the affinity and selectivity of exemplary compound 2. Structure 30 actually represents two isomers because of the introduction of a new chiral center on the side chain. Both of these isomers are synthesized individually because optically pure side chain moieties can be prepared from commercially available optically pure starting material (Table 8, where references for each step are known to those of skill in the art).

Figure 15:
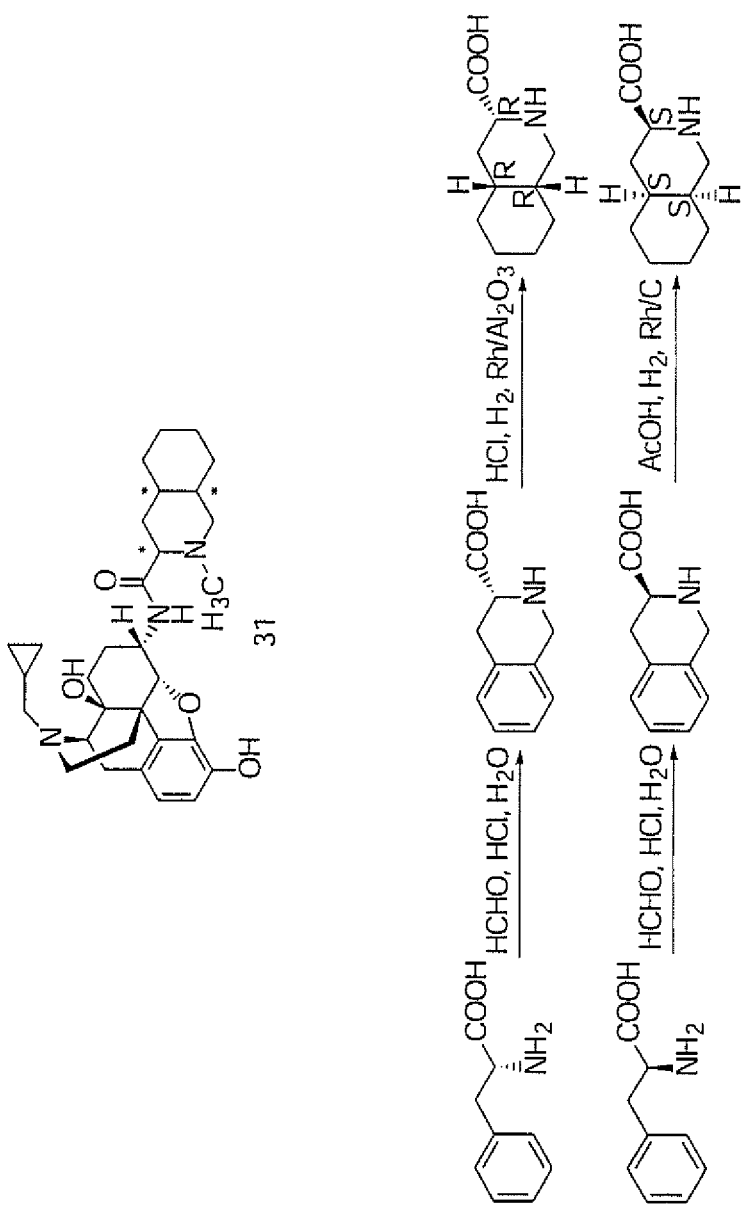
FIG. 15. Isomers and chemical synthesis scheme of compound 31.
Figure 16:
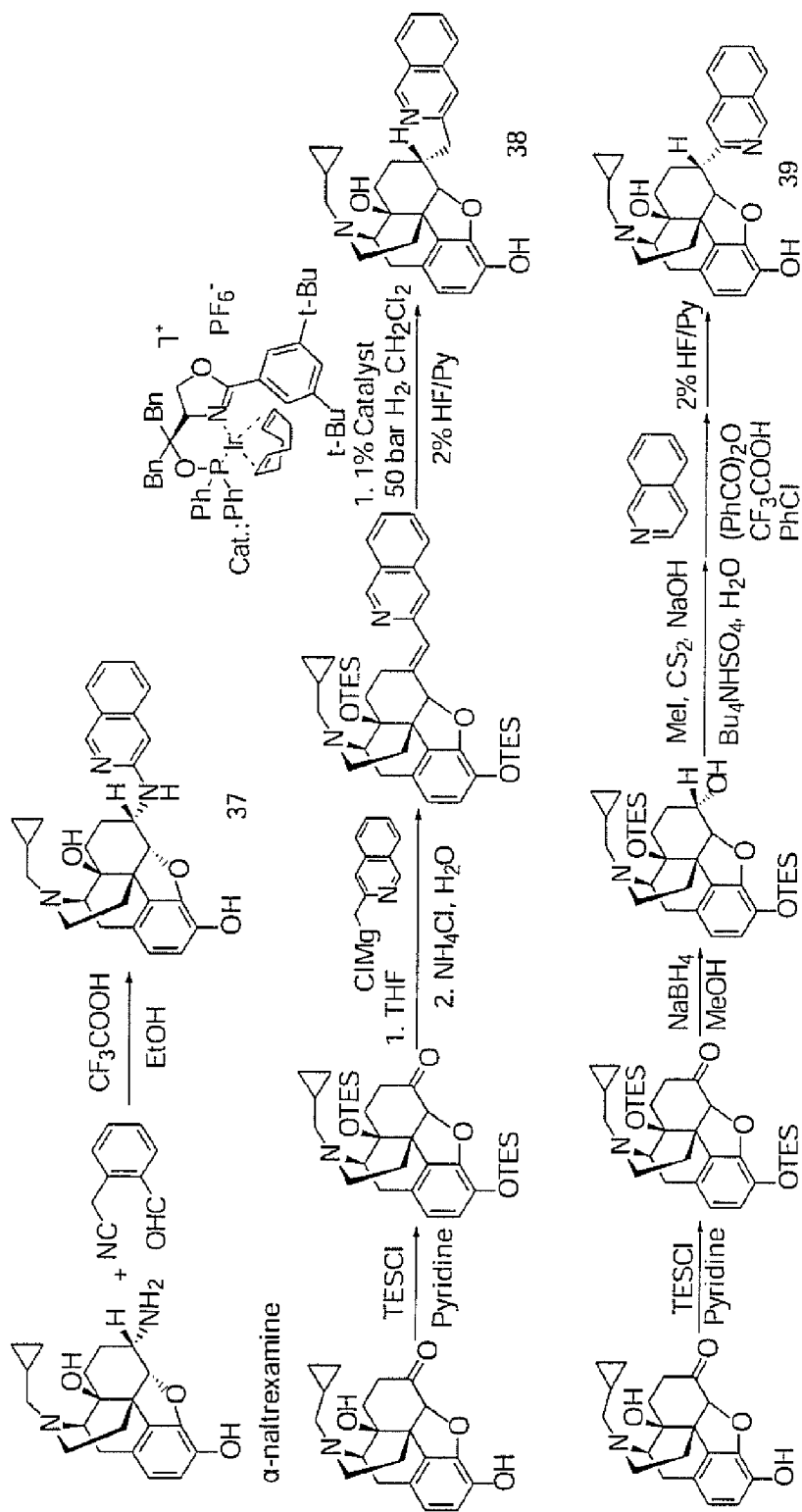
FIG. 16. Exemplary chemical synthesis routes for compound 37, 38 and 39.

Compound 31 (FIG. 15) has a totally saturated side chain moiety. Compound 31 actually is related to the synthesis of eight different isomers because there are three chiral centers in the side chain. At least two isomers can be synthesized following reported procedures [Repala R T, Lavagnino E R, Shepard E R, Farkas E. Journal of the American Chemical Society 1957, 79, 3770-2; Roberts N A, Martin J A, Kinchington D, Broadhurst A V, Craig J C, Duncan I B, Galpin S A, Handa B K, Kay J, Kröhn A, et al. Science. 1990, 248(4953), 358-61; Martin J A, Redshaw S. Eur. Pat. Appl. (1991), 17 pp. EP 432695 A2; Chirgadze N Y, Schacht A L, Smith G F, Willey M R. PCT Int. Appl. (1995), 129 pp. WO 9523608 A1 19950908 CAN 123:306600 AN 1995:899178; Shuman R T, Rothenberger R B, Campbell C S, Smith G F, Gifford-Moore D S, Paschal J W, Gesellchen P D. J Med Chem. 1995, 38(22), 4446-53.]. Depending on the affinity of compound 29 and 30 for the MOR, these two isomers are prepared and their affinity for the MOR is checked to verify the importance of aromaticity of the side chain (FIG. 16).

TABLE 8
The availability of side chain moieties for the newly designed derivatives of exemplary compound 2
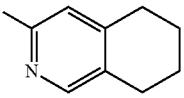

TABLE 8-continued

The availability of side chain moieties for the newly designed derivatives of exemplary compound 2

| Target compound | Side chain moiety | Chemical synthetic preparation route |
|---|---|---|

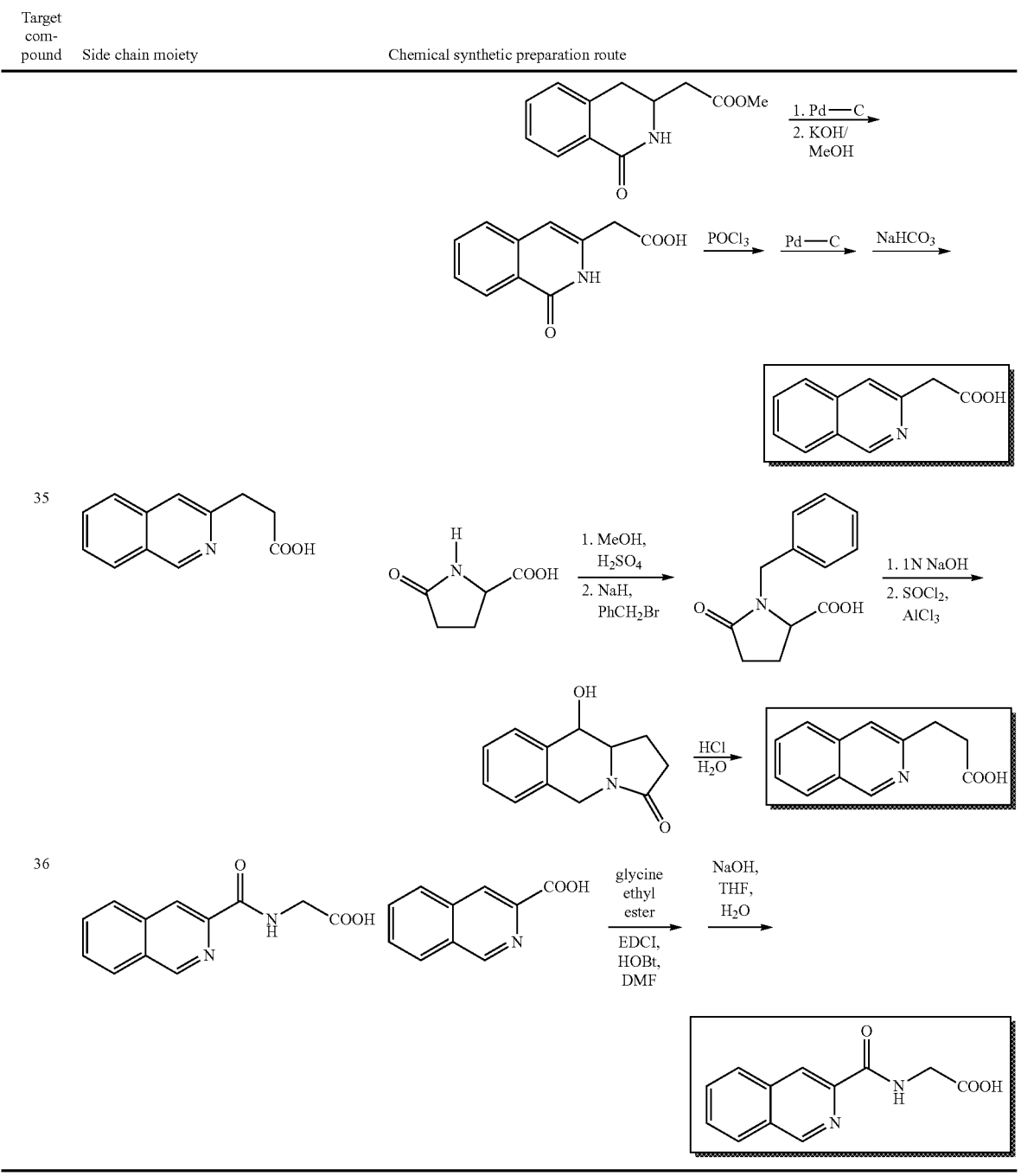

Figure 5:
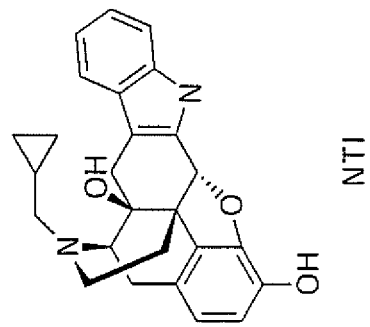
FIG. 5. The kappa opioid receptor selective antagonist norBNI, GNTI and the delta opioid receptor selective antagonist NTI.
Figure 5:
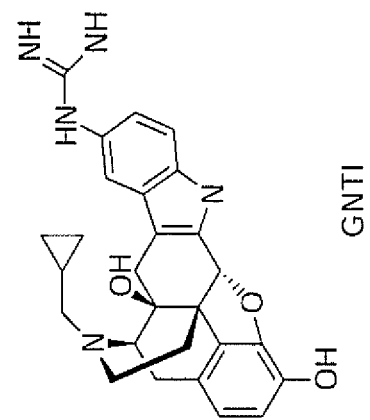
Figure 5:
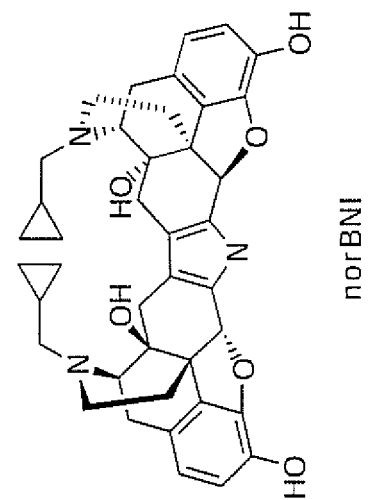
Figure 17:
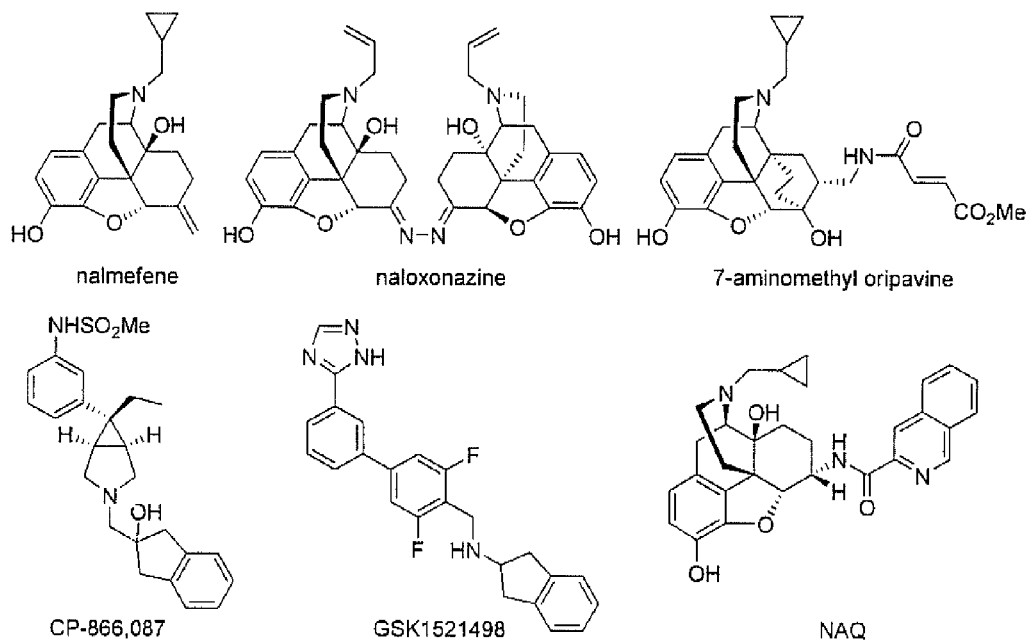
FIG. 17. Representative MOR antagonists currently used as therapeutic agents or under clinical and preclinical investigation.

For compounds 29 to 36, their synthetic routes will be the same as in FIG. 5. For compounds 37, 38 and 39, new synthetic routes have been designed (FIG. 14 FIG. 17). Compound 37 can be synthesized under acidic conditions [Zdrojewski T, Jonczyk A. Tetrahedron 1995, 51(45), 12439-44; Jonczyk A, Lipiak D, Sienkiewicz K. Synlett 1991, (7), 493-6.]. Similar to the preparation of compound 25, the preparation of compound 38 involves the stereoselective reduction of a double bond intermediate [Lightfoot A, Schnider P, Pfaltz A. Angewandte Chemie, International Edition, 1998, 37(20), 2897-2899; Blackmond D G, Lightfoot A, Pfaltz A, Rosner T, Schnider P, Zimmermann N. Chirality 2000, 12(5-6), 442-9; Blankenstein J, Pfaltz A. Angewandte Chemie, International Edition, 2001, 40(23), 4445-4447; Menges F, Pfaltz A. Advanced Synthesis & Catalysis 2002, 344(1), 40-44; Pfaltz A, Blankenstein J, Hilgraf R, Hormann E, Mcintyre S, Menges F, Schonleber M, Smidt S P, Wustenberg B, Zimmermann N. Advanced Synthesis & Catalysis 2003, 345(1+2), 33-44]. The starting material to synthesize compound 39 is TES-protected β-naltrexol, and it can be prepared stereoselectively using NaBH4 reduction under low temperature [Uwai K, Uchiyama H, Sakurada S, Kabuto C, Takeshita M. Bioorganic & medicinal chemistry 2004, 12(2), 417-21]. The rest of the steps are similar to the preparation of compound 26.

For purposes of example and without limitation, thirteen new compounds as derivatives of exemplary compound 2 have been proposed. The synthesis of these thirteen ligands includes the multiple-step preparation of at least nine of side chain moieties as starting material (Table 8).

Characterization and biological testing of these compounds is carried out essentially as described in Examples 1 and 2.

Example 5

Design, Synthesis, and Pharmacological Characterization of 17-Cyclopropylmethyl-3,14β-dihydroxy-4, 5α-epoxy-6α-(isoquinoline-3'-carboxamido)morphinan (NAQ) Analogues as Potent Opioid Receptor Ligands A series of 17-cyclopropylmethyl-3,14β-dihydroxy-4,5α-epoxy-6α-(isoquinoline-3'-carboxamido)morphinan (NAQ) analogues was designed, synthesized, and pharmacologically characterized to study its structure-activity relationship (SAR) at the mu opioid receptor (MOR). The competition binding assay showed substitutions at the 1'- and/or 4'-position of the isoquinoline ring (compounds 4-10) retained or increased the MOR selectivity over the kappa opioid receptor (KOR) while still possessing above 20-fold MOR selectivity over the delta opioid receptor (DOR). In comparison, substitutions at the 6'- and/or 7'-position of the isoquinoline ring (compounds 11-14), extension of the spacer between the epoxymorphinan skeleton and the isoquinoline ring (compounds 1-3), or saturation of the isoquinoline side chain (compounds 15 and 16) decreased the MOR selectivity. Substitutions at the 6'- and/or 7'-position of the isoquinoline ring also reduced the MOR efficacy of the ligands in the [35S] GTPγS assay. Among them, compound 11 acted as an opioid receptor low efficacy partial agonist in the warm-water tail immersion assay and produced less severe withdrawal symptoms compared to naltrexone in the morphine-pelleted mice. Molecular dynamics simulation studies of compound 11 with MOR, KOR and DOR indicated the non-bonded interaction energy to be the following: MOR≈KOR<DOR, which was consistent with the binding data. Collectively, the current findings provide valuable insights for future development of MOR selective ligands and their potential therapeutic applications.

Introduction

There are three main types of opioid receptor (OR): mu (MOR), kappa (KOR) and delta (DOR), all of which belong to the class A rhodopsin-like G protein-coupled receptor (GPCR) family.[1-3] As do other ORs, the MOR interacts with G☐i/o in the intracellular medium.[4] Following MOR activation, the opening of G protein-gated inwardly rectifying K+ (GIRK) channels,[5] inhibition of voltage-gated Ca2+ channels (VGCC),[6] and reduction of intracellular adenylate cyclase-mediated cyclic adenosine monophosphate (cAMP) production[7] occur. All of these cascades lead to membrane potential decrease, neuronal excitability and neurotransmitter release, as well as downstream signaling through their second messenger systems that ultimately affect gene expression.[8] Behavioral effects manifested through the MOR include antinociception as well as reward-related behaviors such as substance (opioid, alcohol) abuse and addiction.[8-10]

As highlighted in the 2013 World Drug Report, "Opioids remained the most commonly reported group of substances involved in drug-related deaths".[11] Opioid overdose is a major cause of mortality. The currently available treatment for opioid overdose is by injecting opioid antagonists, such as naloxone (short action), and naltrexone (long action).[12,13] Opioid abuse and addiction is a risk factor for opioid overdose. The MOR full agonist methadone, partial agonist buprenorphine, and antagonist naltrexone are used to treat opioid addiction presently.[14-16] Although these three medications serve as "proof-of-concept" that targeting MOR would deliver therapeutic effect for opioid addiction, their associated shortcomings, such as overdose risk or hepatotoxicity, call for new molecules with improved pharmacologic properties.[17-19] In this context, scientists and researchers have identified and developed a number of MOR ligands.[20-31] Some of the most recent representative antagonists are illustrated in FIG. 17. Among them, nalmefene has been approved by the European Medicines Agency as an "as-needed" adjunctive treatment for alcohol dependence, 25 whereas N-(3-((1R,5S,6R)-6-ethyl-3-((2-hydroxy-2,3-dihydro-1H-inden-2-yl)methyl)-3-azabicyclo[3.1.0]hexan-6-yl)phenyl) methanesulfonamide (CP-866,087) dose-dependently decreased alcohol intake in preclinical models 23 and yet no results have been reported for its clinical study (ClinicalTrials.gov Identifier: NCT00147576). N-((3,5-Difluoro-3'-(1H-1,2,4-triazol-5-yl)biphenyl-4-yl)methyl)-2,3-dihydro-1H-inden-2-amine (GSK1521498) significantly reduced hedonic responses to sweetened dairy products and calorific intake in binge-eating obese subjects and are currently under further development to treat alcohol addiction.[30,31] Naloxonazine, an irreversible MOR antagonist, attenuated the locomotor activity induced by acute methamphetamine in mice.[21] 7-Aminomethyl oripavine was recently reported to have irreversible MOR antagonism similar to β-funaltrexamine (β-FNA).[24] The latter was able to reduce fat intake in fat-preferring mice.[28] Collectively, some MOR ligands showed therapeutic benefit for substance addiction, such as alcohol and food, while very limited success has been achieved for opioid addiction.

Our research interest in developing MOR selective antagonists for neurological disorder treatment led to the identification of one potent and highly selective MOR ligand NAQ (FIG. 9), a C(6)-isoquinoline substituted naltrexone derivative based on a MOR homology model and the "messageaddress" concept (FIG. 17).[22] NAQ acted as a low-efficacy MOR partial agonist in the [35S]GTPγS binding assay by itself, but antagonized the effects of the MOR full agonist [D-Ala2-MePhe4-Gly(ol)5]enkephalin (DAMGO) in the [35S]GTPγS binding assay and the MOR full agonist morphine in the warm-water tail immersion assay.[22,29] Moreover, NAQ was recently found to be more efficacious and less susceptible to tolerance than naltrexone in reducing high concentration alcohol (30%) consumption in C57BL/6J mice by intermittent access (unpublished results). We herein report the structureactivity relationship (SAR) studies of a series of NAQ analogues. All the newly synthesized NAQ analogues were first evaluated for their affinity, selectivity, and function in an OR radioligand competition binding assay, the MOR [35S]GTPγS binding assay, and the acute antinociceptive agonistic and antagonistic effects in the warm-water tail immersion assay. One selected compound (11, NNQ) was then tested for opioid withdrawal symptoms in chronic morphine-dependent mice. This ligand (NNQ) was also docked into the recently-determined crystal structures of the ORs followed by molecular dynamics to gain insight into its OR selectivity profile.

Results and Discussion
Molecular Design.
Previous modeling studies in which NAQ was docked into the recently-determined crystal structures of MOR, KOR and DOR yielded two different binding sites as alternative "address" domains that interacted with the side chain of NAQ: one located at the top of transmembrane helices 6 and 7, and the other at the interface of helix 5 and extracellular loop 2 (ECL2).[32] While several residues (such as Trp318 and Lys303) within the "address" domains of the MOR were proposed to form favorable hydrogen bonding or aromatic stacking interactions with the side chain of NAQ, others (such as Glu229) may also provide favorable interactions upon modification of the NAQ side chain.[32] To further expand our understating of the postulated "address" domains and more importantly, to study the SAR of NAQ, a series of its analogues were designed based on the modeling study[32] and Craig plots[33], varying the following features: the substitutions on the isoquinoline ring, the distance between the isoquinoline ring and the epoxymorphinan skeleton, and the aromatic character of the C(6) side chain. Different functional groups were chosen as the substituents of the isoquinoline ring to cover all the quadrants of the Craig plots and thus to have a wide range of the partition constant π, the Hammett substituent constant σ, and the resonance constant ER values for appropriate SAR Studies.

Chemistry. The synthesis of the newly designed NAQ analogues was achieved readily (FIG. 21, Table 8).[34-38] Briefly, naltrexone underwent reductive amination with benzylamine and sodium borohydride, followed by catalytic hydrogenation in the presence of the concentrated hydrochloric acid to yield 6α-naltrexamine dihydrocholoride (6α-NTA.2HCl)[39] in a total yield of 79%. A variety of substituted isoquinoline-3-carboxylic acids or its saturated counterparts (see Supporting Information) were then coupled to 6α-NTA.2HCl using EDCI/HOBt. After treating the coupling mixture with K2CO3 in methanol, the NAQ analogues were then obtained by silica gel column purification in yields ranging from 29% to 89%.

Biology. In Vitro and In Vivo Pharmacological Studies. The newly synthesized NAQ analogues were first evaluated in the radioligand competition binding assay and the MOR [35S] GTPγS functional assay on OR-transfected Chinese hamster ovarian (CHO) cell membranes for their binding affinity, selectivity and MOR agonism/antagonism in vitro. They were further tested in the behavioral tail immersion assay for their functional activity in vivo. The KOR and the DOR [35S]GTPγS functional assays (in vitro) were also conducted for two selected compounds, 4 and 11. Compound 11, showing antagonism in the tail immersion assay, was then examined in the opioid withdrawal assays (in vivo). Naltrexone (NTX) was also tested as a control in all the assays.

In Vitro Radioligand Binding Assay and the MOR [35S] GTPγS Functional Assay. The competitive radioligand binding assay was performed on monoclonal OR-expressed CHO cell membranes as described previously.[22,29,34-38] [3H] Naloxone (NLX), [3H]naltrindole (NTI), and [3H]diprenorphine (DPN) were used to label the MOR, the DOR and the KOR, respectively. The MOR [35S]GTPγS binding assay was conducted to determine the Gi/o agonism/antagonism of each new ligand at the MOR as described previously.[22,29,34-38] The results were interpreted as potency (EC50) and the relative efficacy (% Emax) of each compound to the MOR full agonist DAMGO for MOR activation.

As seen in Table 8, all sixteen NAQ analogues retained subnanomolar to nanomolar binding affinity at the MOR.

TABLE 8

Binding Affinity, Selectivity and MOR [$^{35}$S]GTPγS Efficacy for NAQ Analogues.$^a$

| Compd. | R | $K_i$ (nM) | | | Selectivity | | MOR [$^{35}$S]GTPγS Binding | |
|---|---|---|---|---|---|---|---|---|
| | | μ | κ | δ | κ/μ | δ/μ | EC$_{50}$ (nM) | % E$_{max}$ of DAMGO |
| NTX | NA | 0.33 ± 0.02 | 1.44 ± 0.11 | 143.5 ± 13.7 | 4.4 | 435 | 0.16 ± 0.04 | 5.4 ± 0.8 |
| NAQ | (2-methyl isoquinoline) | 1.11 ± 0.07 | 13.3 ± 1.1 | 161.9 ± 15.0 | 12 | 146 | 3.3 ± 0.4 | 20.8 ± 1.2 |
| 1 | (2-ethyl isoquinoline) | 1.20 ± 0.04 | 1.10 ± 0.15 | 12.5 ± 0.7 | 0.9 | 10 | 4.6 ± 0.6 | 18.6 ± 1.1 |
| 2 | (2-propyl isoquinoline) | 0.68 ± 0.05 | 1.61 ± 0.04 | 8.4 ± 0.7 | 2.4 | 12 | 1.14 ± 0.11 | 27.38 ± 0.35 |
| 3 | (N-ethyl isoquinoline-3-carboxamide) | 2.7 ± 1.4 | 0.61 ± 0.04 | 9.2 ± 0.4 | 0.2 | 3.4 | 14.1 ± 4.1 | 13.9 ± 1.9 |

TABLE 8-continued
Binding Affinity, Selectivity and MOR [$^{35}$S]GTPγS Efficacy for NAQ Analogues.[a]
| Compd. | R | K$_i$ (nM) μ | κ | δ | Selectivity κ/μ | δ/μ | MOR [$^{35}$S]GTPγS Binding EC$_{50}$ (nM) | % E$_{max}$ of DAMGO |
|---|---|---|---|---|---|---|---|---|
| 4 (NCQ) | 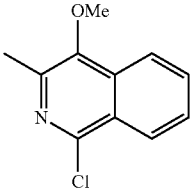 | 0.55 ± 0.01 | 22.2 ± 2.1 | 33.9 ± 0.5 | 40 | 62 | 1.74 ± 0.13 | 51.0 ± 0.4 |
| 5 | 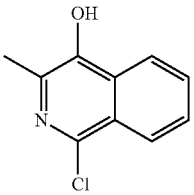 | 0.73 ± 0.07 | 18.3 ± 1.9 | 17.4 ± 1.8 | 25 | 24 | 1.23 ± 0.09 | 19.8 ± 0.08 |
| 6 | 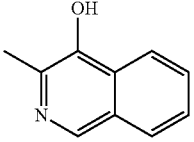 | 0.45 ± 0.02 | 4.0 ± 0.4 | 32.8 ± 1.5 | 8.9 | 73 | 1.06 ± 0.03 | 20.5 ± 0.9 |
| 7 | 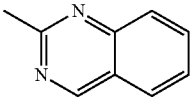 | 1.11 ± 0.06 | 5.1 ± 0.3 | 78.8 ± 0.7 | 4.6 | 71 | 6.0 ± 1.5 | 21.6 ± 0.8 |
| 8 | 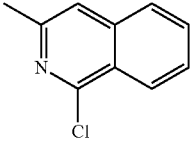 | 1.26 ± 0.04 | 10.8 ± 1.2 | 79.8 ± 2.4 | 8.6 | 63 | 2.62 ± 0.38 | 26.4 ± 0.9 |
| 9 | 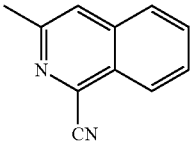 | 0.99 ± 0.07 | 10.1 ± 0.5 | 129.9 ± 9.6 | 10 | 131 | 3.32 ± 0.24 | 37.5 ± 0.7 |
| 10 | 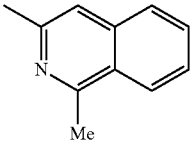 | 2.1 ± 0.2 | 29.1 ± 0.7 | 117.5 ± 7.3 | 14 | 56 | 7.2 ± 0.5 | 22.2 ± 0.4 |
| 11 (NNQ) | 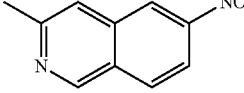 | 5.7 ± 1.7 | 27.9 ± 2.0 | 94.7 ± 1.1 | 4.9 | 16 | 31.5 ± 18.7 | 12.5 ± 1.4 |
| 12 | 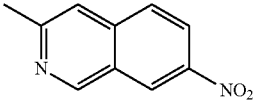 | 3.6 ± 1.1 | 16.0 ± 1.4 | 55.3 ± 1.8 | 4.5 | 16 | 42.7 ± 23.7 | 13.4 ± 0.6 |

TABLE 8-continued

Binding Affinity, Selectivity and MOR [$^{35}$S]GTPγS Efficacy for NAQ Analogues.[a]

| Compd. | R | $K_i$ (nM) | | | Selectivity | | MOR [$^{35}$S]GTPγS Binding | |
|---|---|---|---|---|---|---|---|---|
| | | μ | κ | δ | κ/μ | δ/μ | EC$_{50}$ (nM) | % E$_{max}$ of DAMGO |
| 13 | (3-methylisoquinolin-7-yl)-N(Me)Me | 4.4 ± 0.4 | 88.0 ± 6.9 | 68.6 ± 2.5 | 20 | 16 | 4.70 ± 0.62 | 6.32 ± 0.30 |
| 14 | 3-methyl-6,7-dimethoxyisoquinoline | 13.4 ± 0.4 | 61.0 ± 2.8 | 69.2 ± 4.8 | 4.6 | 5.2 | 85.2 ± 8.6 | 14.0 ± 0.4 |
| 15 | N-Me tetrahydroisoquinoline | 2.9 ± 1.3 | 6.76 ± 0.54 | 9.3 ± 0.3 | 2.3 | 3.2 | 19.4 ± 10.3 | 24.8 ± 1.3 |
| 16 | N-Me tetrahydroisoquinoline with N(Me) | 1.79 ± 0.06 | 4.91 ± 0.23 | 4.5 ± 0.1 | 2.7 | 2.5 | 11.4 ± 0.9 | 26.2 ± 0.6 |

[a]The values are the means ± S.E.M. of four independent experiments. [$^3$H]Naloxone, [$^3$H]naltrindole and [$^3$H]diprenorphine were used to label MOR, DOR and KOR, respectively. The percentage stimulation to DAMGO is the E$_{max}$ of the compound compared to that of DAMGO (normalized to 100%).

Of note, substitution at the 6'- and/or 7'-position of the isoquinoline ring (11-14), regardless of the electronic properties, most significantly decreased the MOR affinity compared to NAQ, with 14 showing two-digit nanomolar potency at the MOR.

In comparison to NAQ, the effects of the different C(6) side chains on the KOR binding affinity varied more significantly than for the MOR affinity. The extended spacer (13) and the saturated ring system (15 and 16) enhanced the KOR binding, with a more profound impact by the former (8- to 22-fold increase). Two phenomena were observed for the substitutions on the 1'- and/or 4'-position of the isoquinoline ring: 1',4'-disubstitution (4 and 5) or an electron-donating group at the 1'-position (10) slightly reduced the KOR binding affinity, whereas the substitution at the 4'-position (6 and 7) or an electron-withdrawing group at the 1'-position (8 and 9) slightly increased the KOR binding. In contrast, substitution at the 6'- and/or 7'-position of the isoquinoline ring (11-14) impaired KOR affinity, especially by electron-donating groups (13 and 14). Compared to the MOR binding data, an extended spacer (1-3), an electron-withdrawing group at the 4'-, 6'-, or 7'-position (7, 11, and 12), an electron-donating group at both 6'- and 7'-positions (14), or a saturated ring system (15 and 16) moderately decreased the MOR/KOR selectivity, while 1',4'-disubstitution (4 and 5), 1'-substitution (8-10), or an electron-donating group at the 4'- or 7'-position (6 and 13) yielded comparable or improved MOR/KOR selectivity, relative to NAQ. Compound 4 had the highest MOR/KOR selectivity in this series of NAQ analogues, nearly 10-fold higher than that of naltrexone.

Compared to NAQ, all of the investigated C(6) side chains increased the DOR binding affinity in the following order: an extended spacer (1-3)≈a saturated ring system (15 and 16)>an electron-donating group at the 4'-position of the isoquinoline ring (4-6)>an electron-withdrawing group at the 4'-position (compound 7) and substitution at 1'-, 6'-, and/or 7'-position (8-14). With respect to the MOR binding affinity, an extended spacer (1-3), a substitution at 6'- and/or 7'-position (11-14), or a saturated ring system (15 and 16) showed little MOR/DOR selectivity, whereas substitutions with different electronic characteristics at the 1'- and/or 4'-position of the isoquinoline ring (4-10), except for 5, showed >50-fold MOR/DOR selectivity. Compound 9 with a 1'-cyano group, the most MOR/DOR-selective ligand in this series of NAQ analogues, displayed a similar MOR/DOR selectivity as NAQ.

The majority of the newly synthesized NAQ analogues showed less than 30% of the MOR stimulation (normalized to the effect of 3 μM DAMGO) in the [35S]GTPγS binding assay, except for 4 and 9 (Table 8). Among them, compound 3 with a glycine-unit spacer and 11-14 carrying substitutions with different electronic characteristics at the 6'- and/or 7'-position of the isoquinoline ring had less than 15% MOR agonism relative to DAMGO. Compound 13 behaved similarly to naltrexone with marginal MOR agonism (<7%). Substitution at the 6'- and/or 7'-position of the isoquinoline ring (11-14) thus induced less MOR stimulation than substitution at the 1'- and/or 4'-position (4-10). Furthermore, an electron-withdrawing group at the 1'-position of the isoquinoline ring (8 and 9) promoted higher MOR activation than an electron-donating group (10). A saturated ring system (15 and 16) also slightly increased the MOR agonism. Compound 13 had the lowest MOR efficacy in this series of NAQ analogues, whereas 4 with 1',4'-disubstituents showed the highest MOR efficacy. Interestingly, NAQ and each of its analogues examined here were 1 to 2 orders of magnitude less potent than naltrexone in the MOR [35S]GTPγS binding assay, especially for 11, 12 and 14 (≥200-fold).

Collectively, the structure-activity relationship study of these NAQ analogues identified five novel ligands (4, 5, 9, 10, and 13) with over 10-fold MOR/KOR and MOR/DOR selectivity. Among them, 4 and 13 displayed the highest and the lowest MOR efficacy, respectively.

Warm-Water Tail Immersion Assay.

The warm-water tail immersion assay is a test of pain response to warm water to measure the effectiveness of analgesics.[40] The advantage of this assay is its relative reproducibility compared to the hot plate test and thus was employed in the current study. Each newly synthesized NAQ analogue was tested for its ability to produce antinociception and/or to antagonize the antinociceptive effects of morphine.

Figure 18A:
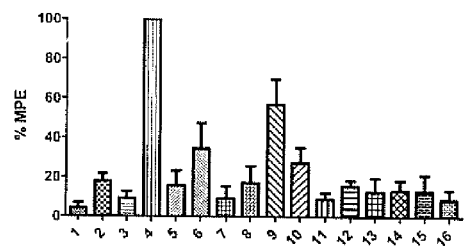
FIGS. 18A and 18B. Warm-water tail immersion assay (n≥6). (A) Antinociceptive effects of NAQ analogues 1-16 at 10 mg/kg; (B) Blockage of the antinociceptive effect of morphine (10 mg/kg) by NAQ analogues 1-3, 5-16, and naltrexone (NTX) at 1 mg/kg.
Figure 18:
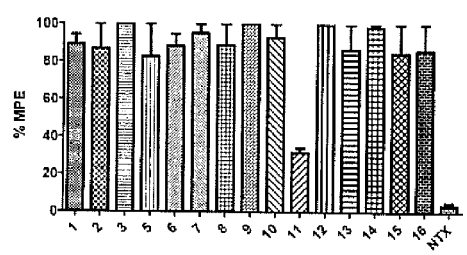

FIG. 18A depicts the antinociceptive effects of the sixteen NAQ analogues (numbered on the X axis) at 10 mg/kg. The results are interpreted as the percentage of maximum possible effect (% MPE). Compound 4 (NCQ), which showed the highest MOR efficacy in the in vitro [35S]GTPγS binding assay, acted as a full agonist in the in vivo warm-water tail immersion assay, resembling the MOR full agonist morphine. The ED50 values of 4 and morphine were calculated to be 0.73 (0.55-0.97), and 3.24 (2.44-4.31) mg/kg (95% CL), respectively. Compound 9 produced a 56.9±12.7% MPE, which was also consistent with its moderate MOR efficacy in the [35S]GTPγS binding assay. The % MPEs of the remaining NAQ analogues, except for 6 and 10, were less than 20%, indicating either weak OR agonism or low CNS permeability.

FIG. 18B depicts the antinociceptive effect of morphine (10 mg/kg) in the presence of each newly synthesized NAQ analogue (1 mg/kg). Due to the full agonism of 4, it was not tested in this antagonism study. Compound 11 (NNQ) appeared to moderately block the antinociceptive effect of morphine whereas the other NAQ analogues had marginal impact on the antinociceptic effect of morphine. The calculated AD50 value for 11 was 0.92 (0.511.67) mg/kg (95% CL), which was less potent than the MOR antagonists naloxone and naltrexone, collectively (Table 9).

TABLE 9

AD$_{50}$ Values of Compound 11 for Antagonizing Morphine (10 mg/kg) Antinociceptive Effect in Warm-Water Tail Immersion Assay.[a]

| Compd. | AD$_{50}$ values (mg/kg (95% CL)) |
|---|---|
| Naloxone[b] | 0.05 (0.03-0.09) |
| Naltrexone | 0.006 (0.003-0.014) |
| NAQ[b] | 0.45 (0.27-0.78) |
| 11 (NNQ) | 0.92 (0.51-1.67) |

[a]All drugs and test compounds were administered to a group of at least six mice subcutaneously (s.c.).
[b]Data taken from Li, et al.[22]

The KOR and DOR [35S]GTPγS Binding Assays for Two New Compounds.

To further understand the underlying mechanisms of 4 (full agonist) and 11 (partial agonist/antagonist) in the warm-water tail immersion assay, KOR and DOR [35S]GTPγS functional assays employing these two lead compounds were performed as described earlier. The KOR full agonist 2-(3,4-dichlorophenyl)-N-methyl-N-[(1R,2R)-2-pyrrolidin-1-ylcyclohexyl]acetamide 17 (U50,488)[41] and DOR full agonist 4-[(R)-[(2S,5R)-4-allyl-2,5-dimethylpiperazin-1-yl](3-methoxyphenyl)methyl]-N,N-diethylbenzamide 18 (SNC80)[42] were included in the assays as reference compounds for a maximal effect at the KOR and the DOR, respectively. As seen in Table 10, compared to naltrexone and NAQ, 4 acted as a low-potency KOR partial agonist with low efficacy (7.1±0.5%).

TABLE 10

KOR and DOR [35S]GTPγS Efficacy for Compounds 4 and 11[a]

| | KOR [35S]GTPγS Binding | | DOR [35S]GTPγS Binding | | Functional Selectivity | |
|---|---|---|---|---|---|---|
| | EC$_{50}$ | % E$_{max}$ of | EC$_{50}$ | % E$_{max}$ of | | |
| Compd. | (nM) | U50,488 | (nM) | SNC80 | κ/μ | δ/μ |
| NTX | 0.81 ± 0.08 | 20.8 ± 0.9 | 4.4 ± 1.6 | 5.6 ± 0.6 | 5.1 | 28 |
| NAQ | 10.9 ± 7.9 | 13.1 ± 2.0 | 98.6 ± 23.7 | 53.5 ± 5.4 | 3.3 | 30 |
| 4 (NCQ) | 26.4 ± 3.9 | 7.1 ± 0.5 | 32.6 ± 5.1 | 54.8 ± 0.1 | 15 | 19 |
| 11 (NNQ) | 62.6 ± 10.4 | 21.1 ± 0.4 | 108.1 ± 0.8 | 67.7 ± 2.0 | 2.0 | 3.4 |

[a]The values are the means ± S.E.M. of three independent experiments. The percentage stimulation compared to U50,488 (17) or SNC80 (18) is the E$_{max}$ of the compound compared to that of U50,488 (17, 3 μm) or SNC80 (18, 5 μm).

Compound 11 displayed a comparable KOR efficacy to naltrexone, but nearly 80-fold less potent than naltrexone. Although 11 had a relatively higher KOR efficacy than NAQ, its potency was nearly 6-fold weaker. NAQ, 4 and 11 all had ~10-fold higher efficacy than naltrexone at the DOR. However, they were 7- to 25-fold less potent compared to naltrexone. With respect to their relative efficacies in the different OR [35S]GTPγS binding assays, 4 retained moderate MOR/DOR functional selectivity compared to naltrexone and NAQ while displaying a significantly higher MOR/KOR functional selectivity than either naltrexone or NAQ. Compound 11, however, exhibited substantially less MOR/DOR functional selectivity than either naltrexone or NAQ and showed similar MOR/KOR functional to naltrexone and NAQ. Thus, the full agonism of compound 4 in the warm-water tail immersion assay was primarily mediated by the MOR while the partial agonism of 11 could be mediated by all three ORs. Because the analgesic effect of morphine has been mainly attributed to MOR activation, the antagonism of 11 in the tail immersion assay could be due to its action at the MOR.

Opioid Withdrawal Assays.

Figure 19A:
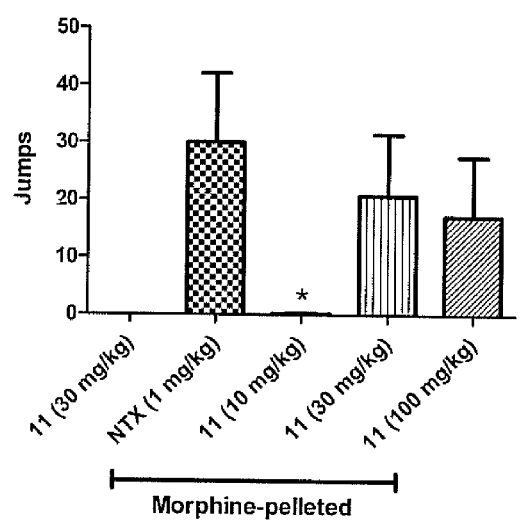
FIGS. 19A and 19B. Compound 11 in opioid-withdrawal assays in chronic morphine-exposed mice (n≥6): (A) Escape jumps; (B) Wet-dog shakes. * indicates P<0.05, compared to naltrexone (NTX).
Figure 19B:
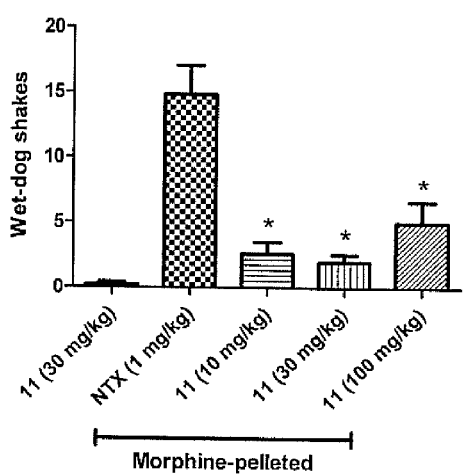

Since 11 antagonized the antinociceptive effect of morphine in the warm-water tail immersion assay, it was further tested in the chronic opioid withdrawal assays in morphine-pelleted mice. Compound 11 did not induce any withdrawal symptoms in placebo-pelleted mice at 30 mg/kg (FIGS. 19A and B; first column). Withdrawal sings occurred almost immediately after injection of naltrexone (1 mg/kg) in morphine-pelleted mice and gave 30.0±12.1 escape jumps and 14.8±2.2 wet-dog shakes (FIGS. 19A and B; second column). Compound 11 did not precipitate significant jumps in mice until 30 mg/kg and reached a plateau at 100 mg/kg (FIG. 19A; columns 3-5). Compared to naltrexone, compound 11 produced significantly less wet-dog shakes, even at a dose as high as 100 mg/kg (FIG. 19B; columns 3-5). Thus, 11 had marginal opioid withdrawal potential at a dose 10-fold of its AD50 value and caused less severe withdrawal symptoms than naltrexone overall. Such observation provides a very promising potential for compound 11 as a drug addiction treatment agent.

Molecular Modeling Studies.

Previously two plausible docking poses of NAQ were identified with the epoxymorphinan core occupying the "message" domain in our recently reported study on C(6)-heterocyclic substituted naltrexamine derivatives.[32] The model indicated that the C(6) side chain of NAQ could either interact with the residues close to the top of helices 6 and 7 (Site 1) or residues close to the top of helix 5 (Site 2). To provide insight into the selectivity profile of 11 (NNQ) compared to NAQ and guide future research, molecular modeling studies of NNQ with three ORs were conducted. Molecular dynamics (MD) simulations were carried out for all three receptors embedded in a lipid bilayer and solvated with water to allow the receptor-ligand complexes to equilibrate in their natural biological environment. Energy analyses were then performed on the resulting NNQ-OR complexes. The most favorable non-bonded interaction energy, calculated using NAMD Energy, between NNQ and its surrounding environment (including protein and water molecules) within different cutoff distances of the ligand were determined and are shown in Table 11.

TABLE 11

NNQ-OR Interaction Energies (kcal/mol).

| Radius[a] (Å) | MOR-NNQ | | | KOR-NNQ | | | DOR-NNQ | | |
|---|---|---|---|---|---|---|---|---|---|
| | E[b] | VDW[c] | Total | E[b] | VDW[c] | Total | E[b] | VDW[c] | Total |
| 10 | −13.76 | −71.64 | −85.40 | −22.52 | −66.35 | −88.87 | −8.37 | −63.49 | −71.86 |
| 8 | −14.69 | −69.89 | −84.58 | −21.43 | −66.04 | −87.47 | −8.18 | −63.24 | −71.42 |
| 6 | −17.44 | −67.83 | −85.27 | −23.00 | −62.90 | −85.90 | −6.71 | −63.82 | −70.53 |
| 5 | −16.45 | −63.89 | −80.34 | −19.27 | −58.52 | −77.79 | −11.70 | −60.49 | −72.19 |

[a]Distance from the docked ligand NNQ;
[b]E: Electrostatic interaction;
[c]VDW: Van der Waals' interaction.

The choice of cutoff distance from the ligand generally did not affect the non-bonded interaction energy between the receptor and the ligand NNQ significantly, except for those of MOR and KOR at 5 Å, in which a moderate increase of energy was observed compared to the corresponding values at larger cutoff radii. Less favorable Van der Waals' (VDW) interactions contributed to the increased total interaction energy for the MORNNQ complex at 5 Å, whereas both less favorable electrostatic and VDW interactions led to a higher total interaction energy for the KOR-NNQ complex at 5 Å. In contrast, the decreased VDW interaction for the DOR-NNQ complex at 5 Å comparing to other cutoff radii, was well-compensated by the more favorable electrostatic interaction at this distance. Thus, the total energy for the DORNNQ complex remained the same.

Figure 20A:
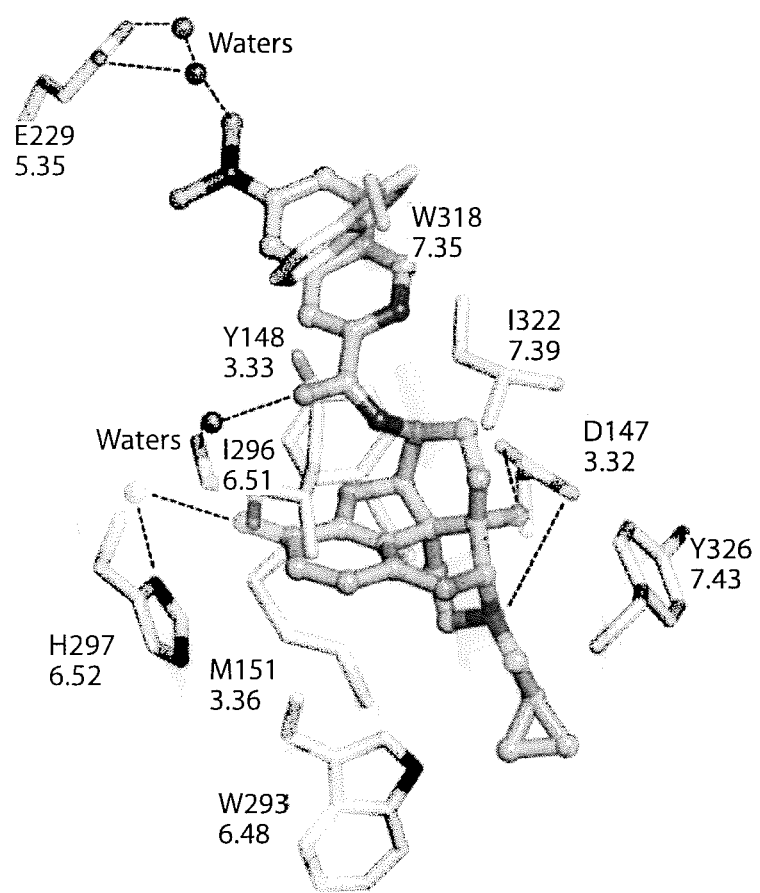
FIG. 20A-C NNQ interaction poses after a 15-ns MD simulation with three OR models: (A) MOR; (B) KOR; (C) DOR. NNQ is represented by balls and sticks (green carbon atoms) and the interacting OR residues are shown as capped sticks. Ionic interactions and hydrogen bonds are shown with black dashed lines. OR amino acid residues are labeled with their sequence number and Ballesteros-Weinstein index.
Figure 20B:
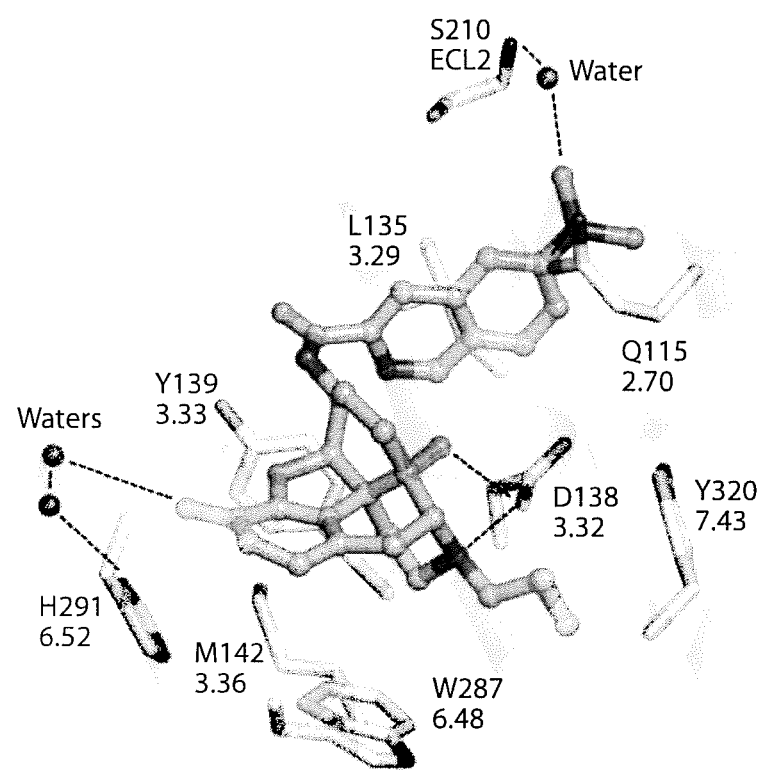
Figure 20C:
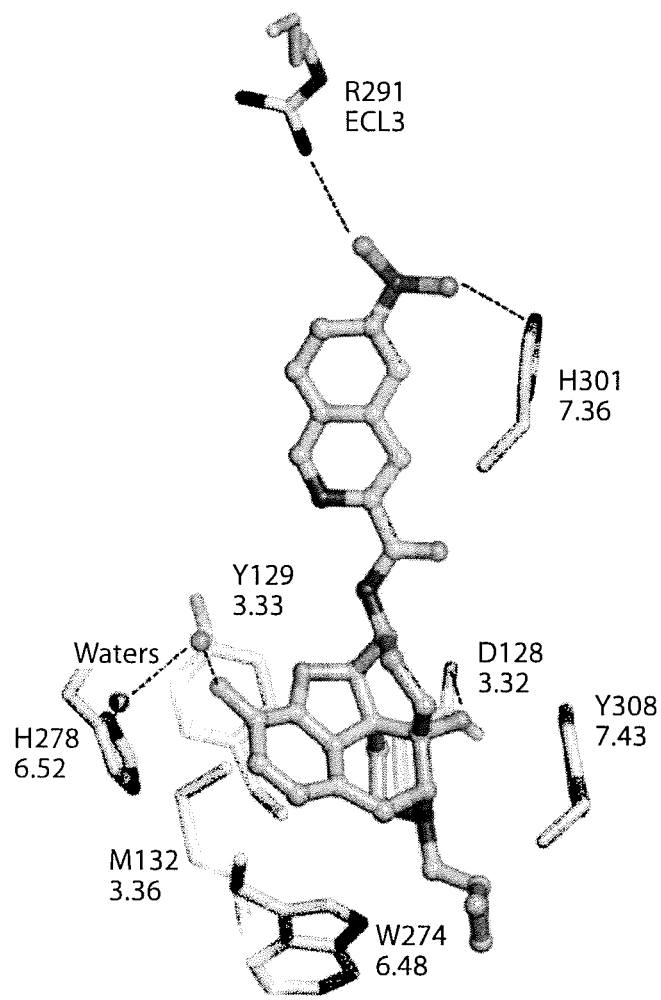

The binding poses associated with the lowest energy for NNQ in the three ORs are shown in FIGS. 20A-C. Similar poses were obtained for NNQ in the current studies compared to the previous modeling study wherein NAQ was used as the ligand.[32] In particular, the epoxymorphinan core remained in its crystallographically-determined binding site obtained using other naltrexone-based ligands and generally maintained the same interactions as previously observed.[43-45] However, the orientation of the 6'-substituent, located in the extracellular loop 'address' regions of the ORs,[46] was much more varied. For the MORNNQ complex, the pose with the most favorable non-bonded interactions directed the 6'-nitro group toward the top of helix 5 (Site 2), interacting with Glu229 5.35 through two bridging water molecules (FIG. 20A). However, the KOR-NNQ and the DOR-NNQ complexes showed a preference for other sites. In the KOR-NNQ complex (FIG. 20B), the isoquinoline ring was placed between helix 2 and helix 3 with interactions between the 6'-nitro group and Gln115 2.70 and also with the backbone NH group of Ser210ECL2 via a water molecule. In the DOR-NNQ complex (FIG. 20C), the isoquinoline ring was oriented toward helix 7 with the nitro group interacting with Arg291ECL3 and His301 7.36 via direct hydrogen bond interactions. We hypothesized that the presence of a glutamate residue at the 5.35 position in MOR, instead of an aspartate residue (one carbon shorter than glutamate) in the KOR and the DOR, allowed for the formation and maintenance of a more stable hydrogen bonding network in the MOR than in the other two ORs; hence NNQ showed a preference for Site 2 in the MOR. In the KOR-NNQ complex, NNQ preferred a different binding pocket yet still attained favorable interactions with Ser210ECL2 and Gln115 2.70 without substantially affecting the interactions between the epoxymorphinan skeleton and the KOR. However, in the DOR-NNQ complex, interactions between the nitro group and the Arg291ECL3 and the His301 7.36 residues were accompanied by loss of directionality in Asp128 3.32 residue. This resulted in the loss of the hydrogen bond interaction between the carboxylate group of Asp 128 and the protonated N(17) atom of the epoxymorphinan skeleton, with only a hydrogen bond formed between Asp128 and the 14-hydroxyl group. This loss of favorable interaction was also reflected by the relatively high electrostatic interaction energy for the DOR-NNQ complex, compared to the MOR-NNQ and KOR-NNQ complexes (Table 1). The relatively unfavorable electrostatic interaction energy obtained for DOR was also the major contributor to relatively unfavorable total interaction energy for DOR compared to the other two ORs. The total interaction energies for the ORs followed the trend MOR<KOR<DOR at 5 Å, a trend also observed in the measured binding affinity of NNQ at the three ORs (Table 8). The generally favorable interaction energies at all three ORs also provide an explanation for the relatively low selectivity of 11 among the three OR subtypes (Table 8).

Conclusions

In conclusion, a series of NAQ analogues was designed, synthesized, and pharmacologically characterized to study its structure-activity relationships. All newly synthesized ligands bound to the MOR with sub-nanomolar to nanomolar affinity. Substitutions at the 1'- and/or 4'-position of the isoquinoline ring retained or increased the MOR selectivity over the KOR while still possessing over 20-fold MOR selectivity over the DOR, whereas substitutions at the 6'- and/or 7'-position of the isoquinoline ring decreased the MOR selectivity. A two-atom spacer and aromatic ring were preferred for optimal MOR selectivity. Substitutions at the 6'- and/or 7'-position of the isoquinoline ring also decreased the MOR efficacy in the [35S]GTPγS binding assay. Overall, 4 showed the highest MOR selectivity and MOR efficacy in the in vitro study. Among this series of NAQ analogues, 4 behaved as a full agonist in the warm-water tail immersion assay, while 11 acted as a partial agonist or an antagonist in the absence or presence of morphine. The full agonism of 4 in the in vivo study is mediated primarily by the MOR while the partial agonism of 11 was an effect mediated by all three ORs. Nevertheless, 11 exerted its antagonism mainly through the MOR. Furthermore, 11 produced less severe withdrawal symptoms than naltrexone in the chronic opioid withdrawal assay. Molecular dynamics simulation studies of compound 11 based on the crystal structures of the three ORs revealed that the orientation of its 6'-nitro group varied considerably in the structurally different 'address' regions of the ORs. Collectively, the current study identified a novel lead compound (11, NNQ) carrying interesting pharmacological profiles which warrants further study for its potential application in treatment of different neurological disorders.

Experimental Section

Chemical Synthesis. General Methods. Reagents were purchased from either Sigma-Aldrich or Alfa Aesar. TLC analyses were carried out on the Analtech Uniplate F254 plates. Chromatographic purification was carried out on silica gel (230~400 mesh, Merck) columns. Melting points were obtained with a Fisher scientific micro melting point apparatus without correction. All IR spectra were acquired on a Nicolet iS10 instrument. Proton (400 MHz) and Carbon-13 (100 MHz) nuclear magnetic resonance (NMR) spectra were recorded at ambient temperature with tetramethylsilane as the internal standard on Varian Mercury 400 MHz NMR spectrometer. LC-MS analysis was performed on a Waters Micromass QTOF-II instrument (ESI source), or an Applied Bio Systems 3200 Q trap with a turbo V source for TurbolonSpray. HPLC analysis was done with a Varian ProStar 210 system on Microsorb-MV 100-5 C8/C18 column (250 mm×4.6 mm) at 254 nm eluting with acetonitrile (0.1% TFA)/water (50/50) at 1 m/min over 15 to 45 min. Elemental analysis was conducted by Atlantic Microlab, Inc. All the analytical methods listed above were used to determine the purity of the newly synthesized compounds and their purity was confirmed to be ≥95%. Yields were not maximized.

General Procedure for Amide Coupling/Saponification Reaction.

On an ice-water bath, to the solution of acid (3 eq) in anhydrous DMF (7 mL), was added 1-ethyl-3-(3-dimethylaminopropyl)carbodiimide hydrochloride (EDCI, 3 eq), hydrobenzotriazole (HOBt, 3 eq), 4 Å molecular sieves, and TEA (8.0 eq) with $N_2$ protection. Fifteen minutes later, a solution of 6α-naltrexamine hydrochloride (19, 1.0 eq) in DMF (5 mL) was added dropwise. The resulted mixture was allowed to warm up to ambient temperature gradually. Upon completion of the reaction, the mixture was then filtered through celite. The filtrate was concentrated to remove DMF. Methanol (10 mL), and $K_2CO_3$ (3 eq) were then added to the residue and stirred at ambient temperature overnight. The mixture was then filtered through celite again. The filtrate was concentrated to remove methanol. The residue was partitioned between $CH_2Cl_2$ (50 mL) and brine (50 mL). The organic layer was separated and dried over anhydrous $MgSO_4$, concentrated under reduced pressure. The residue was then purified by column chromatography, eluting with $CH_2Cl_2$/MeOH (1% $NH_3.H_2O$) to afford the corresponding compound as free base. Upon confirmation of the structure by $^1$H NMR and $^{13}$C NMR, the compound was then transformed into hydrochloride salt by dissolving the free base in MeOH (0.1 mL) and DCM (2 mL), adding HCl methanol solution (1.25 M, 4 eq) under an ice-water bath, and stirred for 5 min. Diethyl ether (10 mL) was then added. Two hours later, the precipitate was collected by filtration, dried in vacuum to give the target compound as hydrochloride salt, which was used in the HPLC, LC-MS, and elemental analysis.

Figure 21:
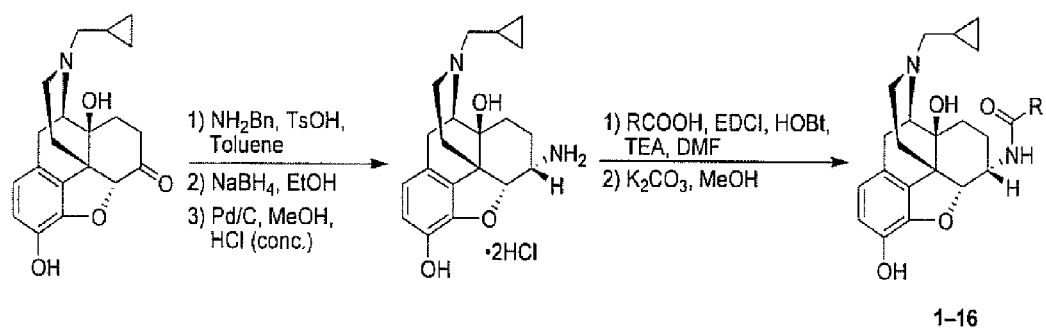
FIG. 21 shows the synthetic route used to generate exemplary NAQ analogues.

FIG. 21 shows the synthetic route used to generate NAQ analogues 1-16.

17-Cyclopropylmethyl-3,14β-dihydroxy-4,5α-epoxy-6α-[2-(isoquinolin-3-yl)acetamido)morphinan (1)

The title compound was prepared following the general procedure in 70% yield. Hydrochloride salt: $^1$H NMR (400 MHz, DMSO-$d_6$) 69.67 (s, 1H), 9.31 (brs, 1H, exchangeable), 8.84 (brs, 1H, exchangeable), 8.37 (d, J=8.56 Hz, 1H), 8.33 (d, J=8.04 Hz, 1H), 8.17-8.15 (m, 2H), 8.04 (t, J=7.58 Hz, 1H), 7.87 (t, J=7.46 Hz, 1H), 6.75 (d, J=8.12 Hz, 1H), 6.58 (d, J=8.16 Hz, 1H), 6.29 (brs, 1H), 4.64 (d, J=3.88 Hz, 1H), 4.45 (m, 1H), 4.06 (s, 2H), 3.90 (d, J=6.64 Hz, 1H), 3.34 (d, J=19.96 Hz, 1H), 3.26 (m, 1H), 3.09-2.97 (m, 2H), 2.94 (m, 1H), 2.70 (m, 1H), 2.43 (m, 1H), 1.87 (m, 1H), 1.62 (m, 1H), 1.50-1.35 (m, 2H), 1.08-0.95 (m, 2H), 0.67 (m, 1H), 0.61 (m, 1H), 0.47 (m, 1H), 0.39 (m, 1H); $^{13}$C NMR (100 MHz, DMSO-$d_6$) δ 169.19, 148.48, 147.37, 141.37, 140.74, 140.50, 138.04, 131.87, 131.35, 130.11, 128.49, 127.87, 126.71, 123.43, 121.08, 119.65, 89.12, 71.00, 63.70, 59.21, 47.52, 47.17, 47.11, 40.01, 31.67, 30.62, 25.02, 21.02, 6.86, 6.24, 3.42. MS m/z found 512.2699 (M+H)⁺. IR (Diamond, cm⁻¹) $v_{max}$ 3232.8, 1651.9, 1615.6, 1236.4, 1117.6, 765.6, 747.5. mp 203° C. dec.

17-Cyclopropylmethyl-3,14β-dihydroxy-4,5α-epoxy-6α-[3-(isoquinolin-3-yl)propanamido)morphinan (2)

The title compound was prepared following the general procedure in 89% yield. $^1$H NMR (400 MHz, CDCl₃) δ 9.19 (s, 1H), 7.92 (d, J=8.2 Hz, 1H), 7.74 (d, J=8.2 Hz, 1H), 7.66 (dt, J=1.04 Hz, 6.95 Hz, 1H), 7.54 (m, 2H), 6.73 (d, J=8.04 Hz, 1H), 6.49 (d, J=8.12 Hz, 1H), 6.41 (d, J=8.44 Hz, 1H, exchangeable), 4.49 (m, 2H), 3.27 (m, 2H), 3.06 (d, J=5.12 Hz, 1H), 2.99 (d, J=18.52 Hz, 1H), 2.69 (dt, J=3.28 Hz, 7.32 Hz, 2H), 2.63 (m, 1H), 2.54 (dd, J=6.48 Hz, 18.56 Hz, 1H), 2.33 (m, 2H), 2.18 (m, 2H), 1.65 (m, 1H), 1.55-1.43 (m, 2H), 1.28 (m, 1H), 0.83 (m, 2H), 0.52 (m, 2H), 0.11 (m, 2H); $^{13}$C NMR (100 MHz, CDCl₃) δ 171.63, 153.19, 151.90, 145.73, 137.74, 136.68, 131.10, 130.81, 127.63, 127.22, 126.86, 126.29, 125.74, 119.39, 119.13, 117.66, 89.77, 69.45, 62.25, 59.64, 47.00, 45.89, 43.28, 36.56, 33.44, 33.15, 28.84, 22.84, 21.25, 9.33, 3.92, 3.84. MS m/z found 526.2 (M+H)⁺. IR (Diamond, cm⁻¹) $v_{max}$ 1628.3, 1502.9, 1117.4, 859.0, 748.0. mp 106-108° C.

17-Cyclopropylmethyl-3,14β-dihydroxy-4,5α-epoxy-6α-[2-(isoquinoline-3-carboxamido)acetamido}morphinan (3)

The title compound was prepared following the general procedure in 72% yield. $^1$H NMR (400 MHz, CD₃OD) δ9.24 (s, 1H), 8.49 (s, 1H), 8.12 (d, J=8.12 Hz, 1H), 8.02 (d, J=8.12 Hz, 1H), 7.81 (dt, J=1.28 Hz, 7.54 Hz, 1H), 7.75 (dt, J=1.16

Hz, 7.50 Hz, 1H), 6.63 (d, J=8.08 Hz, 1H), 6.49 (d, J=8.12 Hz, 1H), 4.58 (d, J=3.36 Hz, 1H), 4.51 (dt, J=4.19 Hz, 12.95 Hz, 1H), 4.20 (s, 2H), 3.12 (d, J=6.68 Hz, 1H), 3.03 (d, J=18.6 Hz, 1H), 2.63 (d, J=7.00 Hz, 1H), 2.58 (dd, J=6.90 Hz, 18.70 Hz, 1H), 2.35 (m, 1H), 2.33 (m, 1H), 2.26 (d, J=11.72 Hz, 2H), 1.71 (dt, J=9.24 Hz, 14.80 Hz, 1H), 1.55 (m, 1H), 1.48 (d, J=9.60 Hz, 1H), 1.42 (dd, J=8.80 Hz, 14.80 Hz, 1H), 1.03 (m, 1H), 0.85 (m, 1H), 0.51 (m, 2H), 0.13 (m, 2H); $^{13}$C NMR (100 MHz, CD$_3$OD) δ 170.44, 167.48, 152.91, 147.11, 144.33, 139.39, 137.12, 132.46, 132.13, 131.24, 130.40, 129.08, 128.89, 126.78, 121.35, 120.21, 118.40, 90.52, 71.10, 63.33, 60.63, 48.36, 47.73, 44.42, 43.69, 34.83, 30.43, 23.73, 21.72, 10.15, 4.59, 4.07. MS m/z found 555.3 (M+H)$^+$. IR (Diamond, cm$^{-1}$) ν$_{max}$ 3295.8, 2928.6, 1651.7, 1505.9, 1231.8. mp 138-140° C.

17-Cyclopropylmethyl-3,14β-dihydroxy-4,5α-epoxy-6α-(1-chloro-4-methoxyisoquinoline-3-carboxamido)morphinan (4)

The title compound was prepared following the general procedure in 70% yield. $^1$H NMR (400 MHz, CDCl$_3$) δ 8.33-8.30 (m, 2H), 8.10 (d, J=8.44 Hz, 1H, exchangeable), 7.86-7.76 (m, 2H), 6.71 (d, J=8.08 Hz, 1H), 6.56 (d, J=8.12 Hz, 1H), 4.84-4.78 (m, 2H), 4.15 (s, 3H), 3.14 (d, J=6.04 Hz, 1H), 3.06 (d, J=18.48 Hz, 1H), 2.69-2.60 (m, 2H), 2.42-2.23 (m, 4H), 1.90-1.79 (m, 2H), 1.58 (d, J=10.44 Hz, 1H), 1.47 (m, 1H), 1.18 (m, 1H), 0.87 (m, 1H), 0.54 (m, 2H), 0.14 (m, 2H); $^{13}$C NMR (100 MHz, CDCl$_3$) δ 162.45, 152.84, 145.24, 143.86, 137.28, 134.72, 133.27, 131.48, 130.96, 130.13, 129.15, 126.66, 126.08, 123.52, 119.27, 117.06, 90.50, 69.59, 63.81, 62.28, 59.73, 47.37, 46.20, 43.23, 33.57, 29.24, 22.92, 21.09, 9.40, 3.94, 3.87. MS m/z found 562.5 (M+H)$^+$. IR (Diamond, cm$^{-1}$) ν$_{max}$ 3256.8, 1652.1, 1503.9, 1313.2, 1117.0, 945.5, 768.8, 726.8. mp 202-204° C.

17-Cyclopropylmethyl-3,14β-dihydroxy-4,5α-epoxy-6α-(1-chloro-4-hydroxyisoquinoline-3-carboxamido)morphinan (5)

The title compound was prepared following the general procedure in 44% yield. Hydrochloride salt: $^1$H NMR (400 MHz, DMSO-d$_6$) δ 13.61 (s, 1H, exchangeable), 9.42 (s, 1H, exchangeable), 8.88 (brs, 1H, exchangeable), 8.37 (m, 1H), 8.32 (m, 1H), 8.25 (d, J=8.72 Hz, 1H, exchangeable), 8.03-8.01 (m, 2H), 6.75 (d, J=8.08 Hz, 1H), 6.63 (d, J=8.12 Hz, 1H), 6.36 (s, 1H, exchangeable), 4.85 (d, J=3.96 Hz, 1H), 4.71 (m, 1H), 3.93 (d, J=6.96 Hz, 1H), 3.41-3.27 (m, 2H), 3.15-3.05 (m, 2H), 2.96 (m, 1H), 2.72 (m, 1H), 2.50 (m, 1H), 1.94 (dt, J=8.97 Hz, 15.36 Hz, 1H), 1.69-1.66 (m, 2H), 1.50 (dd, J=8.92 Hz, 15.32 Hz, 1H), 1.19-1.08 (m, 2H), 0.70 (m, 1H), 0.63 (m, 1H), 0.49 (m, 1H), 0.42 (m, 1H); $^{13}$C NMR (100 MHz, CD$_3$OD) δ 169.81, 155.29, 147.22, 140.78, 140.56, 132.36 (×2), 131.39, 130.59, 129.87, 127.42, 124.28, 122.98, 121.92, 121.12, 120.04, 89.14, 71.05, 63.73, 59.10, 47.23, 46.83, 31.62, 30.32, 24.92, 21.19, 6.85, 6.28, 3.34 (×2). MS m/z found 548.3 (M+H)$^+$. IR (Diamond, cm$^{-1}$) ν$_{max}$ 3076.8, 2952.6, 1620.6, 1532.1, 1319.0, 1118.3, 1032.3, 948.3, 768.0. mp 207-210° C.

17-Cyclopropylmethyl-3,14β-dihydroxy-4,5α-epoxy-6α-(4-hydroxyisoquinoline-3-carboxamido) morphinan (6)

The title compound was prepared following the general procedure in 60% yield. $^1$H NMR (400 MHz, CDCl$_3$) δ 13.36 (s, 1H, exchangeable), 8.58 (s, 1H), 8.34 (d, J=8.04 Hz, 1H), 8.29 (d, J=8.44 Hz, 1H, exchangeable), 7.90 (d, J=7.64 Hz, 1H), 7.75-7.67 (m, 2H), 6.74 (d, J=8.08 Hz, 1H), 6.56 (d, J=8.12 Hz, 1H), 4.79 (m, 2H), 3.14 (d, J=6.52 Hz, 1H), 3.06 (d, J=18.48 Hz, 1H), 2.69-2.61 (m, 2H), 2.42-2.24 (m, 4H), 1.87 (dt, J=9.01 Hz, 14.54 Hz, 1H), 1.77 (m, 1H), 1.60 (m, 1H), 1.47 (dd, J=9.22 Hz, 14.14 Hz, 1H), 1.19 (m, 1H), 0.87 (m, 1H), 0.57-0.53 (m, 2H), 0.14 (m, 2H); $^{13}$C NMR (100 MHz, CDCl$_3$) δ 169.20, 155.12, 145.36, 141.77, 137.42, 131.39, 130.87, 129.94, 129.58, 128.31, 127.14, 126.04, 122.79, 122.13, 119.42, 117.29, 90.41, 69.62, 62.25, 59.76, 47.45, 45.93, 43.17, 33.72, 29.33, 22.99, 21.04, 9.40, 3.95, 3.87. MS m/z found 514.2514 (M+H)$^+$. IR (Diamond, cm$^{-1}$) ν$_{max}$ 3211.9, 1624.9, 1529.8, 1456.4, 1118.2, 952.0, 764.1, 745.5. mp 128-131° C.

17-Cyclopropylmethyl-3,14β-dihydroxy-4,5α-epoxy-6α-(4-quinazoline-2-carboxamido)morphinan (7)

The title compound was prepared following the general procedure in 63% yield. $^1$H NMR (400 MHz, CDCl$_3$) δ 9.45 (s, 18H), 8.45 (d, J=8.96 Hz, 1H), 8.17 (d, J=8.44 Hz, 1H), 7.99-7.93 (m, 2H), 7.72 (dt, J=0.76 Hz, 7.52 Hz, 18H), 6.73 (d, J=8.08 Hz, 1H), 6.56 (d, J=8.12 Hz, 1H), 4.88 (m, 1H), 4.82 (d, J=4.4 Hz, 1H), 3.14 (d, J=6.16 Hz, 1H), 3.06 (d, J=18.48 Hz, 1H), 2.69-2.60 (m, 2H), 2.42-2.22 (m, 4H), 1.89-1.80 (m, 2H), 1.58 (m, 1H), 1.48 (m, 1H), 1.25 (m, 1H), 0.88 (m, 1H), 0.55 (m, 2H), 0.14 (m, 2H); $^{13}$C NMR (100 MHz, CDCl$_3$) δ 162.07, 160.68, 153.97, 149.87, 145.26, 137.59, 134.77, 130.92, 129.38, 129.22, 127.15, 125.79, 124.87, 119.25, 117.33, 90.08, 69.65, 62.32, 59.68, 47.32, 46.70, 43.28, 33.44, 28.95, 22.96, 21.13, 9.35, 3.91, 3.84. MS m/z found 499.2515 (M+H)$^+$. IR (Diamond, cm$^{-1}$) ν$_{max}$ 3369.5, 1675.0, 1506.4, 1117.3, 777.8. mp 151-153° C.

17-Cyclopropylmethyl-3,14β-dihydroxy-4,5α-epoxy-6α-(1-chloroisoquinoline-3-carboxamido)morphinan (8)

The title compound was prepared following the general procedure in 29% yield. $^1$H NMR (400 MHz, CDCl$_3$) δ 8.55 (s, 1H), 8.36 (d, J=8.24 Hz, 1H), 8.18 (d, J=8.76 Hz, 1H, exchangeable), 7.99 (d, J=7.52 Hz, 1H), 7.83-7.75 (m, 2H), 6.74 (d, J=8.12 Hz, 1H), 6.57 (d, J=8.12 Hz, 1H), 4.86-4.81 (m, 2H), 3.13 (d, J=6.52 Hz, 1H), 3.07 (d, J=18.48 Hz, 1H), 2.69-2.61 (m, 2H), 2.42-2.24 (m, 4H), 1.89-1.73 (m, 2H), 1.62 (d, J=8.96 Hz, 1H), 1.48 (m, 1H), 1.21 (m, 1H), 0.88 (m, 1H), 0.57-0.53 (m, 2H), 0.15-0.12 (m, 2H); $^{13}$C NMR (100 MHz, CDCl$_3$) δ 162.82, 150.33, 145.21, 142.79, 137.88, 137.42, 131.80, 130.86, 130.00, 128.68, 127.93, 126.58, 125.94, 120.68, 119.33, 117.22, 90.35, 69.63, 62.31, 59.72, 47.39, 46.46, 43.24, 33.59, 29.15, 22.95, 21.13, 9.40, 3.90, 3.82. MS m/z found 532.2002 (M+H)$^+$. IR (diamond, cm$^{-1}$) ν$_{max}$ 3380.5, 2926.0, 1656.5, 1506.2, 1259.8, 1116.5, 1033.8, 988.7, 786.4. mp 210-212° C.

17-Cyclopropylmethyl-3,14β-dihydroxy-4,5α-epoxy-6α-(1-cyanoisoquinoline-3-carboxamido)morphinan (9)

The title compound was prepared following the general procedure in 40% yield. $^1$H NMR (400 MHz, CDCl$_3$) δ 8.82 (s, 1H), 8.39 (m, 1H), 8.16 (d, J=8.68 Hz, 1H, exchangeable), 8.09 (m, 1H), 7.92-7.87 (m, 2H), 6.75 (d, J=8.08 Hz, 1H), 6.61 (d, J=8.08 Hz, 1H), 4.84 (m, 2H), 3.15 (d, J=6.36 Hz, 1H), 3.08 (d, J=18.48 Hz, 1H), 2.69-2.63 (m, 2H), 2.42-2.27 (m, 4H), 1.89-1.79 (m, 2H), 1.60 (m, 1H), 1.50 (m, 1H), 1.30

(m, 1H), 0.87 (m, 1H), 0.55 (m, 2H), 0.15 (m, 2H); $^{13}$C NMR (100 MHz, CDCl$_3$) δ 162.39, 144.98, 144.18, 137.62, 136.51, 133.16, 132.48, 131.38, 130.70, 130.08, 128.97, 125.63, 125.52, 124.35, 119.56, 117.44, 115.46, 89.90, 69.72, 62.31, 59.69, 47.35, 46.61, 43.36, 33.42, 28.78, 22.96, 21.21, 9.43, 3.95, 3.87. MS m/z found 523.2339 (M+H)$^+$. Salt: IR (diamond, cm$^{-1}$) ν$_{max}$ 3076.2, 2161.7, 1507.3, 1318.1, 1116.8, 1033.1, 793.8, 748.9. mp 251° C. dec.

17-Cyclopropylmethyl-3,14β-dihydroxy-4,5α-epoxy-6α-(1-methylisoquinolin-3-carboxamido)morphinan (10)

The title compound was prepared following the general procedure in 65% yield. $^1$H NMR (400 MHz, CDCl$_3$) δ 8.54 (d, J=8.44 Hz, 1H, exchangeable), 8.45 (s, 1H), 8.11 (d, J=8.20 Hz, 1H), 7.93 (d, J=7.92 Hz, 1H), 7.73-7.63 (m, 2H), 6.72 (d, J=8.08 Hz, 1H), 6.56 (d, J=8.08 Hz, 1H), 4.87-4.84 (m, 2H), 3.13 (d, J=6.40 Hz, 1H), 3.06 (d, J=18.48 Hz, 1H), 2.93 (s, 3H), 2.68-2.60 (m, 2H), 2.41-2.22 (m, 4H), 1.88-1.80 (m, 2H), 1.58 (m, 1H), 1.48 (dd, J=8.94 Hz, 11.70 Hz, 1H), 1.23 (m, 1H), 0.87 (m, 1H), 0.55 (m, 2H), 0.14 (m, 2H); $^{13}$C NMR (100 MHz, CDCl$_3$) δ 164.29, 157.57, 145.29, 142.41, 137.30, 136.10, 131.04, 130.41, 128.86, 128.61, 128.47, 126.12, 125.67, 119.15, 119.08, 116.96, 90.57, 69.63, 62.34, 59.71, 47.38, 46.17, 43.27, 33.53, 29.11, 22.94, 22.48, 21.31, 9.41, 3.92, 3.83. MS m/z found 512.2569 (M+H)$^+$. Salt: IR (diamond, cm$^{-1}$) ν$_{max}$ 3207.9, 1660.7, 1506.7, 1457.6, 1320.3, 1117.4, 1032.6, 782.8. mp 224° C. dec.

17-Cyclopropylmethyl-3,14β-dihydroxy-4,5α-epoxy-6α-(6-nitroisoquinoline-3-carboxamido)morphinan (11)

The title compound was prepared following the general procedure in 62% yield. $^1$H NMR (400 MHz, DMSO-d$_6$) δ 9.63 (s, 1H), 9.27 (d, J=1.96 Hz, 1H), 9.16 (brs, 1H), 8.94 (s, 1H), 8.53 (d, J=8.96 Hz, 1H), 8.51 (d, J=8.32 Hz, 1H), 8.49 (dd, J=2.18 Hz, 9.02 Hz, 1H), 6.63 (d, J=8.08 Hz, 1H), 6.51 (d, J=8.08 Hz, 1H), 4.67-4.62 (m, 2H), 3.12 (d, J=6.4 Hz, 1H), 3.01 (d, J=18.56 Hz, 1H), 2.51-2.50 (m, 2H), 2.38-2.32 (m, 2H), 2.29-2.14 (m, 2H), 1.71 (dt, J=9.22 Hz, 14.47 Hz, 1H), 1.60 (t, J=11.24 Hz, 1H), 1.46-1.37 (m, 2H), 1.05 (m, 1H), 0.90 (m, 1H), 0.50 (m, 2H), 0.14 (m, 2H); $^{13}$C NMR (100 MHz, DMSO-d$_6$) δ 162.58, 152.04, 148.56, 145.39, 144.61, 138.01, 135.04, 130.76, 130.64, 130.36, 124.81, 124.45, 122.33, 121.31, 118.89, 117.22, 88.73, 69.12, 61.23, 58.69, 46.56, 45.86, 42.80, 33.49, 29.23, 22.36, 20.64, 8.98, 3.84, 3.37. MS m/z found 543.7 (M+H)$^+$. IR (Diamond, cm$^{-1}$) ν$_{max}$ 3368.3, 1663.2, 1630.6, 1531.8, 1507.1, 1457.3, 1341.8, 1116.3. mp 141-143° C.

17-Cyclopropylmethyl-3,14β-dihydroxy-4,5α-epoxy-6α-(7-nitrosoquinoline-3-carboxamido)morphinan (12)

The title compound was prepared following the general procedure in 37% yield. $^1$H NMR (400 MHz, CDCl$_3$) δ 9.37 (s, 1H), 9.00 (m, 1H), 8.73 (s, 1H), 8.53 (dd, J=2.06 Hz, 8.94 Hz, 1H), 8.46 (d, J=8.64 Hz, 1H), 8.16 (d, J=8.96 Hz, 1H), 6.73 (d, J=8.04 Hz, 1H), 6.58 (d, J=8.04 Hz, 1H), 4.89-4.82 (m, 2H), 3.15 (d, J=6.36 Hz, 1H), 3.08 (d, J=18.4 Hz, 1H), 2.70-2.61 (m, 2H), 2.42-2.24 (m, 4H), 1.89-1.82 (m, 2H), 1.62-1.59 (m, 1H), 1.49 (dd, J=9.28 Hz, 12.4 Hz, 1H), 1.23-1.19 (m, 1H), 0.88 (m, 1H), 0.56 (m, 2H), 0.14 (m, 2H); $^{13}$C NMR (100 MHz, CDCl$_3$) δ 163.03, 152.80, 147.13, 146.82, 145.21, 138.68, 137.28, 130.91, 130.14, 128.33, 126.12, 124.42, 124.22, 119.98, 119.41, 117.08, 90.45, 69.61, 62.21, 59.71, 47.41, 46.46, 43.19, 33.62, 29.16, 22.94, 21.09, 9.39, 3.96, 3.86. MS m1 found 543.6 (M+H)$^+$. IR (Diamond, cm$^{-1}$) ν$_{max}$ 3367.7, 1664.1, 1631.3, 1522.7, 1508.7, 1487.5, 1459.2, 1342.9, 1117.0. mp 230° C. dec.

17-Cyclopropylmethyl-3,14β-dihydroxy-4,5α-epoxy-6α-(7-dimethylaminoisoquinoline-3-carboxamido)morphinan (13)

The title compound was prepared following the general procedure in 75% yield. $^1$H NMR (400 MHz, CDCl$_3$) δ 8.91 (s, 1H), 8.45 (s, 1H), 8.32 (d, J=8.72 Hz, 1H, exchangeable), 7.80 (d, J=9.08 Hz, 1H), 7.34 (dd, J=9.12 Hz, 2.48 Hz, 1H), 6.94 (d, J=2.16 Hz, 1H), 6.73 (d, J=8.08 Hz, 1H), 6.55 (d, J=8.12 Hz, 1H), 4.86-4.79 (m, 2H), 3.20-3.00 (m, 8H), 2.68-2.59 (m, 2H), 2.38-2.27 (m, 4H), 1.90-1.76 (m, 2H), 1.59 (m, 1H), 1.46 (m, 1H), 1.16 (m, 1H), 0.87 (m, 1H), 0.57-0.52 (m, 2H), 0.15-0.11 (m, 2H); $^{13}$C NMR (100 MHz, CDCl$_3$) δ 164.63, 150.28, 149.12, 145.46, 140.09, 137.49, 131.73, 130.99, 129.02, 128.27, 125.88, 120.54, 120.22, 119.19, 117.21, 104.52, 90.72, 69.62, 62.31, 59.75, 47.33, 46.07, 43.22, 40.42 (×2), 33.62, 29.38, 22.95, 21.21, 9.39, 3.94, 3.86. MS m/z found 541.3001 (M+H)$^+$. IR (Diamond, cm$^{-1}$) ν$_{max}$ 3375.0, 1616.2, 1518.4, 1504.5, 1156.4, 810.0, 726.1. mp 268° C. dec.

17-Cyclopropylmethyl-3,14β-dihydroxy-4,5α-epoxy-6α-(6,7-dimethoxyisoquinoline-3-carboxamido)morphinan (14)

The title compound was prepared following the general procedure in 72% yield. $^1$H NMR (400 MHz, DMSO-d$_6$) δ 9.16 (s, 1H, exchangeable), 9.13 (s, 1H), 8.42 (m, 2H), 7.625 (s, 1H), 7.619 (s, 1H), 6.63 (d, J=8.0 Hz, 1H), 6.50 (d, J=8.04 Hz, 1H), 4.92 (brs, 1H, exchangeable), 4.61 (m, 2H), 3.97 (s, 3H), 3.95 (s, 3H), 3.09 (d, J=6.48 Hz, 1H), 3.00 (d, J=18.52 Hz, 1H), 2.65-2.56 (m, 2H), 2.40-2.27 (m, 2H), 2.26-2.13 (m, 2H), 1.69 (dt, J=9.32 Hz, J=14.49 Hz, 1H), 1.56 (m, 1H), 1.45-1.36 (m, 2H), 0.99 (m, 1H), 0.88 (m, 1H), 0.50 (m, 2H), 0.13 (m, 2H); $^{13}$C NMR (100 MHz, DMSO-d$_6$) δ 163.46, 153.21, 151.30, 148.62, 145.38, 141.84, 137.89, 132.08, 130.70, 125.69, 124.88, 118.75, 118.45, 117.09, 106.20, 105.80, 89.00, 69.06, 61.19, 58.71, 55.86, 55.74, 46.55, 45.52, 42.65, 33.62, 29.27, 22.25, 20.69, 9.06, 3.74, 3.36. MS m/z found 558.7 (M+H)$^+$. IR (Diamond, cm$^{-1}$) ν$_{max}$ 3486.3, 3382.4, 1669.1, 1506.4, 1457.0, 1250.1, 1220.7, 1177.2, 1004.9, 830.7. mp 250° C. dec.

17-Cyclopropylmethyl-3,14β-dihydroxy-4,5α-epoxy-6α-[(S)-(2-methyl-1,2,3,4-tetrahydroisoquinoline-3-carboxamido)]morphinan (15)

The title compound was prepared following the general procedure in 87% yield. $^1$H NMR (400 MHz, CDCl$_3$) δ 7.15-7.09 (m, 3H), 7.01 (m, 1H), 6.69 (d, J=8.08 Hz, 1H), 6.53 (d, J=8.16 Hz, 1H), 4.93 (brs, 1H), 4.66 (d, J=4.64 Hz, 1H), 4.52 (m, 1H), 3.78 (d, J=14.96 Hz, 1H), 3.64 (d, J=14.92 Hz, 1H), 3.29 (t, J=6.92 Hz, 1H), 2.99-3.05 (m, 4H), 2.64 (d, J=5.84 Hz, 1H), 2.55 (dd, J=6.50 Hz, 18.46 Hz, 1H), 2.43 (s, 3H), 2.33 (dd, J=3.6 Hz, 6.40 Hz, 2H), 2.22 (m, 2H), 1.48-1.66 (m, 3H), 1.19 (m, 1H), 0.81-0.95 (m, 2H), 0.53 (m, 2H), 0.11 (m, 2H); $^{13}$C NMR (100 MHz, CDCl$_3$) δ 172.03, 145.06, 137.57, 133.94, 133.17, 130.81, 128.23, 126.91, 126.26, 126.18, 125.61, 119.29, 117.43, 89.73, 69.51, 64.56, 62.25, 59.67, 55.88, 47.13, 45.74, 43.29, 42.07, 33.28, 29.49, 28.62, 22.86, 21.29, 9.40, 3.90, 3.85. MS m/z found 516.7 (M+H)$^+$. IR (Diamond, cm$^{-1}$) $v_{max}$ 3200.0, 2930.5, 1641.3, 1504.4, 1253.9, 1118.8. mp 137-139° C.

17-Cyclopropylmethyl-3,14β-dihydroxy-4,5α-epoxy-6α-(7-dimethylamino-2-methyl-1,2,3, 4-tetrahydroisoquinoline-3-carboxamido)morphinan (16)

The title compound was prepared following the general procedure in 76% yield. MS m/z found 559.3 (M+H)$^+$.

Biological Evaluation. Drugs.

Morphine sulfate was purchased from Mallinckrodt (St. Louis, Mo.). Naloxone and naltrexone were purchased from Sigma-Aldrich (St. Louis, Mo.). All drugs and test compounds were dissolved in pyrogen-free isotonic saline (Baxter Healthcare, Deerfield, Ill.).

Animals.

Male Swiss-Webster mice (Harlan, Indianapolis, Ind.) weighing 25 to 30 g were housed six per cage in animal care quarters at 22±2° C. on a 12 h light/dark cycle. Food and water were available ad libitum. The mice were brought to a test room (22±2° C., 12 h light/dark cycle), marked for identification, and allowed 18 h to recover from transport and handling. Protocols and procedures were approved by the Institutional Animal Care and Use Committee at Virginia Commonwealth University Medical Center and complied with the recommendations of the International Association for the Study of Pain.

In Vitro Competitive Radioligand Binding and Functional Assay.

The radioligand binding assay and the [$^{35}$S]GTPγS binding assay were conducted using monoclonal OR-expressed Chinese hamster ovarian (CHO) cell lines as described previously.[22,29,36,37] Briefly, for the competition binding assay, [$^3$H]NLX, [$^3$H]DPN, and [$^3$H]NTI were used to label the MOR, the KOR, and the DOR, respectively. Aliquots of a membrane protein (30 μg) were incubated with the corresponding radioligand in the presence of different concentrations of the ligand under investigation in TME buffer (50 mM Tris, 3 mM MgCl$_2$, 0.2 mM EGTA, pH 7.7) at 30° C. for 1.5 h. The bound radioactive ligand was separated from the free radioligand by filtration using the Brandel harvester (Biomedical Research & Development Laboratories, MD). Specific (i.e., OR-related) binding was determined as the difference in binding obtained in the absence and presence of 5 μM naltrexone, 5 μM U50,488, and 5 μM SNC80 for the MOR, the KOR, and the DOR, respectively. The potency of the drugs in displacing the specific binding of the radioligand was determined by linear regression analysis of Hill plots. The IC$_{50}$ values were determined and converted to K$_i$ values using the Cheng-Prusoff equation. The [$^{35}$S]GTPγS functional assays were conducted in the same cell membranes used for the receptor binding assays. Membrane proteins (10 μg) were incubated with varying concentrations of compounds, GDP (10 μM) and 0.1 nM [$^{35}$S]GTPγS in assay buffer (50 mM Tris, 3 mM MgCl$_2$, 100 mM NaCl, 0.2 mM EGTA, pH 7.7) for 1.5 h at 30° C. Nonspecific binding was determined with 20 μM unlabeled GTPγS. DAMGO (3 μM), U50,488 (5 μM), and SNC80 (5 μM) were included in the assay for a maximal effect of a full agonist for the MOR, KOR, and DOR, respectively.

In Vivo Assays. Tail Immersion Test.

The warm-water tail immersion assay was performed according to Coderre and Rollman[47] using a water bath with the temperature maintained at 56±0.1° C. Before injecting, the baseline latency (control) of the mice was determined. Only mice with a reaction time from 2 to 4 s were used. The average baseline latency for the experiment was 3.0±0.1 s. The test latency after drug treatment was assessed at the appropriate time, and a 10 s maximum cutoff time was imposed to prevent tissue damage. Antinociception was quantified according to the method of Harris and Pierson[48] as the percentage of maximum possible effect (% MPE), which was calculated as: % MPE=[(test latency−control latency)/(10−control latency)]×100. Percent MPE was calculated for each mouse using at least six mice per drug.

Opioid Withdrawal Assays.

A 75 mg morphine pellet was implanted into the base of the neck of male Swiss Webster mice following the reported procedure.[29] The animals were allowed to recover in their home cages before testing. Mice were then allowed for 30 minutes habituation to an open-topped, square, clear Plexiglas observation chamber (26×26×26 cm$^3$) with lines partitioning the bottom into quadrants before given antagonist. Withdrawal was precipitated at 72 hours from pellet implantation with naltrexone (1.0 mg/kg, s.c.), and the testing compound (s.c.) at indicated doses. Withdrawal commenced within 3 minutes after antagonist administration. Escape jumps and wet dog shakes were quantified by counting their occurrences over 20 minutes for each mouse using at least six mice per drug.

Statistical Analysis.

One-way ANOVA followed by the post hoc Dunnett test were performed to assess significance using the Prism 3.0 software (GraphPad Software, San Diego, Calif.).

Molecular Modeling Studies.

The molecular structure of the ligand (11, NNQ) was sketched in SYBYL-X 2.0, and its Gasteiger-Hückel charges were assigned before energy minimization (10,000 iterations) with the Tripos force field (TFF). The X-ray crystal structures for MOR (4DKL)[44], KOR (4DJH)[45] and DOR (4EJ4)[43] were retrieved from PDB Data Bank. SYBYL-X 2.0 was also used to prepare the obtained protein coordinates for ligand docking by extracting the crystallized ligand and the fusion protein at intracellular loop 3, followed by addition of hydrogen atoms and subsequent energy minimization of only the added hydrogen atoms. Automated docking on these "cleaned" receptor structures was performed utilizing a genetic algorithm-based docking program GOLD 5.2.[49] The binding site was defined to include all atoms within 10 Å of the γ-carbon atom of Asp$^{3.32}$ for the three opioid crystal structures along with a hydrogen bond constraint between the N(17) nitrogen atom and the carboxylate group oxygen atoms of Asp$^{3.32}$. The best CHEM-PLP-scored solutions were chosen for molecular dynamics (MD) studies. Gaps in the protein sequence including those due to extraction of the fusion proteins were modeled and refined employing MODELLER9v10.[50,51] Force field parameter and topology files for NNQ were generated utilizing SwissParam.[52] Density functional theory (DFT) calculations at the 6-31 G* level were employed to calculate partial atomic charges of the NNQ atoms using NWChem 6.0.[53] Coordinates for the spatial arrangement of the receptors within the lipid bilayer were retrieved from the Orientations of Proteins in Membranes (OPM) database.[54] The simulation system, consisting of the receptor-ligand complex embedded in a lipid (POPC) bilayer surrounded with saline solution (0.15 M NaCl) was created in VMD 1.9.1[55] using the CHARMM force field topology file[56,57]. All simulations were performed under hybrid CHARMM force field parameters that included protein, lipids and ligand with a time-step of 2 femtoseconds (fs). Periodic boundary conditions were employed, and Particle Mesh Ewald (PME) summation was used to calculate long-range electrostatic interactions. Non-bonded interactions were calculated with a smooth cutoff between 10 to 12 Å with a frequency of 1 fs.

The temperature was maintained at 310 K via Langevin dynamics. All molecular modeling simulations were performed using NAMD 2.8[58]. MD simulations were carried out in four stages. In the first stage, equilibration of the fluid-like lipid bi-layer was performed via minimization (1000 iterations) followed by NPT equilibration (pressure equilibration, 0.5 fs) of the lipid tails only. In the second stage, an NPT equilibration of the system was run for a period of 1 ns with harmonic constraints placed on protein and NNQ atoms (5 kcal/(mol-Å)). The harmonic restraint was released in stage 3 and the entire system was equilibrated using the NVT canonical ensemble for a further 1 ns. The final production run was conducted for 15 ns using an NVT ensemble. Energy landscape analysis was performed using the NAMD Energy 1.4 plug-in; non-bonded interaction analyses were performed at various distances with a dielectric constant of 6.5.59 The best-scored poses based on the NAMD non-bonded interactions were selected for further analysis.

Abbreviations Used cAMP, cyclic adenosine monophosphate; CHO, Chinese hamster ovary; DAMGO, [D-Ala$^2$-MePhe$^4$-Gly(ol)$^5$]enkephalin; DFT, density functional theory; DOR, delta opioid receptor, DPN, diprenorphine; EDCI, 1-ethyl-3-(3-dimethylaminopropyl)carbodiimide; β-FNA, β-funaltrexamine; GIRK, G protein-gated inwardly rectifying K$^+$; GPCR, G protein-coupled receptor; HOBt, hydrobenzotriazole; KOR, kappa opioid receptor, MD, molecular dynamics; MOR, mu opioid receptor, NLX, naloxone; NTX, naltrexone; NTI, naltrindole; NAQ, 17-cyclopropylmethyl-3,14β-dihydroxy-4,5α-epoxy-6α-(isoquinoline-3'-carboxamido)morphinan; OR, opioid receptor; PME, Particle Mesh Ewald; OPM, Orientations of Proteins in Membranes; SAR, structure-activity relationship; TFF, Tripos Force Field; VGCC, voltage-gated Ca$^{2+}$ channels.

REFERENCES FOR EXAMPLE 5

(1) Dhawan, B. N.; Cesselin, F.; Raghubir, R.; Reisine, T.; Bradley, P. B.; Portoghese, P. S.; Hamon, M. International Union of Pharmacology. XII. Classification of Opioid Receptors. *Pharmacol. Rev.* 1996, 48, 567-592.
(2) Janecka, A.; Fichna, J.; Janecki, T. Opioid Receptors and Their Ligands. *Curr. Top. Med. Chem.* 2004, 4, 1-17.
(3) Waldhoer, M.; Bartlett, S. E.; Whistler, J. L. Opioid Receptors. *Annu. Rev. Biochem.* 2004, 73, 953-990.
(4) Chakrabarti, S.; Prather, P. L.; Yu, L.; Law, P. Y.; Loh, H. H. Expression of the Mu-Opioid Receptor in CHO Cells: Ability of Mu-Opioid Ligands to Promote Alpha-azidoanilido[$^{32}$P]GTP Labeling of Multiple G Protein Alpha Subunits. *J. Neurochem.* 1995, 64, 2534-2543.
(5) Miyake, M.; Christie, M. J.; North, R. A. Single Potassium Channels Opened by Opioids in Rat Locus Ceruleus Neurons. *Proc. Natl. Acad. Sci. U.S.A.* 1989, 86, 3419-3422.
(6) Ortiz-Miranda, S. I.; Dayanithi, G.; Coccia, V.; Custer, E. E.; Alphandery, S.; Mazuc, E.; Treistman, S.; Lemos, J. R. µ-Opioid Receptor Modulates Peptide Release from Rat Neurohypophysial Terminals by Inhibiting Ca$^{2+}$ Influx. *J. Neuroendocrinol.* 2003, 15, 888-894.
(7) Barchfeld, C. C.; Maasen, Z. F.; Medzihradsky, F. Receptor-Related Interactions of Opiates with PGE-Induced Adneylate Cyclase in Brain. *Life Sci.* 1982, 31, 1661-1665.
(8) Thorsell, A. The µ-Opioid Receptor and Treatment Response to Naltrexone. *Alcohol Alcohol.* 2013, 48, 402-408.
(9) Herz, A. Multiple Opiate Receptors and Their Functional Significance. *J. Neural Transm., Suppl.* 1983, 18, 227-233.
(10) Sadée, W.; Wang, Z. Agonist Induced Constitutive Receptor Activation as a Novel Regulatory Mechanism. Mu Receptor Regulation. *Adv. Exp. Med. Biol.* 1995, 373, 85-90.
(11) World Drug Report 2013. Report from the United Nations Office on Drugs and Crime, (available online at the web site for unodc.org.
(12) Adams, W. A.; Robinson, K. J.; Jones, R. S.; Edwards, G. B. Overdose During Chemical Restraint in a Black Rhinoceros (*Diceros bicornis*). *Vet. Anaesth. Analg.* 2005, 32, 53-57.
(13) White, J. M.; Irvine, R. J. Mechanisms of Fatal Opioid Overdose. *Addiction* 1999, 94, 961-972.
(14) Bart, G. Maintenance Medication for Opiate Addiction: The Foundation of Recovery. *J. Addict. Dis.* 2012, 31, 207-225.
(15) Stotts, A. L.; Dodrill, C. L.; Kosten, T. R. Opioid Dependence Treatment: Options in Pharmacotherapy. *Expert Opin. Pharmacother.* 2009, 10, 1727-1740.
(16) Veilleux, J. C.; Colvin, P. J.; Anderson, J.; York, C.; Heinz, A. J. A Review of Opioid Dependence Treatment: Pharmacological and Psychosocial Interventions to Treat Opioid Addiction. *Clin. Psychol. Rev.* 2010, 30, 155-166.
(17) Isbell, H.; Vogel, V. H. The Addiction Liability of Mathadon (Amidone, Dolophine, 10820) and Its Use in the Treatment of the Morphine Abstinence Syndrome. *Am. J. Psychiatry* 1949, 105, 909-914.
(18) Minozzi, S.; Amato, L.; Vecci, S.; Davoli, M.; Kirchmayer, U.; Verster, A. Oral Naltrexone Maintenance Treatment for Opioid Dependence. *Cochrane Database Syst. Rev.* 2011, CD001333.
(19) Walsh, S. L.; Preston, K. L.; Stitzer, M. L.; Cone, E. J.; Bigelow, G. E. Clinical Pharmacology of Buprenorphine: Ceiling Effects at High Doses. *Clin. Pharmacol. Ther.* 1994, 55, 569-580.
(20) Broadbear, J. H.; Sumpter, T. L.; Burke, T. F.; Husbands, S. M.; Lewis, J. W.; Woods, J. H.; Traynor, J. R. Methocinnamox Is a Potent, Long-Lasting, and Selective Antagonist of Morphine-Mediated Antinociception in the Mouse: Comparison with Clocinnamox, β-Funaltrexamine, and β-Chlornaltrexamine. *J. Pharmacol. Exp. Ther.* 2000, 294, 933-940.
(21) Chien, C.-C.; Lee, Y.-J.; Fan, L.-W.; Ho, I.-K.; Tien, L.-T. Naloxonazine, a Specific Mu-Opioid Receptor Antagonist, Attenuates the Increment of Locomotor Activity Induced by Acute Methamphetamine in Mice. *Toxicol. Lett.* 2012, 212, 61-65.
(22) Li, G.; Aschenbach, L. C.; Chen, J.; Cassidy, M. P.; Stevens, D. L.; Gabra, B. H.; Selley, D. E.; Dewey, W. L.; Westkaemper, R. B.; Zhang, Y. Design, Synthesis, and Biological Evaluation of 6α- and 6β-N-Heterocyclic Substituted Naltrexamine Derivatives as µ Opioid Receptor Selective Antagonists. *J. Med. Chem.* 2009, 52, 1416-1427.
(23) McHardy, S. F.; Heck, S. D.; Guediche, S.; Kalman, M.; Allen, M. P.; Tu, M.; Bryce, D. K.; Schmidt, A. W.; Vanase-Frawley, M.; Callegari, E.; Doran, S.; Grahame, N. J.; McLean, S.; Liras, S. Discovery of CP-866,087, a Mu Opioid Receptor Antagonist for the Treatment of Alcohol Abuse and Dependence. *MedChemComm* 2011, 2, 1001-1005.
(24) Moynihan, H. A.; Derrick, I.; Broadbear, J. H.; Greedy, B. M.; Aceto, M. D.; Harris, L. S.; Purington, L. C. S.; Thomas, M. P.; Woods, J. H.; Traynor, J. R.; Husbands, S. M.; Lewis, J. W. Fumaroylamino-4,5-epoxymorphinans and Related Opioids with Irreversible µ Opioid Receptor Antagonist Effects. *J. Med. Chem.* 2012, 55, 9868-9874.

(25) Niciu, M. J.; Arias, A. J. Targeted Opioid Receptor Antagonists in the Treatment of Alcohol Use Disorders. *CNS Drugs* 2013, 27, 777-787.

(26) Sally, E. J.; Xu, H.; Dersch, C. M.; Hsin, L.-W.; Chang, L.-T.; Prisinzano, T. E.; Simpson, D. S.; Giuvelis, D.; Rice, K. C.; Jacobson, A. E.; Cheng, K.; Bilsky, E. J.; Rothman, R. B. Identification of a Novel "Almost Neutral" µ-Opioid Receptor Antagonist in CHO Cells Expressing the Cloned Human µ-Opioid Receptor. *Synapse* 2010, 64, 280-288.

(27) Schmidhammer, H.; Burkard, W. P.; Eggstein-Aeppli, L.; Smith, C. F. C. Synthesis and Biological Evaluation of 14-Alkoxymorphinans. 2. (−)-N-(Cyclopropylmethyl)-4,14-dimethoxymorphinan-6-one, a Selective p Opioid Receptor Antagonist. *J. Med. Chem.* 1989, 32, 418-421.

(28) South, T.; Deng, C.; Huang, X.-F. AM 251 and β-Funaltrexamine Reduce Fat Intake in a Fat-Preferring Strain of Mouse. *Behav. Brain Res.* 2007, 181, 153-157.

(29) Yuan, Y.; Li, G.; He, H.; Stevens, D. L.; Kozak, P.; Scoggins, K. L.; Mitra, P.; Gerk, P. M.; Selley, D. E.; Dewey. W. L.; Zhang, Y. Characterization of 6α- and 6β-N-Heterocyclic Substituted Naltrexamine Derivatives as Novel Leads to Development of Mu Opioid Receptor Selective Antagonists. *ACS Chem. Neurosci.* 2011, 2, 346-351.

(30) Ziauddeen, H.; Chamberlain, S. R.; Nathan, P. J.; Koch, A.; Maltby, K.; Bush, M.; Tao, W. X.; Napolitano, A.; Skeggs, A. L.; Brooke, A. C.; Cheke, L.; Clayton, N. S.; Sadaf Farooqi, I.; O'Rahilly, S.; Waterworth, D.; Song, K.; Hosking, L.; Richards, D. B.; Fletcher, P. C.; Bullmore, E. T. Effects of the Mu-Opioid Receptor Antagonist GSK1521498 on Hedonic and Consummatory Eating Behaviour: A Proof of Mechanism Study in Binge-Eating Obese Subjects. *Mol. Psychiatry* 2013, 18, 1287-1293.

(31) Ziauddeen, H.; Nathan, P. J.; Dodds, C.; Maltby, K.; Miller, S. R.; Waterworth, D.; Song, K.; Warren, L.; Hosking, L.; Zucchetto, M.; Bush, M.; Johnson, L. V.; Sarai, B.; Mogg, K.; Bradley, B. P.; Richards, D. B.; Fletcher, P. C.; Bullmore, E. T. The Effects of Alcohol on the Pharmacokinetics and Pharmacodynamics of the Selective Mu-Opioid Receptor Antagonist GSK1521498 in Healthy Subjects. *J. Clin. Pharmacol.* 2013, 53, 1078-1090.

(32) Zaidi, S. A.; Amatt, C. K.; He, H.; Selley, D. E.; Mosier, P. D.; Kellogg, G. E.; Zhang, Y. Binding Mode Characterization of 6α- and 6β-N-Heterocyclic Substituted Naltrexamine Derivatives via Docking in Opioid Receptor Crystal Structures and Site-Directed Mutagenesis Studies: Application of the "Message-Address" Concept in Development of Mu Opioid Receptor Selective Antagonists. *Bioorg. Med. Chem.* 2013, 21, 6405-6413.

(33) Craig, P. N. Interdependence between Physical Parameters and Selection of Substituent Groups for Correlation Studies. *J. Med. Chem.* 1971, 14, 680-684.

(34) Yuan, Y.; Elbegdorj, O.; Beletskaya, I. O.; Selley, D. E.; Zhang, Y. Structure Activity Relationship Studies of 17-Cyclopropylmethyl-3,14β-dihydroxy-4,5α-epoxy-6α-(isoquinoline-3'-carboxamido)morphinan (NAQ) Analogues as Potent Opioid Receptor Ligands: Preliminary Results on the Role of Electronic Characteristics for Affinity and Function. *Bioorg. Med. Chem. Lett.* 2013, 23, 5045-5048.

(35) Yuan, Y.; Elbegdorj, O.; Chen, J.; Akubathini, S. K.; Beletskaya, I. O.; Selley, D. E.; Zhang, Y. Structure Selectivity Relationship Studies of 17-Cyclopropylmethyl-3,14β-dihydroxy-4,5α-epoxy-6β-[(4'-pyridyl)carboxamido]morphinan Derivatives toward the Development of the Mu Opioid Receptor Antagonists. *Bioorg. Med. Chem. Lett.* 2011, 21, 5625-5629.

(36) Yuan, Y.; Elbegdorj, O.; Chen, J.; Akubathini, S. K.; Zhang, F.; Stevens, D. L.; Beletskaya, I. O.; Scoggins, K. L.; Zhang, Z.; Gerk, P. M.; Selley, D. E.; Akbarali, H. I.; Dewey, W. L.; Zhang, Y. Design, Synthesis, and Biological Evaluation of 17-Cyclopropylmethyl-3,14β-dihydroxy-4,5α-epoxy-6β-[(4'-pyridyl)carboxamido]morphinan Derivatives as Peripheral Selective µ Opioid Receptor Agents. *J. Med. Chem.* 2012, 55, 10118-10129.

(37) Yuan, Y.; Zaidi, S. A.; Elbegdorj, O.; Aschenbach, L. C. K.; Li, G.; Stevens, D. L.; Scoggins, K. L.; Dewey, W. L.; Selley, D. E.; Zhang, Y. Design, Synthesis, and Biological Evaluation of 14-Heteroaromatic-Substituted Naltrexone Derivatives: Pharmacological Profile Switch from Mu Opioid Receptor Selectivity to Mu/Kappa Opioid Receptor Dual Selectivity. *J. Med. Chem.* 2013, 56, 9156-9169.

(38) Zhang, Y.; Elbegdorj, O.; Yuan, Y.; Beletskaya, I. O.; Selley, D. E. Opioid Receptor Selectivity Profile Change via Isosterism for 14-O-Substituted Naltrexone Derivatives. *Bioorg. Med. Chem. Lett.* 2013, 23, 3719-3722.

(39) Sayre, L. M.; Portoghese, P. S. Stereospecific Synthesis of the 6α- and 6β-Amino Derivatives of Naltrexone and Oxymorphone. *J. Org. Chem.* 1980, 45, 3366-3368.

(40) Janssen, P. A. J.; Niemegeers, C. J. E.; Dony, J. G. H. The Inhibitory Effect of Fentanyl and Other Morphine-Like Analgesics on the Warm Water Induced Tail Withdrawal Reflex in Rats. *Arzneim. Forsch.* 1963, 13, 502-507.

(41) Von Voightlander, P. F.; Lewis, R. A. U-50,488, a Selective Kappa Opioid Agonist: Comparison to Other Reputed Kappa Agonists. *Prog. Neuro-Psychopharmacol. Biol. Psychiatry* 1982, 6, 467-470.

(42) Calderon, S. N.; Rothman, R. B.; Porreca, F.; Flippen-Anderson, J. L.; McNutt, R. W.; Xu, H.; Smith, L. E.; Bilsky, E. J.; Davis, P.; Rice, K. C. Probes for Narcotic Receptor Mediated Phenomena. 19. Synthesis of (+)-4-[(αR)-α-((2S,5R)-4-Allyl-2,5-dimethyl-1-piperazinyl)-3-methoxybenzyl]-N,N-diethylbenzamide (SNC 80): A Highly Selective, Nonpeptide δ Opioid Receptor Agonist. *J. Med. Chem.* 1994, 37, 2125-2128.

(43) Granier, S.; Manglik, A.; Kruse, A. C.; Kobilka, T. S.; Thian, F. S.; Weis, W. I.; Kobilka, B. K. Structure of the δ-Opioid Receptor Bound to Naltrindole. *Nature* 2012, 485, 400-404.

(44) Manglik, A.; Kruse, A. C.; Kobilka, T. S.; Thian, F. S.; Mathiesen, J. M.; Sunahara, R. K.; Pardo. L.; Weis, W. I.; Kobilka, B. K.; Granier, S. Crystal Structure of the µ-Opioid Receptor Bound to a Morphinan Antagonist. *Nature* 2012, 485, 321-326.

(45) Wu, H.; Wacker, D.; Mileni, M.; Katritch, V.; Han, G. W.; Vardy, E.; Liu, W.; Thompson, A. A.; Huang, X.-P.; Carroll, F. I.; Mascarella, S. W.; Westkaemper, R. B.; Mosier, P. D.; Roth, B. L.; Cherezov, V.; Stevens, R. C. Structure of the Human ic-Opioid Receptor in Complex with JDTic. *Nature* 2012, 485, 327-332.

(46) Filizola, M.; Devi, L. A. How Opioid Drugs Bind to Receptors. *Nature* 2012, 485, 314-316.

(47) Coderre, T. J.; Rollman, G. B. Naloxone Hyperalgesia and Stress-Induced Analgesia in Rats. *Life Sci.* 1983, 32, 2139-2146.

(48) Harris, L. S.; Pierson, A. K. Some Narcotic Antagonists in the Benzomorphan Series. *J. Pharmacol. Exp. Ther.* 1964, 143, 141-148.

(49) Jones, G.; Willett, P.; Glen, R. C.; Leach, A. R.; Taylor, R. Development and Validation of a Genetic Algorithm for Flexible Docking. *J. Mol. Biol.* 1997, 267, 727-748.

(50) Eswar, N.; Eramian, D.; Webb, B.; Shen, M.-Y.; Sali, A. Protein Structure Modeling with MODELLER. *Methods Mol. Biol.* 2008, 426, 145-159.

(51) Fiser, A.; Do, R. K. G.; Sali, A. Modeling of Loops in Protein Structures. *Protein Sci.* 2000, 9, 1753-1773.
(52) Zoete, V.; Cuendet, M. A.; Grosdidier, A.; Michielin, O. SwissParam: A Fast Force Field Generation Tool for Small Organic Molecules. *J. Comput. Chem.* 2011, 32, 2359-2368.
(53) Valiev, M.; Bylaska, E. J.; Govind, N.; Kowalski, K.; Straatsma, T. P.; Van Dam, H. J. J.; Wang, D.; Nieplocha, J.; Apra, E.; Windus, T. L.; de Jong, W. A. NWChem: A Comprehensive and Scalable Open-Source Solution for Large Scale Molecular Simulations. *Comput. Phys. Commun.* 2010, 181, 1477-1489.
(54) Lomize, M. A.; Lomize, A. L.; Pogozheva, I. D.; Mosberg, H. I. OPM: Orientations of Proteins in Membranes Database. *Bioinformatics* 2006, 22, 623-625.
(55) Humphrey, W.; Dalke, A.; Schulten, K. VMD: Visual Molecular Dynamics. *J. Mol. Graph.* 1996, 14, 33-38.
(56) Feller, S. E.; Gawrisch, K.; MacKerell, A. D., Jr. Polyunsaturated Fatty Acids in Lipid Bilayers: Intrinsic and Environmental Contributions to Their Unique Physical Properties. *J. Am. Chem. Soc.* 2002, 124, 318-326.
(57) MacKerell, A. D., Jr.; Feig, M.; Brooks, C. L., III. Extending the Treatment of Backbone Energetics in Protein Force Fields: Limitations of Gas-Phase Quantum Mechanics in Reproducing Protein Conformational Distributions in Molecular Dynamics Simulations. *J. Comput. Chem.* 2004, 25, 1400-1415.
(58) Phillips, J. C.; Braun, R.; Wang, W.; Gumbart, J.; Tajkhorshid, E.; Villa, E.; Chipot, C.; Skeel, R. D.; Kalé, L.; Schulten, K. Scalable Molecular Dynamics with NAMD. *J. Comput. Chem.* 2005, 26, 1781-1802.
(59) Kukic, P.; Farrell, D.; Mcintosh, L. P.; Garcia-Moreno E., B.; Jensen, K. S.; Toleikis, Z.; Teilum, K.; Nielsen, J. E. Protein Dielectric Constants Determined from NMR Chemical Shift Perturbations. *J. Am. Chem. Soc.* 2013, 135, 16968-16976.
(60) Ballesteros, J. A.; Weinstein, H. Integrated Methods for the Construction of Three-Dimensional Models and Computational Probing of Structure-Function Relationships in G-Protein Coupled Receptors. *Methods Neurosci.* 1995, 25, 366-428.

EXAMPLE 6

Structure Activity Relationship Studies of 17-cyclopropylmethyl-3,14β-dihydroxy-4,5α-epoxy-6α-(isoquinoline-3'-carboxamido)morphinan (NAQ) Analogues as Potent Opioid Receptor Ligands:
Exemplary Results on the Role of Electronic Characteristics for Affinity and Function Abstract 17-Cyclopropylmethyl-3,14β-dihydroxy-4,5α-epoxy-6α-(isoquinoline-3'-carboxamido)morphinan (NAQ) was previously designed following the "message-address" concept and was identified as a potent and highly selective mu opioid receptor (MOR) ligand based on its pharmacological profile. We here report the preliminary structure activity relationship (SAR) studies of this novel lead compound. For the new ligands synthesized as NAQ analogues, their binding assay results showed that a longer spacer and a saturated ring system of the side chain were unfavorable for their MOR selectivity over the kappa and delta opioid receptors. In contrast, substitutions with different electronic properties at either 1'- or 4'-position of the isoquinoline ring of the side chain were generally acceptable for reasonable MOR selectivity. The majority of NAQ analogues retained low efficacy at the MOR compared to NAQ in the $^{35}$S-GTP[γS] binding assays while electron-withdrawing groups at 1'-position of the isoquinoline ring induced higher MOR stimulation than electron-donating groups did. In summary, the electronic characteristics of substituents at 1'- or 4'-position of the isoquinoline ring in NAQ seem to be critical and need to be further tuned up to achieve higher MOR selectivity and lower MOR stimulation.

Naltrexone (FIG. 22) has long been used for opioid addiction and alcoholism treatment.[1,2] It exerted its function mainly through blocking the mu opioid receptor (MOR).[1,2] Despite the demonstrated efficacy, its hepatotoxicity and inverse agonism on the MOR in opioid-dependent state compromised its clinical applications.[3-5] Furthermore, naltrexone bound to the MOR and the kappa opioid receptor (KOR) with similar affinity.[6] Naltrexone also possessed moderate efficacy at the KOR,[7] which was proposed to counteract its therapeutic efficiency for addiction treatment.[8]

Figure 22:
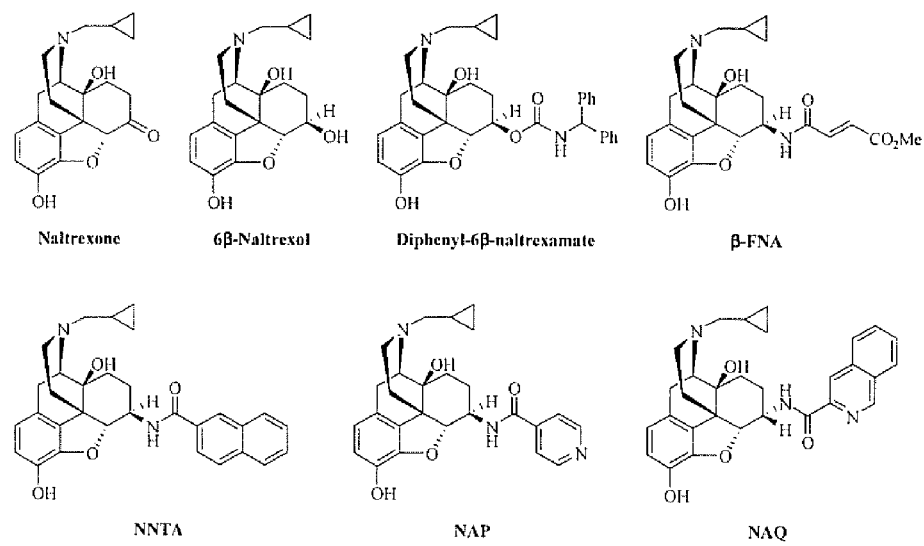
FIG. 22. Naltrexone and examples of its C6-substituted derivatives.

So far, a variety of molecules have been synthesized based on the skeleton of naltrexone. Most of the modifications happened at the C6-position by introducing a f-configuration substituent. These efforts provided a number of pharmacologically interesting compounds (FIG. 22). Among them, 6β-naltrexol is the major metabolite of naltrexone and it acted as a neutral MOR antagonist and a KOR inverse agonist.[9-11] Deveau research group recently reported that diphenyl-6β-naltrexamate carried improved MOR selectivity over both the delta opioid receptor (DOR) and KOR compared to 6β-naltrexol.[12] β-funaltrexamine (β-FNA), N-naphthoyl-β-naltrexamine (NNTA), and N-isonicotinoyl-β-naltrexamine (NAP) were the amide derivatives of 6β-naltrexamine. β-FNA was a MOR irreversible antagonist with reversible KOR agonist activity.[13] NNTA selectively and potently activated the mu/kappa opioid receptor heteromers without inducing significant physical dependence and place preference in its $ED_{50}$ dose range.[14] NAP acted as a peripheral MOR antagonist and significantly increased mouse gastrointestinal transit with an $ED_{50}$ around 0.0088 mg/kg. NAP also only displayed marginal withdrawing symptoms at a dose as high as 10 mg/kg.[15]

In contrast, only a few reports have described the 6α-configuration derivatives of naltrexone.[16-18] A thorough analysis of the binding data of these compounds revealed that the 6α-isomers generally carried higher MOR selectivity over the KOR than the corresponding 6β-isomers.[16,17] More recently, 17-cyclopropylmethyl-3,14β-dihydroxy-4,5α-epoxy-6α-(isoquinoline-3'-carboxamido)morphinan (NAQ, FIG. 22) was found to be more efficacious and less susceptible to tolerance than naltrexone in reducing high concentration alcohol consumption in C57BL/6J mice by intermittent access.[19] However, NAQ also acted as a DOR partial agonist with relative high efficacy and moderate potency in the $^{35}$S-GTP[γS] binding assays.[20] There have been reports that the DOR was associated with morphine dependence in mice.[21-23] Thus a ligand without DOR agonism would be ideal for therapeutic purpose. To achieve that, we herein report the structure activity relationship (SAR) studies of NAQ, focusing on the spacer length between the epoxymorphinan skeleton and the isoquinoline ring (side chain), and the electronic properties of the side chain.

Figure 23:
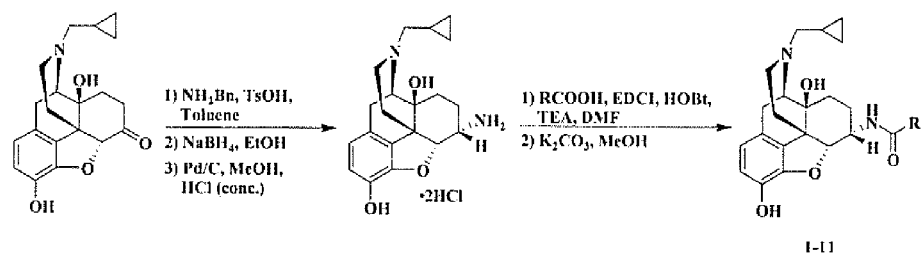
FIG. 23. Exemplary two-step synthetic route for NAQ analogues.

The syntheses of these NAQ analogues were achieved in two steps (FIG. 23).[16] Briefly, reductive amination of naltrexone with benzylamine and sodium borohydride followed by catalytic hydrogenation in the presence of hydrochloric acid furnished 6α-naltrexamine dihydrochloride (6α-NTA.2HCl) in a total yield of 79%.[24] A variety of substituted isoquinoline-3-carboxylic acids were then coupled to 6α-NTA.2HCl via EDCI/HOBt method. After treatment with $K_2CO_3$ in methanol, NAQ analogues were obtained with moderate yields.

These new NAQ analogues were then screened in the in vitro opioid receptor binding assays and MOR $^{35}$S-GTP[γS] functional assays according to the procedures reported previously with minor revision (see Supplementary Information).[6,16] Naltrexone and NAQ were tested along under the same conditions for comparison (Table 12).

TABLE 12

Binding affinity, selectivity and MOR $^{35}$S-GTP[γS] functional assay results for NAQ analogues.[a]

| Compd | R | $K_i$ (nM) μ | $K_i$ (nM) κ | $K_i$ (nM) δ | Selectivity κ/μ | Selectivity δ/μ | MOR $^{35}$S-GTP[γS] Binding EC$_{50}$ (nM) | MOR $^{35}$S-GTP[γS] Binding % E$_{max}$ of DAMGO |
|---|---|---|---|---|---|---|---|---|
| NTX | NA | 0.33 ± 0.02 | 1.44 ± 0.11 | 143.5 ± 13.7 | 4.4 | 435 | 0.16 ± 0.04 | 5.4 ± 0.8 |
| NAQ | 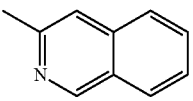 | 1.11 ± 0.07 | 13.3 ± 1.1 | 161.9 ± 15.0 | 12 | 146 | 3.3 ± 0.4 | 20.8 ± 1.2 |
| 1 | 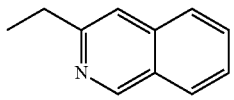 | 1.20 ± 0.04 | 1.10 ± 0.15 | 12.5 ± 0.7 | 0.9 | 10 | 4.6 ± 0.6 | 18.6 ± 1.1 |
| 2 | 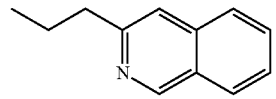 | 0.68 ± 0.05 | 1.61 ± 0.04 | 8.4 ± 0.7 | 2.4 | 12 | 1.14 ± 0.11 | 27.38 ± 0.35 |
| 3 | 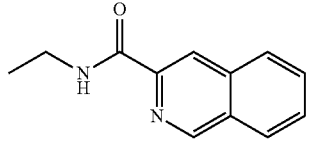 | 2.7 ± 1.4 | 0.61 ± 0.04 | 9.2 ± 0.4 | 0.2 | 3.4 | 14.1 ± 4.1 | 13.9 ± 1.9 |
| 4 | 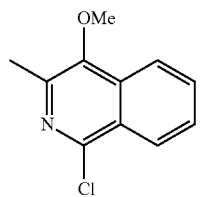 | 0.55 ± 0.01 | 22.2 ± 2.1 | 33.9 ± 0.5 | 40 | 62 | 1.74 ± 0.13 | 51.0 ± 0.4 |
| 5 | 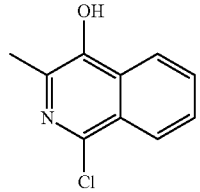 | 0.73 ± 0.07 | 18.3 ± 1.9 | 17.4 ± 1.8 | 25 | 24 | 1.23 ± 0.09 | 19.8 ± 0.8 |
| 6 | 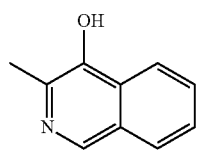 | 0.45 ± 0.02 | 4.0 ± 0.4 | 32.8 ± 1.5 | 8.9 | 73 | 1.06 ± 0.03 | 20.5 ± 0.9 |
| 7 | 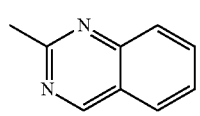 | 1.11 ± 0.06 | 5.1 ± 0.3 | 78.8 ± 0.7 | 4.6 | 71 | 6.0 ± 1.5 | 21.6 ± 0.8 |

TABLE 12-continued

Binding affinity, selectivity and MOR $^{35}$S-GTP[γS] functional assay results for NAQ analogues.[a]

| Compd | R | $K_i$ (nM) | | | Selectivity | | MOR $^{35}$S-GTP[γS] Binding | |
|---|---|---|---|---|---|---|---|---|
| | | μ | κ | δ | κ/μ | δ/μ | $EC_{50}$ (nM) | % $E_{max}$ of DAMGO |
| 8 | 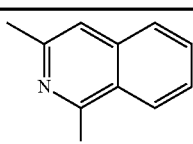 | 1.26 ± 0.04 | 10.8 ± 1.2 | 79.8 ± 2.4 | 8.6 | 63 | 2.62 ± 0.38 | 26.4 ± 0.9 |
| 9 | 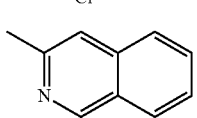 | 2.1 ± 0.2 | 29.1 ± 0.7 | 117.5 ± 7.3 | 14 | 56 | 7.2 ± 0.5 | 22.2 ± 0.4 |
| 10 | 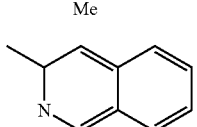 | 0.99 ± 0.07 | 10.1 ± 0.5 | 129.9 ± 9.6 | 10 | 131 | 3.32 ± 0.24 | 37.5 ± 0.7 |
| 11 | 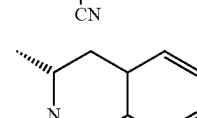 | 2.9 ± 1.3 | 6.76 ± 0.54 | 9.3 ± 0.3 | 2.3 | 3.2 | 19.4 ± 10.3 | 24.8 ± 1.3 |

[a]The values were the means ± S.E.M. of four independent experiments. [$^3$H]Naloxone, [$^3$H]Naltrindole, and [$^3$H]diprenorphine were used to label the MOR, the DOR and the KOR, respectively. The percentage stimulation to DAMGO was the $E_{max}$ of the compound compared to that of DAMGO (normalized to 100%). Naltrexone (NTX), and NAQ were tested along under the same conditions.

All the NAQ analogues retained high binding affinity to the MOR within subnanomolar to nanomolar range. While they all bound to the MOR as potently as NAQ, it seemed that the electron-donating groups at the 4'-position of the isoquinoline ring (compounds 4-6) were favorable for MOR-ligand interactions whereas the less rigid ring system (11) was disadvantageous for MOR binding.

There was around 10-fold decrease in the KOR binding affinity for NAQ compared to that of naltrexone. The longer spacer (compounds 1-3) moderately enhanced ligands' KOR binding affinity compared to NAQ. Electron-withdrawing groups at 4'-position of the isoquinoline ring (compound 7) and saturated ring system (compound 11) slightly improved their KOR binding affinity, whereas electron-donating groups showed reduced KOR binding affinity except for compound 6. Regarding to their MOR selectivity, it thus seemed that a longer spacer, electron-withdrawing groups at 4'-position, or a saturated ring system yielded decreased MOR selectivity over the KOR while electron-withdrawing groups at 1'-position (compounds 8 and 10), and electron-donating groups at both 1'- and 4'-positions (compounds 4-6, and 9) gave comparable or improved MOR selectivity over the KOR, relative to NAQ. Compound 4 showed the highest MOR selectivity over the KOR in this series of compounds (nearly 10 times higher than that of naltrexone).

NAQ showed similar binding affinity as naltrexone at the DOR. A longer spacer (compounds 1-3) and a saturated ring system (compound 11) significantly improved ligand DOR binding affinity (>13 fold). Electron-donating groups at 4'-position of the isoquinoline ring (compounds 4-6) also modestly augmented DOR affinity, whereas an electron-withdrawing group at 4'-position (compound 7) and substitutions at 1'-position (compounds 8-10), regardless of their electronic characteristics, were only marginally in favor of DOR binding, compared to NAQ. With respect to their MOR selectivity, it thus appeared that a longer spacer and a saturated ring system were devastating for MOR selectivity over the DOR, while substitutions with different electronic properties at either 1'- or 4'-position of the isoquinoline ring were tolerant with over 20-fold MOR selectivity over the DOR. Being the most selective one in this series of ligands, compound 10 displayed a similar MOR selectivity over the DOR to NAQ.

The majority of NAQ analogues demonstrated less than 30% of MOR stimulation in the $^{35}$S-GTP[γS] binding assay, except for compounds 4 and 10 (Table 12). No conclusive SAR could be drawn except that electron-withdrawing groups at 1'-position of the isoquinoline ring (compounds 8 and 10) seemed to promote more MOR activation than an electron-donating group (compound 9). Compound 3 with the longest spacer carried the lowest efficacy in this series of compounds whereas compound 4 showed the highest efficacy on the MOR. To be noticed, NAQ and all its analogues were 1 to 2 order of magnitudes less potent than naltrexone in the $^{35}$S-GTP[γS] binding assay.

In conclusion, a series of NAQ analogues as 6α-naltrexamine derivatives, were synthesized for structure activity relationship studies with respect to the spacer length between the epoxymorphinan skeleton and the isoquinoline ring (side chain), electronic characteristics of the side chain, and rigidity of the side chain. Opioid receptor binding assays showed that a longer spacer and a less rigid side chain were unfavorable for MOR selectivity over the KOR and the DOR. This study identified four NAQ analogues (compounds 4, 5, 9, and 10) with ≥10-fold selectivity over the KOR and the DOR, which was comparable to that of cyprodime[25]. Among them, compound 4 resembled to buprenorphine[26] in the in vitro functional studies as a MOR partial agonist while carrying greatly improved MOR selectivity, which should be beneficial for drug abuse and addiction treatment.

REFERENCES FOR EXAMPLE 6

1. Gonzalez, J. P.; Brogden, R. N. Drugs 1988, 35, 192.
2. Ray, L. A.; Chin, P. F.; Miotto, K. CNS Neurol. Disord. Drug Targets 2010, 9, 13.
3. Minozzi, S.; Amato, L.; Vecchi, S.; Davoli, M.; Kirchmayer, U.; Verster, A. Cochrane Database Syst. Rev. 2011, CD001333.
4. Sadie, W.; Wang, D.; Bilsky, E. J. Life Sci. 2005, 76, 1427.
5. Garbutt, J. C. Curr. Pharm. Des. 2010, 16, 2091.
6. Yuan, Y.; Elbegdorj, O.; Chen, J.; Akubathini, S. K.; Zhang, F.; Stevens, D. L.; Beletskaya, 1. O.; Scoggins, K. L.; Zhang, Z.; Gerk, P. M.; Selley, D. E.; Akbarali, H. I.; Dewey, W. L.; Zhang, Y. J. Med. Chem. 2012, 55, 10118.
7. Wentland, M. P.; Lou, R.; Lu, Q.; Bu, Y.; Denhardt, C.; Jin, J.; Ganorkar, R.; VanAlstine, M. A.; Guo, C.; Cohen, D. J.; Bidlack, J. M. Bioorg. Med. Chem. Lett. 2009, 19, 2289.
8. Wee, S.; Koob, G. F. Psychopharmacol. 2010, 210, 121.
9. Ferrari, A.; Del Bertolotti, M. I.; Utri, A.; Avico, U.; Sternieri, E. Drug Alcohol Depend. 1998, 52, 211.
10. Wang, D.; Raehal, E. L.; Bilsky, E. J.; Sadee, W. J. Neurochem. 2001, 77, 1590.
11. Wang, D.; Sun, X.; Sadee, W. J. Pharmacol. Exp. Ther. 2007, 321, 544.
12. Pelotte, A. L.; Smith, R. M.; Ayestas, M.; Dersch, C. M.; Bilsky, E. J.; Rothman, R. B.; Deveau, A. M. Bioorg. Med. Chem. Lett. 2009, 19, 2811.
13. Ward, S. J.; Portoghese, P. S.; Takemori, A. E. J. Pharmacol. Exp. Ther. 1982, 220, 494.
14. Yekkirala, A. S.; Lunzer, M. M.; McCurdy, C. R.; Powers, M. D.; Kalyuzhny, A. E.; Roerig, S. C.; Portoghese, P. S. Proc. Natl. Acad. Sci. USA 2011, 108, 5098.
15. Yuan, Y.; Stevens, D. L.; Braithwaite, A.; Scoggins, K. L.; Bilsky, E. J.; Akbarali, H. I.; Dewey, W. L.; Zhang Y. Bioorg. Med. Chem. Lett. 2012, 22, 4731.
16. Li, G.; Aschenbach, L. C.; Chen, J.; Cassidy, M. P.; Stevens, D. L.; Gabra, B. H.; Selley, D. E.; Dewey, W. L.; Westkaemper, R. B.; Zhang, Y. J. Med. Chem. 2009, 52, 1416.
17. Ghirmai, S.; Azar, M. R.; Polgar, W. E.; Berzetei-Gurske, I.; Cashman, J. R. J. Med. Chem. 2008, 51, 1913.
18. Metzger, J.; Jung, G.; Bessler, W. G.; Hoffmann, P.; Strecker, M.; Lieberknecht, A.; Schmidt, U. J. Med. Chem. 1991, 34, 1969.
19. Warner, J. A.; Yuan, Y.; Zhang, Y.; Miles, M. F. Unpublished results.
20. Yuan, Y.; Li, G.; He, H.-J; Stevens, D. L.; Kozak, P.; Scoggins, K. L.; Mitra, P.; Gerk, P. M.; Selley, D. E.; Dewey, W. L.; Zhang, Y. ACS Chem. Neurosci. 2011, 2, 346.
21. Sánchez-Blázquez, P.; Garcia-Espina, A.; Garzón, J. J. Pharmacol. Exp. Ther. 1997, 280, 1423.
22. Miyamoto, Y.; Portoghese, P. S.; Takemori, A. E. J. Pharmacol. Exp. Ther. 1993, 264, 1141.
23. Abdelhamid, E. E.; Sultana, M.; Portoghese, P. S.; Takemori, A. E. J. Pharmacol. Exp. Ther. 1991, 258, 299.
24. Sayre, L. M.; Portoghese, P. S. J. Org. Chem. 1980, 45, 3366.
25. Spetea, M.; Schuellner, F.; Moisa, R. C.; Berzetei-Gurske, I. P.; Schraml, B.; Doerfler, C.; Aceto, M. D.; Harris, L. S.; Coop, A.; Schmidhammer, H. J. Med. Chem. 2004, 47, 3242.
26. Huang, P.; Kehner, G. B.; Cowan, A.; Liu-Chen, L.-Y. J. Pharmacol. Exp. Ther. 2001, 297, 688.

EXAMPLE 7

Design, Synthesis, and Biological Evaluation of 17-Cyclopropylmethyl-3,14β-dihydroxy-4,5α-epoxy-6β-[(4'-pyridyl)carboxamido]morphinan Derivatives as Peripheral Selective Mu Opioid Receptor Agents Abstract Peripheral selective mu opioid receptor (MOR) antagonists could alleviate the symptoms of opioid-induced constipation (OIC) without compromising the analgesic effect of opioids. However, a variety of adverse effects were associated with them, partially due to their relatively low MOR selectivity. NAP, a 6β-N-4'-pyridyl substituted naltrexamine derivative, was identified previously as a potent and highly selective MOR antagonist mainly acting within the peripheral nervous system. The noticeable diarrhea associated with it prompted the design and synthesis of its analogues in order to study its structure-activity relationship. Among them, compound 8 showed improved pharmacological profiles compared to the original lead, acting mainly at peripheral while increasing the intestinal motility in morphine-pelleted mice ($ED_{50}$=0.03 mg/kg). The slight decrease of the $ED_{50}$ compared to the original lead was well compensated by the unobserved adverse effect. Hence, this compound and similar compounds could be used in treating OIC, and other disorders (e.g., alcohol and drug addiction), in subjects (human and animal) in need thereof.

Introduction

Opioids are the mainstay for cancer and non-cancer pain management.[1-3] However, their use is often associated with multiple side effects, such as dependence, respiratory depression, sedation, dizziness, pruritus, urinary retention and bowel dysfunction.[4] Among them, the most common and distressing one is probably constipation. The prevalence of opioid-induced constipation (OIC) varies from 9.3 to 95% among different population investigated.[5-13] Moreover, unlike other adverse effects of opioids, tolerance to constipation rarely develops.[14]

Three subtypes of opioid receptors are implicated in their pharmacology, designated as the mu opioid receptor (MOR), the kappa opioid receptor (KOR), and the delta opioid receptor (DOR), respectively. The pathomechanism of OIC is mainly attributed to the activation of the peripheral MOR in the gastrointestinal (GI) tract,[15-17] although central effects cannot be fully ruled out.[18-20] It has been demonstrated that "excitation" of MOR delayed gastric emptying and intestinal transit, reduced water and electrolytes secretion, and increased intestinal liquid reabsorption, which subsequently led to OIC.[21-25]

The traditional treatment of OIC employing laxatives provides less than satisfying and predictable results. A survey showed that only 46% of opioid-treated patients who required laxative therapy achieved the desired results half of the time, comparing to an 84% satisfaction rate in the control group.[26] Several other pharmacological interventions have also been applied to address OIC with some encouraging outcomes, for example, opioid switch (such as switching from morphine to transdermal fentanyl,[27-30] transdermal buprenorphine,[31] methadone,[32] or a novel MOR agonist/norepinephrine reuptake inhibitor, tapentadol[33-35]), 5-HT$_4$ agonists (such as Prucalopride[36]), and type-2 chloride channel (ClC-2) activators (such as Lubiprostone[37]). However, controversial results have also been reported for each of these agents.[38-40]

Figure 24:
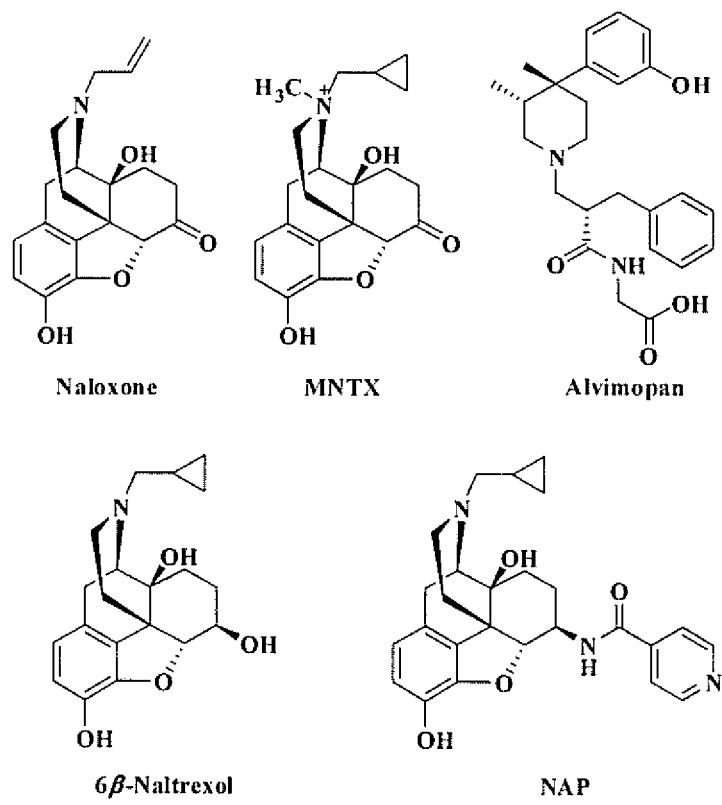
FIG. 24. Compounds for Mechanism-based pharmacological interventions of OIC.

An essential reason that the aforementioned therapies are less effective and satisfactory for OIC is that they do not directly address the underlying mechanism of OIC. As pointed out earlier, a molecule that could selectively block the peripheral MOR function would be of therapeutic interest for OIC. Naloxone (FIG. 24), a relative mu and kappa-selective opioid antagonist ($K_i$ value ratios, $\delta/\mu \approx 96$, $\delta/\kappa \approx 69$),[41] has low systemic bioavailability (~2%) due to its significant hepatic first-pass,[42] and its role in OIC has been extensively studied for over a decade. Yet reversal of desired analgesia and/or precipitation of withdrawal symptoms are frequently seen with modestly improved laxation for immediate-release naloxone.[43-46] A fixed combination of prolonged-release (PR) naloxone and PR oxycodone (1:2) overcame these drawbacks and significantly improved bowel function.[47-49] Given its predetermined "recipe", this medication is not applicable to patients who have either liver disease or need other opioid analgesics and it is only approved in thirteen European countries.[49,50] Therefore, a systemic MOR antagonist still doesn't seem to be an ideal and universal resolution for OIC.

As for peripheral selective MOR antagonists, due to their restricted ability to cross the blood-brain barrier (BBB), they were able to relieve OIC without compromising the central analgesic effect and inducing withdrawal symptoms by themselves.[51] The first drug of this class, methylnaltrexone (MNTX, FIG. 24),[52] in its subcutaneous formation, was approved in 2008 for palliative-care patients who are suffering from OIC when laxative therapy is insufficient.[53] The FDA approval was based on two major clinical trials, in which 48%, and 62% patients had laxation within 4 hours after the first dose of MNTX, as compared with 15%, and 14% patients on placebo, respectively.[54,55] Several clinical trials investigating the efficacy of oral MNTX for OIC/opioid-induced bowel dysfunction (OIBD) were completed, but no results have been published. Although three of four reported clinical trials have shown that oral alvimopan (FIG. 24), another peripheral selective MOR antagonist, is efficacious in improving spontaneous bowel movement (SBM) compared to placebo, the myocardial infarction associated with long term use restrained its application for OIC.[56-60]

In light of the debilitating and troublesome impact of OIC on patients' quality of life and the relative low efficiency of MNTX to induce SBM ($\leq 62\%$),[54,55] it has been the center of great interest to develop novel peripheral MOR antagonists. At least four new agents are under clinical development right now.[61] Among them, one is a PEGylated modified naloxone that was well reviewed.[62] The structures of the rest of the compounds have not been disclosed. But all molecules showed enhanced SBMs versus placebo without impeding central antinociception in early clinical trials.[62,63] Preliminary research published not long ago by Yancey-Wrona and colleagues revealed that 6β-naltrexol (FIG. 24) inhibits morphine-induced slowing of GI transit in healthy opioid-naive volunteers by acting as a peripheral selective opioid antagonist.[64] Although it is too early to tell whether any of these new molecules will eventually replace MNTX, they do serve as "proof-of-concept" that specifically blocking MOR in the GI tract can improve symptoms of OIC.

In an effort to develop highly selective opioid antagonists, a 6β-N-4'-pyridyl substituted naltrexamine derivative, NAP (FIG. 24), was identified as a peripheral selective MOR antagonist based on its in vitro/in vivo pharmacological assays and pharmacokinetic studies.[65-68] The $ED_{50}$ of NAP is 0.0088 mg/kg in the GI transit assay, which makes it a useful compound to address the peripheral side effects of opioids. However, the incidence of diarrhea associated with high doses of NAP requires further structure-activity relationship (SAR) studies with concentration on its C(6)-pyridyl ring system, which was proposed to interact as an alternate "address" domain with MOR based on the "message-address" concept.[65] Thus a series of new ligands were rationally designed, synthesized and biologically evaluated as the second generation of molecular modeling aided drug design. At least one new compound with improved pharmacological profiles compared to the initial lead has been identified.

Results and Discussion

Molecular Design.

Figure 25A:
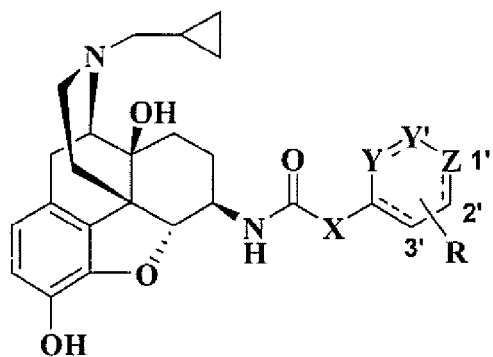
FIGS. 25(A) and (B). (A) Schematic representation of exemplary NAP derivatives, (B) Exemplery NAP analogues synthetic route.

Docking studies of NAP into the homology models of the three opioid receptors revealed a preferred binding mode for NAP to MOR over DOR and KOR through aromatic stacking and a putative hydrogen-bonding via the nitrogen atom on the pyridyl ring.[65] On the basis of our modeling study and the Craig Plot, the following features were taken into account when designing the new NAP analogues to facilitate its structure-selectivity relationship (SSR) study: electronic/steric/hydrophobic effects of the C(6)-pyridyl ring, the length of the spacer between the C(6)-pyridyl ring and the morphinan skeleton, and the aromatic property of the C(6) side chain (FIG. 25A).

Chemistry.

Figure 25B:
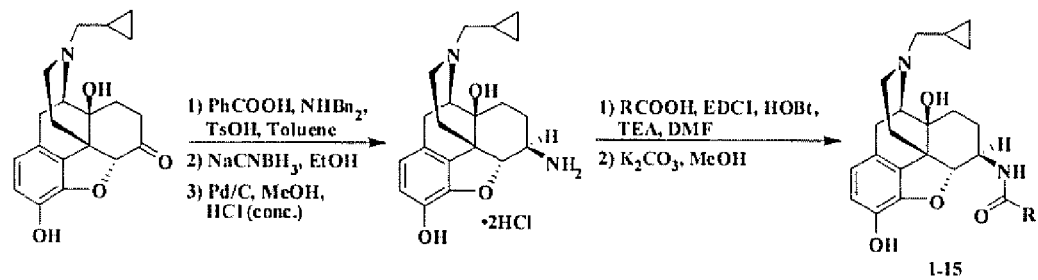

Fifteen NAP derivatives were synthesized in a similar to that presented in FIG. 25B.[65, 69] Briefly, stereo-selective reductive amination of naltrexone with dibenzylamine followed by catalytic hydrogenation-deprotection under acidic condition furnished 6β-naltrexamine (6β-NTA)[70] dihydrocholoride in a total yield of 50%. Then a variety of substituted N-containing heterocyclic acids, obtained either through commercial resources or prepared in house (see Supporting Information), were coupled with 6β-NTA employing EDC/HOBt method. After treated with $K_2CO_3$, the 6-monosubstituted NAP analogues were thus obtained, with yield ranging from 44 to 88%.

Biology.

The synthesized NAP analogues were first evaluated in the radioligand binding assay and $^{35}$S-GTP[γS] functional assay (in vitro). Then selected ligands were further advanced to in vivo behavioral (tail flick) and functional activity (charcoal gavage and intestinal motility) tests.

In Vitro Radioligand Binding and $^{35}$S-GTP[γS] Functional Assays.

To determine the binding affinity and selectivity of these novel NAP analogues to three subtype opioid receptors, the competitive radioligand binding assay was performed on monocloned opioid receptor-expressed Chinese Hamster Ovarian (CHO) cells as described previously.[65,66] [$^3$H]naloxone, [$^3$H]naltrindole (NTI), and [$^3$H]nor-binaltorphimine (norBNI) or [$^3$H]diprenorphine (DPN) were used to label MOR, DOR and KOR, respectively. The results are summarized in Table 13.

TABLE 13

Binding Affinity and MOR $^{35}$S-GTP[γS] Binding Assay Results for NAP Derivatives$^a$

| Compd | R | $K_i$ (nM) | | | Selectivity | | MOR $^{35}$S-GTP[γS] Binding | |
|---|---|---|---|---|---|---|---|---|
| | | μ | δ | κ | δ/μ | κ/μ | EC$_{50}$ (nM) | % E$_{max}$ of DAMGO |
| NTX$^b$ | N/A | 0.26 ± 0.02 | 117.1 ± 8.9 | 5.15 ± 0.26 | 450 | 20 | ND | 7.75 ± 0.20$^c$ |
| CTAP$^b$ | N/A | 2.02 ± 0.71 | 1441 ± 106 | 1013 ± 175 | 713 | 501 | ND | 1.99 ± 0.92$^c$ |
| NAP$^b$ | 4-pyridyl | 0.37 ± 0.07 | 277.5 ± 8.0 | 60.7 ± 5.6 | 747 | 163 | 1.14 ± 0.38 | 22.72 ± 0.84 |
| 1 | 2-Cl-4-pyridyl | 0.10 ± 0.04 | 602.5 ± 22.3 | 0.15 ± 0.04 | 6111 | 1.5 | 0.83 ± 0.03 | 58.20 ± 1.47 |
| 2 | 2-Br-4-pyridyl | 0.63 ± 0.18 | 173.7 ± 134.9 | 0.18 ± 0.03 | 276 | 0.3 | 1.19 ± 0.57 | 50.80 ± 2.85 |
| 3 | 2-CN-4-pyridyl | 1.25 ± 0.55 | 75.3 ± 7.0 | 0.13 ± 0.01$^d$ | 60 | 0.1 | 10.00 ± 0.80 | 43.13 ± 1.82 |
| 4 | 2-CH$_3$-4-pyridyl | 0.39 ± 0.20 | 90.1 ± 17.1 | 0.58 ± 0.12 | 232 | 1.5 | 1.13 ± 0.14 | 43.32 ± 2.80 |
| 5 | 2-OMe-4-pyridyl | 0.60 ± 0.23 | 160.4 ± 6.6 | 0.46 ± 0.04$^d$ | 267 | 0.8 | 7.89 ± 0.61 | 25.32 ± 4.36 |
| 6 | 3-Cl-4-pyridyl | 0.67 ± 0.28 | 502.4 ± 70.1 | 19.9 ± 7.7 | 746 | 30 | 2.32 ± 1.76 | 24.86 ± 1.83 |
| 7 | 3-Br-4-pyridyl | 0.45 ± 0.13 | 128.0 ± 61.2 | 2.83 ± 0.60 | 285 | 6 | 1.31 ± 0.59 | 23.23 ± 0.35 |
| 8 (NMP) | 3-CH$_3$-4-pyridyl | 0.58 ± 0.25 | 273.6 ± 1.8 | 96.7 ± 12.2 | 470 | 166 | 1.52 ± 0.26 | 30.63 ± 0.55 |
| 9 | 3-OMe-4-pyridyl | 0.43 ± 0.02 | 103.9 ± 3.9 | 4.28 ± 0.46$^d$ | 242 | 10.0 | —$^e$ | —$^e$ |

TABLE 13-continued

Binding Affinity and MOR $^{35}$S-GTP[γS] Binding Assay Results for NAP Derivatives$^a$

| Compd | R | $K_i$ (nM) μ | δ | κ | Selectivity δ/μ | κ/μ | MOR $^{35}$S-GTP[γS] Binding EC$_{50}$ (nM) | % E$_{max}$ of DAMGO |
|---|---|---|---|---|---|---|---|---|
| 10 | 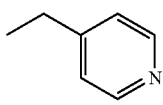 | 0.85 ± 0.16 | 865.6 ± 135.2 | 9.01 ± 0.61 | 1017 | 10.6 | 2.32 ± 0.64 | 32.78 ± 1.80 |
| 11 | 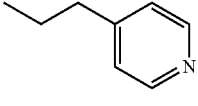 | 0.57 ± 0.41 | 294.0 ± 75.4 | 1.65 ± 0.19 | 516 | 2.9 | 1.46 ± 0.11 | 22.62 ± 1.24 |
| 12 (NGP) | 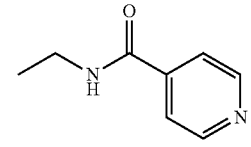 | 0.73 ± 0.59 | 526.1 ± 78.3 | 203.2 ± 67.0 | 719 | 278 | 2.84 ± 0.53 | 22.62 ± 0.66 |
| 13 | 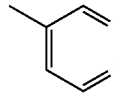 | 2.07 ± 0.41 | 419.9 ± 50.0 | 1.57 ± 0.18$^d$ | 203 | 0.7 | 28.3 ± 4.3 | 27.64 ± 4.54 |
| 14 | 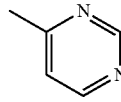 | 2.13 ± 0.31 | 339.6 ± 27.4 | 1.21 ± 0.10$^d$ | 159 | 0.6 | 7.49 ± 0.79 | 17.78 ± 2.71 |
| 15 | 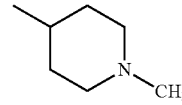 | 0.87 ± 0.38 | 2586 ± 1704 | 6.49 ± 2.36 | 2968 | 7.5 | 5.08 ± 0.43 | 37.24 ± 0.97 |

$^a$The values are the means ± S.E.M. of three independent experiments. [$^3$H]naloxone, [$^3$H]NTI, and [$^3$H]norBNI were used to label MOR, DOR and KOR, respectively, unless as otherwise stated. The percentage stimulation to DAMGO is the E$_{max}$ of the compound compared to that of DAMGO (normalized to 100%). Naltrexone (NTX), and CTAP were tested along as controls under same conditions.
N/A not applicable.
N.D. could not be determined.
$^b$See reference 65.
$^c$At 100 nM, see reference 66.
$^d$[H]DPN was used as the radioligand.
$^e$Not tested.

As seen in Table 13, all exemplary derivatives retained sub-nanomolar to nanomolar affinity for MOR, but the selectivity of MOR over DOR and KOR varied among different substituents on the pyridyl ring, the spacer length between the pyridyl ring and the morphinan skeleton, and the side chain saturation state. Overall most of the ligands bound to the DOR with low affinity of $K_i$ values at three-digit nanomolar concentration. This was in line with their parent compound NAP's high selectivity over the DOR. More particularly, the 3'-analogues appeared to be more potent than their 2'-counterparts for DOR binding (I vs. 6, 13 vs. 14), except for the methyl substitutions. In contrast, chloro-substitution (1, 6) and introduction of a second nitrogen into the pyridyl ring (13, 14) tended to have lower affinity for the DOR whereas bromo- and methoxy-groups (2, 5, 7, 9) were relatively favorable for the DOR binding. Similarly, it seemed the increased spacer length between the pyridyl ring and the morphinan skeleton (10-12) did not influence their low affinity to the DOR very significantly. It thus seemed that a balance between electronic property (affecting hydrogen bonding) and steric hindrance (affecting aromatic stacking) was desired to reach high MOR selectivity over DOR. Nevertheless, the majority of the new analogues displayed over 150-fold MOR selectivity over DOR. Ligands with 2'-chloro substitution on the pyridyl ring (1), one methylene spacer (10), and saturated piperidyl ring (15) even achieved over 1000-fold selectivity. Replacement of the aromatic system in the side chain of NAP with a non-aromatic one (15) caused 10-fold decrease in its binding affinity for DOR, probably due to the loss of aromatic staking interaction[65].

Compared to NAP, two derivatives, 8 and 12, obtained comparable or slightly improved MOR selectivity over KOR, whereas the rest derivatives exhibited decreased selectivity. Nonetheless, 3'-substitution on the pyridyl ring seemed to favor the MOR selectivity over the KOR compared with 2'-substitution regardless of the electronic characteristics while a longer spacer seemed to be beneficial to the MOR selectivity over the KOR (10-12).

Collectively, the structure selectivity relationship study of NAP derivatives thus supported the original hypothesis that interactions of aromatic stacking and hydrogen bonding between an alternative "address" domain in the receptor binding pocket and the 6-position side chain of NAP would facilitate attaining high MOR selectivity over DOR and KOR.[65,69] To be noticed, compounds 6, 8-10, and 12 displayed improved MOR selectivity profile comparing to the marketing drugs MNTX ($K_1$ value ratios, $\delta/\mu \approx 24$, $\kappa/\mu = 10$)[71], and alvimopan ($K_i$ value ratios, $\delta/\mu \approx 6$, $\kappa/\mu \approx 52$)[72].

The $^{35}$S-GTP[γS] binding assay was first conducted on the MOR-expressed CHO cells to determine the efficacy of each new ligand and define whether it acts as a full agonist, a partial agonist, or an antagonist of MOR as illustrated before.[65,66] The results were interpreted as $EC_{50}$ and the relative efficacy of each molecule to the full MOR agonist [D-Ala$^2$-MePhe$^4$-Gly(ol)$^5$]enkephalin (DAMGO) to stimulate G-protein (Table 1). MOR antagonists naltrexone (NTX; 0.1-100 nM) and D-Phe-Cys-Tyr-D-Trp-Arg-Thr-Pen-Thr-NH$_2$ (CTAP; 1-300 nM) were tested along as controls. Both control compounds produced minimal stimulation (<8% relative to DAMGO at 100 nM, Table 1). From Table 13, it seemed most of the NAP analogs act as MOR partial agonists under the tested condition with 1 or 2-digital nanomolar potency. Compound 14 had the lowest efficacy, followed by compounds 12 and 11. As pointed out in the previous report, the 2'-substitution on the pyridyl ring, except for the methoxyl group, appeared to favor MOR agonism (for example, 1 vs. 6, 4 vs. 8),[69] whereas the electronic characteristics, the spacer length, and the side chain saturation state had rather inconsistent/irregular impact.

Given that compounds 8 and 12 showed comparable binding affinity, selectivity and efficacy to the initial lead NAP, they were further characterized by the $^{35}$S-GTP[γS] functional assay on DOR and KOR-expressed CHO cell membranes, respectively (Table 14).

TABLE 14

KOR/DOR $^{35}$S-GTP[γS] Binding Assay
Results for Compounds 8 and 12$^a$

| Compd | KOR $^{35}$S-GTP[γS] Binding | | DOR $^{35}$S-GTP[γS] Binding | |
|---|---|---|---|---|
| | $EC_{50}$ (nM) | % $E_{max}$ of U50,488H | $EC_{50}$ (nM) | % $E_{max}$ of SNC80 |
| NAP$^b$ | 28.8 ± 14.4 | 45.5 ± 4.4 | 15.2 ± 15.2 | 10.2 ± 3.1 |
| 8 (NMP) | 26.4 ± 8.4 | 31.4 ± 3.9 | 38.6 ± 10.0 | 90.2 ± 21.0 |
| 12 (NGP) | 25.0 ± 22.4 | 23.5 ± 1.6 | 19.0 ± 2.9 | 84.3 ± 23.2 |

$^a$The values are the means ± S.E.M. of three independent experiments. The percentage stimulation to U50,488H or SNC80 is the $E_{max}$ of the compound compared to that of U50,488H or SNC80 (normalized to 100%).
$^b$See reference 66.

Both compounds exhibited partial agonism at KOR with relative low efficacy (% $E_{max}$ of U50,488≥5 35%) and low potency ($EC_{50}$s are double digit nanomolar versus single digit nanomolar at MOR). Meanwhile, both ligands 8 and 12 behaved as low potency DOR agonists. The fact that compounds 8 and 12 possessed higher efficacy at DOR but lower efficacy at KOR compared to those of NAP is very crucial since it was believed that KOR activation may cause sedation and dysphoric effects, whereas DOR agonism was regarded to associate with fewer side effects.[73,74] Encouraged by the results from these in vitro assay results, compounds 8 and 12 were subjected to in vivo study to further characterize their pharmacological properties.

Tail Flick Test.

Figure 26:
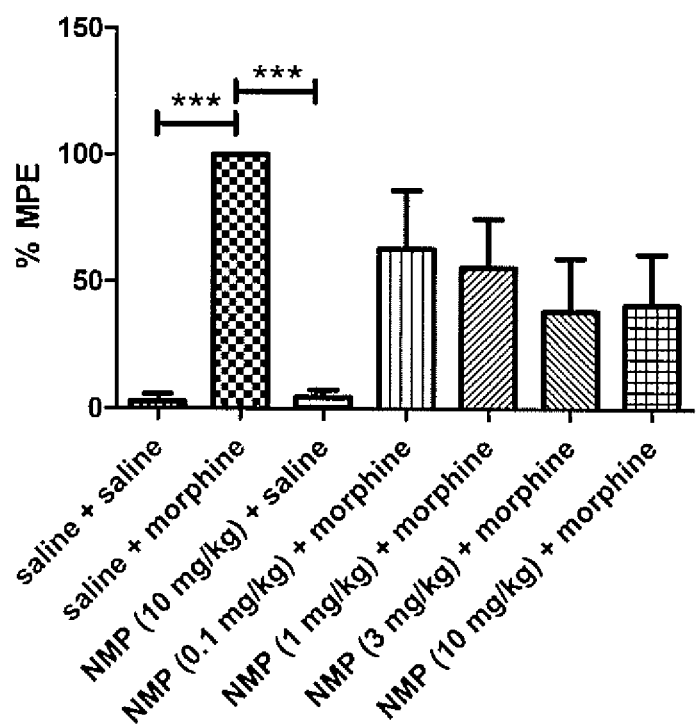
FIGS. 26(A) and (B). Tail flick assay in morphine naïve mice challenged with 10 mg/kg) morphine (n=4; P<0.0005) for (A) NMP (8) and (B) NGP (12).
Figure 26:
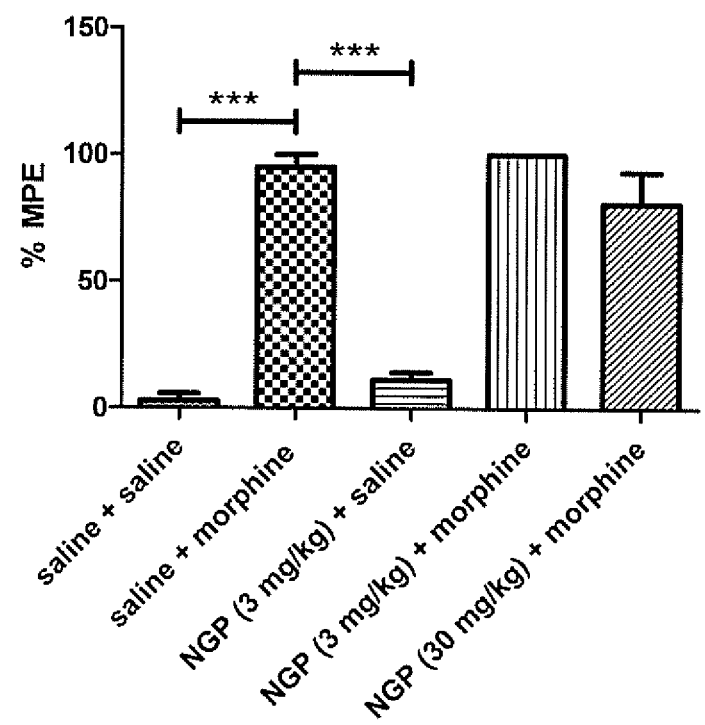

Compounds 8 and 12 were first evaluated for their acute antinociception effects in the tail flick test as previously described.[65] They also were tested for their antagonist ability for the antinociceptive effects of morphine. The percentage maximum possible effect (% MPE) for compounds 8 (10 mg/kg) and 12 (3 mg/kg) are 4.4±2.8%, and 11.2±3.1%, respectively, comparing to a 100% MPE of morphine (10 mg/kg, FIGS. 26A-B). Thus, compound 8 seemed to have no apparent CNS antinociception whereas compound 12 looked like a partial agonist with relatively low efficacy. There was no statistically significant blockage of antinociceptive effect of morphine (10 mg/kg) for compound 8 at the dose as high as 10 mg/kg (FIG. 26A), and no apparent antagonism effect was noticed for compound 12 even up to 30 mg/kg (FIG. 26B). Collectively, both ligands appeared to have marginal effects in CNS at doses ≤10 mg/kg by themselves or challenged with 10 mg/kg of morphine, which makes them more preferable as peripheral selective MOR ligands.

Charcoal Gavage and Intestinal Motility Assays.

The GI transit assay was employed to examine the effects of compounds 8 and 12 on the GI function of morphine-pelleted and morphine naive mice (2 mg/kg, chronic, or 10 mg/kg, acute, respectively). Two mg/kg of morphine was found to decrease GI motility.[75,76] Studies were conducted as described in the literature.[68,77] Results are shown in FIGS. 27A-B and 28A-B, correspondingly.

Figure 27:
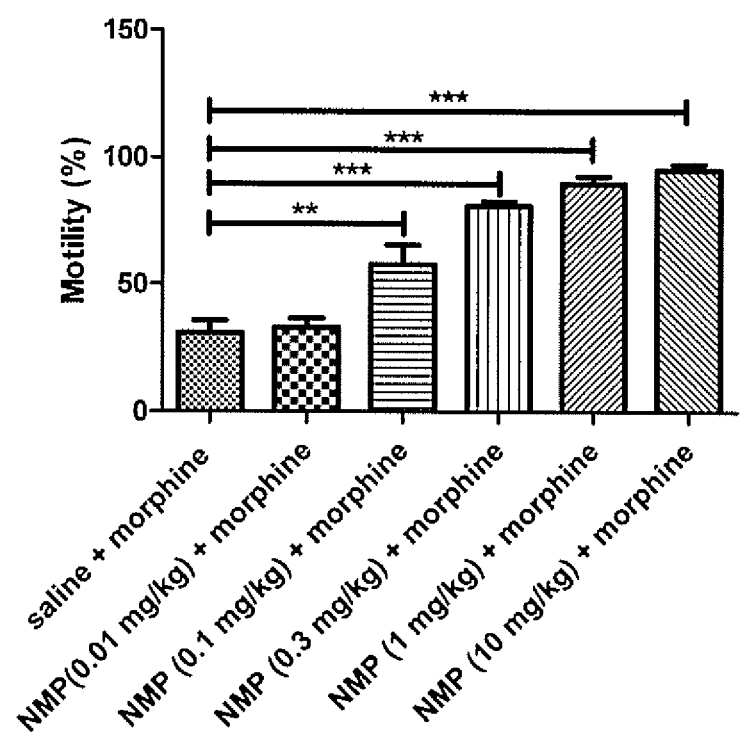
FIGS. 27 (A) and (B). Chronic charcoal gavage and intestinal motility assay in morphine-pelletted mice challenged with 2 mg/kg morphine (n=6; P<0.005, *P<0.0005).
Figure 27B:
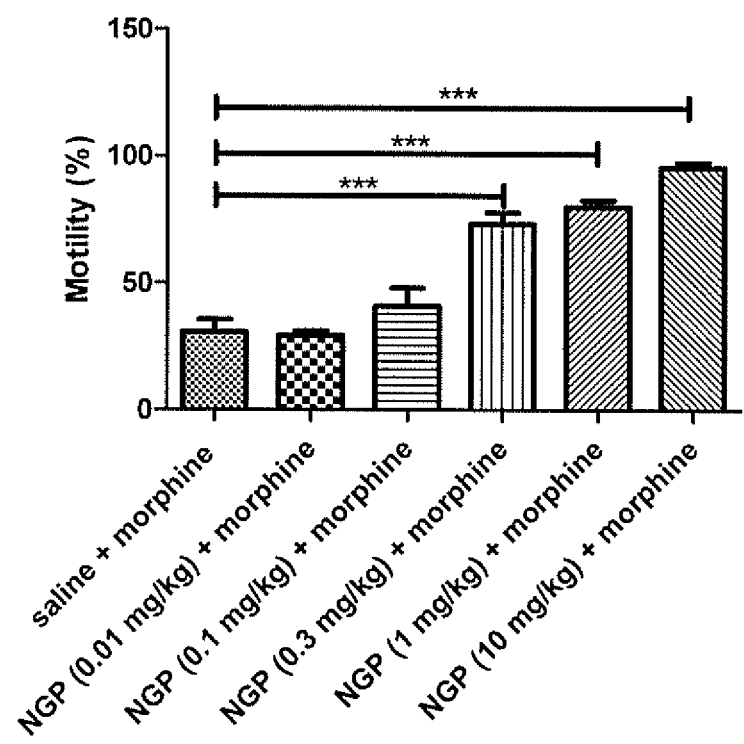

As seen in FIG. 27A, compound 8 showed a dose-response increase of GI motility in the chronic assay in morphine-pelleted mice. Treatments with 0.1, 0.3, 1, and 10 mg/kg of 8 significantly restored the GI transit compared to the control. Similarly, 0.3, 1, and 10 mg/kg of compound 12 also statistically significantly reversed the morphine inhibition of GI motility versus saline (FIG. 27B). No incidence of diarrhea happened at any tested doses of either compound. The calculated $ED_{50}$ for compounds 8 and 12 to reverse the inhibitory effect of morphine are 0.03 and 0.08 mg/kg, respectively. Their relatively reduced potency compared to parent lead NAP might be correlated to their higher efficacy on the DOR as indicated in the in vitro $^{35}$S-GTP[γS] functional assay. As reported by Smith et al., the mouse ileum express both DOR and KOR.[78] Thus, compounds 8 and 12 may inhibit acetylcholine release through their DOR agonism, which might be in facilitation to the GI transit delayed by morphine. Thus the intestinal motility activity of NAP and its derivatives may be associated with both MOR antagonism and DOR agonism for mice. Although the DOR activation effect has a negative impact on GI transit, its presence might also somehow be advantageous as no diarrhea was observed.

Figure 28A:
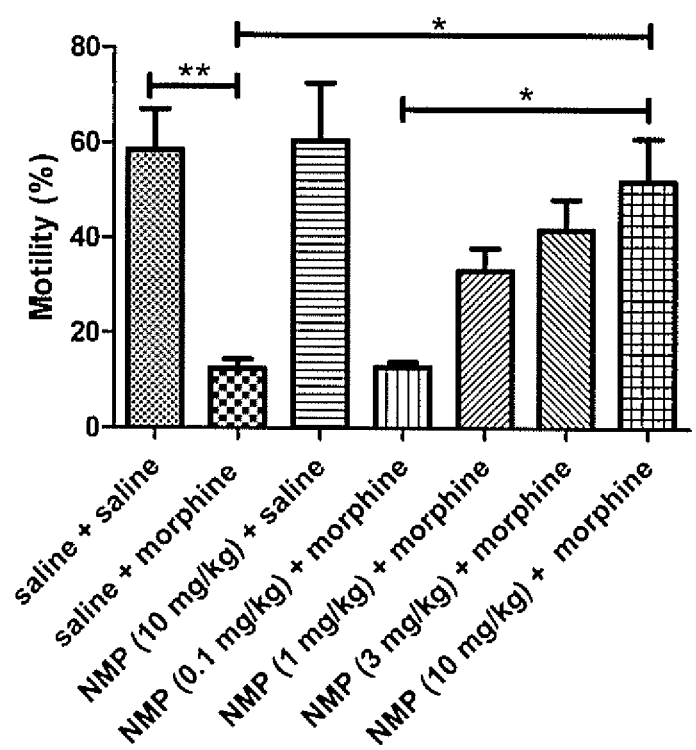
FIGS. 28 (A) and (B). Acute charcoal gavage and intestinal motility assay in morphine naive mice challenged with 10 mg/kg (n=4, *P, 0.05, **P<0.005) for (A) NMP (8) and (B) NGP (12).
Figure 28B:
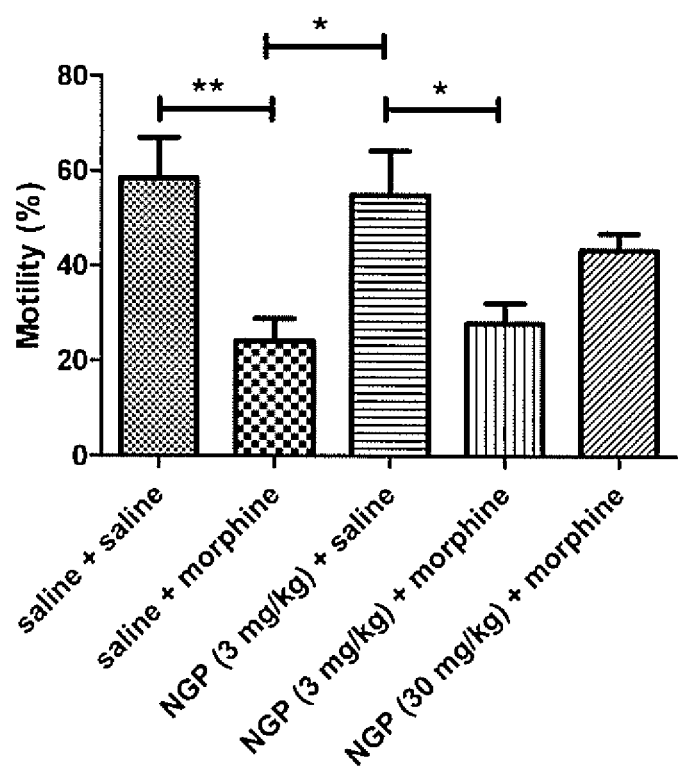

Due to the improved side effect profile of compounds 8 and 12 comparing to that of NAP in the chronic intestinal motility assay, i.e. no incidence of diarrhea, the acute effects of these two novel NAP derivatives on GI transit were further evaluated in morphine-naive mice that were later challenged by 10 mg/kg morphine (FIGS. 28A-B). Morphine (10 mg/kg) significantly reduced the intestinal motility compared to saline (12.4±2.0% vs. 58.4±8.5%, FIG. 28A) while compounds 8 and 12 alone (10 mg/kg) had negligible effect on GI transit versus saline. This was more promising compared to the results of NAP in a similar assay where the intestinal motility decreased at a similar dose of NAP.[68] The acute effect of treatment of compound 8 at 10 mg/kg dose appeared to be a significant recovery of GI motility challenged by 10 mg/kg morphine compared to control while a positive trend was observed as the dose increased, which demonstrated that compound 8 could antagonize the negative impact of morphine on GI tract in morphine-naive mice (EDs) value was 7.85 mg/kg). In contrast, compound 12 was not able to restore the GI motility as effective as compound 8 (FIG. 28B), which is consistent with the observed partial agonism in the tail flick assay for compound 12.

Pharmacokinetics Studies on Bidirectional Transport of Compounds 8 and 12 in Caco-2 Cells.

Figure 29:
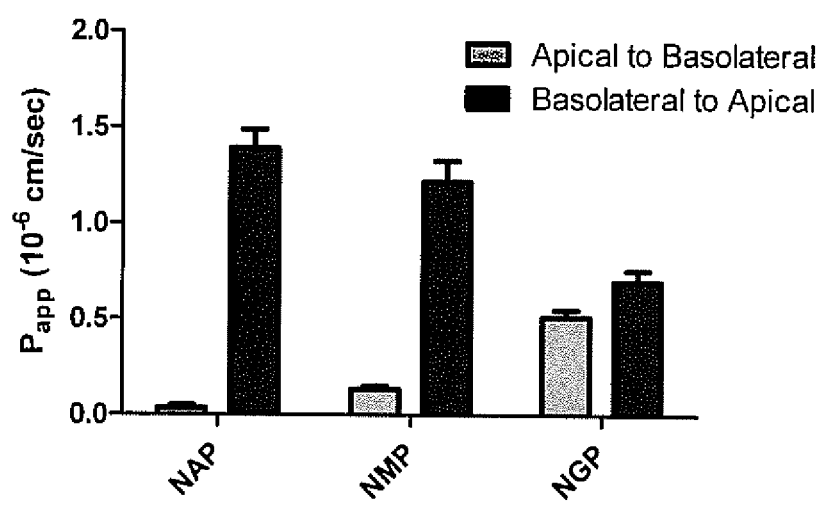
FIG. 29 Graph illustrating bidirectional transport of NAP, NMP (8) and NGP (12) in Caco-2 cells.

To further characterize the permeability of compounds 8 and 12, they were evaluated in Caco-2 cells for their bidirectional transport capacity (FIG. 29). As reported previously,[66,67] the apparent permeability of NAP was significantly low in corresponding to its apparent decreased CNS activity in the in vivo assays. Similarly, compound 8 (NMP) also showed low permeability, which is in line with its peripheral nervous system activity. On the other hand, compound 12 (NGP) showed no significant difference in its bidirectional transport capacity, which matched well with its apparent partial agonism observed in the tail flick assay.

Conclusions

The exemplary MOR antagonists of Example 7 were designed and synthesized based on the original modeling study and the structure of the lead compound, NAP, from the first generation designed molecules. Structure selectivity study of the new series supported the hypothesis that an alternative "address" domain in the receptors distinguished ligand selectivity among three opioid receptors. Among them, compounds 8 and 12, which showed comparable MOR selectivity comparing to that of NAP and marginal CNS effects, also restored the intestinal motility in morphine-pelleted mice, with $ED_{50}$ of 0.03 and 0.08 mg/kg, respectively. The slight decrease of the $ED_{50}$ might be due to the activation of the DOR in the mouse ileum. Nevertheless, the overall pharmacological profiles were enhanced as no diarrhea occurred at tested doses up to 10 mg/kg for both compounds. Due to the high MOR selectivity of compound 8 (NMP) over DOR and KOR, compared to that of MNTX and alvimopan, together with its apparent low CNS permeability, it, and similar analogs, may be provided to subjects for OIC treatment and in other applications (e.g., treatment of drug addiction, etc.).

Experimental Section

Chemical Synthesis. General Methods. Chemical reagents were purchased from either Sigma-Aldrich or Alfa Aesar. TLC analyses were carried out on Analtech Uniplate F254 plates. Chromatographic purification was accomplished on silica gel columns (230-400 mesh, Merck). Melting points were obtained with a Fisher scientific micro melting point apparatus without correction. IR spectra were recorded on either a Nicolet iS10 or a Nicolet Avatar 360 FT-IR Instrument. Proton (400 MHz) and Carbon-13 (100 MHz) nuclear magnetic resonance (NMR) spectra were acquired at ambient temperature with tetramethylsilane as the internal standard on a Bruker Ultrashield 400 Plus spectrometer. MS analysis was performed on an Applied Bio Systems 3200 Q trap with a turbo V source for TurbolonSpray. HPLC analysis was done with a Varian ProStar 210 system on Microsorb-MV 100-5 C8/C18 column (250 mm×4.6 mm) at 254 nm eluting with acetonitrile (0.1% TFA)/water (50/50 or 35/65) at 1 mL/min over 30 min. Elemental analysis was conducted in Atlantic Microlab, Inc. Specific rotation was gained on the JASCO DIP-1000 Digital Polarimeter and given as the mean value of three measurements. All above analytical methods were used to determine purity of the newly synthesized compounds and their purity is confirmed so forth as ≥95%.

General Procedure for Amide Coupling/Hydrolysis Reaction.

On an ice-water bath, to a solution of acid (3 eq) in anhydrous DMF (3 mL), was added N-(3-dimethylaminopropyl)-N'-ethylcarbodiimide hydrochloride (EDCI, 3 equiv), hydrobenzotriazole (HOBt, 3 equiv), 4 Å molecular sieves, and TEA (5.0 eq) with $N_2$ protection. Fifteen minutes later, a solution of 6β-naltroxamine hydrochloride (1.0 eq) in DMF (1 mL) was added dropwise. The resulted mixture was allowed to warm up to ambient temperature gradually. Upon completion of the reaction, the mixture was then filtered through celite. The filtrate was concentrated to remove DMF. Methanol (5 mL), and $K_2CO_3$ (2 eq) were then added to the residue and stirred at ambient temperature overnight. The mixture was then filtered through celite again. The filtrate was concentrated to remove methanol. The residue was partitioned between $CH_2Cl_2$ (50 mL) and brine (50 mL). The organic layer was separated and dried over anhydrous $MgSO_4$, concentrated under reduced pressure. The residue was then purified by column chromatography, eluenting with $CH_2Cl_2$/MeOH (1% $NH_3.H_2O$) to afford the corresponding compound as free base. Upon confirmation by $^1H$ NMR and $^{13}C$ NMR, the free base was then transformed into hydrochloride salt by soluting in MeOH (0.1 mL) and DCM (2 mL), adding HCl methanol solution (1.25 M, 4 eq) with an ice-water bath, and stirred for 5 min. Diethyl ether (10 mL) was then added. Two hours later, the precipitate was collected by filtration, dried in vacuum to give the target compound as hydrochloride salt, which was used in the HPLC, MS, specific rotation and elemental analysis.

17-Cyclopropylmethyl-3,14β-dihydroxy-4,5α-epoxy-6β-{[4'-(2'-chloropyridyl)]carboxamido}morphinan (1)

The title compound was obtained following the general procedure as a yellow solid, in 88% yield. $[\alpha]^{25}_D$ -105.64° (c=1.0, MeOH). $^1H$ NMR (300 MHz, $CDCl_3$) δ 8.43 (d, J=5.1 Hz, 1H), 8.08 (d, J=8.7 Hz, 1H), 7.73 (m, 1H), 7.62 (dd, J=5.4 Hz, 1.5 Hz, 1H), 6.61 (d, J=8.1 Hz, 1H), 6.54 (d, J=8.1 Hz, 1H), 4.71 (d, J=6.0 Hz, 1H), 3.98 (m, 1H), 3.16 (d, J=5.7 Hz, 1H), 3.03 (d, J=18.6 Hz, 1H), 2.65 (m, 2H), 2.38 (d, J=6.6 Hz, 2H), 2.19 (m, 2H), 2.02 (m, 1H), 1.67 (m, 2H), 1.49 (m, 2H), 0.85 (m, 1H), 0.55 (m, 2H), 0.13 (m, 2H); $^{13}C$ NMR (75 MHz, $CDCl_3$) δ 200.8, 164.1, 154.6, 152.5, 150.6, 144.6, 139.5, 130.7, 124.9, 122.5, 120.3, 117.9, 92.3, 70.6, 62.4, 59.6, 51.5, 47.6, 44.1, 35.3, 31.9, 29.5, 23.5, 9.6, 4.3, 4.1. MS m/z found 482.6 $(M+H)^+$. IR (KBr, $cm^{-1}$) $v_{max}$ 3250.3, 1660.3, 1550.4, 1498.7, 1317.8, 1136.8. mp >250° C. Anal. ($C_{26}H_{28}ClN_3O_4.2HCl.1.5H_2O$) C, H, N.

17-Cyclopropylmethyl-3,14β-dihydroxy-4,5α-epoxy-6β-{[4'-(2'-bromopyridyl)]carboxamido}morphinan (2)

The title compound was obtained following the general procedure as a light yellow solid, in 62% yield. $[\alpha]^{25}_D$ -141.75° (c=1.0, MeOH). $^1H$ NMR (300 MHz, $CDCl_3$) δ 8.41 (d, J=5.1 Hz, 1H), 8.19 (d, J=8.7 Hz, 1H), 7.91 (m, 1H), 7.68 (dd, J=5.4 Hz, 1.5 Hz, 1H), 6.60 (d, J=8.4 Hz, 1H), 6.55 (d, J=8.1 Hz, 1H), 4.80 (d, J=6.6 Hz, 1H), 3.91 (m, 1H), 3.19 (d, J=5.4 Hz, 1H), 3.05 (d, J=18.3 Hz, 1H), 2.68 (m, 2H), 2.39 (m, 2H), 2.19 (m, 3H), 1.70 (m, 2H), 1.46 (m, 2H), 0.85 (m, 1H), 0.55 (m, 2H), 0.15 (m, 2H); $^1H$ NMR (300 MHz, $CD_3OD$) δ 8.54 (d, J=4.8 Hz, 1H), 8.04 (d, J=1.2 Hz, 1H), 7.81 (dd, J=5.4 Hz, 1.5 Hz, 1H), 6.71 (m, 2H), 4.71 (d, J=7.8 Hz, 1H), 3.90 (m, 1H), 3.43 (m, 1H), 3.24 (m, 1H), 2.85 (m, 3H), 2.62 (m, 1H), 2.40 (m, 2H), 2.02 (m, 1H), 1.77-1.53 (m, 4H), 1.02 (m, 1H), 0.67 (m, 2H), 0.32 (m, 2H); $^{13}C$ NMR (75 MHz, $CD_3OD$) δ 204.7, 166.2, 152.1, 146.4, 143.7, 143.6, 142.4, 132.1, 127.4, 122.2, 120.6, 119.0, 92.5, 71.8, 64.0, 59.9, 53.8, 48.7, 46.4, 31.4, 31.1, 25.3, 23.9, 9.4, 5.2, 4.1. MS m/z found 526.1 $(M+H)^+$. IR (KBr, $cm^{-1}$) $v_{max}$ 3398.9, 1673.2, 1544.0, 1498.7, 1472.9, 1324.4, 1130.3. mp >250° C. Anal. ($C_{26}H_{28}BrN_3O_4.2HCl.1.5H_2O$) C, H, N.

17-Cyclopropylmethyl-3,14β-dihydroxy-4,5α-epoxy-6β-{[4'-(2'-cyanopyridyl)]carboxamido}morphinan (3)

The title compound was obtained following the general procedure as a light yellow solid, in 48% yield. $[\alpha]^{25}_D$ −146.120 (c=0.5, MeOH). Hydrochloride salt: $^1$H NMR (400 MHz, DMSO-d$_6$) δ 9.15 (s, 1H), 8.76 (m, 1H), 8.68 (brs, 1H), 8.25 (dd, J=0.64, 1.44 Hz, 1H), 7.95 (dd, J=1.62, 5.06 Hz, 1H), 6.55 (d, J=8.16 Hz, 1H), 6.49 (d, J=8.16 Hz, 1H), 6.02 (s, 1H), 4.62 (d, J=7.76 Hz, 1H), 3.69 (d, J=5.16 Hz, 1H), 3.54-3.48 (m, 1H), 3.19 (m, 2H), 2.94-2.85 (m, 2H), 2.68 (m, 1H), 2.27 (m, 1H), 2.26 (m, 1H), 1.78-1.69 (m, 1H), 1.60 (m, 1H), 1.43 (m, 1H), 1.34-1.21 (m, 2H), 0.89 (m, 1H), 0.50 (m, 1H), 0.42 (m, 1H), 0.35 (m, 1H), 0.24 (m, 1H); $^{13}$C NMR (100 MHz, DMSO-d$_6$) δ 162.16, 152.15, 142.42, 142.00, 141.34, 133.25, 129.51, 126.43, 125.28, 120.60, 119.41, 117.96, 117.19, 89.54, 69.63, 61.65, 56.69, 51.64, 46.46, 45.60, 29.27, 27.30, 23.45, 23.01, 5.70, 5.10, 2.62. MS m/z found 473.6 (M+H)$^+$. IR (Diamond, cm$^{-1}$) ν$_{max}$ 3084.0, 2234.1, 1655.9, 1536.6, 1503.1, 1323.1, 1128.0, 1031.0, 919.8, 857.9, 747.8. mp 251° C. dec.

17-Cyclopropylmethyl-3,14β-dihydroxy-4,5α-epoxy-6β-{[4'-(2'-methylpyridyl)]carboxamido}morphinan (4)

The title compound was obtained following the general procedure as a light yellow solid, in 66% yield. $[\alpha]^{25}_D$ −202.18° (c=1.0, MeOH). $^1$H NMR (400 MHz, CDCl$_3$) δ 8.58 (d, J=5.2 Hz, 1H), 7.49 (s, 1H), 7.39 (d, J=8.8 Hz, 1H), 7.31 (d, J=5.2 Hz, 1H), 6.73 (d, J=8.0 Hz, 1H), 6.57 (d, J=8.4 Hz, 1H), 4.49 (d, J=6.0 Hz, 1H), 4.12 (m, 1H), 3.13 (d, J=6.0 Hz, 1H), 3.04 (d, J=18.4 Hz, 1H), 2.65 (m, 2H), 2.60 (s, 3H), 2.38 (d, J=4.8 Hz, 2H), 2.21 (d, J=7.6 Hz, 2H), 1.81 (m, 1H), 1.67 (m, 1H), 1.58 (m, 1H), 1.53 (m, 2H), 0.86 (m, 1H), 0.54 (d, J=8.0 Hz, 2H), 0.14 (d, J=4.8 Hz, 2H); $^{13}$C NMR (100 MHz, CDCl$_3$) δ 164.88, 158.92, 148.87, 143.11, 141.90, 140.04, 130.53, 123.97, 121.26, 119.11, 118.27, 118.01, 91.47, 70.23, 62.13, 59.15, 51.06, 47.23, 43.87, 31.39, 29.21, 23.67, 23.41, 22.53, 9.30, 3.94, 3.66; Hydrochloride salt: $^1$H NMR (400 MHz, DMSO-d$_6$) δ 9.34 (brs, 1H, exchangeable), 9.01 (d, J=7.2 Hz, 1H, exchangeable), 8.88 (brs, 1H, exchangeable), 8.64 (d, J=4.8 Hz, 1H), 7.76 (s, 1H), 7.66 (d, J=4.8 Hz, 1H), 6.73 (d, J=8.4 Hz, 1H, Ar—H), 6.66 (d, J=8.0 Hz, 1H, Ar—H), 6.23 (brs, 1H), 4.82 (d, J=8.0 Hz, 1H), 3.89 (m, 1H), 3.69 (m, 1H), 3.36 (m, 2H), 3.06 (m, 2H), 2.85 (m, 1H), 2.57 (s, 3H), 2.45 (m, 2H), 1.90 (m, 1H), 1.78 (m, 1H), 1.59 (m, 1H), 1.44 (m, 2H), 1.07 (m, 1H), 0.67 (m, 1H), 0.59 (m, 1H), 0.50 (m, 1H), 0.42 (m, 1H); $^{13}$C NMR (100 MHz, DMSO-d$_6$) δ 163.92, 158.14, 148.51, 142.23, 142.04, 141.34, 129.60, 121.23, 120.60, 119.30, 118.81, 117.90, 89.62, 69.66, 61.53, 56.64, 51.37, 46.46, 45.58, 29.29, 27.28, 23.59, 23.43, 23.02, 5.73, 5.13, 2.62. MS m/z found 462.4 (M+H)$^+$. IR (Diamond, cm$^{-1}$) ν$_{max}$ 3181.9, 3057.7, 2936.5, 1661.1, 1609.4, 1543.5, 1505.1, 1452.0, 1346.1, 1273.8, 1240.9, 1125.0, 1032.3. mp 248° C. dec. Anal. (C$_{27}$H$_{31}$N$_3$O$_4$.HCl.2H$_2$O) C, H, N.

17-Cyclopropylmethyl-3,14β-dihydroxy-4,5α-epoxy-6β-{[4'-(2'-methoxypyridyl)]carboxamido}morphinan (5)

The title compound was prepared by following the general procedure in 62% yield. $[\alpha]^{25}_D$ −179.44° (c=0.8, MeOH). Hydrochloride salt: $^1$H NMR (400 MHz, DMSO-d$_6$) δ 8.94 (d, J=8.04 Hz, 1H), 8.88 (brs, 1H), 8.31 (d, J=5.24 Hz, 1H), 7.40 (dd, J=5.2 Hz, 1.2 Hz, 1H), 7.25 (m, 1H), 6.73 (d, J=8.0 Hz, 1H), 6.65 (d, J=8.4 Hz, 1H), 4.83 (d, J=8.0 Hz, 1H), 3.90 (m, 4H), 3.67 (m, 1H), 3.34 (m, 2H), 3.05 (m, 2H), 2.86 (m, 1H), 2.45 (m, 2H), 1.90 (m, 1H), 1.78 (m, 1H), 1.58 (m, 1H), 1.43 (m, 2H), 1.08 (m, 1H), 0.67 (m, 1H), 0.59 (m, 1H), 0.52 (m, 1H), 0.41 (m, 1H); $^{13}$C NMR (100 MHz, DMSO-d$_6$) δ 164.10, 163.63, 147.53, 144.34, 141.98, 141.24, 129.49, 120.52, 119.26, 117.86, 114.55, 108.25, 89.51, 69.60, 61.59, 56.61, 53.51, 51.27, 46.39, 45.51, 29.23, 27.23, 23.47, 22.94, 5.63, 5.02, 2.54. MS m/z found 478.2 (M+H)$^+$. IR (Diamond, cm$^{-1}$) ν$_{max}$ 3390.5, 3172.6, 3116.7, 1659.7, 1617.9, 1547.9, 1422.0, 1372.2, 1329.2, 1276.0, 1131.8, 1033.6, 919.4, 859.7, 811.6. mp 244-248° C. dec. Anal. (C$_{27}$H$_{31}$N$_3$O$_5$.2HCl.2.5H$_2$O) C, H, N.

17-Cyclopropylmethyl-3,14β-dihydroxy-4,5α-epoxy-6β-{[4'-(3'-chloropyridyl)]carboxamido}morphinan (6)

The title compound was obtained following the general procedure as a light yellow solid, in 68% yield. $[\alpha]^{25}_D$-155.77° (c=1.0, MeOH). $^1$H NMR (300 MHz, CDCl$_3$) δ 8.61 (m, 1H), 8.51 (d, J=4.8 Hz, 1H), 7.56 (d, J=9.3 Hz, 1H), 7.39 (m, 1H), 6.72 (d, J=8.4 Hz, 1H), 6.57 (d, J=8.1 Hz, 1H), 4.51 (d, J=6.6 Hz, 1H), 4.04 (m, 1H), 3.10 (d, J=5.7 Hz, 1H), 3.04 (d, J=18.3 Hz, 1H), 2.63 (m, 2H), 2.38 (d, J=6.6 Hz, 2H), 2.18 (d, J=8.1 Hz, 2H), 1.90 (m, 1H), 1.74-1.62 (m, 2H), 1.54-1.47 (m, 2H), 0.82 (m, 1H), 0.54 (m, 2H), 0.14 (m, 2H); $^1$H NMR (300 MHz, CD$_3$OD) δ 8.62 (m, 1H), 8.54 (d, J=4.5 Hz, 1H), 7.50 (m, 1H), 6.62 (m, 2H), 4.51 (d, J=7.8 Hz, 1H), 3.83 (m, 1H), 3.13 (m, 2H), 2.68 (m, 2H), 2.41 (m, 2H), 2.17 (m, 2H), 1.94 (m, 1H), 1.76 (m, 1H), 1.58 (m, 2H), 1.39 (m, 1H), 0.87 (m, 1H), 0.54 (m, 2H), 0.16 (m, 2H); $^{13}$C NMR (75 MHz, CD$_3$OD) δ 167.0, 150.8, 149.1, 145.1, 143.7, 142.1, 132.5, 129.8, 125.4, 124.2, 120.3, 120.7, 92.8, 71.8, 63.7, 60.3, 53.8, 49.0, 45.5, 31.8, 31.4, 25.5, 23.7, 10.3, 4.7, 4.4. MS m/z found 482.4 (M+H)$^+$. IR (KBr, cm$^{-1}$) ν$_{max}$ 3198.6, 1653.9, 1498.7, 1317.8, 1123.9, 1033.4. mp 230° C. dec. Anal. (C$_{26}$H$_{28}$ClN$_3$O$_4$.2HCl.H$_2$O) C, H, N.

17-Cyclopropylmethyl-3,14β-dihydroxy-4,5α-epoxy-6β-{[4'-(3'-bromopyridyl)]carboxamido}morphinan (7)

The title compound was obtained following the general procedure as a light yellow solid, in 51% yield. $[\alpha]^{25}_D$ −141.16° (c=1.0, MeOH). $^1$H NMR (300 MHz, CDCl$_3$) δ 8.71 (m, 1H), 8.53 (d, J=5.1 Hz, 1H), 7.48 (d, J=9.0 Hz, 1H), 7.29 (d, J=4.5 Hz, 1H), 6.71 (d, J=8.1 Hz, 1H), 6.56 (d, J=8.4 Hz, 1H), 4.52 (d, J=6.6 Hz, 1H), 4.03 (m, 1H), 3.09 (d, J=5.7 Hz, 1H), 3.03 (d, J=18.6 Hz, 1H), 2.65 (m, 2H), 2.36 (d, J=6.0 Hz, 2H), 2.17 (d, J=8.1 Hz, 2H), 1.89 (m, 1H), 1.74-1.61 (m, 2H), 1.53-1.46 (m, 2H), 0.82 (m, 1H), 0.53 (d, J=7.5 Hz, 2H), 0.13 (d, J=4.5 Hz, 2H); $^{13}$C NMR (75 MHz, CD$_3$OD) 168.0, 153.2, 149.5, 147.5, 143.7, 142.1, 132.5, 125.4, 124.3, 120.3, 119.0, 118.7, 92.8, 71.8, 63.7, 60.3, 53.8, 49.0, 45.5, 31.8, 31.4, 25.5, 23.7, 10.3, 4.7, 4.4. MS m/z found 526.6 (M+H)$^+$. IR (KBr, cm$^{-1}$) ν$_{max}$ 3398.9, 1653.9, 1550.4, 1505.2, 1330.7, 1123.9. mp 235° C. dec. Anal. (C$_{26}$H$_{28}$BrN$_3$O$_4$.2HCl.2H$_2$O) C, H, N.

17-Cyclopropylmethyl-3,14β-dihydroxy-4,5α-epoxy-6β-{[4'-(3'-methylpyridyl)]carboxamido}morphinan (8)

The title compound was obtained following the general procedure as a white solid, in 88% yield. $[\alpha]^{25}_D$ −141.45°

(c=1.0, MeOH). $^1$H NMR (300 MHz, CDCl$_3$) δ 8.53 (m, 2H), 7.23 (d, J=5.4 Hz, 1H), 6.87 (d, J=9.0 Hz, 1H), 6.78 (d, J=7.8 Hz, 1H), 6.62 (d, J=7.8 Hz, 1H), 4.48 (d, J=5.7 Hz, 1H), 4.12 (m, 1H), 3.14 (d, J=5.7 Hz, 1H), 3.07 (d, J=18.9 Hz, 1H), 2.67 (m, 2H), 2.43 (s, 3H), 2.39 (m, 2H), 2.22 (m, 2H), 1.89 (m, 1H), 1.69 (m, 2H), 1.55 (m, 2H), 0.85 (m, 1H), 0.56 (m, 2H), 0.16 (m, 2H); $^{13}$C NMR (75 MHz, CDCl$_3$) δ 167.5, 151.3, 147.0, 143.6, 143.0, 140.3, 131.1, 130.8, 124.1, 121.1, 119.3, 118.3, 92.0, 70.5, 62.3, 59.4, 53.6, 51.4, 47.6, 44.1, 29.7, 24.0, 22.7, 16.7, 9.5, 4.2, 3.9. MS m/z found 462.2 (M+H)$^+$. IR (KBr, cm$^{-1}$) $v_{max}$ 3424.8, 1653.9, 1544.0, 1505.2, 1317.8, 1130.3. mp 211° C. dec. Anal. (C$_{27}$H$_{31}$N$_3$O$_4$.2HCl.0.2H$_2$O) C, H, N.

17-Cyclopropylmethyl-3,14β-dihydroxy-4,5α-epoxy-6β-{[4'-(3'-methoxylpyridyl)]carboxamido}morphinan (9)

The title compound was obtained following the general procedure as a light yellow solid, in 60% yield. [α]$^{25}_D$ −145.47° (c=0.5, MeOH). Hydrochloride salt: $^1$H NMR (400 MHz, DMSO-d$_6$) δ 8.88 (brs, 1H), 8.76 (brs, 1H), 8.71 (d, J=8.16 Hz, 1H), 8.54 (brs, 1H), 7.80 (m, 1H), 6.74 (d, J=8.00 Hz, 1H), 6.66 (d, J=8.12 Hz, 1H), 4.87 (d, J=7.64 Hz, 1H), 4.08 (s, 3H), 3.88-3.70 (m, 2H), 3.36-3.32 (m, 2H), 3.12-3.05 (m, 2H), 2.87 (m, 1H), 2.47 (m, 2H), 2.02-1.89 (m, 1H), 1.74 (m, 1H), 1.62 (m, 1H), 1.46-1.35 (m, 2H), 1.09 (m, 1H), 0.68 (m, 1H), 0.60 (m, 1H), 0.52 (m, 1H), 0.42 (m, 1H); $^{13}$C NMR (100 MHz, DMSO-d$_6$) δ 162.95, 155.65, 153.65, 152.38, 142.15, 141.28, 129.68, 121.76, 120.60, 119.26, 117.97, 92.59, 89.91, 69.71, 61.45, 56.92, 56.69, 51.27, 46.49, 45.68, 29.52, 27.29, 23.58, 23.00, 21.18, 5.72, 5.10, 2.63. MS m/z found 478.6 (M+H)$^+$. IR (Diamond, cm$^{-1}$) $v_{max}$ 3068.3, 1655.7, 1525.6, 1503.5, 1319.4, 1255.5, 1125.2, 1032.1, 1006.7, 800.7. mp 225° C. dec.

17-Cyclopropylmethyl-3,14β-dihydroxy-4,5α-epoxy-6β-[2'-(pyridine-4"-yl)acetamido]morphinan (10)

The title compound was obtained following the general procedure as a yellow solid, in 44% yield. [α]$^{25}_D$ −15.30° (c=1.0, MeOH). $^1$H NMR (300 MHz, CDCl$_3$) δ 8.32 (d, J=5.1 Hz, 2H), 7.45 (d, J=7.5 Hz, 1H), 7.18 (d, J=5.1 Hz, 2H), 6.69 (d, J=8.1 Hz, 1H), 6.54 (d, J=7.8 Hz, 1H), 4.59 (d, J=7.2 Hz, 1H), 3.87 (m, 1H), 3.68 (d, J=15.0 Hz, 1H), 3.48 (d, J=15.6 Hz, 1H), 3.05 (m, 2H), 2.62 (m, 2H), 2.38 (d, J=6.0 Hz, 2H), 2.17 (d, J=6.9 Hz, 2H), 1.81 (m, 2H), 1.58-1.28 (m, 3H), 0.84 (m, 1H), 0.55 (d, J=8.1 Hz, 2H), 0.14 (d, J=4.5 Hz, 2H); $^{13}$C NMR (75 MHz, CD$_3$OD) δ 171.8, 150.1 (×2), 147.7, 143.7, 142.0, 132.5, 126.3 (×2), 125.3, 120.2, 118.7, 93.2, 71.8, 63.8, 60.3, 53.3, 49.0, 45.5, 43.2, 31.8, 31.4, 25.7, 23.7, 10.3, 4.7, 4.3. MS m/z found 462.3 (M+H)$^+$. IR (KBr, cm$^{-1}$) $v_{max}$ 3398.9, 3243.8, 3069.3, 1660.3, 1640.0, 1556.9, 1501.8, 1317.8, 1130.3. mp 210° C. dec. Anal. (C$_{27}$H$_{31}$N$_3$O$_4$.2HCl.2H$_2$O) C, H, N.

17-Cyclopropylmethyl-3,14β-dihydroxy-4,5α-epoxy-6β-[3'-(pyridine-4"-yl)propanamido]morphinan (11)

The title compound was obtained as a yellow solid, in 49% yield. [α]$^{25}_D$ −102.63° (c=1.5, MeOH). $^1$H NMR (400 MHz, CDCl$_3$) δ 8.47 (m, 2H), 7.14 (m, 3H), 6.71 (d, J=8.0 Hz, 1H), 6.53 (d, J=8.0 Hz, 1H), 4.30 (d, J=6.4 Hz, 1H), 3.84 (m, 1H), 3.07 (d, J=5.6 Hz, 1H), 3.00 (d, J=18.4 Hz, 1H), 2.94 (t, J=7.4 Hz, 2H), 2.58 (m, 2H), 2.48 (t, J=7.6 Hz, 2H), 2.35 (d, J=6.4 Hz, 2H), 2.11 (m, 2H), 1.69 (m, 1H), 1.61-1.54 (m, 2H), 1.43 (m, 2H), 0.86 (m, 1H), 0.52 (d, J=8.0 Hz, 2H), 0.12 (d, J=4.8 Hz, 2H); Hydrochloride salt: $^1$H NMR (400 MHz, DMSO-d$_6$) δ 9.36 (brs, 1H, exchangeable), 8.82 (brs, 1H, exchangeable), 8.55 (d, J=4.4 Hz, 2H), 8.22 (d, J=7.6 Hz, 1H, exchangeable), 7.44 (d, J=5.2 Hz, 2H), 6.72 (d, J=8.0 Hz, 1H), 6.63 (d, J=8.0 Hz, 1H), 6.17 (brs, 1H, exchangeable), 4.51 (d, J=8.0 Hz, 1H, C$_5$—H), 3.83 (m, 1H, C$_6$—H), 3.45-3.20 (m, 3H, buried in water peak), 3.10-2.97 (m, 2H), 2.91 (t, J=7.4 Hz, 2H), 2.84 (m, 1H), 2.48-2.32 (m, 4H), 1.64 (m, 2H), 1.44 (m, 2H), 1.32 (m, 1H), 1.06 (m, 1H), 0.67 (m, 1H), 0.58 (m, 1H), 0.50 (m, 1H), 0.40 (m, 1H); $^{13}$C NMR (100 MHz, DMSO-d$_6$) δ 170.44, 146.83 (×2), 141.92, 141.03, 139.0, 129.49, 124.73 (×2), 120.54, 119.26, 117.72, 89.72, 69.49, 61.46, 56.52, 50.44, 46.28, 45.41, 35.33, 30.30, 29.15, 27.14, 23.45, 22.81, 5.55, 5.03, 2.46. MS m/z found 476.4 (M+H)$^+$. IR (Diamond, cm$^{-1}$) $v_{max}$ 3065.4, 1652.1, 1556.5, 1501.4, 1463.3, 1319.1, 1159.8, 1128.6. mp 205° C. dec. Anal. (C$_{28}$H$_{33}$N$_3$O$_4$.2HCl.0.5H$_2$O) C, H, N.

17-Cyclopropylmethyl-3,14β-dihydroxy-4,5α-epoxy-6β-{2'-[(pyridine-4"-yl)carboxamido]acetamido}morphinan (12)

The title compound was obtained following the general procedure as a white solid, in 74% yield. [α]$^{25}_D$ −126.340 (c=1.0, MeOH). $^1$H NMR (300 MHz, CDCl$_3$) δ 8.55 (d, J=4.5 Hz, 2H), 8.41 (m, 1H, exchangeable), 7.74 (d, J=6.9 Hz, 1H, exchangeable), 7.64 (d, J=4.8 Hz, 2H), 6.67 (d, J=7.8 Hz, 1H), 6.53 (d, J=8.1 Hz, 1H), 4.57 (d, J=6.6 Hz, 1H), 4.28 (m, 1H), 4.08 (d, J=13.2 Hz, 1H), 3.82 (m, 1H), 3.03 (m, 2H), 2.58 (m, 2H), 2.35 (d, J=5.1 Hz, 2H), 2.11 (m, 2H), 1.89 (m, 1H), 1.60 (m, 2H), 1.37 (m, 2H), 0.81 (m, 1H), 0.52 (d, J=7.5 Hz, 2H), 0.11 (d, J=3.9 Hz, 2H); $^{13}$C NMR (75 MHz, CDCl$_3$) δ 169.5, 166.0, 150.2 (×2), 142.5, 140.7, 140.3, 131.3, 124.4, 121.5 (×2), 119.5, 117.8, 92.5, 70.5, 62.4, 59.3, 52.1, 47.8, 44.2, 43.6, 30.9, 30.2, 24.7, 22.8, 9.6, 4.2, 4.0. MS m/z found 505.7 (M+H)$^+$. IR (KBr, cm$^{-1}$) $v_{max}$ 3398.9, 1653.9, 1544.0, 1498.7, 1317.8, 1246.7, 1123.9. mp 215° C. dec. Anal. (C$_{28}$H$_{32}$N$_4$O$_5$.2HCl.3H$_2$O) C, H, N.

17-Cyclopropylmethyl-3,14β-dihydroxy-4,5α-epoxy-6β-[(2'-pyridazine) carboxamido]morphinan (13)

The title compound was prepared by following the general procedure in 68% yield. [α]$^{25}_D$ −150.27° (c=0.8, MeOH). Hydrochloride salt: $^1$H NMR (400 MHz, DMSO-d$_6$) δ 9.60 (dd, J=1.8 Hz, 1.2 Hz, 1H), 9.47 (dd, J=5.2 Hz, 1.2 Hz, 1H), 9.33 (d, J=8.0 Hz, 1H, exchangeable), 8.89 (brs, 1H, exchangeable), 8.08 (dd, J=5.6 Hz, 2.4 Hz, 1H), 6.73 (d, J=8.0 Hz, 1H), 6.66 (d, J=8.4 Hz, 1H), 6.25 (brs, 1H, exchangeable), 4.82 (d, J=7.6 Hz, 1H), 3.88 (d, J=4.8 Hz, 1H), 3.73 (m, 1H), 3.37 (m, 2H), 3.07 (m, 2H), 2.86 (m, 1H), 2.44 (m, 2H), 1.91 (m, 1H), 1.80 (m, 1H), 1.61 (m, 1H), 1.42 (m, 2H), 1.09 (m, 1H), 0.67 (m, 1H), 0.60 (m, 1H), 0.51 (m, 1H), 0.41 (m, 1H); $^{13}$C NMR (100 MHz, DMSO-d$_6$) δ 162.48, 152.09, 148.58, 141.92, 141.27, 130.96, 129.43, 124.03, 120.54, 119.34, 117.88, 89.43, 69.57, 64.79, 56.61, 51.45, 46.38, 45.53, 29.21, 27.21, 23.40, 22.93, 5.63, 5.02, 2.53. MS (ESI) m/z: 449.54 (M+H)$^+$. IR (Diamond, cm$^{-1}$) $v_{max}$: 3172.3, 3054.0, 1659.2, 1541.3, 1503.4, 1455.8, 1124.8, 1032.3, 1012.5, 919.0, 896.2. mp 213-216° C. dec. Anal. (C$_{25}$H$_{28}$N$_4$O$_4$.2HCl) C, H, N.

17-Cyclopropylmethyl-3,14β-dihydroxy-4,5α-epoxy-6β-[(2'-pyrimidine) carboxamido]morphinan (14)

The title compound was prepared by following the general procedure in 62% yield. $[\alpha]^{25}_D$ −190.45° (c=0.5, MeOH). Hydrochloride salt: $^1$H NMR (400 MHz, DMSO-$d_6$) δ 9.37 (s, 1H), 9.30 (d, J=8.8 Hz, 1H), 9.09 (d, J=4.8 Hz, 1H), 8.87 (brs, 1H), 8.0 (d, J=4.4 Hz, 1H), 6.68 (d, J=8.4 Hz, 1H), 6.66 (d, J=8.4 Hz, 1H), 6.25 (brs, 1H), 5.0 (d, J=7.6 Hz, 1H), 3.87 (d, J=4.8 Hz, 1H), 3.70 (m, 1H), 3.32 (m, 2H), 3.06 (m, 2H), 2.86 (m, 1H), 2.44 (m, 2H), 2.02 (m, 1H), 1.76 (d, J=14.0 Hz, 1H), 1.53 (m, 1H), 1.42 (m, 2H), 1.09 (m, 1H), 0.67 (m, 1H), 0.6 (m, 1H), 0.51 (m, 1H), 0.41 (m, 1H); $^{13}$C NMR (100 MHz, DMSO-$d_6$) δ 162.32, 159.67, 157.86, 156.36, 142.09, 141.32, 129.68, 120.59, 119.26, 118.60, 117.88, 89.59, 69.67, 64.88, 56.63, 51.15, 46.45, 45.59, 29.49, 27.27, 23.50, 23.01, 5.74, 5.13, 2.63. MS (ESI) m/z: 449.50 (M+H)$^+$. IR (Diamond, cm$^{-1}$)$\nu_{max}$ 3071.0, 1667.7, 1514.3, 1455.3, 1322.3, 1236.1, 1127.1, 1033.9, 986.3, 857.9, 664.0. mp 214-217° C. Anal. ($C_{25}H_{23}N_4O_4 \cdot 2HCl \cdot H_2O$) C, H, N.

17-Cyclopropylmethyl-3,14β-dihydroxy-4,5α-epoxy-6β-(1'-methylpiperidine-4'-carboxamido)morphinan (15)

The title compound was obtained following the general procedure as a light yellow solid, in 57% yield. $[\alpha]^{25}_D$ −88.06° (c=1.0, MeOH). $^1$H NMR (300 MHz, CDCl$_3$) δ 7.02 (d, J=8.4 Hz, 1H), 6.65 (d, J=8.1 Hz, 1H), 6.51 (d, J=8.1 Hz, 1H), 4.47 (d, J=6.3 Hz, 1H), 3.86 (m, 1H), 3.11 (d, J=5.7 Hz, 1H), 3.06 (d, J=18.3 Hz, 1H), 2.96-2.89 (m, 2H), 2.64-2.56 (m, 2H), 2.43-2.35 (m, 4H), 2.27-2.26 (m, 4H), 2.19-2.08 (m, 4H), 2.00 (m, 2H), 1.80 (m, 1H), 1.58 (d, J=10.5 Hz, 2H), 1.47 (d, J=8.7 Hz, 2H), 0.83 (m, 1H), 0.53 (d, J=7.2 Hz, 2H), 0.12 (d, J=4.5 Hz, 2H); $^{13}$C NMR (75 MHz, CDCl$_3$) δ 175.0, 143.7, 140.5, 130.8, 123.8, 119.0, 118.6, 91.8, 77.4, 70.3, 62.3, 59.4, 55.1, 50.6, 47.4, 46.1, 44.1, 42.6, 31.8, 29.3, 28.5, 28.4, 23.6, 22.7, 9.5, 4.2, 3.9. MS m/z found 468.6 (M+H)$^+$. IR (KBr, cm$^{-1}$) $\nu_{max}$ 3437.7, 1647.4, 1544.0, 1460.0, 1311.3, 1123.9. mp >250° C. Anal. ($C_{27}H_{37}N_3O_4 \cdot 2HCl \cdot 2.5H_2O$) C, H, N.

Biological Evaluation. Drugs.

Morphine sulfate was purchased from Mallinckrodt, St. Louis, Mo. Naloxone was purchased from Sigma-Aldrich (St. Louis, Mo.). All drugs and test compounds were dissolved in pyrogen-free isotonic saline (Baxter Healthcare, Deerfield, Ill.).

Animals.

Male Swiss-Webster mice (Harlan, Indianapolis, Ind.) weighing 25 to 30 g were housed six per cage in animal care quarters at 22±2° C. on a 12 h light/dark cycle. Food and water were available ad libitum. The mice were brought to a test room (22±2° C., 12 h light/dark cycle), marked for identification, and allowed 18 h to recover from transport and handling. Protocols and procedures were approved by the Institutional Animal Care and Use Committee at Virginia Commonwealth University Medical Center and comply with the recommendations of the International Association for the Study of Pain.

In Vitro Competitive Radioligand Binding and Functional Assay.

The radioligand binding assay and $^{35}$S-GTP[γS]-binding assay were conducted using monocloned opioid receptor expressed in Chinese hamster ovarian (CHO) cell lines as described previously.[65,66,78-81] [$^3$H]naloxone, [$^3$H]NTI, and [$^3$H]norBNI (or [$^3$H]DPN) were used to label the μ, δ, and κ opioid receptors, respectively. Aliquots of a membrane protein (30 μg) were incubated with the corresponding radioligand in the presence of different concentrations of the drug under investigation at 30° C. for 1 h. Specific (i.e., opioid receptor related) binding was determined as the difference in binding obtained in the absence and presence of 10 μM naltrexone. The potency of the drugs in displacing the specific binding of the radioligand was determined from data using linear regression analysis of Hill plots. The IC$_{50}$ values will then be determined and corrected to K$_i$ values using the Cheng-Prusoff equation. Functional assays were conducted in the same cell membranes used for the receptor binding assays. Membrane proteins (10 μg) were incubated with varying concentrations of drugs, GDP (μ: 10 μM; κ and δ: 20 μM) and 0.1 nM $^{35}$S-GTP[γS] in assay buffer for 2 h (μ) or 1.5 h (κ and δ) at 30° C. Nonspecific binding was determined with 10 μM unlabeled GTP[γS]. DAMGO (3 μM), U50,488H (5 μM), and SNC80 (5 μM) were included in the assay for a maximally effective concentration of a full agonist for the μ, κ, and δ opioid receptor, respectively.

In Vivo Assays. Tail Flick Test.

The warm-water tail flick test was performed according to Coderre and Rollman[82] using a water bath with the temperature maintained at 56±0.1° C. Before injecting, the baseline latency (control) of the mice was determined. Only mice with a reaction time from 2 to 4 s were used. The average baseline latency for the experiment was 3.0±0.1 s. The test latency after drug treatment was assessed at the appropriate time, and a 10 s maximum cutoff time was imposed to prevent tissue damage. Antinociception was quantified according to the method of Harris and Pierson[83] as the percentage of maximum possible effect (% MPE), which was calculated as: % MPE=[(test latency−control latency)/(10−control latency)]×100. Percent MPE was calculated for each mouse using at least six mice per drug.

Intestinal Motility Assay.

The GI transit assay was conducted as reported in the literature.[68,77] Briefly, each group of four or six mice received a subcutaneous (s.c.) injection of testing compound at different concentrations or saline at time zero. Five minutes later, morphine (2, or 10 mg/kg) was given subcutaneously. After twenty minutes, a forced meal of charcoal suspension was given via gavage. Thirty minutes following the meal, mice were euthanized and the small intestine was dissected. The distance traveled by the charcoal in the intestine was then measured and expressed as a percentage of the total length of the intestine, from pylorus to cecum.

Statistical Analysis.

One-way ANOVA followed by the post hoc "Dunnett" test were performed to assess significance using the Prism 3.0 software (GraphPad Software, San Diego, Calif.).

Pharmacokinetics. Bidirectional Transport of NAP, NMP, and NGP in Caco-2 Cells.

Caco-2 (passages 45-47; ATCC, Manassas, Va.) cell culture and bidirectional permeability studies with polyester Transwell filters were performed as described previously.[67] Briefly, cells were cultured in Dulbecco's modified Eagle's medium (9.6 g/L glucose) with 10%/fetal bovine serum and supplemented with 100 unit/mL penicillin, 100 μg/mL streptomycin, and 5% nonessential amino acids for 22 days after seeding on 12 mm 0.4 μm #3460 Transwell-Clear inserts (Fisher Scientific) at a density of 80,000 cells/cm$^2$. Drug solutions in Hank's balanced salt solution (buffered with 10 mM HEPES) were added to either the apical or basolateral chambers, with sampling from the receiver chambers up to 2 h. Acetonitrile (50 μL) was then added to the samples and centrifuged. A portion of the supernatants was analyzed by HPLC-UV using an Alltima HP C18 column (3 μm, 4.6×100 mm; Alltech, Deerfield, Ill.) at 270 nm for NAP, and a Microsorb-MV 100-3 C18 (4.6×100 mm; Varian) column for NMP or NGP at 266 nm. Analytes concentration was quantified from standard curves prepared in transport buffer-acetonitrile (4:1). Calibration curves for NAP, NMP, and NGP were all linear in the range of 0.01 to 100 μM ($R^2$=0.999). Apparent permeability was then calculated using the following equation: $P_{app}=J/(A \times C_i)$, where J is the transport rate, A is the surface area of the cell monolayer, and $C_i$ is the initial concentration of the dosing solution.

REFERENCES FOR EXAMPLE 7

(1) Manchikanti, L.; Singh, A. Therapeutic opioids: A ten-year perspective on the complexities and complications of the escalating use, abuse, and nonmedical use of opioids. *Pain Physician* 2008, 11, 863-888.
(2) Svendsen, K. B.; Andersen, S.; Amason, S.; Arner, S.; Breivik, H.; Heiskanen, T.; Kalso, E.; Kongsgaard, U. E.; Sjogren, P.; Strang, P.; Bach, F. W.; Jensen, T. S. Breakthrough pain in malignant and non-malignant diseases: a review of prevalence, characteristics and mechanisms. *Eur. J. Pain* 2005, 9, 195-206.
(3) Cohen, M. Z.; Easley, M. K.; Ellis, C.; Hughes, B.; Ownby, K.; Rashad, B. G.; Rude, M.; Taft, E.; Westbrooks, J. B. JCAHO. Cancer pain management and the JCAHO's pain standards: an institutional challenge. *J. Pain Symptom Manage.* 2003, 25, 519-527.
(4) McNicol, E.; Horowicz-Mehler, N.; Fisk, R. A.; Bennett, K.; Gialeli-Goudas, M.; Chew, P. W.; Lau, J.; Carr, D. Management of opioid side effects in cancer-related and chronic noncancer pain: a systematic review. *J. Pain* 2003, 4, 231-256.
(5) Candrilli, S. D.; Davis, K. L.; Iyer, S. Impact of constipation on opioid use patterns, health care resource utilization, and costs in cancer patients on opioid therapy. *J. Pain Palliat. Care Pharmacother.* 2009, 23, 231-241.
(6) Twycross, R. G.; Lack, S. A. *Symptom control in far advanced cancer: pain relief*; Pitman, London, 1983.
(7) Moore, R. A.; McQuay, H. J. Prevalence of opioid adverse events in chronic non-malignant pain: systematic review of randomised trials of oral opioids. *Arthritis Res. Ther.* 2005, 7, R1046-R1051.
(8) Allan, L.; Hays, H.; Jensen, N. -H.; de Waroux, B. L. P.; Bolt, M.; Donald, R.; Kalso, E. Randomised crossover trial of transdermal fentanyl and sustained release oral morphine for treating chronic non-cancer pain. *BMJ* 2001, 322, 1154-1158.
(9) Kalso, E.; Edwards, J. E.; Moore, R. A.; McQuay, H. J. Opioids in chronic non-cancer pain: systematic review of efficacy and safety. *Pain* 2004, 112, 372-380.
(10) Vainio, A.; Auvinen A. Prevalence of symptoms among patients with advanced cancer: an international collaborative study. *J. Pain Symptom Manage.* 1996, 12, 3-10.
(11) Cook, S. F.; Lanza, L.; Zhou, X.; Sweeney, C. T.; Goss, D.; Hollis, K.; Mangel, A. W.; Fehnel, S. E. Gastrointestinal side effects in chronic opioid users: results from a population-based survey. *Aliment Phmarmacol. Ther.* 2008, 27, 1224-1232.
(12) Bell, T. J.; Panchal, S. J.; Miaskowski, C.; Bolge, S. C.; Milanova, T.; Williamson, R. The prevalence, severity, and impact of opioid-induced bowel dysfunction: results of a US and European Patient Survey (PROBE 1). *Pain Med.* 2009, 10, 35-42.
(13) Sykes N. P. The relationship between opioid use and laxative use in terminally ill cancer patients. *Palliat. Med.* 1998, 12, 375-382.
(14) Ling, G. S. F.; Paul, D.; Simantov, R.; Pasternak, G. W. Differential development of acute tolerance to analgesia, respiratory depression, gastrointestinal transit and hormone release in a morphine infusion model. *Life Sci.* 1989, 45, 1627-1636.
(15) Manara, L.; Bianchi, G.; Ferretti, P.; Tavani, A. Inhibition of gastrointestinal transit by morphine in rats results primarily from direct drug action on gut opioid sites. *J. Pharmacol. Exp. Ther.* 1986, 237, 945-949.
(16) Tavani, A.; Bianchi, G.; Ferretti, P.; Manara, L. Morphine is most effective on gastrointestinal propulsion in rats by intraperitoneal route: evidence for local action. *Life Sci.* 1980, 27, 2211-2217.
(17) Shook, J. E.; Pelton, J. T.; Hruby, V. J.; Burks, T. F. Peptide opioid antagonist separates peripheral and central opioid antitransit effects. *J. Pharmacol. Exp. Ther.* 1987, 243, 492-500.
(18) Kolso, R. J.; Vaught, J. L.; Cowan, A.; Gmerek, D. E.; Porreca, F. Intrathecal morphine slows gastrointestinal transit in rat. *Eur. J. Pharmacol.* 1985, 119, 243-246.
(19) Galligan, J. J.; Burks, T. F. Centrally mediated inhibition of small intestinal transit and motility by morphine in the rat. *J. Pharmacol. Exp. Ther.* 1983, 226, 356-361.
(20) Stewart, J. J.; Weisbrodt, N. W.; Burks, T. F. Centrally mediated intestinal stimulation by morphine. *J. Pharmacol. Exp. Ther.* 1977, 202, 174-181.
(21) De Luca, A.; Coupar, I. M. Insights into opioid action in the intestinal tract. *Pharmacol. Ther.* 1996, 69, 103-115.
(22) Holzer, P. Treatment of opioid-induced gut dysfunction. *Expert Opin. Investig. Drugs* 2007, 16, 181-194.
(23) Fiocchi, R.; Bianchi, G.; Petrillo, P.; Tavani, A. Manara, L. Morphine inhibits gastrointestinal transit in the rat primarily by impairing propulsive activity of the small intestine. *Life Sci.* 1982, 31, 2221-2223.
(24) McKay, J. S.; Linaker, B. D.; Higgs, N. B.; Turnberg, L. A. Studies of the antisecretory activity of morphine in rabbit ileum in vitro. *Gastroenterol.* 1982, 82, 243-247.
(25) Warhust, G.; Smith, G.; Tonge, A.; Tumberg, L. Effects of morphine on net water absorption, mucosal adenylate cyclase activity and $PGE_2$ metabolism in rat intestine. *Eur. J. Pharmacol.* 1983, 86, 77-82.
(26) Pappagallo, M. Incidence, prevalence, and management of opioid bowel dysfunction. *Am. J. Surg.* 2001, 182, 11 S-18S.
(27) Hunt, R.; Fazekas, B.; Thoeme, D.; Brooksbank, M. A comparison of subcutaneous morphine and fentanyl in hospice cancer patients. *J. Pain Symptom Manage.* 1999, 18, 111-119.
(28) Haazen, L.; Noorduin, H.; Megens, A.; Meert, T. The constipation-inducing potential of morphine and transdermal fentanyl. *Eur. J. Pain* 1999, 3, 9-15.
(29) Ahmedzai, S.; Brooks, D. Transdermal fentanyl versus sustained-release oral morphine in cancer pain: preference, efficacy and quality of life. *J. Pain Symptom Manage.* 1997, 13, 254-261.
(30) Donner, B.; Zenz, M.; Tryba, M.; Strumpf, M. Direct conversion from oral morphine to transdermal fentanyl: a multicenter study in patients with cancer pain. *Pain* 1996, 64, 527-534.
(31) Bach, V.; Kamp-Jensen, M.; Jensen, N-H.; Eriksen, J. Buprenorphine and sustained release oral morphine-effect and side-effects in chronic use. *Pain Clinic.* 1991, 4, 87-93.
(32) Mercadante, S.; Casuccio, A.; Fulfaro, F.; Groff, L.; Boffi, R.; Villari, P.; Gebbia, V.; Ripamonti, C. Switching from morphine to methadone to improve analgesia and tolerability in cancer patients: a prospective study. *J. Clin. Oncol.* 2001, 19, 2898-2904.

(33) Tzschentke, T. M.; Christoph, T.; Kögel, B.; Schiene, K.; Hennies, H. H.; Englberger, W.; Haurand, M.; Jahnel, U.; Cremers, T. I.; Friderichs, E.; De Vry, J. (-)-(1R,2R)-3-(3-Dimethylamino-1-ethyl-2-methyl-propyl)-phenol hydrochloride (tapentadol HCl): a novel mu-opioid receptor agonist/norepinephrine reuptake inhibitor with broad-spectrum analgesic properties. *J. Pharmacol. Exp. Ther.* 2007, 323, 265-276.

(34) Vorsanger, G.; Xiang, J.; Biondi, D.; Upmalis, D.; Delfgaauw, J.; Allard, R.; Moskovitz, B. Post hoc analyses of data from a 90-day clinical trial evaluating the tolerability and efficacy of tapentadol immediate release and oxycodone immediate release for the relief of moderate to severe pain in elderly and nonelderly patients. *Pain Res. Manag.* 2011, 16, 245-251.

(35) Etropolski, M.; Kelly, K.; Okamoto, A.; Rauschkolb, C. Comparable efficacy and superior gastrointestinal tolerability (nausea, vomiting, constipation) of tapentadol compared with oxycodone hydrochloride. *Adv. Ther.* 2011, 28, 401-417.

(36) Sloots, C. E.; Rykx, A.; Cools, M.; Kerstens, R.; De Pauw, M. Efficacy and safety of prucalopride in patients with chronic noncancer pain suffering from opioid-induced constipation. *Dig. Dis. Sci.* 2010, 55, 2912-2921.

(37) Sucampo Pharmaceuticals, Inc. website. Available at: http://investor.sucampo.com/phoenix.zhtml?c=201197&p=irol-newsArticle&ID=1655607&highlight=lubiprostone. Accessed on Apr. 10, 2012.

(38) Wirz, S.; Wittmann, M.; Schenk, M.; Schroeck, A.; Schaefer, N.; Mueller, M.; Standop, J.; Kloecker, N.; Nadstawek, J. Gastrointestinal symptoms under opioid therapy: a prospective comparison of oral sustained-release hydromorphone, transdermal fentanyl, and transdermal buprenorphine. *Eur. J. Pain* 2009, 13, 737-743.

(39) Jeong, I. D.; Camilleri, M.; Shin, A.; Iturrino, J.; Boldingh, A.; Busciglio, I.; Burton, D.; Ryks, M.; Rhoten, D.; Zinsmeister, A. R. A randomised, placebo-controlled trial comparing the effects of tapentadol and oxycodone on gastrointestinal and colonic transit in healthy humans. *Aliment. Pharmacol. Ther*. [Online early access]. DOI: 10.1111/j.1365-2036.2012.05040.x. Publised Online: Feb. 21, 2012.

(40) Wong, B. S.; Camilleri, M. Lubiprostone for the treatment of opioid-induced bowel dysfunction. *Expert Opin. Pharmacother.* 2011, 12, 983-990.

(41) Peng, X.; Knapp, B. I.; Bidlack, J. M.; Neumeyer, J. L. Pharmacological properties of bivalent ligands containing butorphan linked to nalbuphine, naltrexone, and naloxone at μ, δ, and κ opioid receptors. *J. Med. Chem.* 2007, 50, 2254-2258.

(42) Handal, K. A.; Schauben, J. L.; Salamone, F. R. Naloxone. *Ann. Emerg. Med.* 1983, 12, 438-445.

(43) Liu, M.; Wittbrodt, E. Low-dose oral naloxone reverses opioid-induced constipation and analgesia. *J. Pain Symptom Manage.* 2002, 23, 48-53.

(44) Meissner, W.; Schmidt, U.; Hartmann, M.; Kath, R.; Reinhart, K. Oral naloxone reverses opioid-induced constipation. *Pain* 2000, 84, 105-109.

(45) Sykes, N. P. An investigation of the ability of oral naloxone to correct opioid-related constipation in patients with advanced cancer. *Palliat. Med.* 1996, 10, 135-144.

(46) Culpepper-Morgan, J. A.; Inturrisi, C. E.; Portenoy, R. K.; Foley, K.; Houde, R. W.; Marsh, F.; Kreek, M. J. Treatment of opioid-induced constipation with oral naloxone: a pilot study. *Clin. Pharmacol. Ther.* 1992, 52, 90-95.

(47) Ahmedzai, S. H.; Nauck, F.; Bar-Sela, G.; Bosse, B.; Leyendecker, P.; Hopp, M. A randomized, double-blind, active-controlled, double-dummy, parallel-group study to determine the safety and efficacy of oxycodone/naloxone prolonged-release tablets in patients with moderate/severe, chronic cancer pain. *Pallial. Med.* 2012, 26, 50-60.

(48) Löwenstein, O.; Leyendecker, P.; Lux, E. A.; Blagden, M.; Simpson, K. H.; Hopp, M.; Bosse, B.; Reimer, K. Efficacy and safety of combined prolonged-release oxycodone and naloxone in the management of moderate/severe chronic non-malignant pain: results of a prospectively designed pooled analysis of two randomised, double-blind clinical trials. *BMC Clin. Pharmacol.* 2010, 10:12.

(49) Holzer, P. Opioid antagonists for prevention and treatment of opioid-induced gastrointestinal effects. *Curr. Opin. Anaesthesiol.* 2010, 23, 616-622.

(50) Mueller-Lissner, S. Fixed combination of oxycodone with naloxone: a new way to prevent and treat opioid-induced constipation. *Adv. Ther.* 2010, 27, 581-590.

(51) Yuan, C. S. Clinical status of methylnaltrexone, a new agent to prevent and manage opioid-induced side effects. *J. Support. Oncol.* 2004, 2, 111-122.

(52) Relistor [package insert], Wyeth Pharmaceuticals Inc and Progenies Pharmaceuticals, Philadelphia, Pa., and Tarrytown, N.Y., 2009.

(53) FDA. Drug approval package: Relistor (methylnaltrexone bromide) subcutaneous injection. Apr. 24, 2008. Available at: http://tinyurl.com/2uby2uf. Accessed Apr. 14, 2012.

(54) Thomas, J.; Karver, S.; Cooney, G. A.; Chamberlain, B. H.; Watt, C. K.; Slatkin, N. E.; Stambler, N.; Kremer, A. B.; Israel, R. J. Methylnaltrexone for opioid-induced constipation in advanced illness. *N. Engl. J. Med.* 2008, 358, 2332-2343.

(55) Slatkin, N.; Thomas, J.; Lipman, A. G.; Wilson, G.; Boatwright, M. L.; Wellman, C.; Zhukovsky, D. S.; Stephenson, R.; Portenoy, R.; Stambler, N.; Israel, R. Methylnaltrexone for opioid-induced constipation in advanced illness patients. *J. Support. Oncol.* 2009, 7, 39-46.

(56) Jansen, J. P.; Lorch, D.; Langan, J.; Lasko, B.; Hermanns, K.; Kleoudis, C. S.; Snidow, J. W.; Pierce, A.; Wurzelmann, J.; Mortensen, E. R. A randomized, placebo-controlled phase 3 trial (Study SB-767905/012) of alvimopan for opioid-induced bowel dysfunction in patients with non-cancer pain. *J. Pain* 2011, 12, 185-193.

(57) Irving, G.; Penzes, J.; Ramjattan, B.; Cousins, M.; Rauck, R.; Spierings, E. L.; Kleoudis, C. S.; Snidow, J. W.; Pierce, A.; Wurzelmann, J.; Mortensen, E. R. A randomized, placebo-controlled phase 3 trial (Study SB-767905/013) of alvimopan for opioid-induced bowel dysfunction in patients with non-cancer pain. *J. Pain* 2011, 12, 175-184.

(58) Webster, L.; Jansen, J. P.; Peppin, J.; Lasko, B.; Irving, G.; Morlion, B.; Snidow, J.; Pierce, A.; Mortensen, E.; Kleoudis, C.; Carter, E. Alvimopan, a peripherally acting mu-opioid receptor (PAM-OR) antagonist for the treatment of opioid-induced bowel dysfunction: results from a randomized, double-blind, placebo-controlled, dose-finding study in subjects taking opioids for chronic non-cancer pain. *Pain* 2008, 137, 428-440.

(59) Paulson, D. M.; Kennedy, D. T.; Donovick, R. A.; Carpenter, R. L.; Cherubini, M.; Techner, L.; Du, W.; Ma, Y.; Schmidt, W. K.; Wallin, B.; Jackson, D. Alvimopan: an oral, peripherally acting, mu-opioid receptor antagonist for the treatment of opioid-induced bowel dysfunction—a 21-day treatment-randomized clinical trial. *J. Pain,* 2005, 6, 184-192.
(60) Bream-Rouwenhorst, H. R.; Cantrell, M. A. Alvimopan for postoperative ileus. *Am. J. Health-Syst. Pharm.* 2009, 66, 1267-1277.
(61) http://clinicaltrials.gov. Key words: OIC. Accessed on Apr. 14, 2012.
(62) Diego, L.; Atayee, R.; Helmons, P.; Hsiao, G.; von Gunten, C. F. Novel opioid antagonists for opioid-induced bowel dysfunction. *Expert Opin. Investig. Drugs* 2011, 20, 1047-1056.
(63) AISK 37, Alkermes website. Available at: http://investor.alkermes.com/phoenix.zhtml?c=92211 &p=irol-newsArticle&ID=1561623&highlight=. Accessed on Apr. 14, 2012.
(64) Yancey-Wrona, J.; Dallaire, B.; Bilsky, E.; Bath, B.; Burkart, J.; Webster, L.; Magiera, D.; Yang, X.; Phelps, M.; Sadee, W. 6β-Naltrexol, a peripherally selective opioid antagonist that inhibits morphine-induced slowing of gastrointestinal transit: an exploratory study. *Pain Med.* 2011, 12, 1727-1737.
(65) Li, G.; Aschenbach, L. C.; Chen, J.-Y.; Cassidy, M. P.; Stevens, D. L.; Gabra, B. H.; Selley, D. E.; Dewey, W. L.; Westkaemper, R. B.; Zhang, Y. Design, synthesis, and biological evaluation of 6α- and 6β-N-heterocyclic substituted naltrexamine derivatives as p opioid receptor selective antagonists. *J. Med. Chem.* 2009, 52, 1416-1427.
(66) Yuan, Y.; Li, G.; He, H.-J; Stevens, D. L.; Kozak, P.; Scoggins, K. L.; Mitra, P.; Gerk, P. M.; Selley, D. E.; Dewey, W. L.; Zhang, Y. Characterization of 6α- and 6β-N-heterocyclic substituted naltrexamine derivatives as novel leads to development of mu opioid receptor selective antagonists. *ACS Chem. Neurosci.* 2011, 2, 346-351.
(67) Mitra, P.; Venitz, J.; Yuan, Y.; Zhang, Y.; Gerk, P. M. Preclinical disposition (in vitro) of novel μ-opioid receptor selective antagonists. *Drug Metab. Dispos.* 2011, 39, 1589-1596.
(68) Yuan, Y.; Stevens, D. L.; Braithwaite, A.; Scoggins, K. L.; Bilsky, E.; Akbarali, H. I.; Dewey, W. L.; Zhang, Y. 6β-N-Heterocyclic substituted naltrexamine derivative as potential lead to develop peripheral mu opioid receptor selective antagonists. *Bioorg. Med. Chem. Lett.* 2012, 22, 4731-4734.
(69) Yuan, Y.; Elbegdorj, O.; Chen, J.; Akubathini, S. K.; Beletskaya, I. O.; Selley, D. E.; Zhang, Y. Structure selectivity relationship studies of 17-cyclopropylmethyl-3,14β-dihydroxy-4,5α-epoxy-6β-[(4'-pyridyl)carboxamido]morphinan derivatives toward the development of the mu opioid receptor antagonists. *Bioorg. Med. Chem. Lett.* 2011, 21, 5625-5629.
(70) Sayre, L. M.; Portoghese, P. S. Stereospecific synthesis of the 6α- and 6β-amino derivatives of naltrexone and oxymorphone. *J. Org. Chem.* 1980, 45, 3366-3368.
(71) Magnan, J.; Paterson, S. J.; Tavani, A.; Kosterlitz, H. W. The binding spectrum of narcotic analgesic drugs with different agonist and antagonist properties. *Naunyn-Schmiedebergs Arch. Pharmacol.* 1982, 319, 197-205.
(72) Zimmerman, D. M.; Gidda, J. S.; Cantrell, B. E.; Schoepp, D. D.; Johnson, B. G.; Leander,
J. D. Discovery of a potent, peripherally selective trans-3,4-dimethyl-4-(3-hydroxyphenyl)piperidine opioid antagonist for the treatment of gastrointestinal motility disorders. *J. Med. Chem.* 1994, 37, 2262-2265.
(73) Spealman, R. D.; Bergman, J. Modulation of the discriminative stimulus effects of cocaine by mu and kappa opioids. *J. Pharmacol. Exp. Ther.* 1992, 261, 607-615.
(74) Rapaka, R. S.; Porreca, F. Development of delta opioid peptides as nonaddicting analgesics. *Pharm. Res.* 1991, 8, 1-8.
(75) Esmaeili-Mahani, S.; Javan, M.; Motamedi, F.; Ahmadiani, A. Post-adrenalectomy changes in the gene expression of specific G-protein subunits involved in morphine sensitization. *Neuropeptides* 2008, 42, 169-175.
(76) Fukuda, H.; Suenaga, K.; Tsuchida, D.; Mantyh, C. R.; Pappas, T. N.; Hicks, G. A.; Dehaven-Hudkins, D. L.; Takahashi, T. The selective mu opioid receptor antagonist, alvimopan, improves delayed GI transit of postoperative ileus in rats. *Brain Res.* 2006, 1102, 63-70.
(77) Ross, G. R.; Gabra, B. H.; Dewey, W. L.; Akbarali, H. I. Morphine Tolerance in the Mouse Ileum and Colon. *J. Pharmacol. Exp. Ther.* 2008, 327, 561-572.
(78) Smith, C. F.; Waldron, C.; Brook, N. A. Opioid receptors in the mouse ileum. *Arch. Int. Pharmacodyn. Ther.* 1988, 291, 122-131.
(79) Bonner, G.; Meng, F.; Akil, H. Selectivity of mu-opioid receptor determined by interfacial residues near the third extracellular loop. *Eur. J. Pharmacol.* 2000, 403, 37-44.
(80) Zhu, J.; Xue, J.-C.; Law, P.-Y.; Claude, P. A.; Luo, L.-Y.; Yin, J.; Chen, C.; Liu-Chen, L.-Y. The region in the mu opioid receptor conferring selectivity for sufentanil over the delta receptor is different from that over the kappa receptor. *FEBS Lett.* 1996, 384, 198-202.
(81) Thompson, C. M.; Wojno, H.; Greiner, E.; May, E. L.; Rice, K. C.; Selley, D. E. Activation of G-proteins by morphine and codeine congeners: insights to the relevance of O- and N-demethylated metabolites at mu- and delta-opioid receptors. *J. Pharmacol. Exp. Ther.* 2004, 308, 547-554.
(82) Coderre, T. J.; Rollman, G. B. Naloxone hyperalgesia and stress-induced analgesia in rats. *Life Sci.* 1983, 32, 2139-2146.
(83) Harris, L. S.; Pierson, A. K. Some narcotic antagonists in the benzomorphan series. *J. Pharmacol. Exp. Ther.* 1964, 143, 141-148.

EXAMPLE 8

17-N and 1'-N-methylation Products of NAP and NMP

Figure 30:
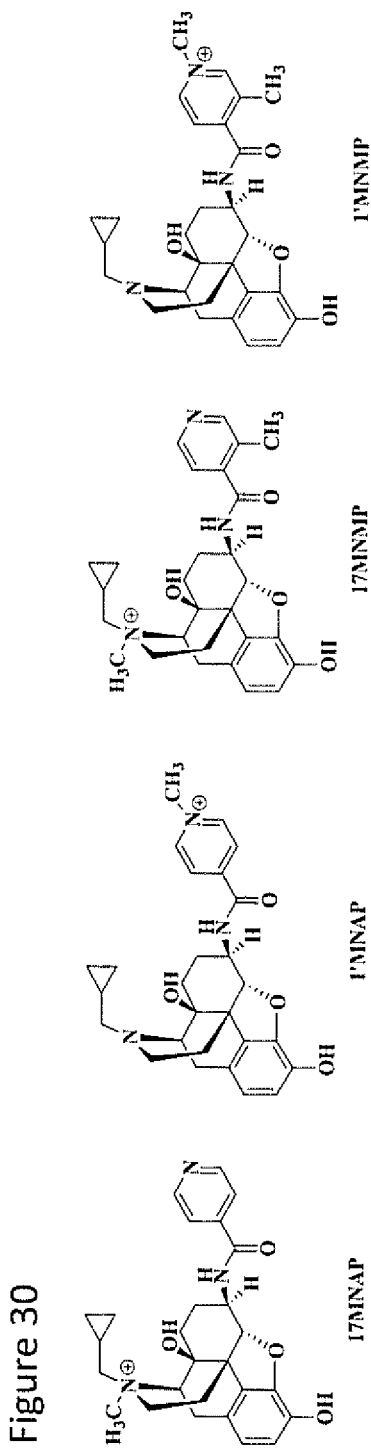
FIG. 30 are exemplary designed methylation products of NAP and NMP.
Figure 31:
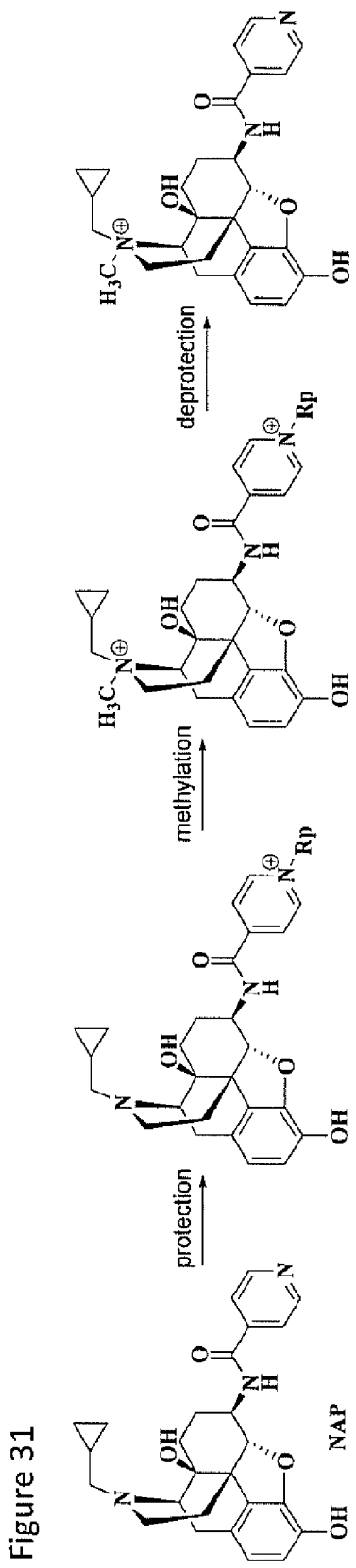
FIG. 31 is a schematic showing an example of protection of the 1'-N-position to achieve 17-N-position methylation of NAP.

Based on the well-known properties of methylnaltrexone (MNTX), conversion of these two leads into their quaternary amine derivatives may increase their polarity, lower lipophilicity, and therefore reinforce their peripheral selectivity to produce more promising drug candidates. Examples of methylated drug candidates include but are not limited to those shown in FIG. 30. These methylation products may be through direct methylation methods on the 17-position or 1'-position. Methylation conditions may vary and could involve use of acetone, methanol, or DMF as a solvent together with a methylation reagent such as methyl iodide. Reactions may occur at 0 C or room temperature using refluxing procedures or sealed tube procedures. FIG. 31 illustrates an exemplary methylation procedure for methylation at the 17-N position. In particular, the 1'-N position is first protected with a proper protection group (Rp) such as borane, carbamate, and triethylborane. Then, methylation can be conducted on the 17-N-position before removing the protecting group. These new agents are highly mu opioid receptor selective compared to other current existing drugs for the same purpose. Also they are highly peripheral system selective with no observable side effects. Thus, they will be useful in the treatment of OIC and other medical conditions (e.g., drug or alcohol addiction).

EXAMPLE 9

1'BNAP AND 17 BNAP

Additional products showing charged and uncharged moieties at the 17 position and at the 1 position on the heteroaromatic ring can be prepared as follows:

0.119 g of NAP (0.229 mmol) was dissolved in 36 ml of acetone so as to obtain a homogeneous solution. To this was added 0.15 mL of Benzyl Bromide (1.26 mmol). The solution was allowed to stir at room temperature under nitrogen for 4 days. After stirring for 4 days the resulting precipitate was collected and dried under vacuum. The filtrate was then concentrated down to one third its volume and allowed to stir for an additional 24 hours and the precipitate collected to produce a second crop. The combined mass was 0.101 g. (70% yield)

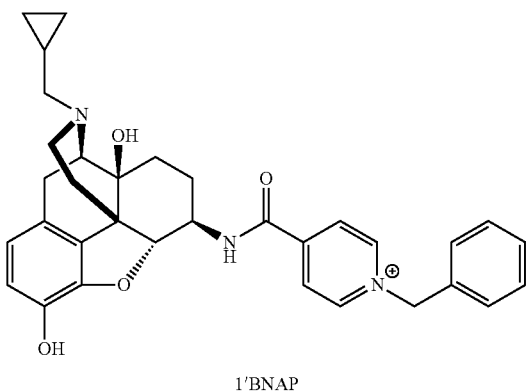

1'BNAP

Similar methods can be applied to prepare the compound below:

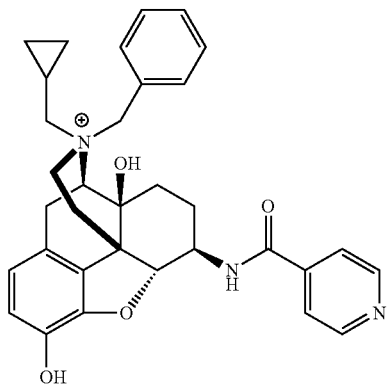

EXA < 17BNAP

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

---

We claim:

1. A selective, non-peptide MOR antagonist of the general formula

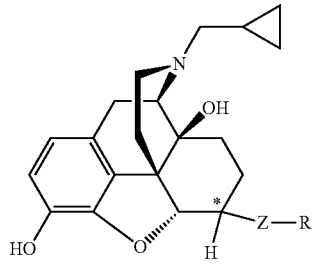

wherein the MOR antagonist may be a racemic mixture or a purified racemate;

the nitrogen (N) at the 17N position may be charged and substituted with a C1-10 aryl or alkaryl, or may be uncharged and unsubstituted;

Z is selected from the group consisting of a substituted or unsubstituted aliphatic moiety; NH; CO; (NHCO)n where n=1-5; (CONH)n where n=1-5; (NHCO)(CH$_2$)n(NHCO), where n=1-5; (NHCO)(CH$_2$)n where n=1-5; (CH$_2$)n(NHCO), where n=1-5; and O;

R is selected from the group consisting of substituted and unsubstituted heteroaromatic rings including without limitation

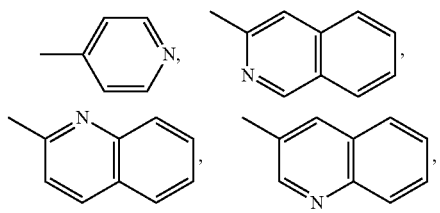

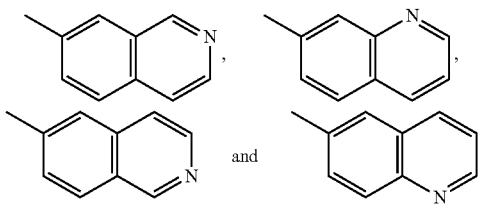

wherein any carbon of said heteroaromatic ring may be bonded to a hydrogen or be substituted with a substitution selected from the group consisting of substituted or unsubstituted C1-5 alkyl, C1-5 alyleether, carboxylic acid, nitrogen, cyano, nitro, halogen, or amino moiety, and where the substitution may be the same or different when more than one carbon is substituted, wherein the nitrogen in the heteroarmatic ring may be charged and substituted with a C-10 alkyl or alkaryl, or be uncharged and unsubstituted; and wherein in addition to the nitrogen substitution in said heteroaromatic ring, one or more carbons within said heteroaromatic ring may be replaced by a substitution selected from the group consisting of N, S, P, and O.

2. The selective, non-peptide MOR antagonist of claim 1 wherein said non-peptide MOR antagonist is represented by the formula

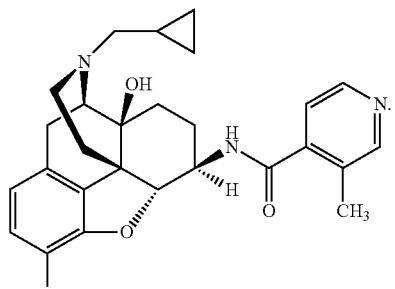

NMP

3. The selective, non-peptide MOR antagonist of claim 1 wherein said non-peptide MOR antagonist is represented by the formula

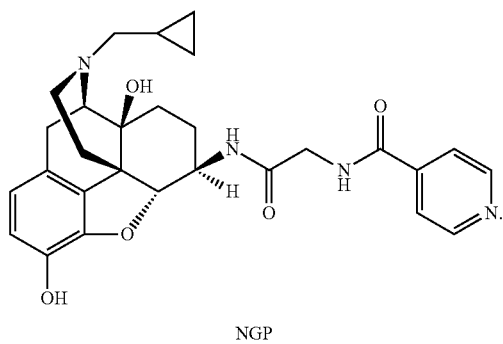

NGP

4. The selective, non-peptide MOR antagonist of claim 1 wherein said non-peptide MOR antagonist is represented by the formula

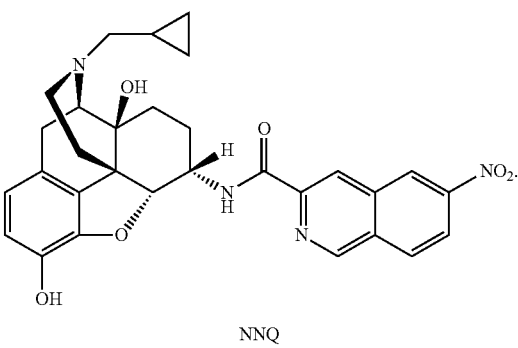

NNQ

5. The selective, non-peptide MOR antagonist of claim 1 wherein said non-peptide MOR antagonist is represented by the formula

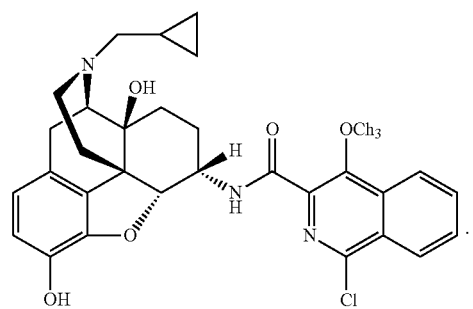

NCQ

6. The selective, non-peptide MOR antagonist of claim 1 wherein said non-peptide MOR antagonist is represented by the formula selected from the group consisting of:

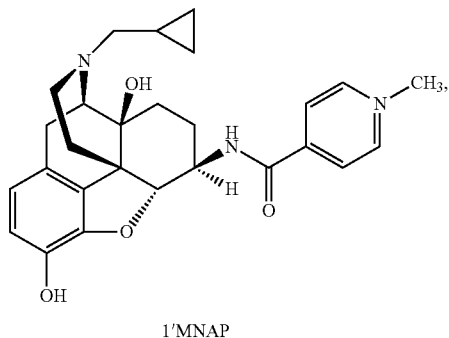

1'MNAP

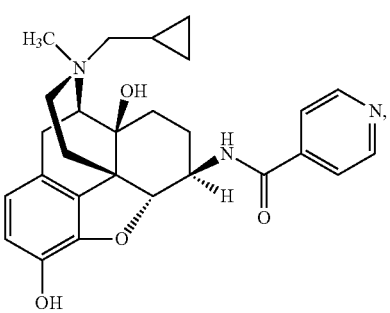

17MNAP

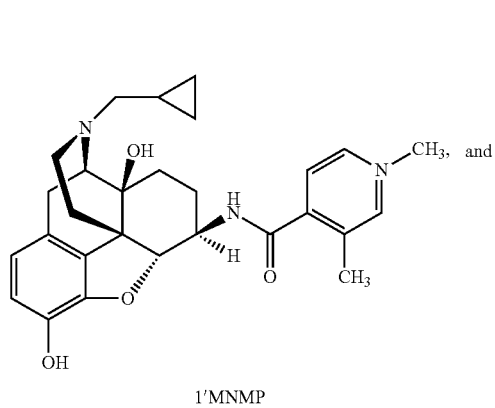

1'MNMP

7. The selective, non-peptide MOR antagonist of claim 1 wherein said non-peptide MOR antagonist is represented by the formula selected from the group consisting of:

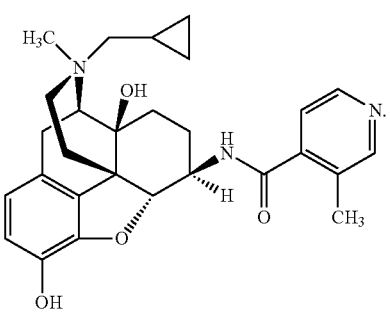

17MNMP

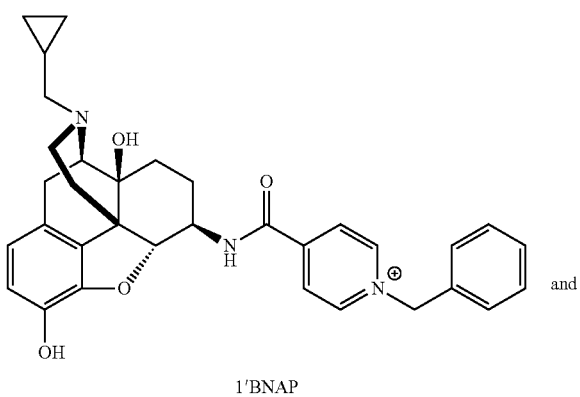

1'BNAP

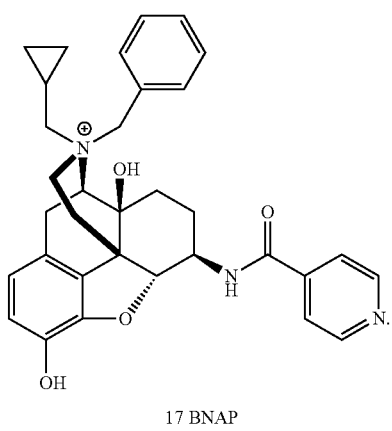

17 BNAP

8. The selective, non-peptide MOR antagonist of claim 1, wherein said non-peptide MOR antagonist is selected from the group consisting of
17-Cyclopropylmethyl-3,14β-dihydroxy-4,5α-epoxy-6β-{[4'-(2'-chloropyridyl)]carboxamido}morphinan;
17-Cyclopropylmethyl-3,14β-dihydroxy-4,5α-epoxy-6β-{[4'-(2'-bromopyridyl)]carboxamido}morphinan;
17-Cyclopropylmethyl-3,14β-dihydroxy-4,5α-epoxy-6β-{[4'-(2'-cyanopyridyl)]carboxamido}morphinan;
17-Cyclopropylmethyl-3,14β-dihydroxy-4,5α-epoxy-6β-{[4'-(2'-methylpyridyl)]carboxamido}morphinan;
17-Cyclopropylmethyl-3,14β-dihydroxy-4,5α-epoxy-6β-{[4'-(2'-methoxypyridyl)]carboxamido}morphinan;
17-Cyclopropylmethyl-3,14β-dihydroxy-4,5α-epoxy-6β-{[4'-(3'-chloropyridyl)]carboxamido}morphinan;
17-Cyclopropylmethyl-3,14β-dihydroxy-4,5α-epoxy-6β-{[4'-(3'-bromopyridyl)]carboxamido}morphinan;
17-Cyclopropylmethyl-3,14β-dihydroxy-4,5α-epoxy-6β-{[4'-(3'-methylpyridyl)]carboxamido}morphinan;
17-Cyclopropylmethyl-3,14β-dihydroxy-4,5α-epoxy-6β-{[4'-(3'-methoxylpyridyl)]carboxamido}morphinan;
17-Cyclopropylmethyl-3,14β-dihydroxy-4,5α-epoxy-6β-[2'-(pyridine-4"-yl)acetamido]morphinan;
17-Cyclopropylmethyl-3,14β-dihydroxy-4,5α-epoxy-6β-[3'-(pyridine-4"-yl)propanamido]morphinan;
17-Cyclopropylmethyl-3,14β-dihydroxy-4,5α-epoxy-6β-{2'-[(pyridine-4"-yl)carboxamido]acetamido}morphinan;
17-Cyclopropylmethyl-3,14β-dihydroxy-4,5α-epoxy-6β-[(2'-pyridazine) carboxamido]morphinan;
17-Cyclopropylmethyl-3,14β-dihydroxy-4,5α-epoxy-6β-[(2'-pyrimidine)carboxamido]morphinan; and
17-Cyclopropylmethyl-3,14β-dihydroxy-4,5α-epoxy-6β-(1'-methylpiperidine-4'-carboxamido)morphinan.

9. The selective, non-peptide MOR antagonist of claim 1, wherein said non-peptide MOR antagonist is selected from the group consisting of
17-Cyclopropylmethyl-3,14β-dihydroxy-4,5α-epoxy-6α-[2-(isoquinolin-3-yl)acetamido)morphinan;
17-Cyclopropylmethyl-3,14β-dihydroxy-4,5α-epoxy-6α-[3-(isoquinolin-3-yl)propanamido)morphinan;
17-Cyclopropylmethyl-3,14β-dihydroxy-4,5α-epoxy-6α-[2-(isoquinoline-3-carboxamido)acetamido}morphinan;
17-Cyclopropylmethyl-3,14β-dihydroxy-4,5α-epoxy-6α-(1-chloro-4-methoxyisoquinoline-3-carboxamido)morphinan;
17-Cyclopropylmethyl-3,14β-dihydroxy-4,5α-epoxy-6α-(1-chloro-4-hydroxyisoquinoline-3-carboxamido)morphinan;
17-Cyclopropylmethyl-3,14β-dihydroxy-4,5α-epoxy-6α-(4-hydroxyisoquinoline-3-carboxamido) morphinan;
17-Cyclopropylmethyl-3,14β-dihydroxy-4,5α-epoxy-6α-(4-quinazoline-2-carboxamido)morphinan;
17-Cyclopropylmethyl-3,14β-dihydroxy-4,5α-epoxy-6α-(1-chloroisoquinoline-3-carboxamido)morphinan;
17-Cyclopropylmethyl-3,14β-dihydroxy-4,5α-epoxy-6α-(1-cyanoisoquinoline-3-carboxamido)morphinan;
17-Cyclopropylmethyl-3,14β-dihydroxy-4,5α-epoxy-6α-(1-methylisoquinolin-3-carboxamido)morphinan;
17-Cyclopropylmethyl-3,14β-dihydroxy-4,5α-epoxy-6α-(6-nitroisoquinoline-3-carboxamido)morphinan;
17-Cyclopropylmethyl-3,14β-dihydroxy-4,5α-epoxy-6α-(7-nitroisoquinoline-3-carboxamido)morphinan;
17-Cyclopropylmethyl-3,14β-dihydroxy-4,5α-epoxy-6α-(7-dimethylaminoisoquinoline-3-carboxamido)morphinan;
17-Cyclopropylmethyl-3,14β-dihydroxy-4,5α-epoxy-6α-(6,7-dimethoxyisoquinoine-3-carboxamido)morphinan;
17-Cyclopropylmethyl-3,14β-dihydroxy-4,5α-epoxy-6α-[(S)-(2-methyl-1,2,3,4-tetrahydroisoquinoline-3-carboxamido)]morphinan; and
17-Cyclopropylmethyl-3,14β-dihydroxy-4,5α-epoxy-6α-(7-dimethylamino-2-methyl-1,2,3,4-tetrahydroisoquinoline-3-carboxamido)morphinan.

10. A method of testing whether or not a candidate compound is a MOR agonist or antagonist, comprising the step of conducting competitive inhibition tests between a radiolabeled MOR agonist and said candidate compound selected from the group consisting of:
17-Cyclopropylmethyl-3,14β-dihydroxy-4,5α-epoxy-6β-{[4'-(2'-chloropyridyl)]carboxamido}morphinan;
17-Cyclopropylmethyl-3,14β-dihydroxy-4,5α-epoxy-6β-{[4'-(2'-bromopyridyl)]carboxamido}morphinan;
17-Cyclopropylmethyl-3,14β-dihydroxy-4,5α-epoxy-6β-{[4'-(2'-cyanopyridyl)]carboxamido}morphinan;
17-Cyclopropylmethyl-3,14β-dihydroxy-4,5α-epoxy-6β-{[4'-(2'-methylpyridyl)]carboxamido}morphinan;
17-Cyclopropylmethyl-3,14β-dihydroxy-4,5α-epoxy-6β-{[4'-(2'-methoxypyridyl)]carboxamido}morphinan;
17-Cyclopropylmethyl-3,14β-dihydroxy-4,5α-epoxy-6β-{[4'-(3'-chloropyridyl)]carboxamido}morphinan;
17-Cyclopropylmethyl-3,14β-dihydroxy-4,5α-epoxy-6β-{[4'-(3'-bromopyridyl)]carboxamido}morphinan;
17-Cyclopropylmethyl-3,14β-dihydroxy-4,5α-epoxy-6β-{[4'-(3'-methylpyridyl)]carboxamido}morphinan;

17-Cyclopropylmethyl-3,14β-dihydroxy-4,5α-epoxy-6β-{[4'-(3'-methoxylpyridyl)]carboxamido}morphinan;

17-Cyclopropylmethyl-3,14β-dihydroxy-4,5α-epoxy-6β-[2'-(pyridine-4"-yl)acetamido]morphinan;

17-Cyclopropylmethyl-3,14β-dihydroxy-4,5α-epoxy-6β-[3'-(pyridine-4"-yl)propanamido]morphinan;

17-Cyclopropylmethyl-3,14β-dihydroxy-4,5α-epoxy-6β-{2'-[(pyridine-4"-yl)carboxamido]acetamido}morphinan;

17-Cyclopropylmethyl-3,14β-dihydroxy-4,5α-epoxy-6β-[(2'-pyridazine)carboxamido]morphinan;

17-Cyclopropylmethyl-3,14β-dihydroxy-4,5α-epoxy-6β-[(2'-pyrimidine)carboxamido]morphinan;

17-Cyclopropylmethyl-3,14β-dihydroxy-4,5α-epoxy-6β-(1'-methylpiperidine-4'-carboxamido)morphinan;

17-Cyclopropylmethyl-3,14β-dihydroxy-4,5α-epoxy-6α-[2-(isoquinolin-3-yl)acetamido]morphinan;

17-Cyclopropylmethyl-3,14β-dihydroxy-4,5α-epoxy-6α-[3-(isoquinolin-3-yl)propanamido]morphinan;

17-Cyclopropylmethyl-3,14β-dihydroxy-4,5α-epoxy-6α-[2-(isoquinoline-3-carboxamido)acetamido]morphinan;

17-Cyclopropylmethyl-3,14β-dihydroxy-4,5α-epoxy-6α-(1-chloro-4-methoxyisoquinoline-3-carboxamido)morphinan;

17-Cyclopropylmethyl-3,14β-dihydroxy-4,5α-epoxy-6α-(1-chloro-4-hydroxyisoquinoline-3-carboxamido)morphinan;

17-Cyclopropylmethyl-3,14β-dihydroxy-4,5α-epoxy-6α-(4-hydroxyisoquinoline-3-carboxamido)morphinan;

17-Cyclopropylmethyl-3,4β-dihydroxy-4,5α-epoxy-6α-(4-quinazoline-2-carboxamido)morphinan;

17-Cyclopropylmethyl-3,14β-dihydroxy-4,5α-epoxy-6α-(1-chloroisoquinoline-3-carboxamido)morphinan;

17-Cyclopropylmethyl-3,14β-dihydroxy-4,5α-epoxy-6α-(1-cyanoisoquinoline-3-carboxamido)morphinan;

17-Cyclopropylmethyl-3,14β-dihydroxy-4,5α-epoxy-6α-(1-methylisoquinolin-3-carboxamido)morphinan;

17-Cyclopropylmethyl-3,14β-dihydroxy-4,5α-epoxy-6α-(6-nitroisoquinoline-3-carboxamido)morphinan;

17-Cyclopropylmethyl-3,14β-dihydroxy-4,5α-epoxy-6α-(7-nitroisoquinoline-3-carboxamido)morphinan;

17-Cyclopropylmethyl-3,14β-dihydroxy-4,5α-epoxy-6α-(7-dimethylaminoisoquinoline-3-carboxamido)morphinan;

17-Cyclopropylmethyl-3,14β-dihydroxy-4,5α-epoxy-6α-(6,7-dimethoxyisoquinoline-3-carboxamido)morphinan;

17-Cyclopropylmethyl-3,14β-dihydroxy-4,5α-epoxy-6α-[(S)-(2-methyl-1,2,3,4-tetrahydroisoquinoline-3-carboxamido)]morphinan; and 17-Cyclopropylmethyl-3,14β-dihydroxy-4,5α-epoxy-6α-(7-dimethylamino-2-methyl-1,2,3,4-tetrahydroisoquinoline-3-carboxamido)morphinan.

11. A method of treating symptoms of addiction related to MOR in a patient in need thereof, comprising administering to said patient a MOR antagonist of general formula

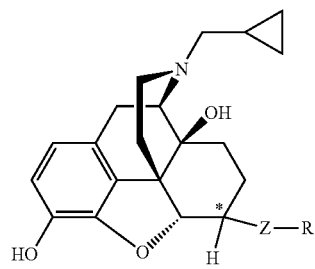

wherein
  the MOR antagonist may be a racemic mixture or a purified racemate;
  the nitrogen (N) at the 17N position may be charged and substituted with a C1-10 alkyl or alkaryl, or may be uncharged and unsubstituted;
  Z is selected from the group consisting of a substituted or unsubstituted aliphatic moiety; NH; CO; (NHCO)n where n=1-5; (CONH)n where n=1-5; (NHCO)(CH$_2$)n(NHCO), where n=1-5; (NHCO)(CH$_2$)n where n=1-5; (CH$_2$)n(NHCO), where n=1-5; and O;
  R is selected from the group consisting of substituted and unsubstituted heteroaromatic rings including without limitation

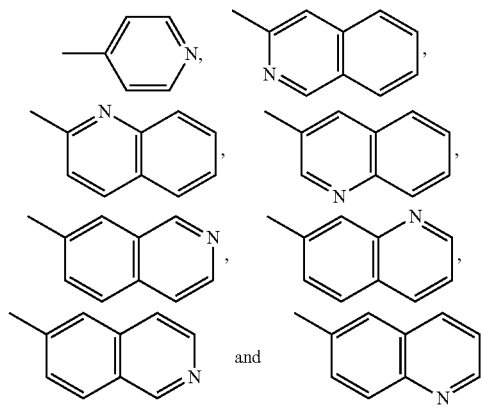

and wherein any carbon of said heteroaromatic ring may be bonded to a hydrogen or be substituted with a substitution selected from the group consisting of substituted or unsubstituted C1-5 alkyl, C1-5 alyleether, carboxylic acid, nitrogen, cyano, nitro, halogen, or amino moiety, and where the substitution may be the same or different when more than one carbon is substituted, wherein the nitrogen in the heteroarmatic ring may be charged and substituted with a C-10 alkyl or alkaryl, or be uncharged and unsubstituted; and wherein in addition to the nitrogen substitution in said heteroaromatic ring, one or more carbons within said heteroaromatic ring may be replaced by a substitution selected from the group consisting of N, S, P, and O.

12. The method of claim 11 wherein said MOR antagonist is selected from the group consisting of:

17-Cyclopropylmethyl-3,14β-dihydroxy-4,5α-epoxy-6β-{[4'-(2'-chloropyridyl)]carboxamido}morphinan;

17-Cyclopropylmethyl-3,14β-dihydroxy-4,5α-epoxy-6β-{[4'-(2'-bromopyridyl)]carboxamido}morphinan;

17-Cyclopropylmethyl-3,14β-dihydroxy-4,5α-epoxy-6β-{[4'-(2'-cyanopyridyl)]carboxamido}morphinan;

17-Cyclopropylmethyl-3,14β-dihydroxy-4,5α-epoxy-6β-{[4'-(2'-methylpyridyl)]carboxamido}morphinan;
17-Cyclopropylmethyl-3,14β-dihydroxy-4,5α-epoxy-6β-{[4'-(2'-methoxypyridyl)]carboxamido}morphinan;
17-Cyclopropylmethyl-3,14β-dihydroxy-4,5α-epoxy-6β-{[4'-(3'-chloropyridyl)]carboxamido}morphinan;
17-Cyclopropylmethyl-3,14β-dihydroxy-4,5α-epoxy-6β-{[4'-(3'-bromopyridyl)]carboxamido}morphinan;
17-Cyclopropylmethyl-3,14β-dihydroxy-4,5α-epoxy-6β-{[4'-(3'-methylpyridyl)]carboxamido}morphinan;
17-Cyclopropylmethyl-3,14β-dihydroxy-4,5α-epoxy-6β-{[4'-(3'-methoxylpyridyl)]carboxamido}morphinan;
17-Cyclopropylmethyl-3,14β-dihydroxy-4,5α-epoxy-6β-[2'-(pyridine-4"-yl)acetamido]morphinan;
17-Cyclopropylmethyl-3,14β-dihydroxy-4,5α-epoxy-6β-[3'-(pyridine-4"-yl)propanamido]morphinan;
17-Cyclopropylmethyl-3,14β-dihydroxy-4,5α-epoxy-6β-{2'-[(pyridine-4"-yl)carboxamido]acetamido}morphinan;
17-Cyclopropylmethyl-3,14β-dihydroxy-4,5α-epoxy-6β-[(2'-pyridazine)carboxamnido]morphinan;
17-Cyclopropylmethyl-3,14β-dihydroxy-4,5α-epoxy-6β-[(2'-pyrimidine)carboxamido]morphinan;
17-Cyclopropylmethyl-3,14β-dihydroxy-4,5α-epoxy-6α-(1'-methylpiperidine-4'-carboxamido)morphinan;
17-Cyclopropylmethyl-3,14β-dihydroxy-4,5α-epoxy-6α-[2-(isoquinolin-3-yl)acetamido)morphinan;
17-Cyclopropylmethyl-3,14β-dihydroxy-4,5α-epoxy-6α-[3-(isoquinolin-3-yl)propanamido)morphinan;
17-Cyclopropylmethyl-3,14β-dihydroxy-4,5α-epoxy-6α-[2-(isoquinoline-3-carboxamido)acetamido)morphinan;
17-Cyclopropylmethyl-3,14β-dihydroxy-4,5α-epoxy-6α-(1-chloro-4-methoxyisoquinoline-3-carboxamido)morphinan;
17-Cyclopropylmethyl-3,14β-dihydroxy-4,5α-epoxy-6α-(1-chloro-4-hydroxyisoquinoline-3-carboxamido)morphinan;
17-Cyclopropylmethyl-3,14β-dihydroxy-4,5α-epoxy-6α-(4-hydroxyisoquinoline-3-carboxamido)morphinan;
17-Cyclopropylmethyl-3,14β-dihydroxy-4,5α-epoxy-6α-(4-quinazoline-2-carboxamido)morphinan;
17-Cyclopropylmethyl-3,14β-dihydroxy-4,5α-epoxy-6α-(1-chloroisoquinoline-3-carboxamido)morphinan;
17-Cyclopropylmethyl-3,14β-dihydroxy-4,5α-epoxy-6α-(1-cyanoisoquinoline-3-carboxamido)morphinan;
17-Cyclopropylmethyl-3,14β-dihydroxy-4,5α-epoxy-6α-(1-methylisoquinolin-3-carboxamido)morphinan;
17-Cyclopropylmethyl-3,14β-dihydroxy-4,5α-epoxy-6α-(6-nitroisoquinoline-3-carboxamido)morphinan;
17-Cyclopropylmethyl-3,14β-dihydroxy-4,5α-epoxy-6α-(7-nitroisoquinoline-3-carboxamido)morphinan;
17-Cyclopropylmethyl-3,14β-dihydroxy-4,5α-epoxy-6α-(7-dimethylaminoisoquinoline-3-carboxamido)morphinan;
17-Cyclopropylmethyl-3,14β-dihydroxy-4,5α-epoxy-6α-(6,7-dimethoxyisoquinoline-3-carboxamido)morphinan;
17-Cyclopropylmethyl-3,14β-dihydroxy-4,5α-epoxy-6α-[(S)-(2-methyl-1,2,3,4-tetrahydroisoquinoline-3-carboxamido)]morphinan; and
17-Cyclopropylmethyl-3,14β-dihydroxy-4,5α-epoxy-6α-(7-dimethylamino-2-methyl-1,2,3,4-tetrahydroisoquinoline-3-carboxamido)morphinan.

13. The method of claim 11 wherein said addiction is opioid addiction.

14. A method of treating opioid induced constipation in a patient in need thereof, comprising
administering to said patient a MOR antagonist of general formula

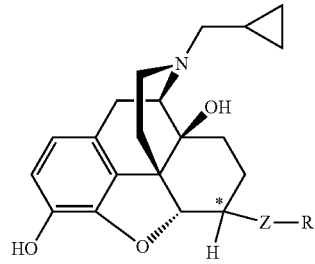

wherein
the MOR antagonist may be a racemic mixture or a purified racemate;
the nitrogen (N) at the 17N position may be charged and substituted with a C1-10 alkyl or alkaryl, or may be uncharged and unsubstituted;
Z is selected from the group consisting of a substituted or unsubstituted aliphatic moiety; NH; CO; (NHCO)n where n=1-5; (CONH)n where n=1-5; (NHCO)(CH$_2$)n (NHCO), where n=1-5; (NHCO)(CH$_2$)n where n=1-5; (CH$_2$)n(NHCO), where n=1-5; and O;
R is selected from the group consisting of substituted and unsubstituted heteroaromatic rings including without limitation

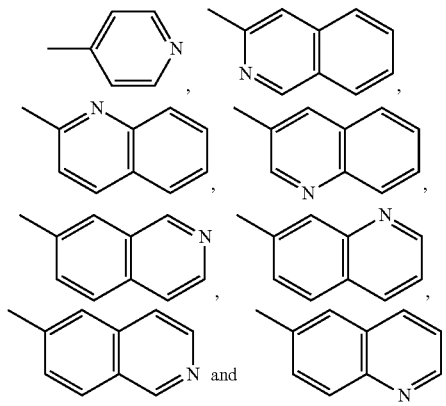

wherein any carbon of said heteroaromatic ring may be bonded to a hydrogen or be substituted with a substitution selected from the group consisting of substituted or unsubstituted C1-5 alkyl, C1-5 alyleether, carboxylic acid, nitrogen, cyano, nitro, halogen, or amino moiety, and where the substitution may be the same or different when more than one carbon is substituted,
wherein the nitrogen in the heteroarmatic ring may be charged and substituted with a C-10 alkyl or alkaryl, or be uncharged and unsubstituted; and
wherein in addition to the nitrogen substitution in said heteroaromatic ring, one or more carbons within said heteroaromatic ring may be replaced by a substitution selected from the group consisting of N, S, P, and O.

15. The method of claim 14 wherein said MOR antagonist is selected from the group consisting of:

17-Cyclopropylmethyl-3,14β-dihydroxy-4,5α-epoxy-6β-{[4'-(2'-chloropyridyl)]carboxamido}morphinan;

17-Cyclopropylmethyl-3,14β-dihydroxy-4,5α-epoxy-6β-{[4'-(2'-bromopyridyl)]carboxamido}morphinan;

17-Cyclopropylmethyl-3,14β-dihydroxy-4,5α-epoxy-6β-{[4'-(2'-cyanopyridyl)]carboxamido}morphinan;

17-Cyclopropylmethyl-3,14β-dihydroxy-4,5α-epoxy-6β-{[4'-(2'-methylpyridyl)]carboxamido}morphinan;

17-Cyclopropylmethyl-3,14β-dihydroxy-4,5α-epoxy-6β-{[4'-(2'-methoxypyridyl)]carboxamido}morphinan;

17-Cyclopropylmethyl-3,14β-dihydroxy-4,5α-epoxy-6β-{[4'-(3'-chloropyridyl)]carboxamido}morphinan;

17-Cyclopropylmethyl-3,14β-dihydroxy-4,5α-epoxy-6β-{[4'-(3'-bromopyridyl)]carboxamido}morphinan;

17-Cyclopropylmethyl-3,14β-dihydroxy-4,5α-epoxy-6β-{[4'-(3'-methylpyridyl)]carboxamido}morphinan;

17-Cyclopropylmethyl-3,14β-dihydroxy-4,5α-epoxy-6β-{[4'-(3'-methoxylpyridyl)]carboxamido}morphinan;

17-Cyclopropylmethyl-3,14β-dihydroxy-4,5α-epoxy-6β-[2'-(pyridine-4"-yl)acetamido]morphinan;

17-Cyclopropylmethyl-3,14β-dihydroxy-4,5α-epoxy-6β-[3'-(pyridine-4"-yl)propanamido]morphinan;

17-Cyclopropylmethyl-3,14β-dihydroxy-4,5α-epoxy-6β-{2'-[(pyridine-4"-yl)carboxamido]acetamido}morphinan;

17-Cyclopropylmethyl-3,14β-dihydroxy-4,5α-epoxy-6β-[(2'-pyridazine) carboxamiido]morphinan;

17-Cyclopropylmethyl-3,14β-dihydroxy-4,5α-epoxy-6β-[(2'-pyrimidine) carboxamido]morphinan;

17-Cyclopropylmethyl-3,14β-dihydroxy-4,5α-epoxy-6β-(1'-methylpiperidine-4'-carboxamido)morphinan;

17-Cyclopropylmethyl-3,14β-dihydroxy-4,5α-epoxy-6α-[2-(isoquinolin-3-yl)acetamido)morphinan;

17-Cyclopropylmethyl-3,14β-dihydroxy-4,5α-epoxy-6α-[3-(isoquinolin-3-yl)propanamido)morphinan;

17-Cyclopropylmethyl-3,14β-dihydroxy-4,5α-epoxy-6α-[2-(isoquinoline-3-carboxamido)acetamido}morphinan;

17-Cyclopropylmethyl-3,14β-dihydroxy-4,5α-epoxy-6α-(1-chloro-4-methoxyisoquinoline-3-carboxamido)morphinan;

17-Cyclopropylmethyl-3,14β-dihydroxy-4,5α-epoxy-6α-(1-chloro-4-hydroxyisoquinoline-3-carboxamido)morphinan;

17-Cyclopropylmethyl-3,14β-dihydroxy-4,5α-epoxy-6α-(4-hydroxyisoquinoline-3-carboxamido)morphinan;

17-Cyclopropylmethyl-3,14β-dihydroxy-4,5α-epoxy-6α-(4-quinazoline-2-carboxamido)morphinan;

17-Cyclopropylmethyl-3,14β-dihydroxy-4,5α-epoxy-6α-(1-chloroisoquinoline-3-carboxamido)morphinan;

17-Cyclopropylmethyl-3,14β-dihydroxy-4,5α-epoxy-6α-(1-cyanoisoquinoline-3-carboxamido)morphinan;

17-Cyclopropylmethyl-3,14β-dihydroxy-4,5α-epoxy-6α-(1-methylisoquinolin-3-carboxamido)morphinan;

17-Cyclopropylmethyl-3,14β-dihydroxy-4,5α-epoxy-6α-(6-nitroisoquinoline-3-carboxamido)morphinan;

17-Cyclopropylmethyl-3,14β-dihydroxy-4,5α-epoxy-6α-(7-nitroisoquinoline-3-carboxamido)morphinan;

17-Cyclopropylmethyl-3,14β-dihydroxy-4,5α-epoxy-6α-(7-dimethylaminoisoquinoline-3-carboxamido)morphinan;

17-Cyclopropylmethyl-3,14β-dihydroxy-4,5α-epoxy-6α-(6,7-dimethoxyisoquinoline-3-carboxamido)morphinan;

17-Cyclopropylmethyl-3,14β-dihydroxy-4,5α-epoxy-6α-[(S)-(2-methyl-1,2,3,4-tetrahydroisoquinoline-3-carboxamido)]morphinan; and 17-Cyclopropylmethyl-3,14β-dihydroxy-4,5α-epoxy-6α-(7-dimethylamino-2-methyl-1,2,3,4-tetrahydroisoquinoline-3-carboxamido)morphinan.

\* \* \* \* \*